United States Patent
Qabar et al.

(10) Patent No.: US 6,372,744 B1
(45) Date of Patent: Apr. 16, 2002

(54) β-SHEET MIMETICS AND METHODS RELATING TO THE USE THEREOF

(75) Inventors: Maher N. Qabar, Redmond; Michael K. McMillan, Bellevue; Michael S. Kahn, Kirkland; John E. Tulinsky, Seattle; Cyprian O. Ogbu; Jessymol Mathew, both of Bellevue, all of WA (US)

(73) Assignee: Molecumetics Ltd., Bellevue, WA (US)

( * ) Notice: Subject to any disclaimer, the term of this patent is extended or adjusted under 35 U.S.C. 154(b) by 0 days.

(21) Appl. No.: 09/501,052

(22) Filed: Feb. 9, 2000

Related U.S. Application Data

(60) Division of application No. 09/022,934, filed on Feb. 12, 1998, now Pat. No. 6,117,896, and a continuation-in-part of application No. 08/797,915, filed on Feb. 10, 1997, now abandoned, and a continuation-in-part of application No. 08/692,420, filed as application No. PCT/US97/13622 on Aug. 4, 1997, now abandoned.

(60) Provisional application No. 60/047,067, filed on May 19, 1997.

(51) Int. Cl.$^7$ .................. A61K 31/5025; A61K 31/503; A61K 31/416; A61K 31/4162; C07D 249/16

(52) U.S. Cl. ...................... 514/248; 514/384; 530/323; 530/332; 548/263.4

(58) Field of Search .............................. 514/384, 248; 544/236, 237; 548/485, 486, 263.4; 530/323, 334

(56) References Cited

U.S. PATENT DOCUMENTS

| | | | | |
|---|---|---|---|---|
| 4,307,094 A | | 12/1981 | Hassall et al. ............... | 424/250 |
| 4,767,871 A | | 8/1988 | Holmes et al. .............. | 548/365 |
| 4,885,023 A | * | 12/1989 | Yamaguchi et al. ..... | 544/255 X |
| 5,180,418 A | * | 1/1993 | Pissiotas et al. ............ | 504/193 |
| 6,117,896 A | * | 9/2000 | Qabar et al. ................. | 514/384 |

FOREIGN PATENT DOCUMENTS

| | | | | |
|---|---|---|---|---|
| CA | 0593525 | * | 3/1960 | ................. 544/236 |
| DE | 0228812 | * | 10/1985 | ................. 544/236 |
| DE | 3813884 | * | 11/1989 | ................. 544/236 |
| EP | 0104484 | * | 4/1984 | ................. 544/236 |
| EP | 0370955 | * | 5/1990 | ................. 544/236 |
| EP | 599 444 A1 | | 6/1994 | |
| EP | 743 319 A1 | | 11/1996 | |
| JP | 59-172491 | * | 9/1984 | ................. 544/236 |
| JP | 01-121290 | * | 5/1989 | ................. 544/236 |
| WO | WO 93/16103 | | 8/1993 | |
| WO | WO 93/23403 | | 11/1993 | |
| WO | WO 95/33751 | | 12/1995 | |
| WO | WO 95/35308 | | 12/1995 | |
| WO | WO 96/19483 | | 6/1996 | |

OTHER PUBLICATIONS

Bauer et al., "Mehrfach ungesättigte Radikalkationen: Regio–und Stereochemie der oxidativen Dimerisierung von Heptafulvenen," *Chem. Ber. 117*: 809–826, 1984.

Hassall et al., "The Design and Synthesis of New Triazolo, Pyrazolo–, and Pyridazo–pyridazine Derivatives as Inhibitors of Angiotensin Converting Enzyme," *J. Chem. Soc. Perkin Trans. I:* 155–164, 1984.

Bernabeu et al., "(2E)–4–Methoxy–2,4–pentadienamides as New Dienes in the Diels–Alder Reaction," *Tetrahedron Letters 37*(20): 3595–3598, 1996.

Boyd et al., "The Chemistry of N–Substituted 3–Amino–1H–2–benzopyran–1–ones and 5–Amino–2,3–dihydrofuran–2–ones. Ene–type Reactions involving Transfer of Acyl Groups. X–Ray Crystal Structure of cis–3,4–Dihydro–4–morpholinocarbonyl–3–p–nitrophenyl–1H–2–benzopyran–1–one," *J. Chem Soc. Perkin Trans. 1:* pp. 1351–1360, 1978.

Baydar et al., "Acyl Analogues of the Ene Reaction," *J. Chem. Soc. Chem. Comm.* pp. 650–652, 1976.

Seguchi, "Ready Alcoholysis of the Cycloadducts (Urazole) of 4–Phenyl–1,2,4–triazole–3,5–dione by Solvent–assisted Backbone Participation," *J. Chem. Soc. Perkin Trans. 1:* pp. 2883–2884, 1991.

Cowley and Stoodley, "Regio–and Stereo–selective Intermolecular Interceptions of a Conjugated N–Acylhydrazonium Ion," *Tetrahedron Letters 35*(42): 7853–7856, 1994.

Aspinall et al., "Enhanced Discrimination by Aza Dienophiles over their Olefinic Counterparts for the Diastereotopic Faces of Methyl (E,E)–5–(2', 3', 4', 6'–Tetra–O–acetyl–β–D–glucopyranosyloxy)penta–2,4–dienoate," *Tetrahedron Letters 35*(20): 3397–3400, 1994.

Adam et al., "Determination of the Triplet Lifetimes of 1,3–Cyclopentadiyl Biradicals Derived from the Photodenitrogenation of Azoalkanes with Time–Resolved Photoacoustic Calorimetry," *J. Org. Chem. 58*: 1477–1482, 1993.

Attwood et al., "The Design and Synthesis of the Angiotensin Converting Enzyme Inhibitor Cilazapril and Related Bicyclic Compounds," *J. Chem. Soc. Perkin Trans. I:* 1011–1019, 1986.

Baldwin et al., "Synthesis Of A Bicyclic γ–Lactam Dipeptide Analogue," *Heterocycles 34*(5): 903–906, 1992.

Colombo et al., "Conformationally Constrained Dipeptides: Synthesis of 7,5–and 6,5–Fused Bicyclic Lactams by Stereoselective Radical Cyclizations," *Tetrahedron Letters 36*(4): 625–628, 1995.

(List continued on next page.)

*Primary Examiner*—Floyd D. Higel
(74) *Attorney, Agent, or Firm*—Seed Intellectual Property Law Group PLLC

(57) ABSTRACT

β-sheet mimetics and methods relating to the same are disclosed. The β-sheet mimetics have utility as protease and kinase inhibitors, as well as inhibitors of transcription factors and protein-protein binding interactions. Methods of the invention include administration of a β-sheet mimetic, or use of the same for the manufacture of a medicament for treatment of a variety of conditions associated with the targeted protease, kinase, transcription factor and/or protein-protein binding interaction.

73 Claims, 6 Drawing Sheets

OTHER PUBLICATIONS

Colombo et al., "Synthesis of 7,5–Fused Bicyclic Lactams by Stereoselective Radical Cyclization," *Tetrahedron Letters* 35(23): 4031–4034, 1994.

Goldschmidt et al., "Activation Of Electron Deficient Cycloheptatrienes By Tricarbonyliron Complexation," *Tetrahedron Letters* 31(46): 6711–6712, 1990.

Grangier et al., "Reactivity of Nucleophilic Uracil Derivatives," *J. Heterocyclic Chem.* 31: 1707–1714, 1994.

Jungheim et al., "Bicyclic Pyrazolidinones, A New Class Of Antibacterial Agent Based On The β–Lactam Model," *Tetrahedron Letters* 28(3): 285;288, 1987.

Li et al., "Conformationally Restricted Peptide Mimetics: The Incorporation of 6,5–Bicyclic Lactam Ring Skeletons into Peptides," *J. Org. Chem.* 60: 8155–8170, 1995.

Lombart and Lubell, "Synthesis of Enantiopure α,ω–Diamino Dicarboxylates and Azabicycloalkane Amino Acids by Claisen Condensation of α–[N–(Phenylfluorenyl)amino] Dicarboxylates," *The Journal of Organic Chemistry* 59(21): 6147–6149, 1994.

Mathews and Tulinsky, "Active–site mimetic of thrombin," *Biological Abstracts* 100(8): 1148, Abstract No. 123166, 1995.

Mayer et al., "A unique geometry of the active site of angiotensin–converting enzyme consistent with structure–activity studies," *Journal of Computer–Aided Molecular Design* 1: 3–16, 1987.

Mueller and Revesz, "Synthesis of 6,5–Fused Bicyclic Lactams as Potential Dipeptide β–Turn Mimetics," *Tetrahedron Letters* 35(24): 4091–4092, 1994.

Nagai et al., "Bicyclic Turned Dipeptide (BTD) as a β–Turn Mimetic: its Design, Synthesis and Incorporation into Bioactive Peptides," *Tetrahedron* 49(17): 3577–3592, 1993.

Roberts et al, "Asymmetric Synthesis of Two–Residue Modules Designed for Mimicry of Beta Strands,"*Tetrahedron Letters* 36(5): 691–694, 1995.

Robl et al., "Dual Metalloprotease Inhibitors. 6. Incorporation of Bicyclic and Substituted Monocyclic Azepinones as Dipeptide Surrogates in Angiotensin–Converting Enzyme/Neutral Endopeptidase Inhibitors," *J. Med. Chem.* 39: 494–502, 1996.

Robl, "Peptidomimetic Synthesis: Utilization of N–Acyliminium Ion Cyclization Chemistry in the Generation of 7,6–and 7,5–Fused Bicyclic Lactams," *Tetrahedron Letters* 35(3): 393–396, 1994.

Slomcyznska et al., "Electrochemical Cyclization of Dipeptides To Form Novel Bicyclic, Reverse–Turn Peptidomimetics. 2. Synthesis and Conformational Analysis of 6,5–Bicyclic Systems," *J. Org. Chem.* 61(4): 1198–1204, 1996.

Songyang et al., "Use of an oriented peptide library to determine the optimal substrates of protein kinases," *Current Biology* 4(11): 973–982, 1994.

Ternansky and Draheim, "[3.3.0] Pyrazolodinones: An Efficient Synthesis Of A New Class Of Synthetic Antibacterial Agents," *Tetrahedron Letters* 31(20): 2805–2808, 1990.

Bird et al., "Activation of Nuclear Transcription Factor NF–kB Interleukin–1 Is Accomplished by Casein Kinase II–mediated Phosphorylation of the p65 Subunit," *The Journal of Biological Chemistry* 272(51): 32606–32612, 1997.

Butt and Karathanasis, "Trancription Factors as Drug Targets: Opportunities for Therapeutic Selectivity," *Gene Expression* 4: 319–336, 1995.

Moynagh et al., "Interleukin–1 activates transcription factor NFkB in glial cells," *Biochem. J.* 294: 343–347, 1993.

Rubartelli and Sitia, "Interleukin Iβ and thioredoxin are secreted through a novel pathway of secretion," *Biochem. Soc. Trans.* 19: 255–259, 1991.

Sen and Packer, "Antioxidant and redox regulation of gene trancription," *FASEB J.* 10: 709–720, 1996.

\* cited by examiner

β-SHEET MIMETICS AND METHODS RELATING TO THE USE THEREOF

CROSS-REFERENCE TO PRIOR APPLICATIONS

This application is a divisional of U.S. patent application Ser. No. 09/022,934, filed Feb. 12, 1998, now U.S. Pat. No. 6,117,896 which application claims the benefit of U.S. Provisional Application No. 60/047,067, filed May 19, 1997, and is a continuation-in-part of U.S. application Ser. No. 08/797,915 filed Feb. 10, 1997 (abandoned) and U.S. application Ser. No. 08/692,420 filed Aug. 5, 1996 (abandoned), filed as application No. PCT/US97/13622, Aug. 4, 1997, abandoned.

TECHNICAL FIELD

This invention relates generally to β-sheet mimetics and, more specifically, to β-sheet mimetics which inhibit biologically active peptides and proteins.

BACKGROUND OF THE INVENTION

The β-sheet conformation (also referred to as a β-strand conformation) is a secondary structure present in many polypeptides. The β-sheet conformation is nearly fully extended, with axial distances between adjacent amino acids of approximately 3.5 Å. The β-sheet is stabilized by hydrogen bonds between NH and CO groups in different polypeptides strands. Additionally, the dipoles of the peptide bonds alternate along the strands which imparts intrinsic stability to the β-sheet. The adjacent strands in the β-sheet can run in the same direction (i.e., a parallel β-sheet) or in opposite directions (i.e., an antiparallel β-sheet). Although the two forms differ slightly in dihedral angles, both are sterically favorable. The extended conformation of the β-sheet conformation results in the amino acid side chains protruding on alternating faces of the β-sheet.

The importance of β-sheets in peptides and proteins is well established (e.g., Richardson, *Nature* 268:495–499, 1977; Halverson et al., *J. Am. Chem Soc.* 113:6701–6704, 1991; Zhang, *J. Biol. Chem.* 266:15591–15596, 1991; Madden et al., *Nature* 353:321–325, 1991). The β-sheet is important in a number of biological protein-protein recognition events, including interactions between proteases and their substrates, protein kinases and their substrates or inhibitors, the binding of SH2 domain containing proteins to their cognate phosphotyrosine containing protein targets, farnesyl transferase to its protein substrates, and MHC I and II and their antigenic peptides, and has been implicated in many disease states.

Inhibitors that mimic the β-sheet structure of biologically active proteins or peptides would have utility in the treatment of a wide variety of conditions. For example, Ras, the protein product of the ras oncogene, is a membrane bound protein involved in signal transduction regulating cell division and growth. Mutations in the ras gene are among the most common genetic abnormalities associated with human cancers (Barbacid, M. "ras genes," 56:779–827, 1987). These mutations result in a growth signal which is always "on," leading to a cancerous cell. In order to localize to the cell membrane, Ras requires prenylation of the cysteine within its C-terminal CaaX sequence by farnesyl transferase (FTase). (In the sequence CaaX "a" is defined as an amino acid with a hydrophobic side chain and "X" is another amino acid.) This post-translational modification is crucial to its activity. Peptidyl inhibitors of FTase with the sequence CaaX have been shown to block or slow the growth of tumors in cell culture and in whole animals (Kohl et al., "Selective inhibition of ras-dependent transformation by a farnesyltransferase inhibitor," *Science* 260:1934–1937, 1993; Buss, J. E. & Marsters, Jr., J. C. "Farnesyl transferase inhibitors: the successes and surprises of a new class of potential cancer chemotherapeutics," *Chemistry and Biology* 2:787–791, 1995).

SH2 domains, originally identified in the src subfamily of PTKs, are noncatalytic sequences and consist of about 100 amino acids conserved among a variety of signal transducing proteins (Cohen et al., *Cell* 80:237–248, 1995). SH2 domains function as phosphotyrosine-binding modules and mediate critical protein-protein associations (Pawson, *Nature* 573–580, 1995). In particular, the role of SH2 domains has been clearly defined as critical signal transducers for receptor tyrosine kinases (RTKs such as EGF-R, PDGF, insulin receptor, etc.). Phosphotyrosine-containing sites on autophosphorylated RTKs serve as binding sites for SH2-proteins and thereby mediate the activation of biochemical signaling pathways (Carpenter, G., *FAESEB J.* 6:3283–3289, 1992; Sierke, S. and Koland, J., *Biochem.* 32:10102–10108, 1993). The SH2 domains are responsible for coupling the activated growth-factor receptors to cellular responses which include alterations in gene expression, cell proliferation, cytoskeletal architecture and metabolism.

At least 20 cytosolic proteins have been identified that contain SH2 domains and function in intracellular signaling. The distribution of SH2 domains is not restricted to a particular protein family, but is found in several classes of proteins, protein kinases, lipid kinases, protein phosphatases, phospholipases, Ras-controlling proteins and some transcription factors. Many of the SH2-containing proteins have known enzymatic activities while others (Grb2 and Crk) function as "linkers" and "adapters" between cell surface receptors and downstream effector molecules (Marengere, L., et al., *Nature* 369:502–505, 1994). Examples of proteins containing SH2 domains with enzymatic activities that are activated in signal transduction include, but are not limited to, the src subfamily of protein tyrosine kinases (src (pp60$^{c\text{-}src}$), abl, lck, fyn, fgr and others), phospholipase-C-γ (PLC-γ), phosphatidylinositol 3-kinase (Pl-3-kinase), p21-ras GTPase activating protein (GAP) and SH2 containing protein tyrosine phosphatases (SH-PTPase) (Songyang et al., *Cell* 72:767–778, 1993). Intracellular tyrosines are phosphorylated when surface receptors are engaged by diverse ligands for growth factor receptors, cytokine receptors, insulin receptor, and antigen-mediated signaling through T- or B-cell receptors. The phosphorylation of proteins at tyrosine residues is critical in the cellular signal transduction, neoplastic transformation and control of the cell cycle. Due to the central role these various SH2-proteins occupy in transmitting signals from activated cell surface receptors into a cascade of additional molecular interactions that ultimately define cellular responses, inhibitors which block specific SH2-protein binding are desirable as agents for a variety of potential therapeutic applications.

Disease areas in which tyrosine phosphorylation and inhibition of SH2 binding represent targets for drug development include the following:

Cancer

SH2 domains which mediate signaling are clearly significant elements in the regulation of oncogene and protooncogene tyrosine kinase activity and cellular proliferation (Carpenter, *Fed. Am. Soc. Exp. Biol. J.* 6:3283–3289, 1992). The SH2 domains define an important set of substrates through which activated RTKs mediate signaling and through which nonreceptor tyrosine kinases associate with RTKs and are thus targets for anticancer drug development. The ability to block interaction of the RTK with the SH2-containing substrate using a mimetic inhibitor provides a means to abrogate signaling and thereby eliminate oncogenic activity. The biological significance is also illustrated by the v-crk oncogene, a protein composed almost entirely of SH domains, which is able to bring about cellular transformation by interacting with phosphotyrosine containing proteins. As above, the ability of inhibitors to block v-crk binding via its SH2 domain to other proteins would be expected to be effective as an anticancer agent.

Immune Regulation

Regulation of many immune responses is mediated through receptors that transmit signals through tyrosine kinases containing SH2 domains. T-cell activation via the antigen specific T-cell receptor (TCR) initiates a signal transduction cascade leading to lymphokine secretion and cell proliferation. One of the earliest biochemical responses following TCR activation is an increase in tyrosine kinase activity. In particular, T-cell activation and proliferation is controlled through T-cell receptor mediated activation of $p56^{lck}$ and $p59^{fyn}$ tyrosine kinases, as well as ZAP-70 and Syk (Weiss and Litman, Cell 76:263–274, 1994) which contain SH2 domains. Additional evidence indicates that several src-family kinases (lck, blk, fyn) participate in signal transduction pathways leading from B-cell antigen receptors and hence may serve to integrate stimuli received from several independent receptor structures. Thus, inhibitors that block interactions of these SH2 domain kinases with their cognate receptors could serve as immunosuppressive agents with utility in autoimmune diseases, transplant rejection or as anti-inflammatory agents as well as anticancer drugs in cases of lymphocytic leukemias.

Additionally, non-transmembrane PTPase containing SH2 domains are known and nomenclature refers to them as SH-PTP1 and SH-PTP2 (Neel, Cell Biology 4:419–432, 1993) SH-PTP1 is identical to PTP1C, HCP or SHP and SH-PTP2 is also known as PTP1D or PTP2C. SH-PTP1 is expressed at high levels in hematopoietic cells of all lineages and all stages of differentiation. Since the SH-PTP1 gene was identified as responsible for the motheaten (me) mouse phenotype, this provides a basis for predicting the effects of inhibitors that would block its interaction with its cellular substates. Thus, inhibition of SH-PTP1 function would be expected to result in impaired T-cell responses to mitogenic stimulation, decreased NK cell function, and depletion of B-cell precursors with potential therapeutic applications as described above.

Diabetes

In Type 2 (non-insulin dependent) diabetes, tyrosine phosphatases (SH-PTP2) counter-balance the effect of activated insulin-receptor kinases and may represent important drug targets. In vitro experiments show that injection of PTPase blocks insulin stimulated-phosphorylation of tyrosyl residues on endogenous proteins. Thus, inhibitors could serve to modulate insulin action in diabetes.

Neural Regeneration

Glial growth factors are ligands that are specific activators of erb-B2 receptor tyrosine kinase ($p185^{erbB2}$) to promote tyrosine phosphorylation and mitogenic responses of Schwann cells. Consequently, regulation of tyrosine phosphorylation by altering activity in Schwann cells following nerve injury could be an important therapeutic strategy. Inhibitors of erb-B2 signaling activity could have a significant role in treatment of tumors of glial cell origin.

Another class of β-sheet mimetics are inhibitors of protein kinases, which include the protein tyrosine kinases and serine/threonine kinases.

A wide variety of cellular substrates for polypeptide growth factor receptors that possess intrinsic tyrosine kinase activity have now been characterized. Although there is a tremendous diversity among the numerous members of the receptors tyrosine-kinases (RTK) family, the signaling mechanisms used by these receptors share many common features. Biochemical and molecular genetic studies have shown that binding of the ligand to the extracellular domain of the RTK rapidly activates the intrinsic tyrosine kinase catalytic activity of the intracellular domain. The increased activity results in tyrosine-specific phosphorylation of a number of intracellular substrates which contain a common sequence motif. Consequently, this causes activation of numerous downstream signaling molecules and a cascade of intracellular pathways that regulate phospholipid metabolism, arachidonate metabolism, protein phosphorylation (involving other protein kinases), calcium mobilization and transcriptional regulation. The growth-factor-dependent tyrosine kinase activity of the RTK cytoplasmic domain is the primary mechanism for generation of intracellular signals that initiate multiple cellular responses. Thus, inhibitors which would serve as alternate substrates or inhibitors of tyrosine kinase activity have the potential to block this signaling.

Many of the RTK subfamilies are recognizable on the basis of architectural similarities in the catalytic domain as well as distinctive motifs in the extracellular ligand binding regions. Based upon these structural considerations, a nomenclature defining several subfamilies of RTKs, each containing several members, has been developed (Hanks, Curr. Opin. Struc. Biol. 1:369–383, 1991; Ullrich, A., and Schlessinger, J. Cell 61:203–212, 1990). Examples of receptor subfamilies referred to on the basis of their prototypic members include: EGF-receptor, insulin receptor, platelet-derived growth factor (PDGF-receptor), fibroblast growth factor receptors (FGFRs), TRK receptor and EPH/ECK receptors. Members in each of these subfamilies represent molecular targets for the development of mimetic inhibitors that would block tyrosine kinase activity and prevent intracellular signal transduction. Several therapeutic areas in which these targets have value are identified below.

Cancer

In addition to mediating normal cellular growth, members of the EGFR family of RTKs are frequently overexpressed in a variety of aggressive epithelial carcinomas and this is thought to directly contribute to malignant tumor development. A number of studies have shown that the EGFR is frequently amplified in certain types of tumors, including glioblastomas, squamous carcinomas, and brain tumors (Wong et al., Proc. Natl. Acad Sci USA 84:6899–6903, 1987). Additionally, HER2/$p185^{erbB2}$ (alternatively referred to as "neu" in the rat), HER3/$p160^{erbB3}$, HER4/$p180^{erbB4}$ (Plowman, G. et al., Proc. Natl. Acad. Sci. USA 90:1746–1750 (1993) are three RTKs which have extensive amino acid sequence homology to the EGFR. HER2/$p185^{erbB2}$ is frequently amplified and overexpressed in human breast tumors and ovarian carcinomas (Wang et al., Proc. Natl. Acad. Sci. USA 84:6899–6903, 1987), and this amplification is correlated with poor patient prognosis. Simultaneous overexpression of $p185^{neu}$ and the EGFR synergistically transforms rodent fibroblasts and this condition is often observed in human cancers. Finally, HER3 expression is amplified in a variety of human adenocarcinomas. Several inhibitors are known which demonstrate inhibitory activity in vitro against the EGFR and block EGF-dependent cell proliferation which indicates therapeutic potential of compounds with this activity. In addition, in human chronic myelogenous leukemia, enhanced tyrosine kinase activity underlies the disease as a consequence of activation of the cellular c-abl protooncogene. Inhibitors would function as anticancer agents.

Angiogenesis

Currently, there are at least seven FGFR members which mediate a diverse array of biological responses, including the capacity to induce angiogenesis. In addition, a group of RTKs with seven lgLs has been proposed to represent a separate subfamily. Its known members, FLT1, FLK1 and FLT4 show a similarity of structure and expression. These receptors mediate the actions of Vascular Endothelial Growth Factor (VEGF). Several lines of evidence indicate that this subfamily of growth factor receptors play an important role in the formation of blood vessels. Since blood vessel formation is a process reactivated by tumors in order to supply oxygen to these cells, β-strand mimetics that inhibit these growth factors' kinase activities could serve to suppress tumor growth through inhibition of angiogenesis.

Restenosis

The PDGF receptor is of great interest as a target for inhibition in the cardiovascular field since it is believed to play a significant role in restenosis after coronary balloon angioplasties and also in atherosclerosis. The release of PDGF by platelets at damaged surfaces of blood vessels results in stimulation of PDGF receptors on vascular smooth muscle cells, and eventual neointimal thickening. A mimetic inhibitor of kinase activity would prevent proliferation and lead to greater successful outcomes from this surgical procedure.

Many components of signal transduction pathways involve phosphorylation of serine/threonine (ser/thr) residues of protein substrates. Some of these substrates are themselves protein kinases whose activity is modulated by phosphorylation. Two prominent ser/thr-specific protein kinases play a central role in signal transduction: cyclic AMP-dependent protein kinase A (PKA) and the protein kinase C (PKC family). Numerous other serine/threonine specific kinases, including the family of mitogen-activated protein (MAP) kinases serve as important signal transduction proteins which are activated in either growth-factor receptor or cytokine receptor signaling. Other protein ser/thr kinases important for intracellular signaling are Calcium-dependent protein kinase (CaM-kinase II) and the c-raf-protooncogene.

PKC plays a crucial role in cell-surface signal transduction for controlling a variety of physiological processes (Nishizuka, *Nature* 334:661–665, 1988) and represents a large family of isoenzymes which differ in their structure and expression in different tissues, as well as their substrate specificity (Hug and Sarre, *Biochem J.* 291:329–343, 1993). Molecular cloning has demonstrated at least 8 isoenzymes. Due to this diversity and differential expression, activation of individual isoenzymes produces differing cell-specific responses: stimulation of growth, inhibition of differentiation, or induction of differentiation. Due to its ability to stimulate cellular proliferation, it represents a target for anticancer drug development (Powis, *Trends in Pharm. Sci.* 12:188–194, 1991). Overexpression of PKC isoenzymes in mammalian cells is correlated with enhanced expression of early protooncogenes such as c-jun, c-fos, c-myc and one overexpressing cell line gives rise to tumors in nude mice.

Therapeutic applications within the area of immune regulation are evident since activation of T-cells by antigens involves activation of PKC. Activated PKC subsequently activates a branch of the signal cascade that is necessary for transcriptional activation of NF-κB, production of IL-2, and ultimately, T-cell proliferation. Inhibitors that block signaling through this branch pathway have been shown to prevent T-cell activation. Thus, mimetics that would function as inhibitors of PKC in T-cells would block signaling and serve as possible immunosuppressants useful in transplant rejection or as anticancer agents for lymphocytic leukemias. Activators of PKC cause edema and inflammation in mouse skin (Hennings et al., *Carcinogenesis* 8:1342–1346, 1987) and thus inhibitors are also expected to serve as potent anti-inflammatory compounds. Such anti-inflammatory activates would find use in asthma, arthritis and other inflammatory mediated processes. In addition, staurosporine and its analogs, UCN01 and CGP4125, which have been characterized as potent PKC inhibitors in vitro, have anti-tumor activity in animal models (Powis, *Trends in Pharm. Sci.* 12:188–194, 1991), and related compounds are being considered for clinical trials.

With regard to protease inhibition, Cathepsin B is a lysosomal cysteine protease normally involved in proenzyme processing and protein turnover. Elevated levels of activity have been implicated in tumor metastasis (Sloane, B. F. et al., "Cathepsin B and its endogenous inhibitors: the role in tumor malignancy," *Cancer Metastasis Rev.* 9:333–352, 1990), rheumatoid arthritis (Werb, Z. "Proteinases and matrix degradation," in Textbook of Rheumatology, Keller, W. N.; Harris, W. D.; Ruddy, S.; Sledge, C. S., Eds., 1989, W. B. Saunder Co., Philadelphia, Pa., pp. 300–321), and muscular dystrophy (Katunuma N. & Kominami E., "Abnormal expression of lysosomal cysteine proteinases in muscle wasting diseases," *Rev. Physiol. Biochem. Pharmacol.* 108:1–20, 1987).

Calpains are cytosolic or membrane bound Ca++– activated proteases which are responsible for degradation of cytoskeletal proteins in response to changing calcium levels within the cell. They contribute to tissue degradation in arthritis and muscular dystrophy (see Wang K. K. & Yuen P. W., "Calpain inhibition: an overview of its therapeutic potential," *Trends Pharmacol. Sci.* 15:412–419, 1994).

Interleukin Converting Enzyme (ICE) cleaves pro-IL-1 beta to IL-1 beta, a key mediator of inflammation, and therefore inhibitors of ICE may prove useful in the treatment of arthritis (see, e.g., Miller B. E. et al., "Inhibition of mature IL-1 beta production in murine macrophages and a murine model of inflammation by WIN 67694, an inhibitor of IL-1 beta converting enzyme," *J. Immunol.* 154:1331–1338, 1995). ICE or ICE-like proteases may also function in apoptosis (programmed cell death) and therefore play roles in cancer, AIDS, Alzheimer's disease, and other diseases in which disregulated apoptosis is involved (see Barr, P. J.; Tomei, L. D., "Apoptosis and its Role in Human Disease," *Biotechnol.* 12:487–493, 1994).

HIV protease plays a key role in the life cycle of HIV, the AIDS virus. In the final steps of viral maturation it cleaves polyprotein precursors to the functional enzymes and structural proteins of the virion core. HIV protease inhibitors were quickly identified as an excellent therapeutic target for AIDS (see Huff, J. R., "HIV protease: a novel chemotherapeutic target for AIDS," *J. Med. Chem.* 34:2305–2314) and have already proven useful in its treatment as evidenced by the recent FDA approval of ritonavir, Crixivan, and saquinavir.

Hepatitis C virus (HCV) is the major cause of non-A and non-B hepatitis in the world today. It is estimated to infect up to 50 million people. Currently there is no satisfactory treatment available to halt the progression of this debilitating disease. During the life cycle of the virus, a polyprotein of about 3000 amino acids is produced and is proteolytically cleaved by host and viral proteases to produce the mature viral gene products. A serine proteinase located within the HCV NS3 protein cleaves at four specific sites to produce non-structural proteins considered essential for viral replication. Hence, inhibitors of HCV protease are attractive targets for drug design, and could be of great therapeutic benefit. (Neddermann et al., *Biol. Chem.* 378:469–476, 1997.)

Angiotensin converting enzyme (ACE) is part of the renin-angiotensin system which plays a central role in the regulation of blood pressure. ACE cleaves angiotensin I to the octapeptide angiotensin II, a potent pressor agent due to its vasoconstrictor activity. Inhibition of ACE has proved therapeutically useful in the treatment of hypertension (Williams, G. H., "Converting-enzyme inhibitors in the treatment of hypertension," *N. Engl. J. Med.* 319:1517–1525, 1989.

Collagenases cleave collagen, the major constituent of the extracellular matrix (e.g., connective tissue, skin, blood vessels). Elevated collagenase activity contributes to arthritis (Krane S. M. et al., "Mechanisms of matrix degradation in rheumatoid arthritis," *Ann. N.Y. Acad. Sci.* 580:340–354, 1990.), tumor metastasis (Flug M. & Kopf-Maier P., "The basement membrane and its involvement in carcinoma cell invasion," *Acta Anat. Basel* 152:69–84, 1995), and other diseases involving the degradation of connective tissue.

Trypsin-like serine proteases form a large and highly selective family of enzymes involved in hemostasis/ coagulation (Davie, E. W. and K. Fujikawa, "Basic mechanisms in blood coagulation," *Ann. Rev.* 799–829, 1975) and complement activation (Muller-Eberhard, H. J., "Complement," *Ann. Rev. Biochem.* 44:697–724, 1975). Sequencing of these proteases has shown the presence of a homologous trypsin-like core with amino acid insertions that modify specificity and which are generally responsible for interactions with other macromolecular components (Magnusson et al., "Proteolysis and Physiological Regulation," *Miami Winter Symposia* 11:203–239, 1976).

Thrombin, a trypsin-like serine protease, acts to provide limited proteolysis, both in the generation of fibrin from fibrinogen and the activation of the platelet receptor, and thus plays a critical role in thrombosis and hemostasis (Mann, K. G., "The assembly of blood clotting complexes on membranes," *Trends Biochem. Sci.* 12:229–233, 1987). Thrombin exhibits remarkable specificity in the removal of fibrinopeptides A and B of fibrinogen through the selective cleavage of only two Arg-Gly bonds of the one-hundred and eighty-one Arg- or Lys-Xaa sequences in fibrinogen (Blomback, H., *Blood Clotting Enzymology*, Seeger, W. H. (ed.), Academic Press, New York, 1967, pp. 143–215).

Many significant disease states are related to abnormal hemostasis, including acute coronary syndromes. Aspirin and heparin are widely used in the treatment of patients with acute coronary syndromes. However, these agents have several intrinsic limitations. For example, thrombosis complicating the rupture of atherosclerotic plaque tends to be a thrombin-mediated, platelet-dependent process that is relatively resistant to inhibition by aspirin and heparin (Fuster et al., "The pathogenesis of coronary artery disease and the acute coronary syndromes," *N. Engl. J. Med.* 326:242–50, 1992).

Thrombin inhibitors prevent thrombus formation at sites of vascular injury in vivo. Furthermore, since thrombin is also a potent growth factor which initiates smooth muscle cell proliferation at sites of mechanical injury in the coronary artery, inhibitors block this proliferative smooth muscle cell response and reduce restenosis. Thrombin inhibitors would also reduce the inflammatory response in vascular wall cells (Harker et al., *Am. J. Cardiol.* 75:122–16B, 1995).

Furthermore, at least two well-defined transcription factors, nuclear factor (NF) κB and activator protein (AP)-1, are regulated by the intracellular reduction-oxidation (redox) state. The regulation of gene expression by the redox state holds promising therapeutic implications. For example, binding sites of the redox-regulated transcription factors NF-κB and AP-1 are located in the promoter region of a large variety of genes that are directly involved in the pathogenesis of diseases, such as AIDS, cancer, atherosclerosis and diabetic complications (Sen and Packer, *FASEB Journal* 10:709–720, 1996). More specifically, the binding of transcription factors such NF-κB and AP-1 to consensus sites on DNA is driven by oxidant-antioxidant homeostasis, especially by the thiol-disulfide balance.

In the case of NF-κB, a physiologically relevant thiol that plays a crucial role in the regulation of NF-κB function is reduced thioredoxin or a reduced thioredoxin-like protein. Thioredoxin is an important protein oxidoreductase with antioxidant functions. Thioredoxin has been found to upregulate DNA binding of activated NF-κB and thus augments gene expression (Schenk et al., *Proc. Natl. Acad. Sci. USA* 91:1672–1676, 1994). Thioredoxin has been implicated in reducing activated cytosolic NF-κB (specifically reduction of cys-62), which may thus contribute to its nuclear translocation and DNA binding (Hayashi et at., *J. Biol. Chem.* 268:11380–11388, 1993).

DNA binding activity of Fos and Jun in the AP-1 complex has also been found to be regulated by the redox state (Abate et al., *Science* 249:1157–1162, 1990). Each protein contains a single conserved cysteine (flanked by lysine and arginine) in its DNA binding domain. This thiol does not appear to be part of a disulfide bond and may exist as a sulfenic or sulfinic acid in its oxidized form. Ref-1, a bifunctional nuclear protein also possessing endonuclease DNA repair activity, stimulates AP-1 DNA binding by reduction of this regulatory cysteine. A Fos mutant in which the critical cysteine was replaced with serine elicited a three-fold increase in AP-1 DNA binding activity and was no longer subject to redox control (Okuno et al., *Oncogene* 8:695–701, 1993). Hence, since at least four members of the fos family, 3 of the jun family, and at least 4 of the ATF/CREB family of transcription factors all contain this conserved cysteine, redox control of transcription factors appears widespread.

As mentioned above, the regulation of transcription factors such as NF-κB and AP-1 have important therapeutic implications. For example, AP-1 is an important mediator of tumor production (Yoshioka et al., *Proc. Natl. Acad. Sci. USA* 92:4972–4976, 1995). Thus, compounds that repress AP-1 transcriptional activity have utility in the treatment of cancer. Furthermore, due to its direct role in regulating responses to inflammatory cytokines and endotoxins, the activation of NF-κB plays an important role in the development of chronic diseases such as rheumatoid arthritis and acute conditions such as septic shock. Autoimmune diseases, such as systemic lupus erythromatus (SLE), and Alzheimer's disease are also believed involved in activation of NF-κB. Similarly, NF-κB plays an important role in the activation of HIV gene expression. Further conditions which are believed to involve NF-κB include the flu, atherosclerosis, oncogenesis and ataxia telangiectasia (AT).

Proteins containing PDZ domains constitute an additional potential target for b-sheet mimetics. These domains of 80–100 amino acid residues mediate protein-protein interactions by binding to a consensus X-Ser/Thr-X-Val sequence at the very carboxyl terminus of proteins. There are also examples of protein interactions via PDZ domains that are internal (or non C-terminal). The crystal structure of liganded and unliganded PDZ domains have been determined and show a six b-strand and two a-helix structure that binds the consensus recognition polypeptide sequence through a b-sheet conformation. Hence, screening of appropriate b-sheet mimetics should prove a valid strategy for targeting PDZ domain-containing proteins. The targets of PDZ domain-containing proteins are varied but important in signal transduction. PSD-95, a membrane associated guanylate kinase contains three PDZ domains, two of which target the Shaker-type K$^+$ channel and the N-methyl-D-aspartate (NMDA) receptor resulting in their clustering that is required for their function. PTPL1/FAP1, a protein tyrosine phosphatase, has five PDZ domains, two of which interact with Fas, a transmembrane protein of the tumor necrosis factor receptor family, that mediates apoptosis in many cell types. Hence, compounds targeting proteins containing the PDZ domains may prove useful as anticancer agents.

Tryptase, a trypsin-like serine protease found exclusively in mast cells, has attracted much interest due to its potential role as a mediator of inflammation. For example, in the lung tryptase is released along with other mediators of inflammation in response to binding of an inhaled antigen to cell-surface IgE receptors (Ishizaka and Ishizaka, *Prog. Allergy* 34:188–235, 1984). Tryptase has also been shown to cleave vasoactive intestinal peptide in vitro (Caughey et al., *J. Phazmacol. Exp. Ther.* 244:133–137, 1988; Tam and Caughey, *Am. J. Respir. Cell Mol. Biol.* 3:27–32, 1990). These results suggest that tryptase may increase bronchoconstriction via proteolysis of bronchodilating peptides in asthma patients. Consistent with this hypothesis is the recent finding that synthetic tryptase inhibitors blocked airway responses in allergic sheep (Clark et al., *Am. J. Respir. Crit. Care Med.* 152:2076–2083, 1995).

Tryptase activates extracellular matrix-degrading proteins prostromelysin (pro-MMP-3) and procollagenase (pro-MMP-1) via MMP-3, suggesting a role for the enzyme in tissue remodeling and inflammation (Gruber et al., *J. Clin. Invest.* 84:8154–8158, 1989) and therefore possibly in rheumatoid arthritis. Additionally, prostromelysin, when activated, has been shown to degrade the extracellular matrix around atherosclerotic plaques. Since abnormally high levels of tryptase-containing mast cells have been found in coronary atheromas, tryptase may play a role in atheromatous rupture (release of the thrombus), the final event of coronary atherosclerosis (Kaartinen et al., *Circulation* 90:1669–1678, 1994).

Other activities of tryptase include the following. Tryptase cleaves fibrinogen but is not inactivated in the presence of endogenous proteinase inhibitors (Schwartz et al., *J. Immunol.* 135:2762–2767, 1985; Ren et al., *J. Immunol.* 159:3540–3548, 1997), and may function as a local anticoagulant. It has been demonstrated to be a potent mitogen for fibroblasts and may be involved in pulmonary fibrosis and interstitial lung disease (Ruoss et al., *J. Clin. Invest.* 88:493–499, 1991). Tryptase may also be responsible for the activation of PAR-2 (proteinase activated receptor-2) on endothelial cells and keratinocytes (Molino et al., *J. Biol. Chem.* 272:4043–4049, 1997).

Given the central role of mast cells in allergic and inflammatory responses, inhibition of tryptase may result in significant therapeutic effects. Inhibitors of tryptase may be useful for preventing or treating asthma, pulmonary fibrosis and interstitial pneumonia, nephritis, hepatic fibrosis, hepatitis, hepatic cirrhosis, scleroderma, psoriasis, atopic dermatitis, chronic rheumatoid arthritis, influenza, Crohn's disease, ulcerative colitis, inflammatory bowel disease, nasal allergy, and atherosclerosis.

Chymase is a chymotrypsin-like protease that is also released from mast cells. It has been demonstrated to cleave angiotensin-I (ang-I) to angiotensin-II (ang-II) with greater efficiency and selectivity than angiotensin-I converting enzyme (ACE) (Okunishi et al., *J. Hypertension* 2: 227–284, 1984; Urata et al., *Circ. Res.* 66: 883–890, 1990). In heart tissue chymase has been shown to be a major source of ang-II production from ang-I (Dell'Italia et al., *Am. J. Physiol.* (*Heart Circ. Physiol.* 38) 269:H2065–H2073, 1996). In addition, increased chymase activity has been demonstrated in balloon-injury induced hypertrophied vessels in dogs (Shiota et al., *FEBS Lett.* 323:239–242, 1993). Such evidence suggests that inhibition of chymase may be therapeutic for hypertension, ischaemic heart disease, and congestive heart failure.

Urokinase-type plasminogen activator (uPA) is a trypsin-like serine proteinase which converts plasminogen to plasmin as part of the fibrinolytic system. It has long been used for thrombolysis in acute massive pulmonary embolism. Other research has shown that uPA is also a key initiator of the extra-cellular proteolytic cascade involved in cellular invasiveness (Mullins and Rohlich, *Biochim. Biophys. Acta* 695: 177–214, 1983; Testa and Quigly, *Cancer Metast. Rev.* 9:353–367, 1990). In addition uPA binds to uPA receptor (uPAR) through its growth factor domain and further modulates the activity of other proteins involved in cell migration. Overexpression of uPA appears to play a part in cancer invasiveness and metastasis; high levels of uPA, PAI-1 (plasminogen activator inhibitor-1), and uPAR correlate with poor patient prognosis. A variety of research in various model systems demonstrates that inhibitors of uPA decrease tumor cell invasiveness and metastasis (Testa and Quigly, ibid; Andreasen et al., *Int J Cancer* 72:1–22, 1997). Hence, inhibition of uPA may be useful in the treatment of breast cancer, prostate cancer, ovarian cancer, human renal cell cancer, gastric cancer, and lung cancer. Recent evidence indicates that inhibitors of uPA may also be useful in the prevention of restenosis (Loskutoff, *Circulation* 96:2772–2774, 1997).

In view of the important biological role played by the β-sheet, there is a need in the art for compounds which can stabilize the intrinsic β-sheet structure of a naturally occurring or synthetic peptide, protein or molecule. There is also a need in the art for making stable β-sheet structures, as well as the use of such stabilized structures to effect or modify biological recognition events which involve β-sheet structures. The present invention fulfills these needs and provides further related advantages.

SUMMARY OF THE INVENTION

Briefly stated, the present invention is directed to β-sheet mimetics and the use thereof, including use for the manufacture of a medicament for achieving therapeutic effects in a warm-blooded animal through one or more of protease inhibition, kinase inhibition, regulation of a transcription factor and/or by inhibiting protein-protein binding interactions. The therapeutic effects result from administering to the warm-blooded animal a therapeutically effective amount of a β-sheet mimetic including a bicyclic ring system, wherein the β-sheet mimetic has the general structure (I) (including pharmaceutically acceptable salts thereof):

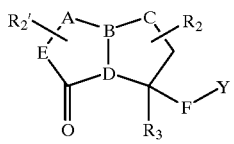
(I)

wherein
  A is selected from —C(=O)—, —(CH$_2$)$_{0-4}$—, —C(=O)(CH$_2$)$_{1-3}$—, —(CH$_2$)$_{1-2}$O— and —(CH$_2$)$_{1-2}$S—;
  B is selected from N and CH;
  C is selected from —C(=O)—, —C(=O) (CH$_2$)$_{1-3}$—, —(CH$_2$)$_{0-3}$—, —O—, —S—, —O—(CH$_2$)$_{1-2}$— and —S(CH$_2$)$_{1-2}$—;
  D is selected from N and C(R$_4$);
  E is selected from

and

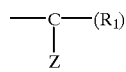

F is an optional carbonyl moiety;
  R$_1$ and R$_4$ are independently selected from amino acid side chain moieties and derivatives thereof;
  R$_2$ and R$_2$' represent one or more ring substituents individually selected from an amino acid side chain moiety and derivatives thereof, or R$_2$ taken together with C or Y forms a fused substituted or unsubstituted homocyclic or heteocyclic ring;
  R$_3$ is selected from an amino acid side chain moiety and derivatives thereof, or taken together with C forms a bridging moiety selected from —(CH$_2$)$_{1-2}$—, —O— and —S—;
  Y and Z represent the remainder of the molecule; and
  any two adjacent CH groups of the bicyclic ring may form a double bond.

In one embodiment where F (i.e., the optional carbonyl moiety) is present and E is —N(Z)—, the compounds of this invention include the following structure (II):

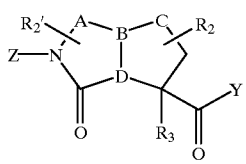
(II)

wherein A, B, C, D, R$_2$, R$_2$', R$_3$, Y and Z are as defined above with regard to structure (I).

In a preferred aspect of this embodiment, A is either —C(=O)— or —(CH$_2$)— and C is —(CH$_2$)$_2$—, as represented by the following structures (IIa) and (IIb):

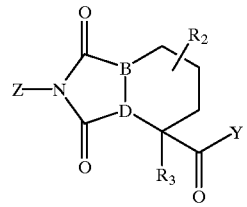
(IIa)

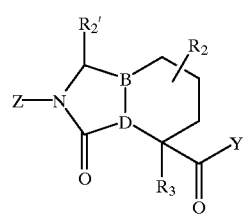
(IIb)

In this embodiment, the six-member ring may be saturated or unsaturated (including aromatic). For example, when B and D of structures (IIa) and (IIb) are both —CH— (and thus constitute adjacent CH groups that may form a double bond), compounds of this invention include the following aromatic structures (IIc) and (IId):

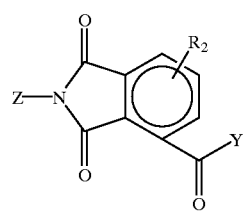
(IIc)

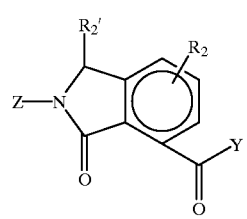
(IId)

Similarly, the following unsaturated compounds having structures (IIe) and (IIf) are also representative of the compounds of structures (IIa) and (IIb):

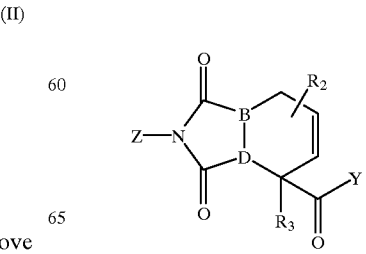
(IIe)

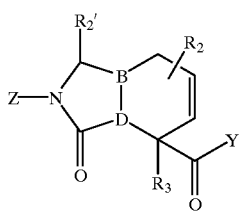
(IIf)

In another embodiment where F is present and E is —C(R$_1$)(NHZ)—, the compounds of this invention include the following structure (III):

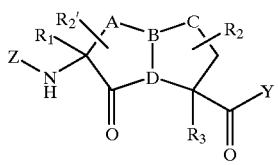
(III)

wherein A, B, C, D, R$_1$, R$_2$, R$_2$', R$_3$, Y and Z are as defined above with regard to structure (I).

In a preferred aspect of this embodiment, A is either —C(=O)— or —(CH$_2$)— and C is —(CH$_2$)$_2$—, as represented by the following structures (IIIa) and (IIIb):

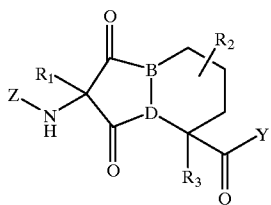
(IIIa)

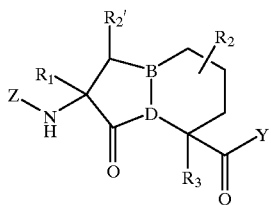
(IIIb)

In this embodiment, the six-member ring may be saturated or unsaturated (including aromatic). For example, when B and D of structures (IIIa) and (IIIb) are both —CH— (and thus constitute adjacent CH groups that may form a double bond), compounds of this invention include the following aromatic structures (IIIc) and (IIId):

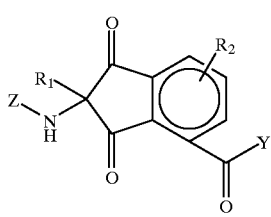
(IIIc)

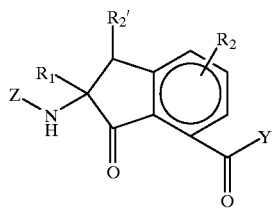
(IIId)

Similarly, the following unsaturated compounds having structures (IIIe) and (IIIf) are also representative of the compounds of structures (IIIa) and (IIIb):

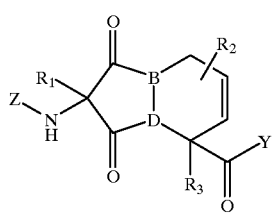
(IIIe)

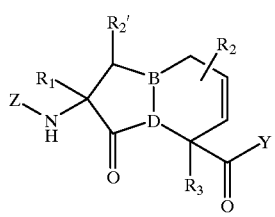
(IIIf)

In a further embodiment when F is present and E is —C(R$_1$)(Z)—, the compounds of this invention include the following structure (IV):

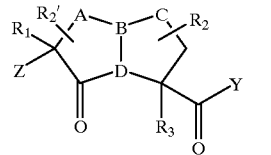
(IV)

wherein A, B, C, D, R$_1$, R$_2$, R$_2$', R$_3$, Y and Z are as defined above with regard to structure (I), and with the proviso that Z does not contain an —NH— moiety attached to the carbon atom having the R$_1$ substituent (and thus distinct from the compounds of structure (III) above).

In a preferred aspect of this embodiment, A is either —(C=O)— or —(CH$_2$)— and C is —(CH$_2$)$_2$—, as represented by the following structures (IVa) and (IVb):

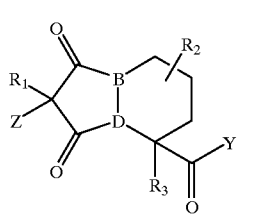
(IVa)

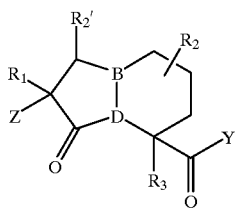
(IVb)

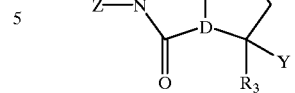
(V)

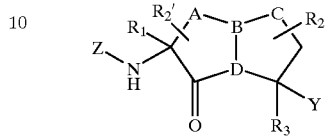
(VI)

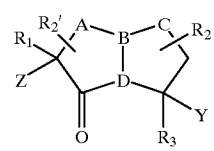
(VII)

In this embodiment, the six-member ring may be saturated or unsaturated (including aromatic). For example, when B and D of structures (IVa) and (IVb) are both —CH— (and thus constitute adjacent CH groups that may form a double bond), compounds of this invention include the following aromatic structures (IVc) and (IVd):

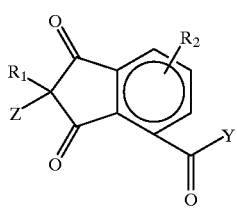
(IVc)

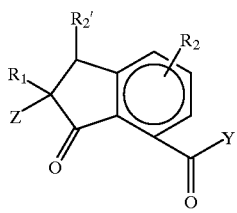
(IVd)

wherein A, B, C, D, $R_1$, $R_2$, $R_2'$, $R_3$, Y and Z are as defined above with regard to structure (I).

In still a further embodiment where $R_3$ taken together with C forms a bridging moiety, compounds of this invention include the following structure (VIII):

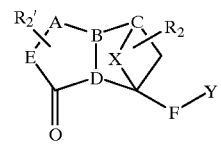
(VIII)

where X is a bridging moiety selected from —$(CH_2)_{1-2}$—, —O— and —S—, and A, B, C, D, E, F, $R_2$, $R_2'$, Y and Z are as defined above with regard to structure (I).

In one aspect of this embodiment where F is present, A is —C(=O)—, C is —$(CH_2)_2$— and E is either —N(Z)— or —C($R_1$)(NHZ)—, compounds of this invention include those of the following structures (VIIIa) and (VIIIb):

Similarly, the following unsaturated compounds having structures (IVe) and (IVf) are also representative of the compounds of structures (IVa) and (IVb):

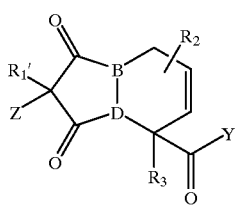
(IVe)

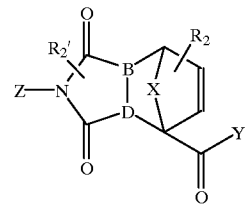
(VIIIa)

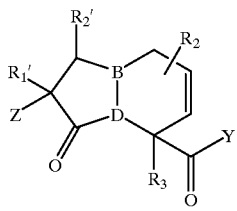
(IVf)

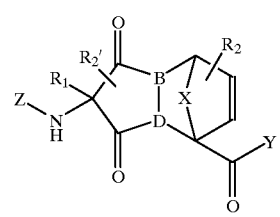
(VIIIb)

In a further embodiment where F is not present and E is either —N(Z)—, —C($R_1$)(NHZ)— or —C($R_1$)(Z)—, the compounds of this invention include the following structures (V), (VI) and (VII):

In yet a further embodiment where F is present, $R_2$ taken together with C forms a substituted or unsubstituted, homocyclic or heterocyclic fused ring as represented by structures (IX) and (X):

(IX)

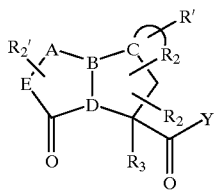

(X)

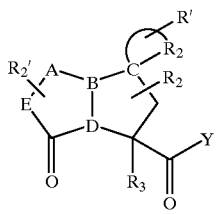

wherein A, B, C, D, E, R$_2$, R$_2'$, R$_3$ and Y are as defined above, and R' is one or more optional ring substituents.

In one aspect of structure (IX), R$_2$ and C taken together form a fused five-, six-, seven- or eight-membered ring as represented by structures (IXa) and (IXb):

(IXa)

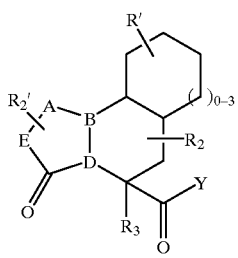

(IXb)

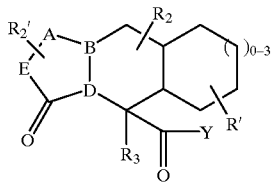

wherein A, B, D, E, R$_2$, R$_2'$, R$_3$, R' and Y are as defined above.

In one aspect of structure (X), R$_2$ and C taken together form a fused five-, six-, seven- or eight-membered ring as represented by structures (Xa) and (Xb):

(Xa)

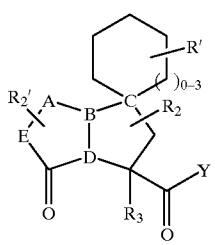

-continued (Xb)

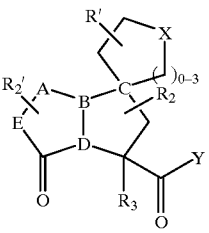

wherein A, B, C, D, E, Y, R$_2$, R$_2'$, R$_3$ and R' are as defined above, and X is selected from —C(=O)—, —NH—, —NR'—, —O— and —S—.

In still a further embodiment where F is present, R$_2$ taken together with Y forms a substituted or unsubstituted, homocyclic or heterocyclic fused ring as represented by structure (XI):

(XI)

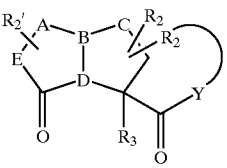

wherein A, B, C, D, E, R$_2$, R$_2'$ and R$_3$ are as defined above.

In one aspect of this embodiment, R$_2$ and Y taken together form a fused five-, six-, seven- or eight-membered ring as represented by structures (XIa) and (XIb):

(XIa)

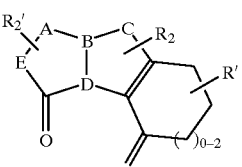

(XIb)

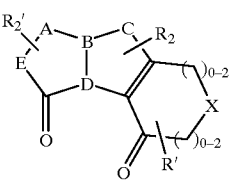

wherein A, B, C, D, E, R$_2$, R$_2'$ and R' are as defined above, R' is an optional substituent, and X is selected from —NH—, —NR'—, —O— and —S—.

These and other aspects of this invention will become apparent upon reference to the following detailed description.

DETAILED DESCRIPTION OF THE INVENTION

Figure 1:
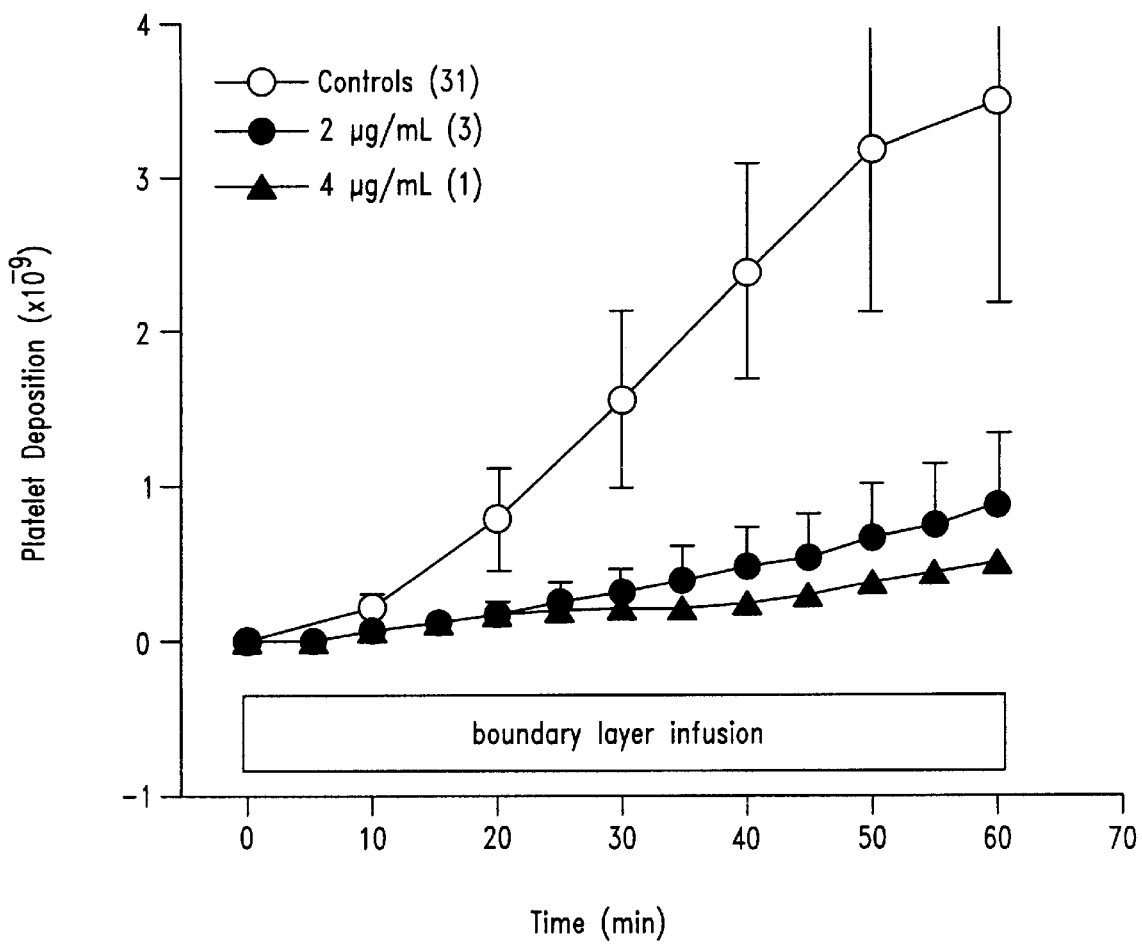
FIG. 1 is a plot showing the effect of various concentrations of structure (20b) on platelet deposition in a vascular graft.

As mentioned above, the β-sheet is an important structural component for many biological recognition events. The β-sheet mimetics of this invention serve to impart and/or stabilize the β-sheet structure of a natural or synthetic peptide, protein or molecule, particularly with regard to conformational stability. In addition, the β-sheet mimetics of this invention are more resistant to proteolytic breakdown, thus rendering a peptide, protein or molecule containing the same more resistant to degradation. The β-sheet mimetic may be positioned at either the C-terminus or N-terminus of the protein, peptide or molecule, or it may be located within the protein, peptide or molecule itself, and more than one β-sheet mimetic of the present invention may be incorporated in a protein, peptide or molecule.

The β-sheet mimetics of this invention are generally represented by structure (I) above, as well as the more specific embodiments represented by structures (II) through (XI). The β-sheet mimetics of this invention may be constructed to mimic the three-dimensional conformation of a β-sheet comprised of naturally occurring L-amino acids, as well as the structure of a β-sheet comprised of one or more D-amino acids. Thus, all stereoconformations of the β-sheet mimetics of structure (I) are within the scope of this invention.

For example, β-sheet mimetics of structure (II) nclude the following structures (II') and (II"):

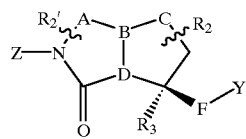
(II')

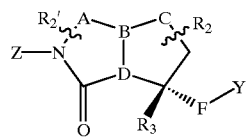
(II")

Similarly, β-sheet mimetics of structure (III) include the following structures (III') through (III""):

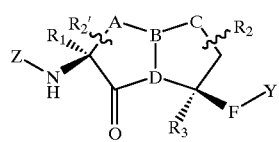
(III')

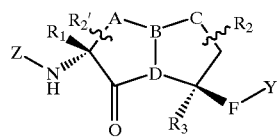
(III")

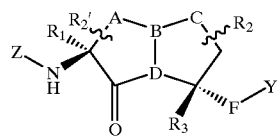
(III''')

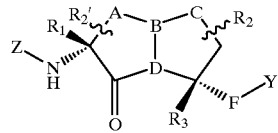
(III'''')

The β-sheet mimetics of structure (IV) include these same stereoconfirmations, but with the "Z—NH" moiety of structures (III') through (III'''') replaced with a "Z" moiety.

As used herein, the term "an amino acid side chain moiety" as used to define the $R_1$, $R_2$, $R_2'$, $R_3$, and $R_4$ moieties represents any amino acid side chain moiety present in naturally occurring proteins, including (but not limited to) the naturally occurring amino acid side chain moieties identified in Table 1 below. Other naturally occurring side chain moieties of this invention include (but are not limited to) the side chain moieties of phenylglycine, 3,5-dibromotyrosine, 3,5-diiodotyrosine, hydroxylysine, naphthylalanine, thienylalanine, γ-carboxyglutamate, phosphotyrosine, phosphoserine and glycosylated amino acids such as glycosylated serine, asparagine and threonine.

TABLE 1

| Amino Acid Side Chain Moiety | Amino Acid |
|---|---|
| —H | Glycine |
| —$CH_3$ | Alanine |
| —$CH(CH_3)_2$ | Valine |
| —$CH_2CH(CH_3)_2$ | Leucine |
| —$CH(CH_3)CH_2CH_3$ | Isoleucine |
| —$(CH_2)_4NH_3^+$ | Lysine |
| —$(CH_2)_3NHC(NH_2)NH_2^+$ | Arginine |
| —$CH_2$-(imidazole, HN—NH$^+$) | Histidine |
| —$CH_2COO^-$ | Aspartic acid |
| —$CH_2CH_2COO^-$ | Glutamic acid |
| —$CH_2CONH_2$ | Asparagine |
| —$CH_2CH_2CONH_2$ | Glutamine |
| —$CH_2$-(phenyl) | Phenylalanine |
| —$CH_2$-(phenyl)-OH | Tyrosine |
| —$CH_2$-(indole) | Tryptophan |
| —$CH_2SH$ | Cysteine |
| —$CH_2CH_2SCH_3$ | Methionine |

TABLE 1-continued

| Amino Acid Side Chain Moiety | Amino Acid |
|---|---|
| —CH$_2$OH | Serine |
| —CH(OH)CH$_3$ | Threonine |

In addition to naturally occurring amino acid side chain moieties, the amino acid side chain moieties of the present invention also include various derivatives thereof. As used herein, a "derivative" of an amino acid side chain moiety includes all modifications and/or variations to naturally occurring amino acid side chain moieties. For example, the amino acid side chain moieties of alanine, valine, leucine, isoleucine, phenylglycine and phenylalanine may generally be classified as lower chain alkyl, aryl or aralkyl moieties. Derivatives of amino acid side chain moieties include other straight chain or branched, cyclic or noncyclic, substituted or unsubstituted, saturated or unsaturated lower chain alkyl, aryl or aralkyl moieties.

As used herein, "lower chain alkyl moieties" contain from 1–12 carbon atoms, "lower chain aryl moieties" contain from 6–12 carbon atoms, and "lower chain aralkyl moieties" contain from 7–12 carbon atoms. Thus, in one embodiment, the amino acid side chain derivative is selected from a $C_{1-12}$ alkyl, a $C_{6-12}$ aryl and a $C_{7-12}$ aralkyl, and in a more preferred embodiment, from a $C_{1-7}$ alkyl, a $C_{6-10}$ aryl and a $C_{7-11}$ aralkyl.

Amino acid side chain derivatives of this invention further include substituted derivatives of lower chain alkyl, aryl and aralkyl moieties, wherein the substituent is selected from (but are not limited to) one or more of the following chemical moieties: —OH, —OR, —COOH, —COOR, —CONH$_2$, —NH$_2$, —NHR, —NRR, —SH, —SR, —SO$_2$R, —SO$_2$H, —SOR and halogen (including F, Cl, Br and I), wherein each occurrence of R is independently selected from a lower chain alkyl, aryl or aralkyl moiety. Moreover, cyclic lower chain alkyl, aryl and aralkyl moieties of this invention include naphthalene, as well as heterocyclic compounds such as thiophene, pyrrole, furan, imidazole, oxazole, thiazole, pyrazole, 3-pyrroline, pyrrolidine, pyridine, pyrimidine, purine, quinoline, isoquinoline and carbazole. Amino acid side chain derivatives further include heteroalkyl derivatives of the alkyl portion of the lower chain alkyl and aralkyl moieties, including (but not limited to) alkyl and aralkyl phosphonates and silanes.

As used in the context of this invention, the term "remainder of the molecule" (as represented by Y and Z) may be any chemical moiety, including (but not limited to) amino acid side chain moieties and derivatives thereof as defined above. For example, when the β-sheet mimetic is located within the length of a peptide or protein, Y and Z may represent amino acids of the peptide or protein. Alternatively, if two or more β-sheet mimetics are linked, the Y moiety of a first β-sheet mimetic may represent a second β-sheet mimetic while, conversely, the Z moiety of the second β-sheet mimetic represents the first β-sheet mimetic.

When the β-sheet mimetic is located at the end of a peptide or protein, or when the β-sheet mimetic is not associated with a peptide or protein, Y and/or Z may represent a suitable terminating moiety. For example, representative terminating moieties for the Z moiety include (but are not limited to) —H, —OH, —R, —C(=O)R and —SO$_2$R (where R is selected from a lower chain alkyl moiety, a lower chain aryl moiety and a lower chain aralkyl moiety), or may be a suitable protecting group for protein synthesis, such as BOC, FMOC and CBZ (i.e., tert-butyloxycarbonyl, 9-fluorenylmethoxycarbonyl and benzyloxycarbonyl, respectively).

Similarly, representative terminating moieties for the Y moiety include (but are not limited to) —H, —OH, —R, —SO$_2$R, —SOR, —SO$_2$NHR, —CF$_3$, —C$_2$F$_5$, —NHOH, —NHNHR, —C(=O)H, —C(=O)R, —C(=O)CF$_3$, —C(=O)OR, —C(=O)CH$_2$OR, —C(=O)NHR, —CH$_2$X', —C(=O)CH$_2$X', —C(=O)C(=O)NRR, —C(=O)CHN$_2$,

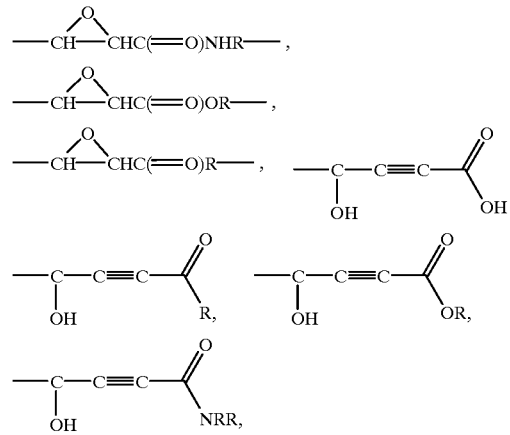

—C(=O)CH=CHC(=O)OH, —C(=O)CH=CHC(=O)R, —C(=O)CH=CHC(=O)OR, —C(=O)CH=CHC(=O)NRR, —CH(OH)CH=CHC(=O)OH, —CH(OH)CH=CHC(=O)R, —CH(OH)CH=CHC(=O)OR, —CH(OH)CH=CHC(=O)NRR, —CH=CHSO$_2$R and —SO$_2$CH=CHR (where X' is Cl, F, Br or I, and each occurrence of R is independently selected from a lower chain alkyl moiety, a lower chain aryl moiety and a lower chain aralkyl moiety), or a heterocyclic moiety, such as pyridine, pyran, thiophan, pyrrole, furan, thiophene, thiazole, benzthiazole, oxazole, benzoxazole, imidazole and benzimidazole.

More specifically, suitable Z and Y terminating moieties of this invention include the following groups:

| Z Moieties | Y Moieties |
|---|---|
| R$^6$—X— | —X—R$^6$ |
| R$^7$—X— | —X—R$^7$ |
| (R$^8$)$_2$N—X— | —X—N(R$^8$)$_2$ |
| R$^9$—O—X— | —X—O—R$^9$ |
| R$^{10}$—S(O)$_p$—X— | —X—S(O)$_p$R$^{10}$ | wherein

X is optionally present and selected from a straight chain or branched, cyclic or noncyclic, saturated or nonsaturated $C_{1-12}$ alkyl optionally substituted with one or more substituents selected from halogen, =O, OR, ONRR, C(O)R, C(O)OR, CN, OC(O)R, C(O)NRR, C(O)NROR, NH$_2$, NO$_2$, NHOR, C(NR), NHR, C(NR)NHR, NHC(NR)NHR, P(OR)$_3$ and SiRRR;

R$^6$ is selected from H, CN, NO$_2$ SiRRR and P(OR)$_3$;

R$^7$ is selected from CO$_{5-14}$ aryl, C$_{4-13}$ heteroaryl, C$_{3-14}$ cycloalkyl, C$_{5-14}$ cycloalkylene, and C$_{2-13}$ heterocycloalkyl, each of which may be optionally substituted with one or more substituents selected from X, halogen, OR, ONRR, C(O)R, C(O)OR, CN, OC(O)

R, NR$_2$, C(O)NRR, C(O)NROR, NRC(O)R, C(NR)NHR, NHC(NR)NHR, NO$_2$ SO$_2$R, SO$_2$NRR, SiRRR, OP(OR)$_3$, CH$_2$P(OR)$_3$ and CF$_2$P(OR)$_3$;

R$^8$ is, at each occurrence, independently selected from H, X, R$^7$, halogen, OR, =C=O, C(O)R, C(O)OR, CN, OC(O)R, NR$_2$, C(O)NRR, NRC(O)R, C(NR)NHR, NO$_2$, SO$_2$R, SO$_2$NRR, SiRRR and P(OR)$_3$, or, taken together, may form a saturated or unsaturated C$_{2-14}$ cycloalkyl optionally substituted with one or more substituents selected from =O, X, R$^7$, halogen, OR, =C=O, C(O)R, C(O)OR, CN, OC(O)R, NR$_2$, C(O)NRR, NRC(O)R, C(NR)NHR, NO$_2$ SO$_2$R, SO$_2$NRR, SiRRR and P(OR)$_3$;

R$^9$ is selected from H, X, R$^7$, halogen C(O)R, C(O)OR, CN, NR$_2$ C(O)NRR, NRC(O)R, C(NR)NHR, NO$_2$, SO$_2$R, SO$_2$NRR, SiRRR and P(OR)$_3$, where p=0–2;

R$^{10}$ is selected from H, X, R$^7$, halogen, OR, C(O)R, C(O)OR, CN, NR$_2$ and C(O)NRR; and each occurrence of R in the above definitions of R$^6$ through R$^{10}$ is independently selected from H, C$_{1-6}$ alkyl, C$_{3-14}$ cycloalkyl, C$_{5-14}$ cycloalkylene, C$_{6-14}$ aryl, C$_{4-13}$ heteroaryl and C$_{2-13}$ heterocycloalkyl, or, when two R groups are present, taken together form a saturated or unsaturated C$_{2-8}$ cycloalkyl.

In the context of protease inhibitors, the Y terminating moiety further includes the following group:

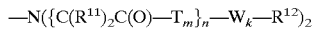

wherein m=0–1;
n=0–20;
k=0–1;

R$^{11}$ is, at each occurrence, independently selected from an amino acid side chain moiety and derivative thereof;

T is, at each occurrence, independently selected from C=O, C(O)—N(R$^{12}$) and N(R$^{12}$);

W is, at each occurrence, independently selected from a C$_{2-14}$ heterocycle; and R$^{12}$ is, at each occurrence, independently selected from H, X, X—R$^6$, X—R$^7$, X—N(R$^8$)$_2$, X—O—R$^9$, X—S(O)$_p$ R$^{10}$ and P(OR)$_3$, or, taken together, may form a saturated or unsaturated C$_{2-14}$ cycloalkyl optionally substituted with one or more substituents selected from halogen, =O, OR, ONRR, C(O)R, C(O)OR, CN, OC(O)R, C(O)NRR, C(O)NROR, NH$_2$, NO$_2$, NHOR, C(NR)NHR, NHC(NR)NHR, P(OR)$_3$ and SiRRR; and R, R$^6$, R$^7$, R$^8$, R$^9$, R$^{10}$, X and p are as defined immediately above;

with the proviso that when n=0 each of R$^{12}$ are not both hydrogen.

In the context of structure (I) above, any two adjacent CH groups of the bicyclic ring may form a double bond. Such double bonds may be present in isolation or conjugation with one or more additional double bonds, including aromatic ring systems. For example, representative isolated double bonds includes compounds of structures (IIe), (IIf), (IIIe), (IIIf), (IVe), (IVf), (VIIIa) and (VIIIb) above. Representative aromatic compounds resulting from conjugated double bonds are depicted by structures (IIc), (IId), (IIIc), (IIId), (IVc) and (IVd) above.

Within a specific embodiment of this invention, β-sheet mimetics are disclosed having structure (II) above, wherein A is —C(=O)—, B is N, C is —(CH$_2$)$_2$— or —C(=O)CH$_2$—, D is N, and the optional carbonyl moiety F is present, as represented by the following structures (IIg), (IIh) and (IIh'):

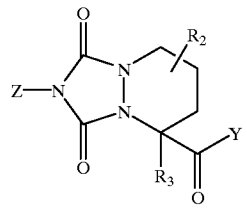
(IIg)

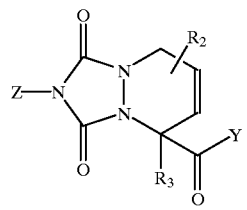
(IIh)

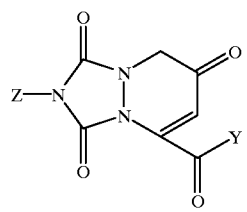
(IIh')

Similarly, when B and D are both OH, representative β-sheet mimetics of this invention include compounds of the following structures (IIi), (IIj) and (IIj'):

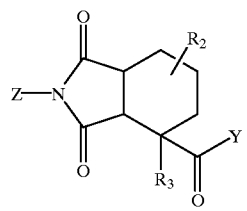
(IIi)

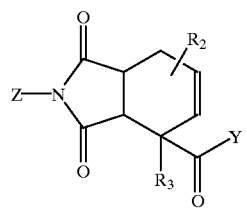
(IIj)

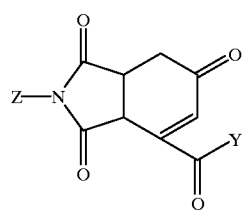
(IIj')

Within another specific embodiment of this invention, β-sheet mimetics are disclosed having structure (III) above. In one aspect of this embodiment, D is N and the compound has the following structure (IIIi):

(IIIi)

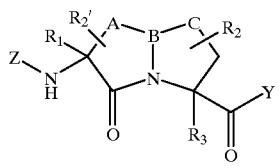

wherein A is selected from —C(=O)—, —(CH$_2$)$_{0-4}$— and —C(=O) (CH$_2$)$_{1-3}$—; B is selected from N and CH; C is selected from —C(=O)— and —(CH$_2$)$_{0-3}$—; and the bicyclic ring system is saturated (i.e., contains no double bonds between adjacent CH groups of the bicyclic ring system).

In this embodiment where B is CH and R$_3$ is hydrogen, compounds are disclosed having the following structures (IIIj), (IIIk) and (IIIl):

(IIIj)

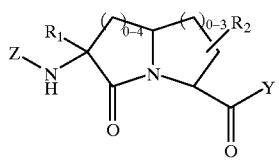

(IIIk)

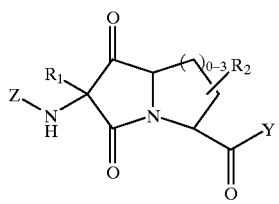

(IIIl)

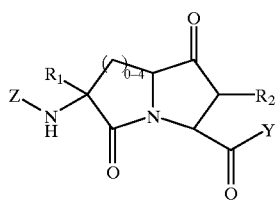

In an embodiment of structure (IIIi) where B is N and R$_3$ is hydrogen, compounds are disclosed having the following structures (IIIm), (IIIn) and (IIIo):

(IIIm)

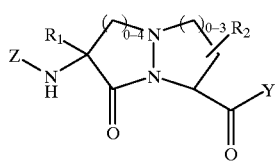

(IIIn)

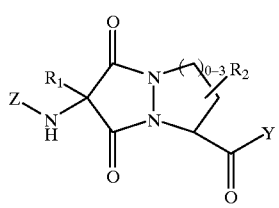

(IIIo)

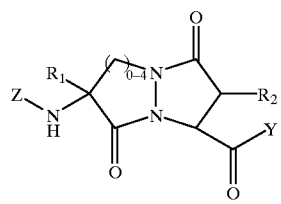

In preferred embodiments of this aspect of the invention, compounds are disclosed having the following structures (IIIp), (IIIq), (IIIr) and (IIIr'):

(IIIp)

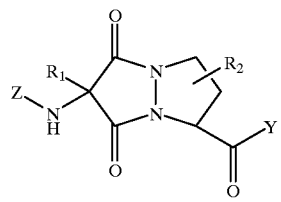

(IIIq)

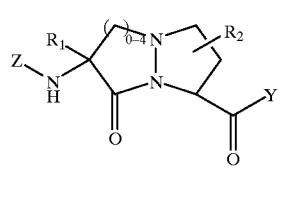

(IIIr)

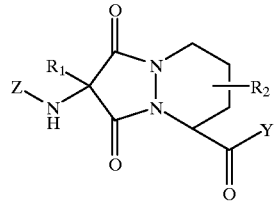

(IIIr')

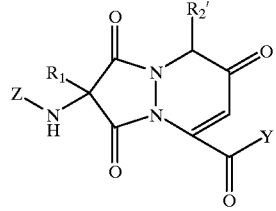

In another embodiment of structure (IIIi) above, compounds are disclosed having the following structure (IIIs):

(IIIs)

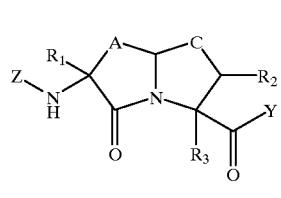

wherein A is selected from —(CH$_2$)$_{0-4}$—, —(CH$_2$)$_{1-2}$O— and —(CH$_2$)$_{1-2}$S—; C is selected from —(CH$_2$)$_{0-3}$—, —O—, —S—, —O(CH$_2$)$_{1-2}$— and —S(CH$_2$)$_{1-2}$—; and the bicyclic ring system is saturated.

In an embodiment of structure (IIIs) where A is —(CH$_2$)$_{0-4}$—, compounds are disclosed having the following structure (IIIt):

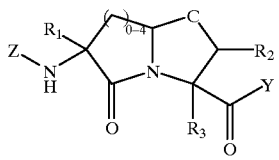
(IIIt)

In an embodiment of structure (IIIs) where A is —(CH$_2$)$_{1-2}$O— or —(CH$_2$)$_{1-2}$S—, compounds are disclosed having the following structures (IIIu) and (IIIv):

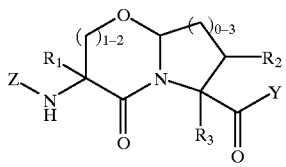
(IIIu)

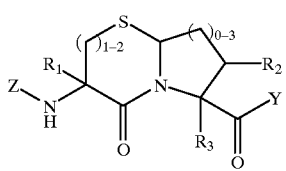
(IIIv)

In an embodiment of structure (IIIs) where C is —(CH$_2$)$_{1-3}$—, compounds are disclosed having the following structure (IIIw):

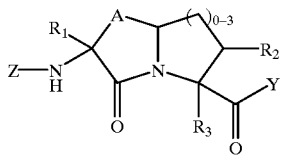
(IIIw)

where A is selected from —(CH$_2$)$_{1-4}$—, —(CH$_2$)$_{1-2}$O— and —(CH$_2$)$_{1-2}$S—.

In an embodiment of structure (IIIs) where C is —O— or —S—, compounds are disclosed having the following structures (IIIx) and (IIIy):

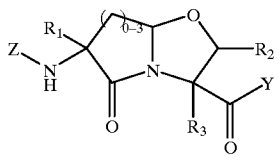
(IIIx)

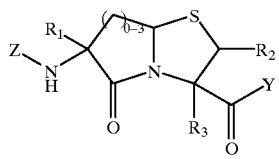
(IIIy)

In an embodiment of structure (IIIs) where C is —O(CH$_2$)$_{1-2}$— or —S(CH$_2$)$_{1-2}$—, compounds are disclosed having the following structures (IIIz) and (IIIza):

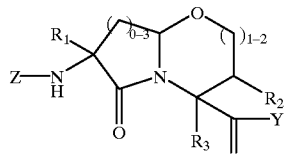
(IIIz)

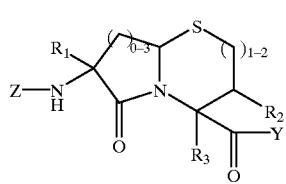
(IIIza)

Within a further embodiment of this invention, β-sheet mimetics are disclosed having strucutre (IV) above. In one aspect of this embodiment, A is —C(=O)—, B is CH or N, C is —(CH$_2$)$_2$— or —C(=O)CH$_2$—, D is N and the optional carbonyl moiety is present, as represented by the following structures (IVg), (IVg'), (IVh) and (IVh'):

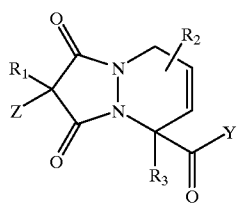
(IVg)

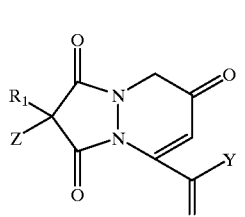
(IVg')

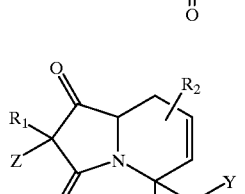
(IVh)

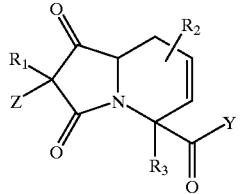

-continued

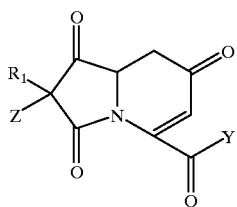
(IVh')

In embodiments of this invention where F is not present, compounds having structures (V), (VI) and (VII) are disclosed. With respect to compounds of structure (V), when A is —C(=O)—, B and D are both CH or N, and C is —(CH$_2$)$_2$—, representative compounds of this invention include the following structures (Va), (Vb) and (Vc):

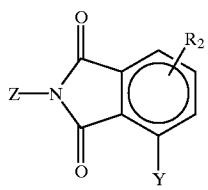
(Va)

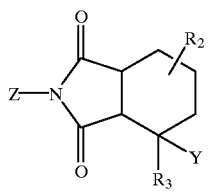
(Vb)

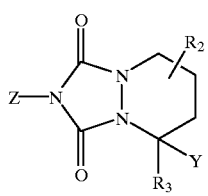
(Vc)

Similarly, in structure (VI), when A is —C(=O)—, B and D are both CH or N, and C is —(CH$_2$)$_2$—, representative compounds of this invention include the following structures (VIa), (VIb) and (VIc):

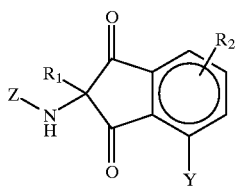
(VIa)

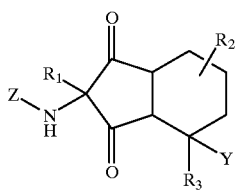
(VIb)

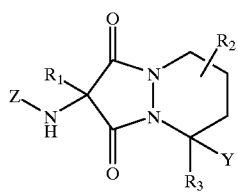
(VIc)

As for structure (VII), when A is —C(=O)—, B and D are both CH or N, and C is —(CH$_2$)$_2$—, representative compounds of this invention include the following structures (VIIa), (VIIb) and (VIIc):

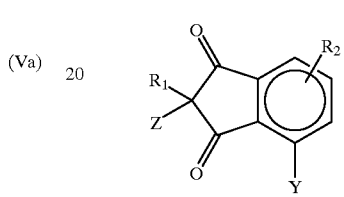
(VIIa)

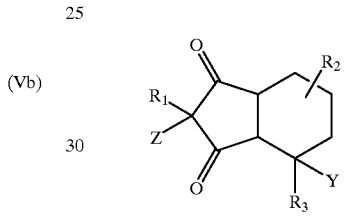
(VIIb)

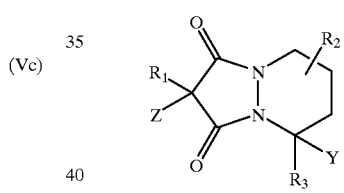
(VIIc)

With regard to compounds of structure (VIII), in one embodiment B and D of structures (VIIIa) and (VIIIb) are both CH or N and X is —S—, —O— or —(CH$_2$)$_2$—, yielding compounds of structures (VIIIc), (VIIId), (VIIIe) and (VIIIf):

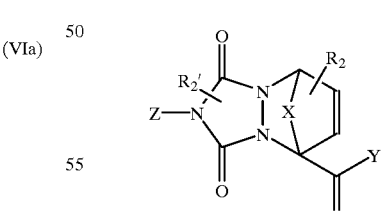
(VIIIc)

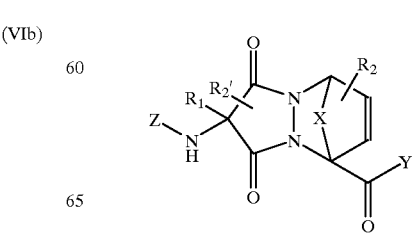
(VIIId)

(VIIIe)

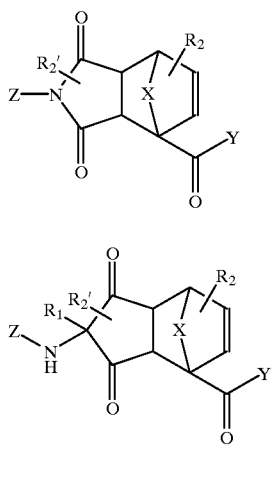

(VIIIf)

In an embodiment of structure (IX), wherein A is —C(=O)—, B and D are both N, E is —N(Z)—, —C(R$_1$)(NHZ)— or —C(R$_1$)(Z)—, and F is present, compounds of this invention include structures (IXc) through (IXh).

(IXc)

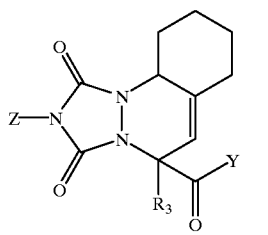

(IXd)

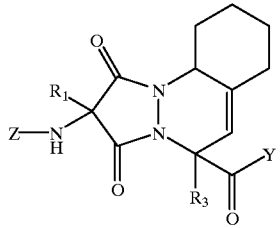

(IXe)

(IXf)

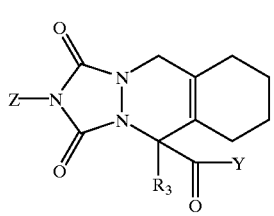

(IXg)

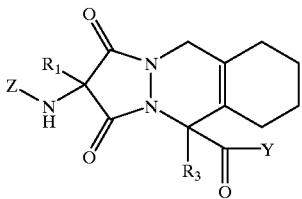

(IXh)

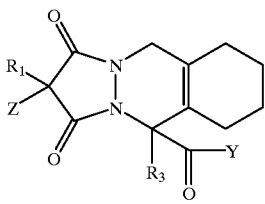

In an embodiment of structure (X), where A is —C(=O)—, B is N, D is N and E is Z—N, compounds of this invention include structures (Xc) and (Xd):

(Xc)

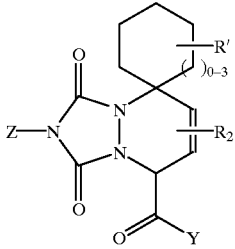

(Xd)

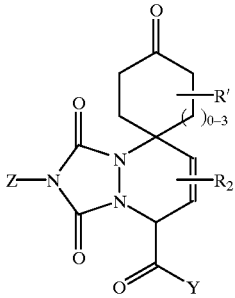

In an embodiment of structure (XI), where A is —C(=O)—, B is N, C is —CH$_2$C(=O)—, D is N and E is Z—N, compounds of this invention include structure (XIc):

(XIc)

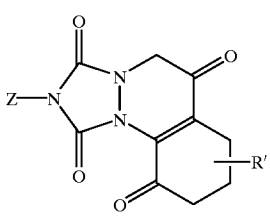

-continued

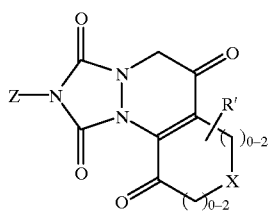

(XId)

The β-sheet mimetics of this invention may be synthesized by one skilled in the art by known organic synthesis techniques. For example, the various embodiments of structure (I) may be synthesized according to the following reaction schemes.

Representative compounds of structure (III) can be synthesized by the following reaction schemes (where n=0–4, p=0–3 and m=0–2):

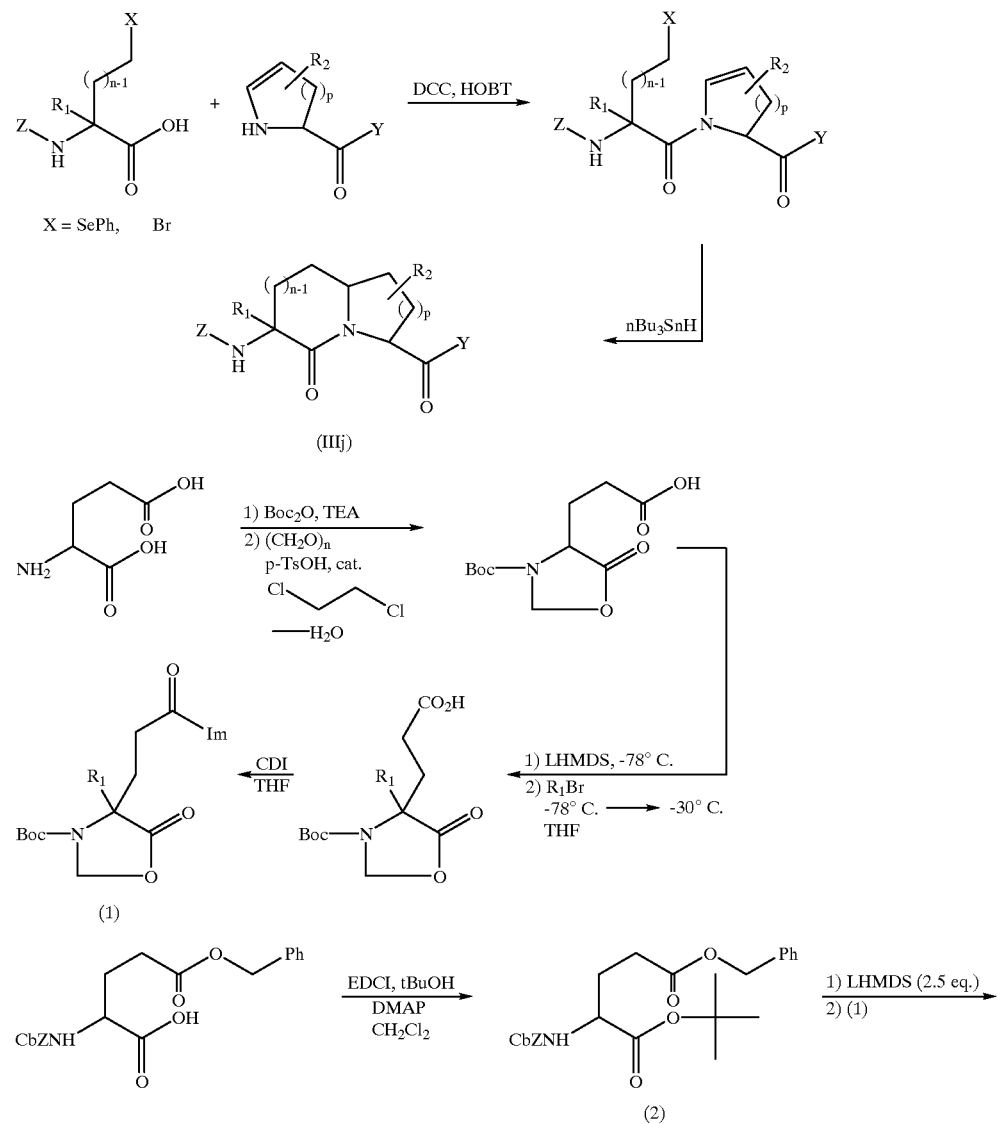

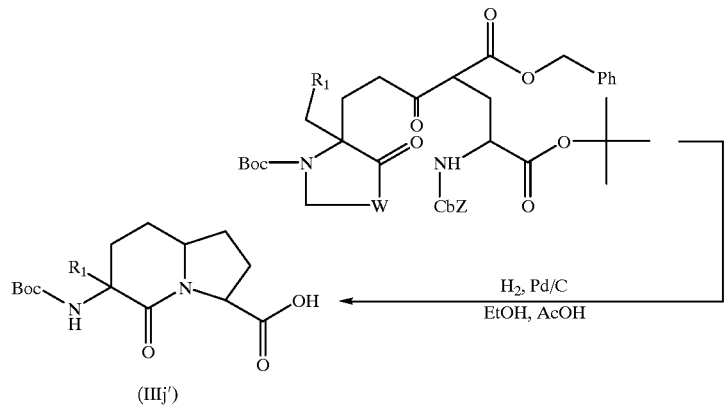
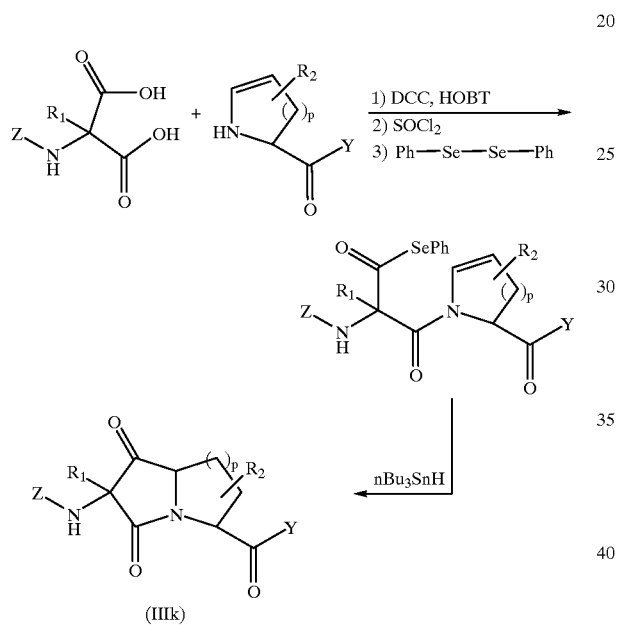
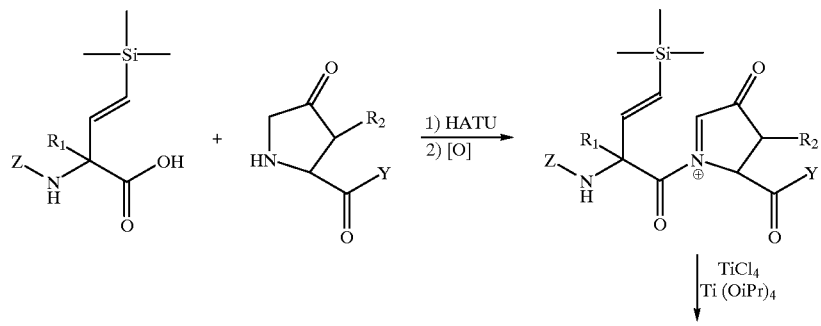

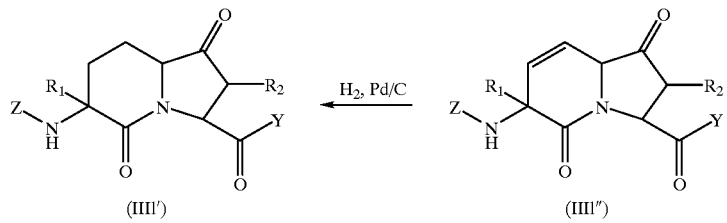

In addition, representative compounds of structure (IIII) having structure (IIIl''') may be synthesized by the following reaction scheme, and when A of structure (IIIl) is —C(=O)(CH$_2$)$_{1-3}$—, a related compound (designated (IIIi') below) can be synthesized by the following reaction scheme:

Representative compounds of structure (IIIi) wherein R$_3$ is an amino acid side chain moiety or derivative thereof may also be prepared according to the above scheme (4).

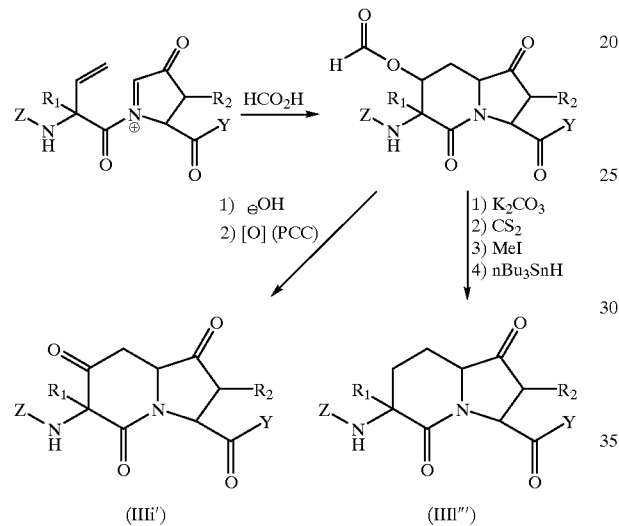

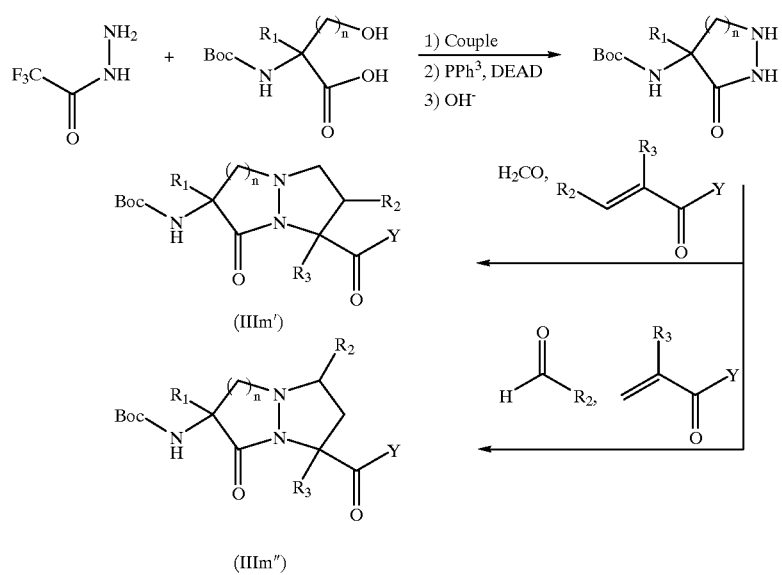

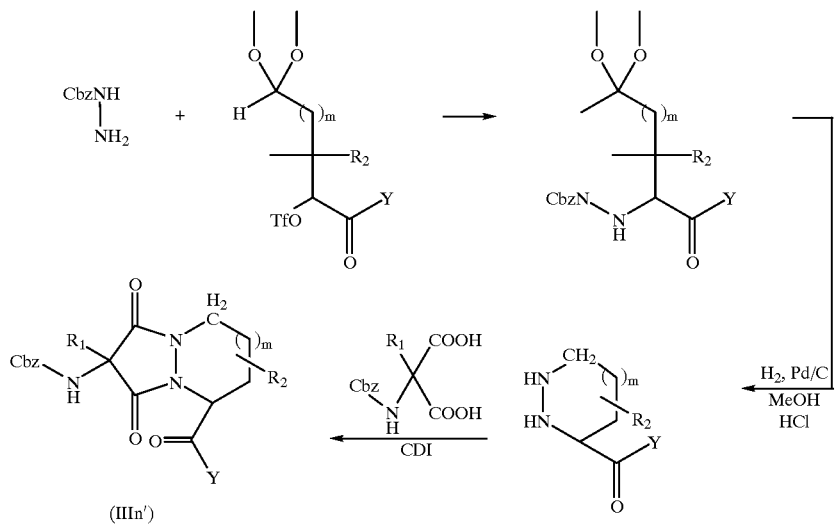
(IIIn′)
Reaction Scheme (6)
Structure (IIIo) can be synthesized by the following reaction scheme:
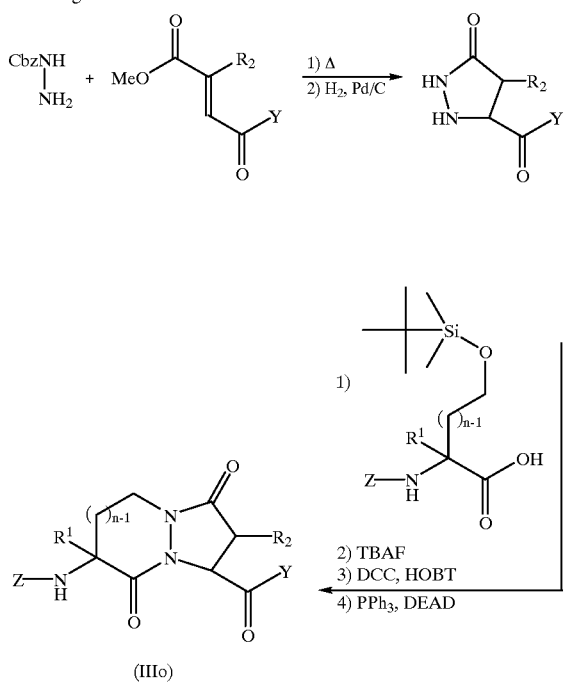
(IIIo)
Reaction Scheme (7)
Representative compounds of structure (IIIp) having structures (IIIp′) and (IIIp″) shown below, can be synthesized by the following reaction scheme:
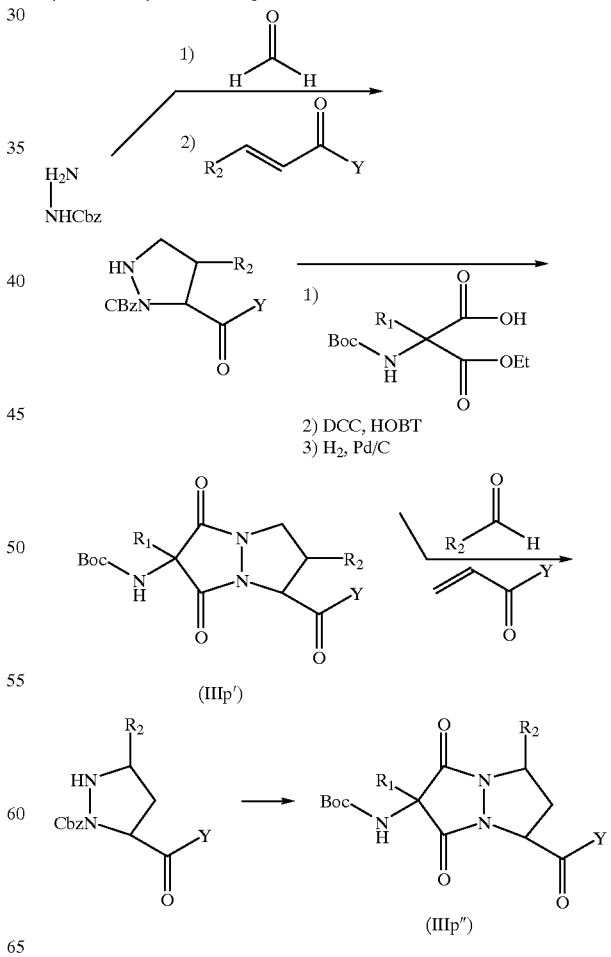
(IIIp′)
(IIIp″)

Reaction Scheme (8)
Representative compounds of structure (IIIq) having structures (IIIq') and (IIIq") can be synthesized by the following reaction scheme (see Jungheim & Sigmund, *J. Org. Chem.* 52:4007-4013, 1987):
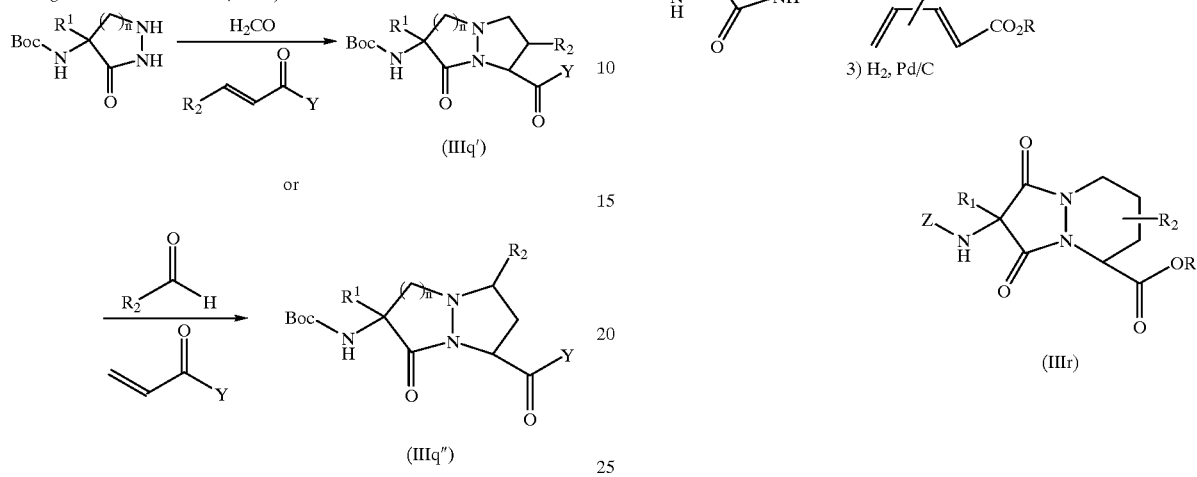
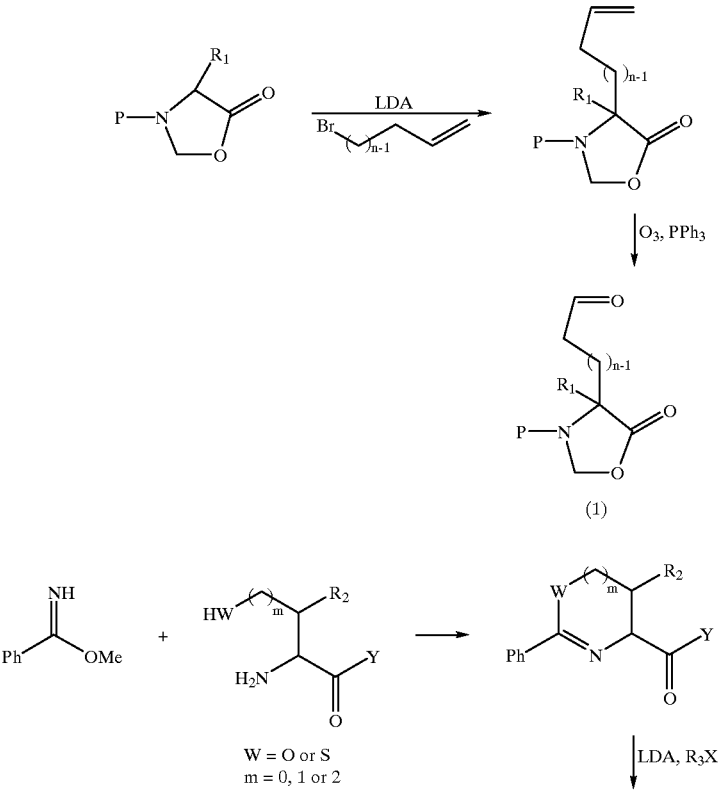

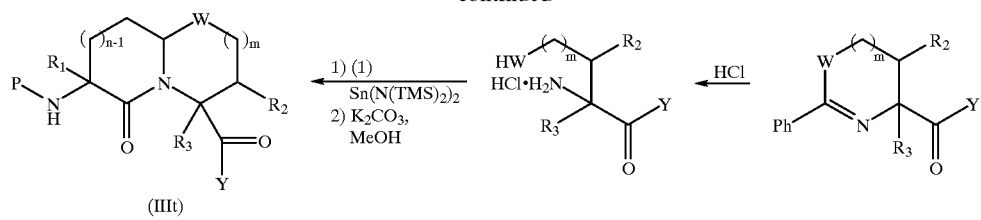
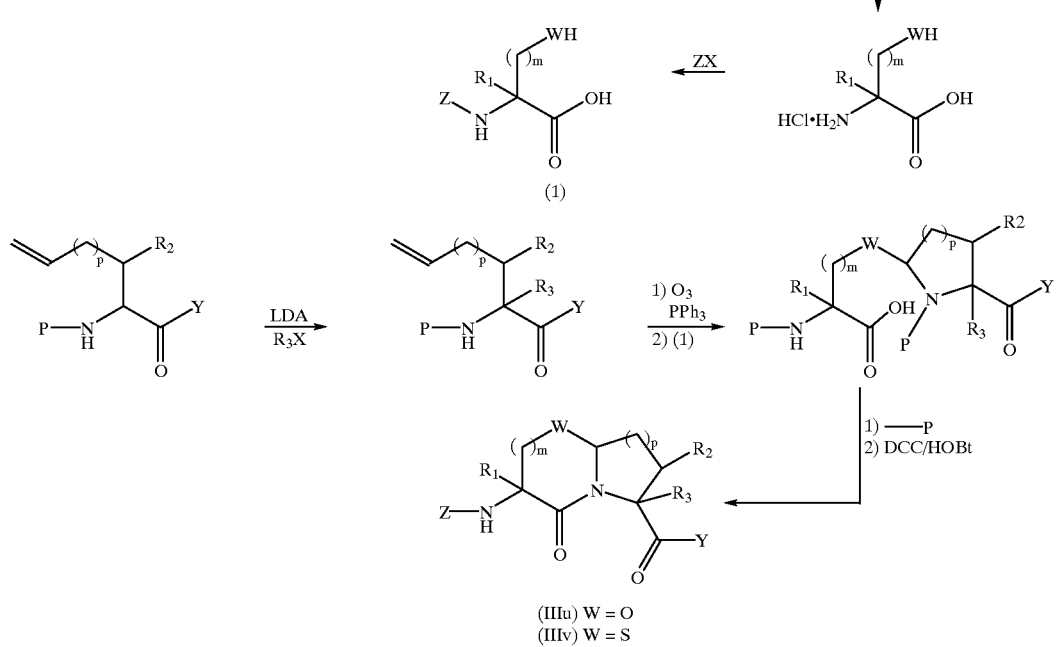
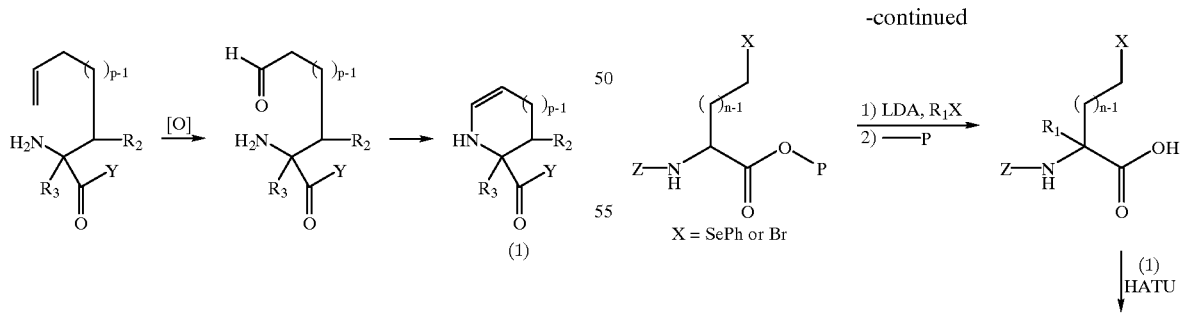

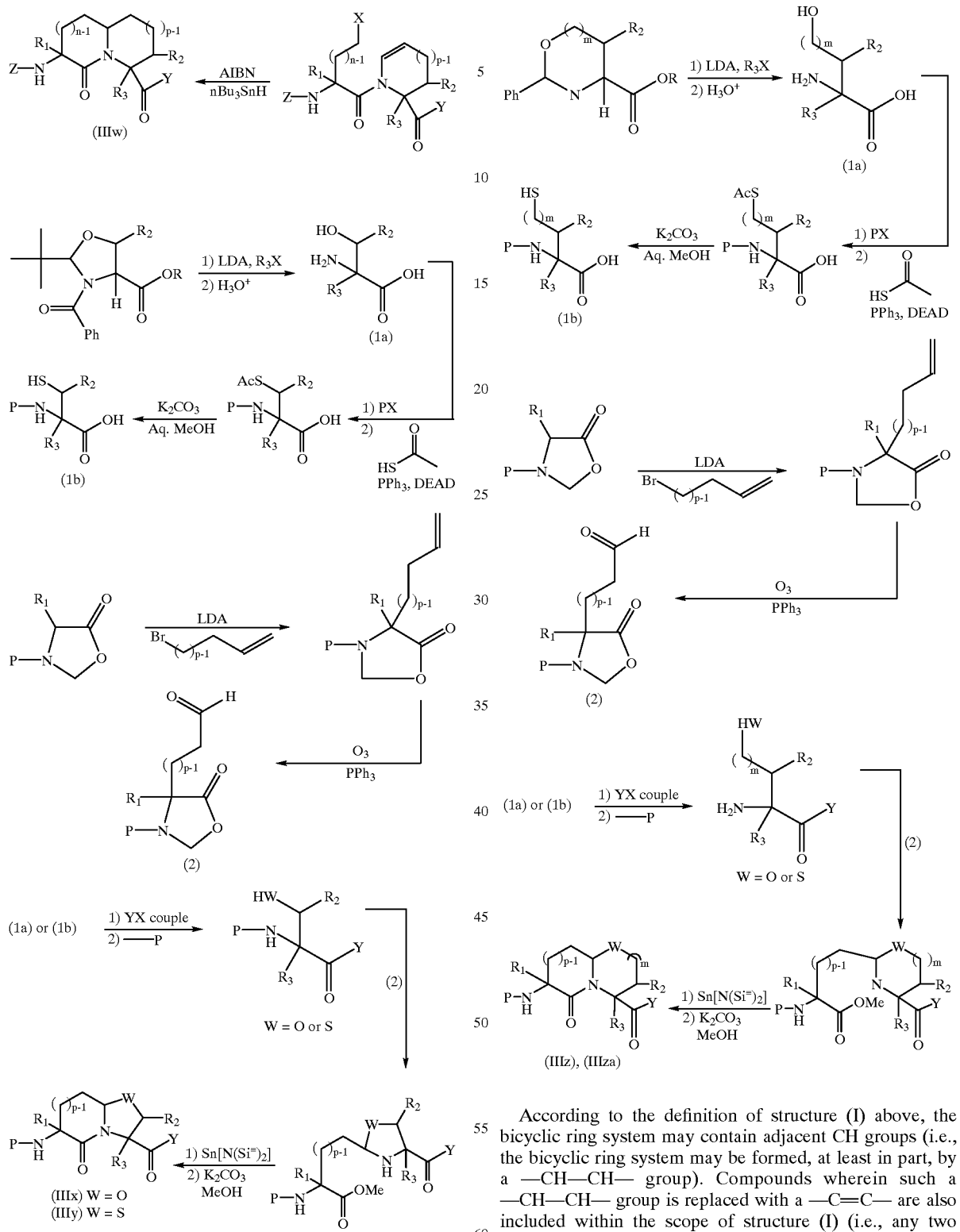

According to the definition of structure (I) above, the bicyclic ring system may contain adjacent CH groups (i.e., the bicyclic ring system may be formed, at least in part, by a —CH—CH— group). Compounds wherein such a —CH—CH— group is replaced with a —C=C— are also included within the scope of structure (I) (i.e., any two adjacent CH groups of the bicyclic ring may together form a double bond).

Reaction Schemes (15), (16) and (17) illustrate further synthetic methodology for preparing representative compounds of structure (III).
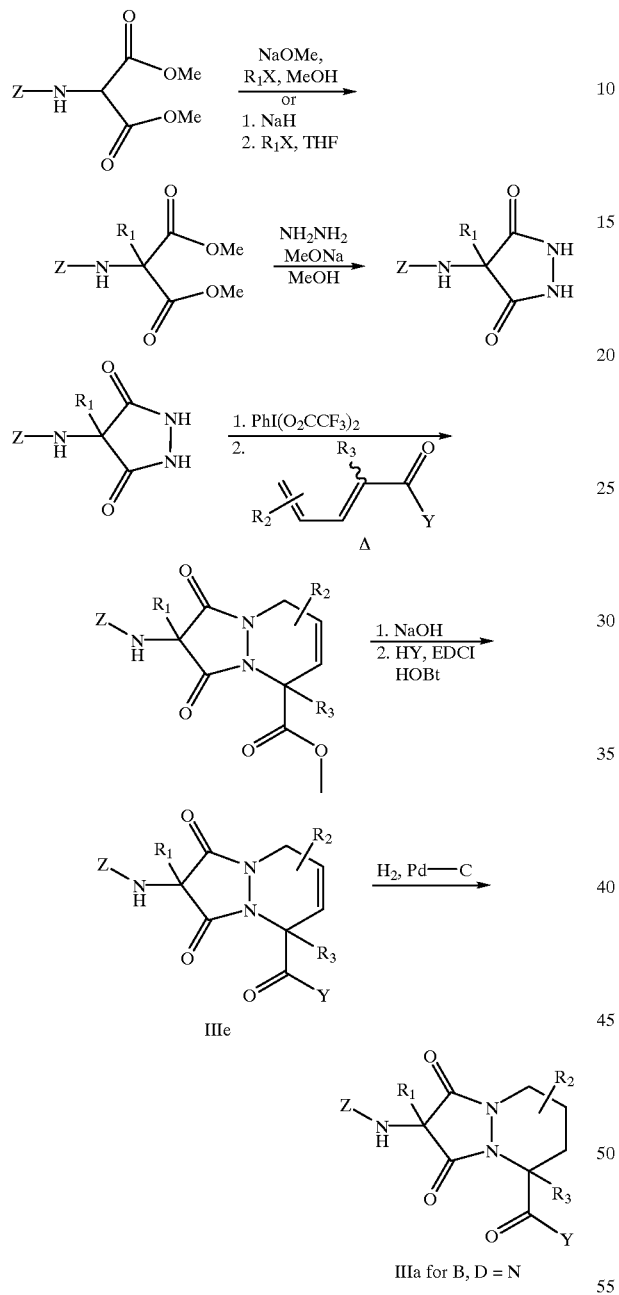
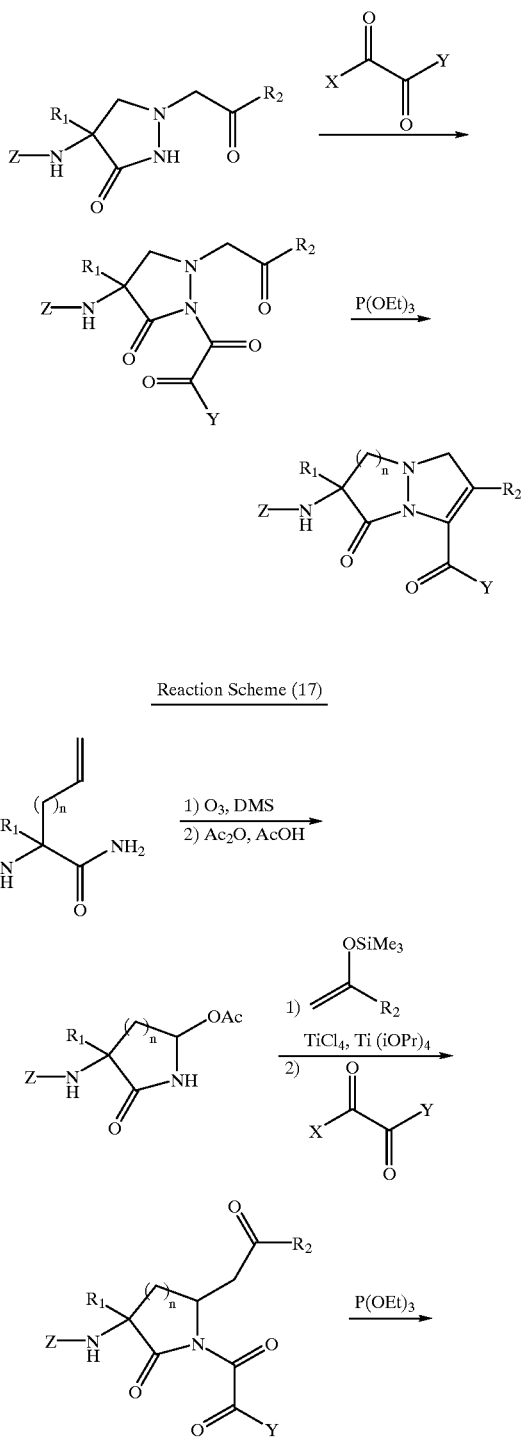
Representative compounds of structure (IV) may be prepared by the following reaction schemes (18) through (21).

Reaction Scheme (18)
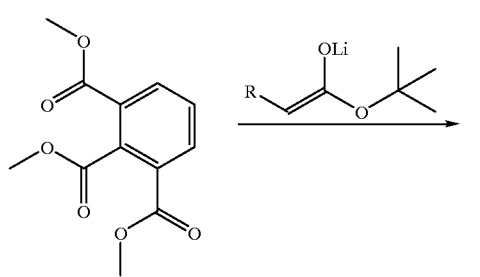
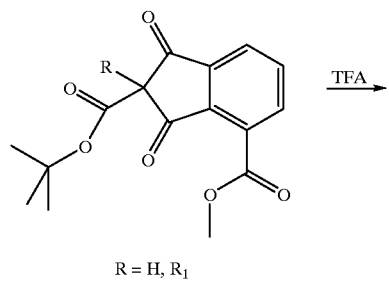
R = H, R₁
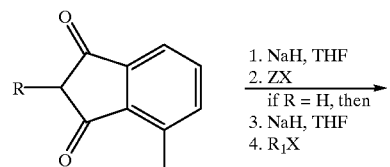
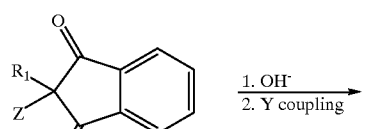
(IVc)
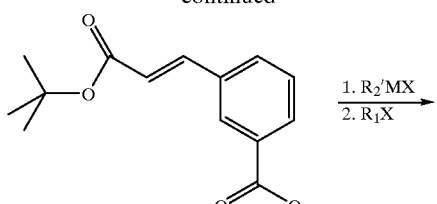
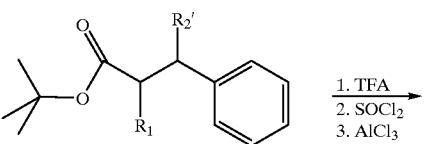
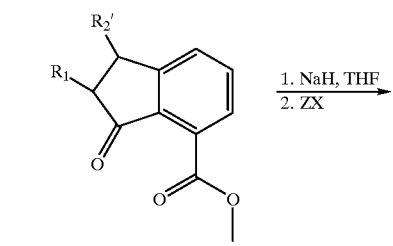
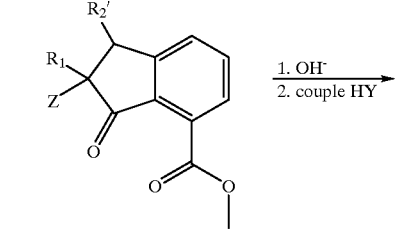
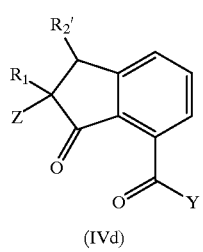
(IVd)
Alternatively, structures (IVc) and (IVd) may be made by reaction scheme (19-1).
Reaction Scheme (19-1)
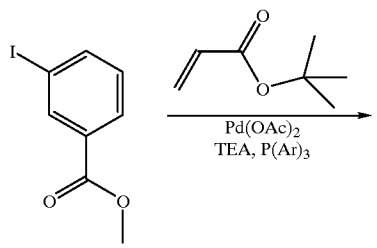
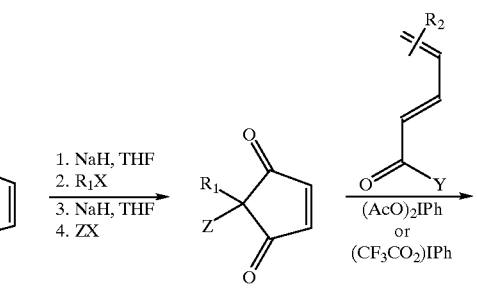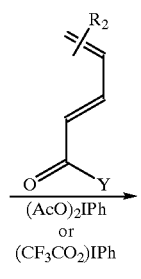

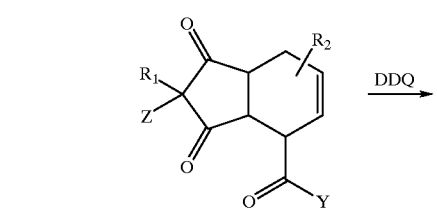
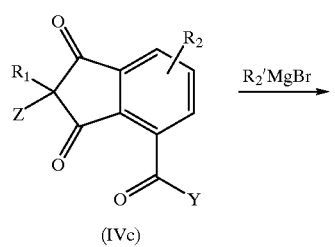
(IVc)
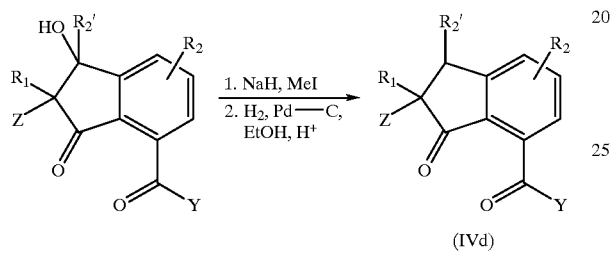
(IVd)
Reaction Scheme (20)
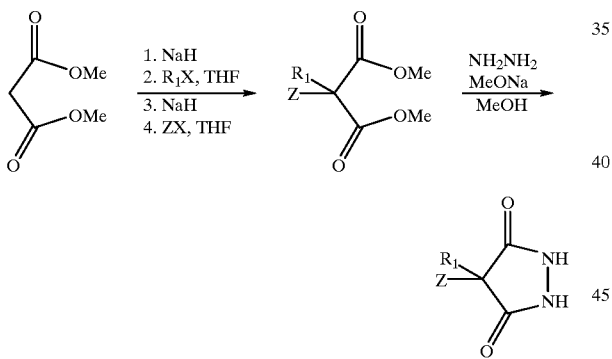
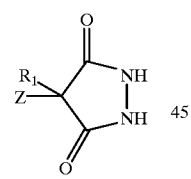
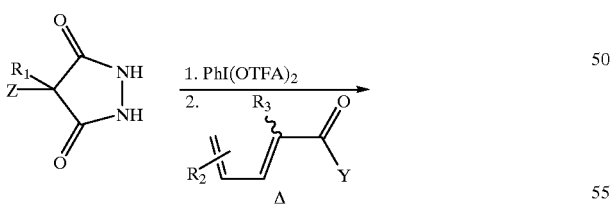
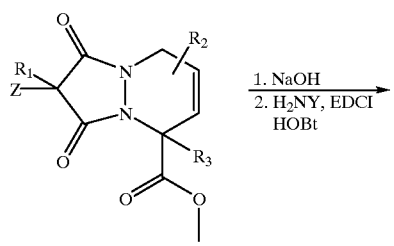
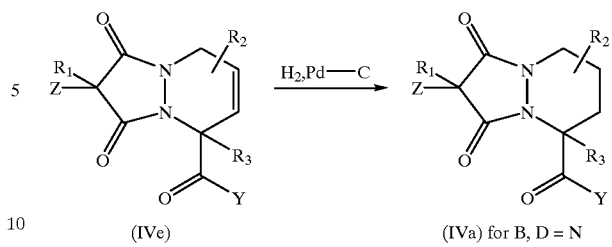
(IVe)  (IVa) for B, D = N
Reaction Scheme (21)
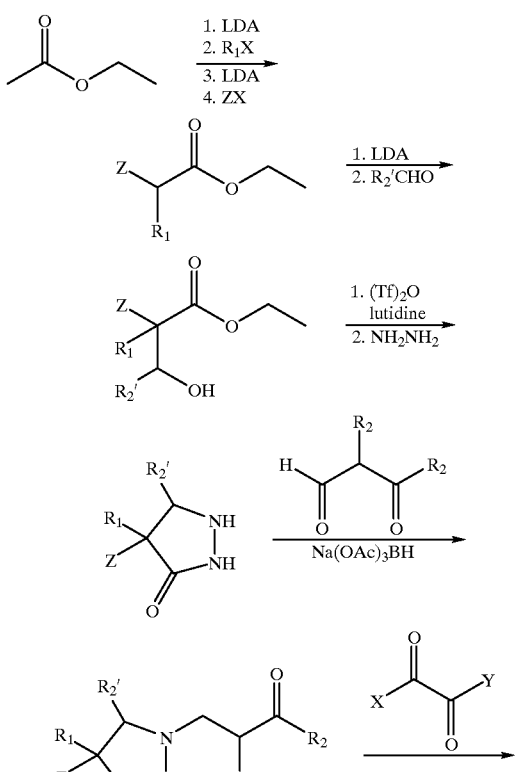

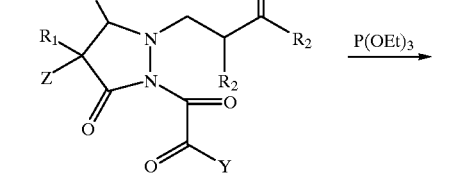
(IVf)

Alternatively, structure (IVf) may be made by the following reaction scheme (21-1).
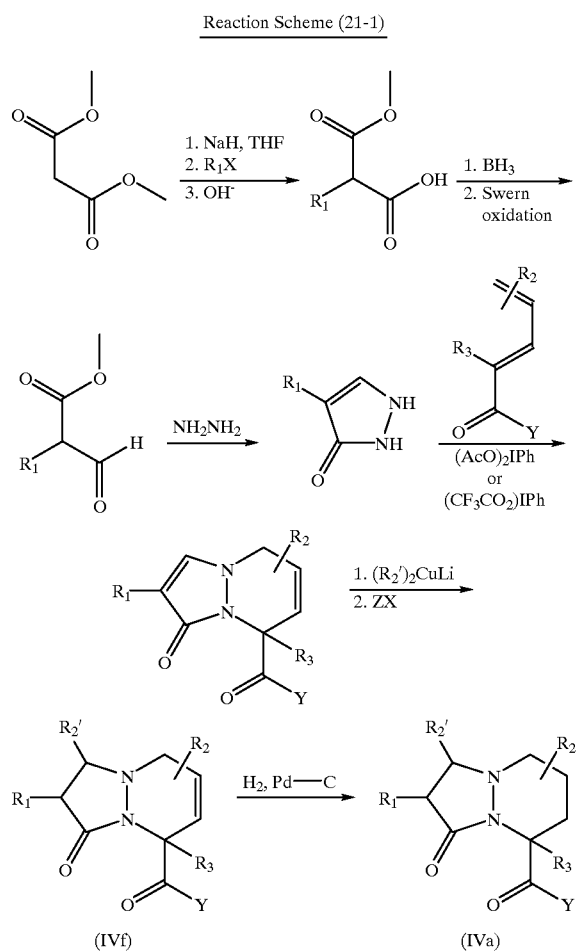
Representative compounds of structure (VIII) may be synthesized either from urazoles or pyrazolidine diones by reaction schemes (22) and (23).
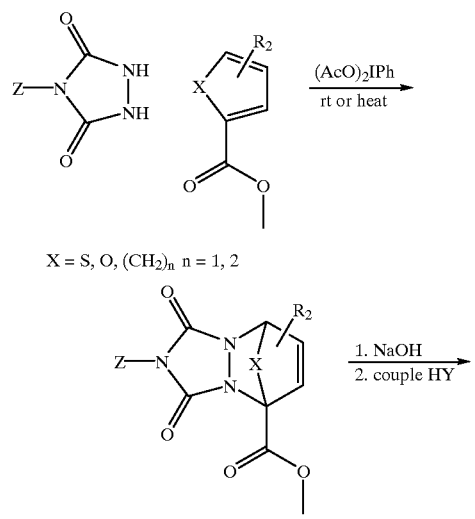
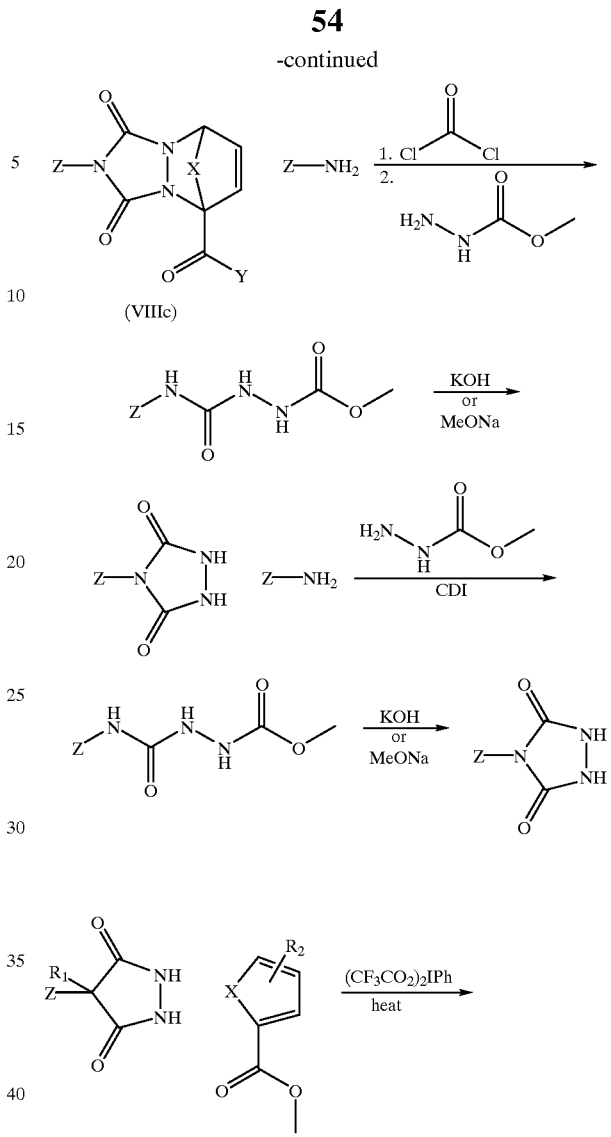
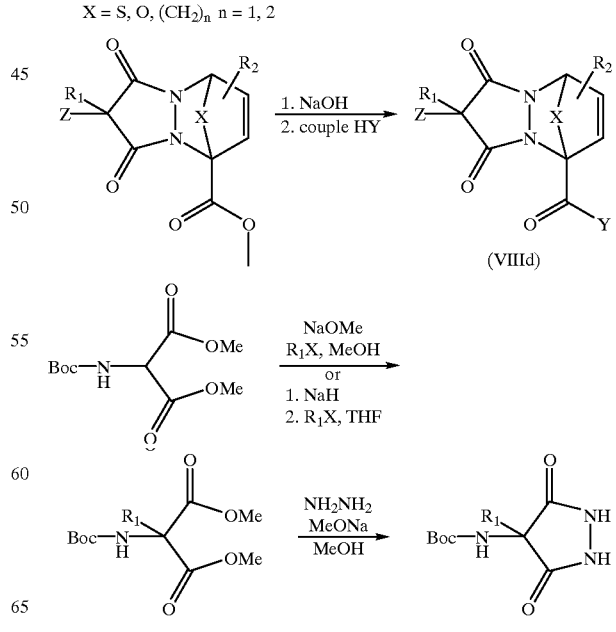

Alternatively, the pyrazolidine dione starting material may be synthesized by the following reaction scheme:
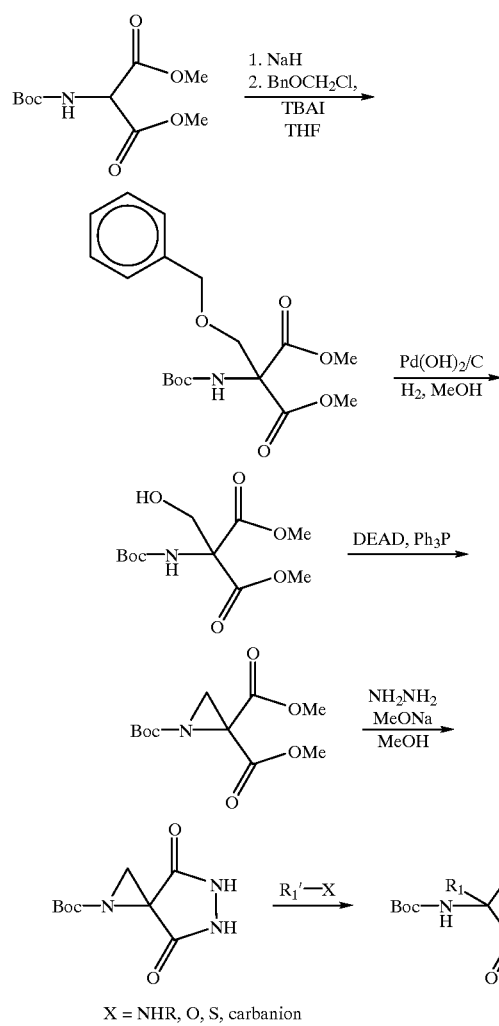
Representative compounds of structure (II) may be synthesized by the following reaction scheme (24):
Reaction Scheme (24)
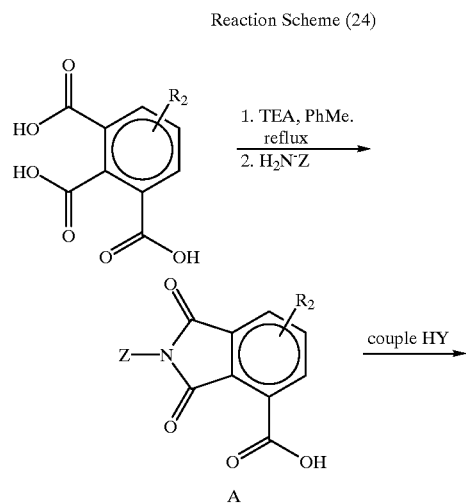
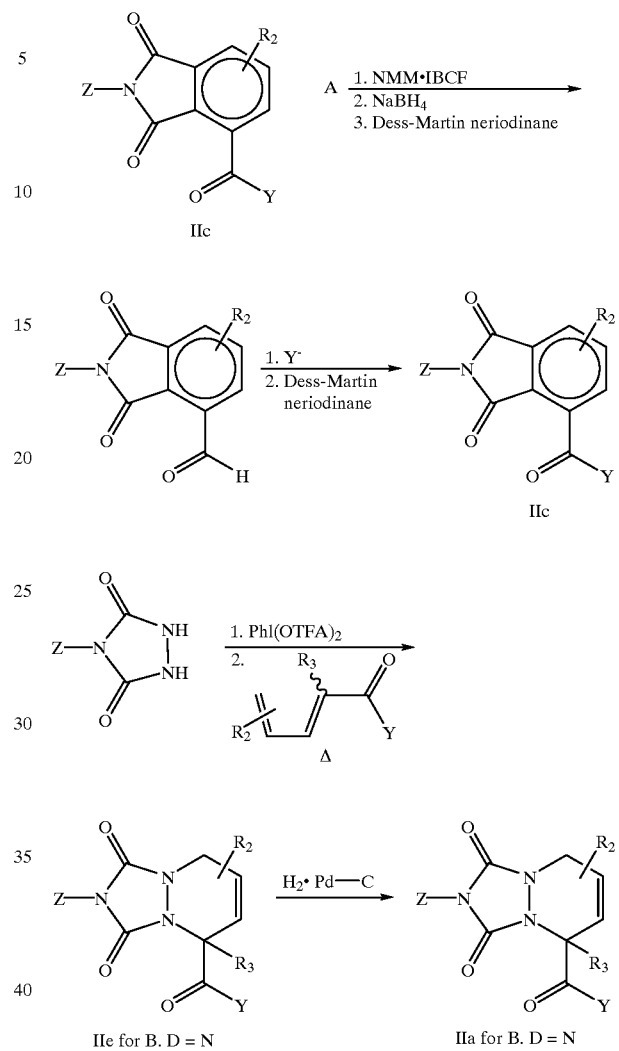
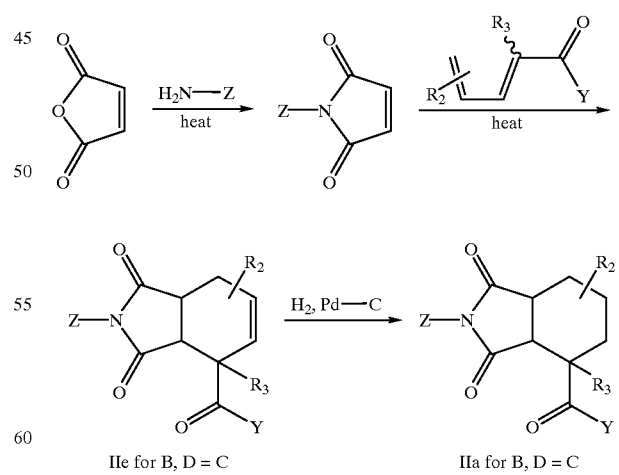
Further representative compounds of structure (II) may be made by the following reaction scheme (25):

Reaction Scheme (25)

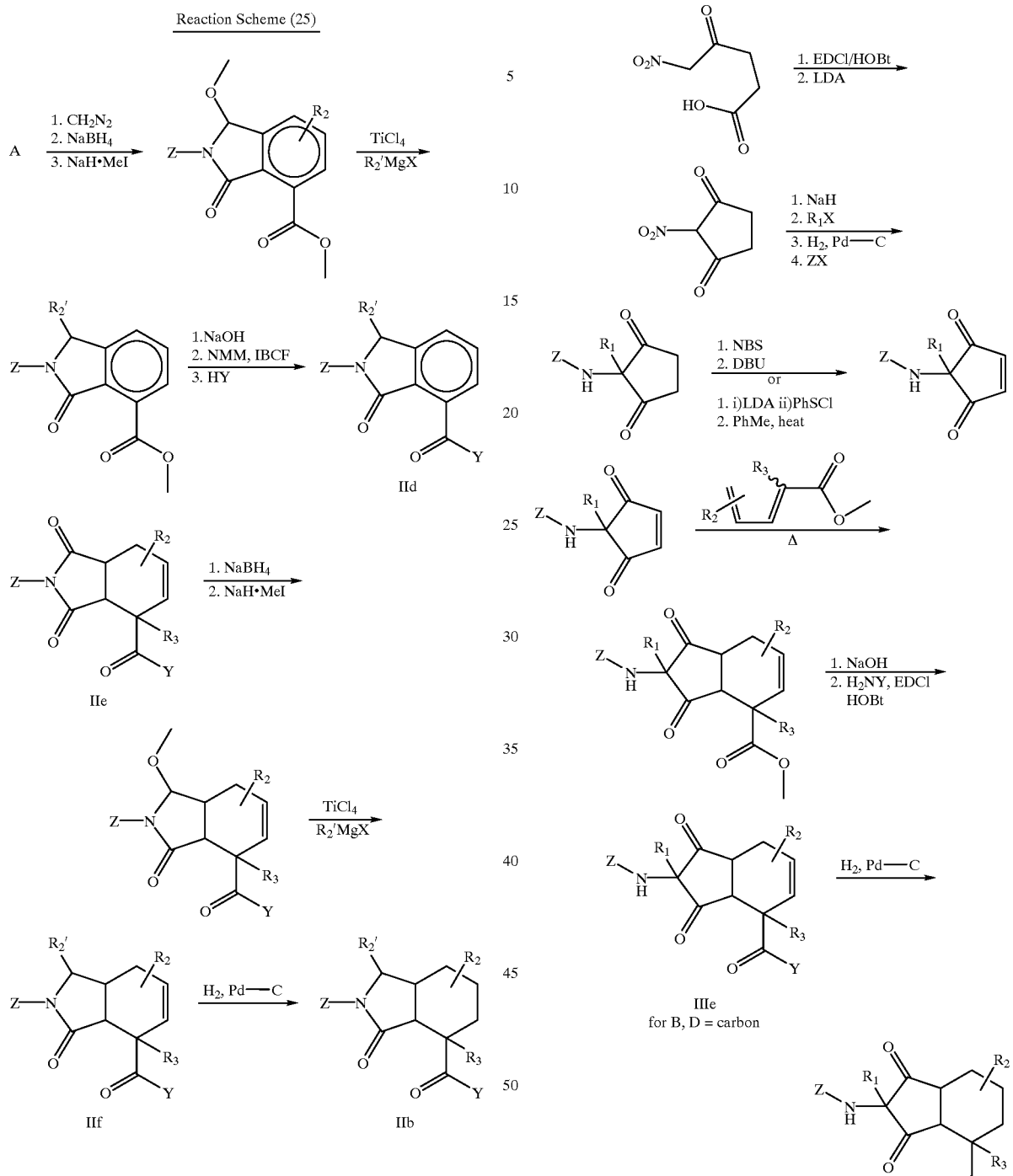

Further representative compounds of structure (III) may be made by the following reaction scheme (26):

Reaction Scheme (26)

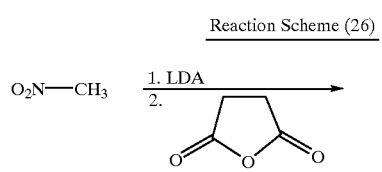

Compounds of structures (V), (VI) and (VII) may be made by the same general techniques as disclosed above for compounds of structures (II), (III) and (IV), with the exception that the respective precursor intermediate does not contain a carbonyl moiety at position F.

Further, compounds of structure (IX) may be prepared according to reaction scheme (27):

Reaction Scheme (27)
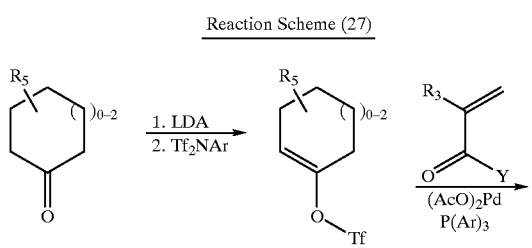
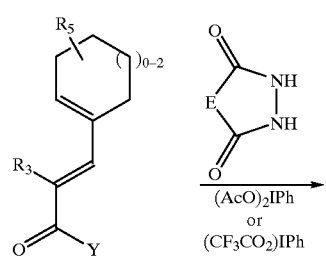
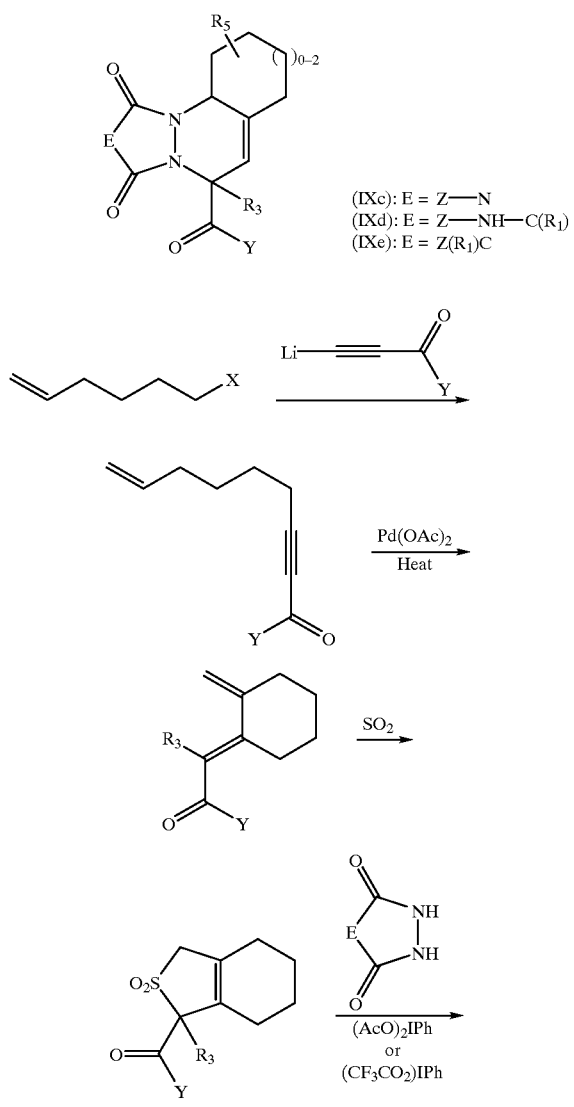
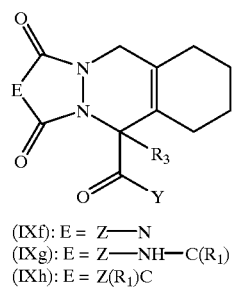
(IXf): E = Z—N
(IXg): E = Z—NH—C(R$_1$)
(IXh): E = Z(R$_1$)C
Representative compounds of structure (IIe) may be made by the following reaction scheme (28):
Reaction Scheme (28)
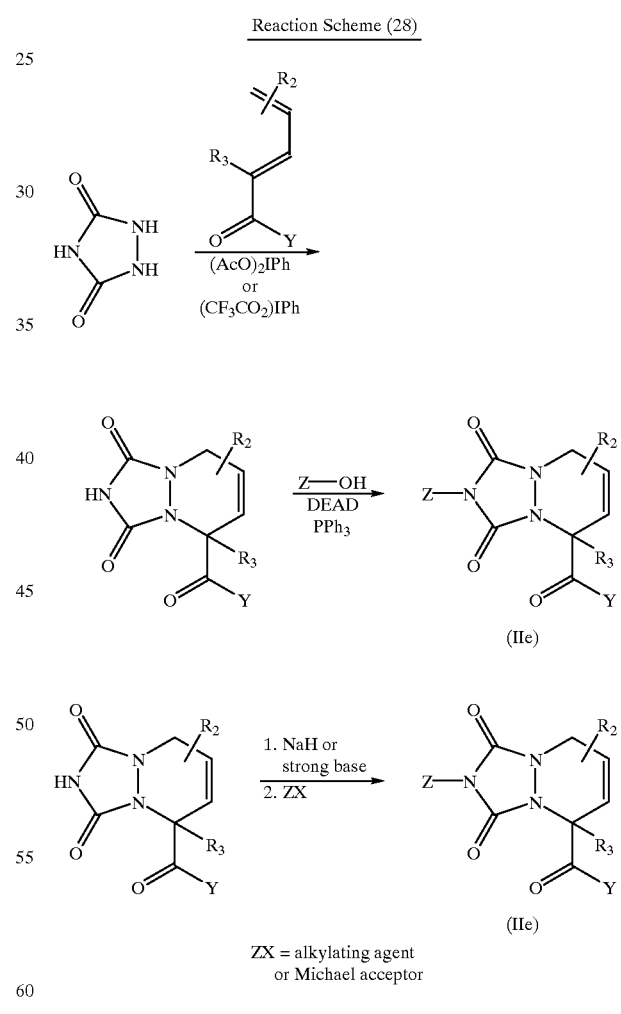
ZX = alkylating agent or Michael acceptor
Representative compounds of structure (X) may be made by the following reaction scheme (29):

Reaction Scheme (29)
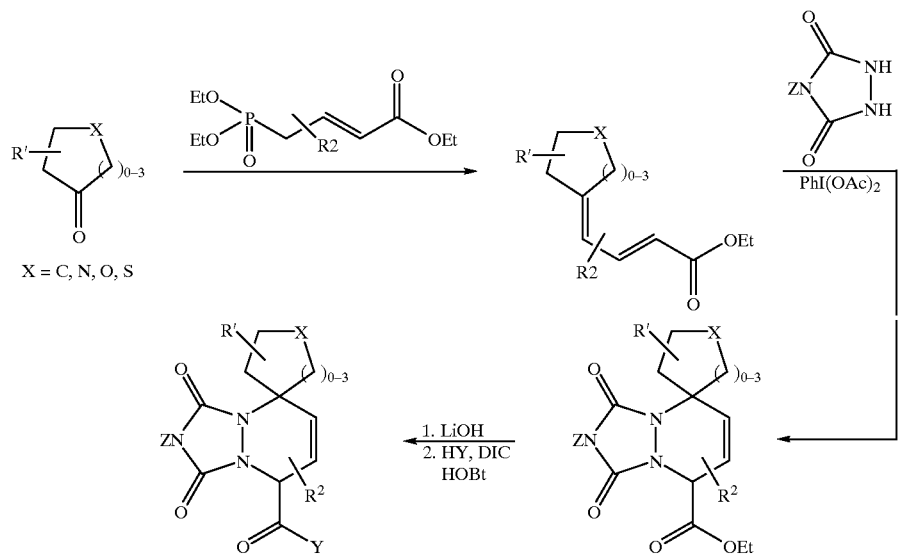
Representative compounds of structure (XIc) may be made by the following reaction scheme (30):
Reaction Scheme (30)
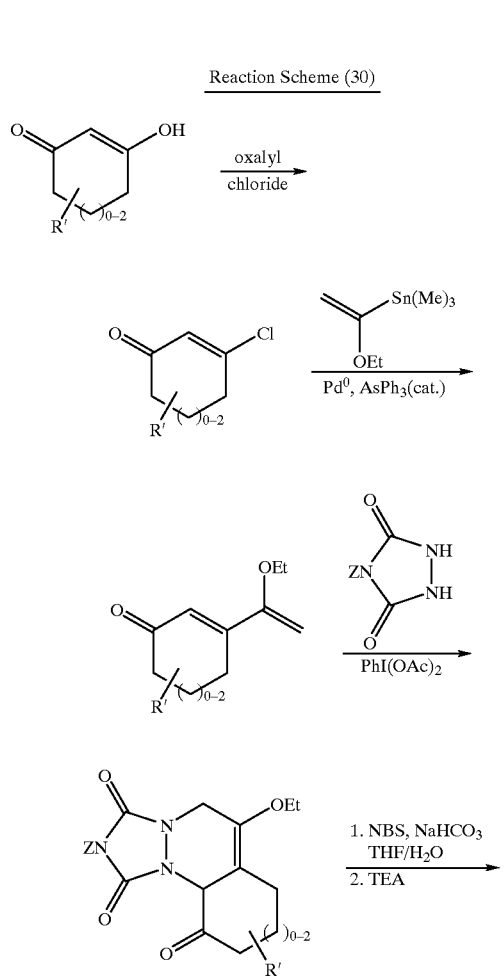
-continued
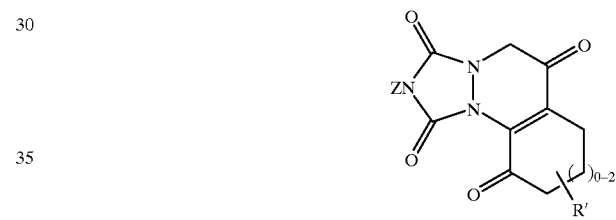
Representative compounds of structure (XId) may be made by the following reaction scheme (31):
Reaction Scheme (31)
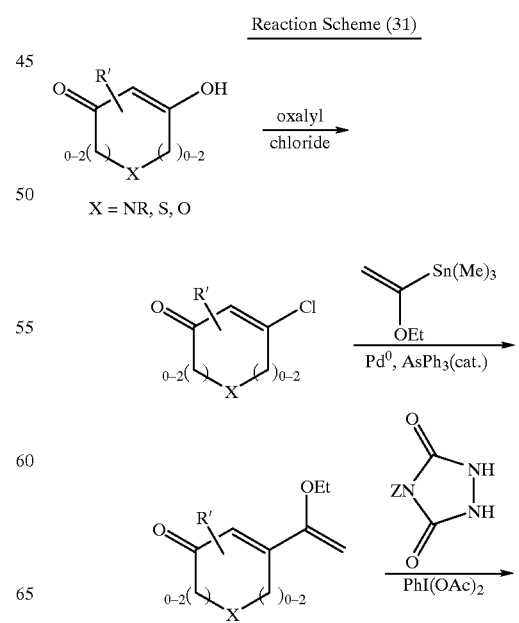

Reaction Scheme (32)
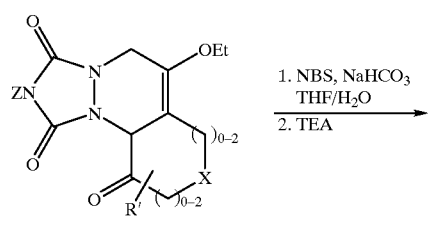
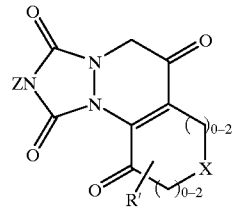
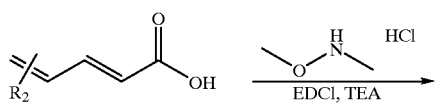
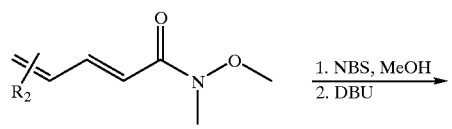
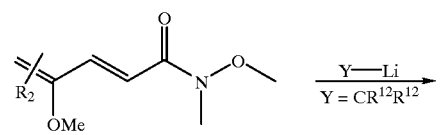
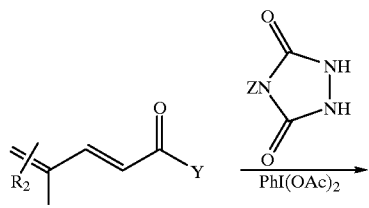
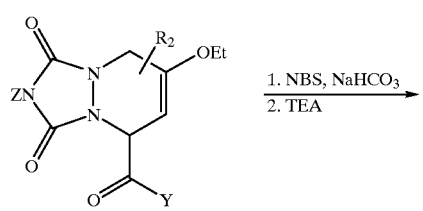
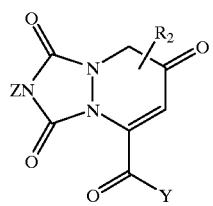
Representative compounds of structure (IIh') may be made by the following reaction schemes (32) and (33):
Reaction Scheme (33)
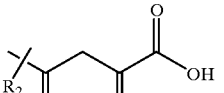
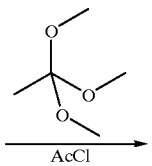
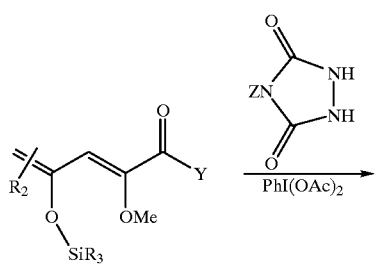
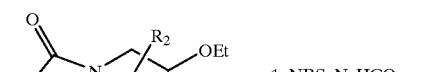
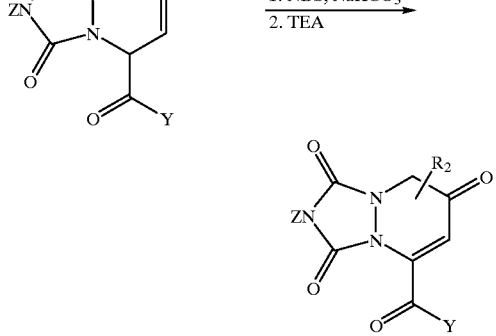
In one embodiment of β-sheet mimetics of this invention, Y groups have the structure:
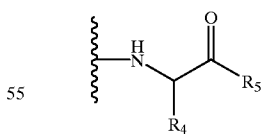
where a preferred stereochemistry is:
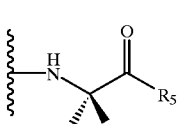

Preferred R$_4$ groups are organoamine moieties having from about 2 to about 10 carbon atoms and at least one nitrogen atom. Suitable organoamine moieties have the chemical formula C$_{2-10}$H$_{4-20}$N$_{1-6}$O$_{0-2}$; and preferably have the chemical formula C$_{3-7}$H$_{7-14}$N$_{1-4}$O$_{0-1}$. Exemplary organoamine moieties of the invention are (wherein R is selected from hydrogen, halogen (e.g., fluorine), lower chain alkyl (e.g., methyl), and hydroxy lower chain alkyl (e.g., hydroxymethyl); and X is selected from CH$_2$, NH, S and O):

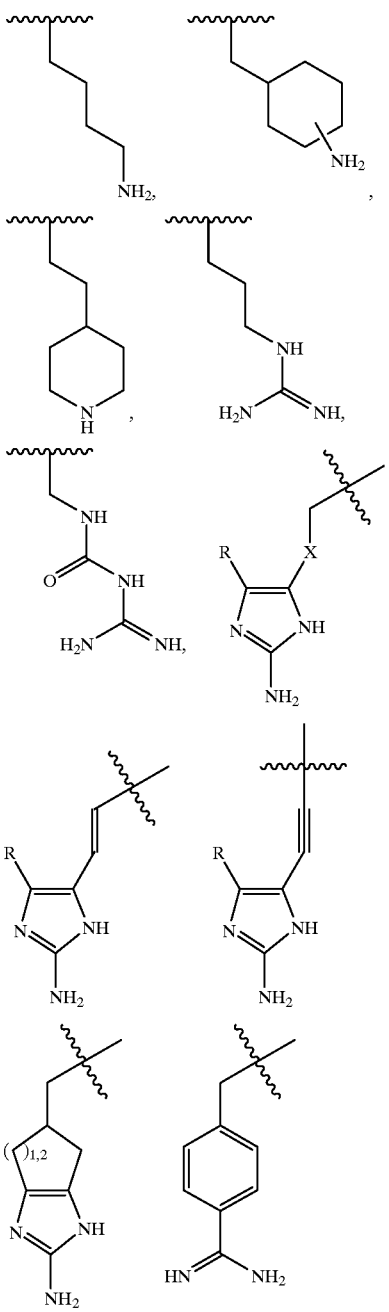

In the above structure, R$_5$ is selected from (a) alkyl of 1 to about 12 carbon atoms, optionally substituted with 1–4 of halide, C$_{1-5}$alkoxy and nitro, (b) —C(=O)NH—C$_{1-5}$alkyl, wherein the alkyl group is optionally substituted with halide or C$_{1-5}$alkoxy, (c) —C(=O)NH—C$_{1-10}$aralkyl where the aryl group may be optionally substituted with up to five groups independently selected from nitro, halide, —NH—(C=O)C$_{1-5}$alkyl, —NH—(C=O)C$_{6-10}$aryl, C$_{1-5}$alkyl and C$_{1-5}$alkoxy, and (d) monocyclic and bicyclic heteroaryl of 4 to about 11 ring atoms, where the ring atoms are selected from carbon and the heteroatoms oxygen, nitrogen and sulfur, and where the heteroaryl ring may be optionally substituted with up to about 4 of halide, C$_{1-5}$alkyl, C$_{1-5}$alkoxy, —C(=O)NHC$_{1-5}$alkyl, —C(=O)NHC$_{6-10}$aryl, amino, —C(=O)OC$_{1-5}$alkyl and —C(=O)OC$_{6-10}$aryl.

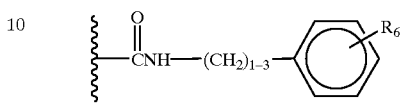

wherein R$_6$ is hydrogen, nitro, halide, NH—C(=O)—C$_{1-5}$alkyl, NH—C(=O)—C$_{6-10}$aryl, C$_1$–C$_5$alkyl and C$_1$–C$_5$alkoxy;

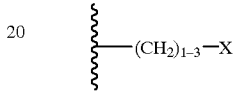

wherein X is halide;

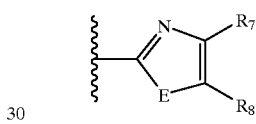

wherein E is —O—, —NH— or —S— and R$_7$ and R$_8$ are independently selected from hydrogen, C$_{1-5}$alkyl, —C(=O)OC$_{1-5}$alkyl, —C(=O)OC$_{6-10}$aryl, —C(=O)NHC$_{1-5}$alkyl and —C(=O)NHC$_{6-10}$aryl; and

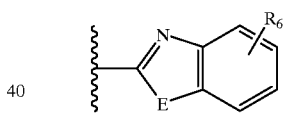

wherein E and R$_6$ are as defined previously.

The β-sheet mimetics of the present invention may be used in standard peptide synthesis protocols, including automated solid phase peptide synthesis. Peptide synthesis is a stepwise process where a peptide is formed by elongation of the peptide chain through the stepwise addition of single amino acids. Amino acids are linked to the peptide chain through the formation of a peptide (amide) bond. The peptide link is formed by coupling the amino group of the peptide to the carboxylic acid group of the amino acid. The peptide is thus synthesized from the carboxyl terminus to the amino terminus. The individual steps of amino acid addition are repeated until a peptide (or protein) of desired length and amino acid sequence is synthesized.

To accomplish peptide (or protein or molecule) synthesis as described above, the amino group of the amino acid to be added to the peptide should not interfere with peptide bond formation between the amino acid and the peptide (i.e., the coupling of the amino acid's carboxyl group to the amino group of the peptide). To prevent such interference, the amino groups of the amino acids used in peptide synthesis are protected with suitable protecting groups. Typical amino protecting groups include, for example, BOC and FMOC groups. Accordingly, in one embodiment of the present invention, the β-sheet mimetics of the present invention bear a free carboxylic acid group and a protected amino group, and are thus suitable for incorporation into a peptide by standard synthetic techniques.

The β-sheet mimetics of this invention may be synthesized on solid support, typically via a suitable linker. The β-sheet mimetics may then be cleaved from the solid support by, for example, aminolysis, and screened as competitive substrates against appropriate agents, such as the chromogenic substrate BAPNA (benzyoylarginine paranitroanalide) (see Eichler and Houghten, *Biochemistry* 32:11035–11041, 1993) (incorporated herein by reference). Alternatively, by employing a suitable linker moiety, such screening may be performed while the β-sheet mimetics are still attached to the solid support.

Once a substrate is selected by the above kinetic analysis, the β-sheet mimetic may be converted into an inhibitor by modifications to the C-terminal—that is, by modification to the Y moiety. For example, the terminal Y moiety may be replaced with —$CH_2Cl$, —$CF_3$, —H, or —C(O)NHR. Appropriate R moieties may be selected using a library of substrates, or using a library of inhibitors generated using a modification of the procedure of Wasserman and Ho (*J. Org. Chem.* 59:4364–4366, 1994) (incorporated herein by reference).

Libraries of compounds containing β-strand templates may be constructed to determine the optimal sequence for substrate recognition or binding. Representative strategies to use such libraries are discussed below.

A representative β-sheet mimetic substrate library may be constructed as follows. It should be understood that the following is exemplary of methodology that may be used to prepare a β-sheet mimetic substrate library, and that other libraries may be prepared in an analogous manner.

In a first step, a library of the following type:

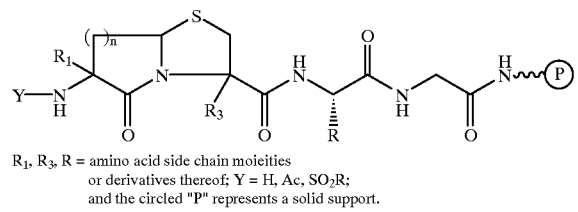

$R_1$, $R_3$, R = amino acid side chain moieties
or derivatives thereof; Y = H, Ac, $SO_2R$;
and the circled "P" represents a solid support.

may be constructed on a solid support (PEGA resin, Meldal, M. *Tetrahedron Lett.* 33:3077–80, 1992; controlled pore glass, Singh et al., *J. Med. Chem.* 38:217–19, 1995). The solid support may then be placed in a dialysis bag (Bednarski et al., *J. Am. Chem. Soc.* 109:1283–5, 1987) with the enzyme (e.g., a protease) in an appropriate buffer. The bag is then placed in a beaker with bulk buffer. The enzymatic reaction is monitored as a function of time by HPLC and materials cleaved from the polymer are analyzed by MS/MS. This strategy provides information concerning the best substrates for a particular target.

The synthesis of the β-sheet mimetic is illustrated by the retrosynthetic procedure shown next:

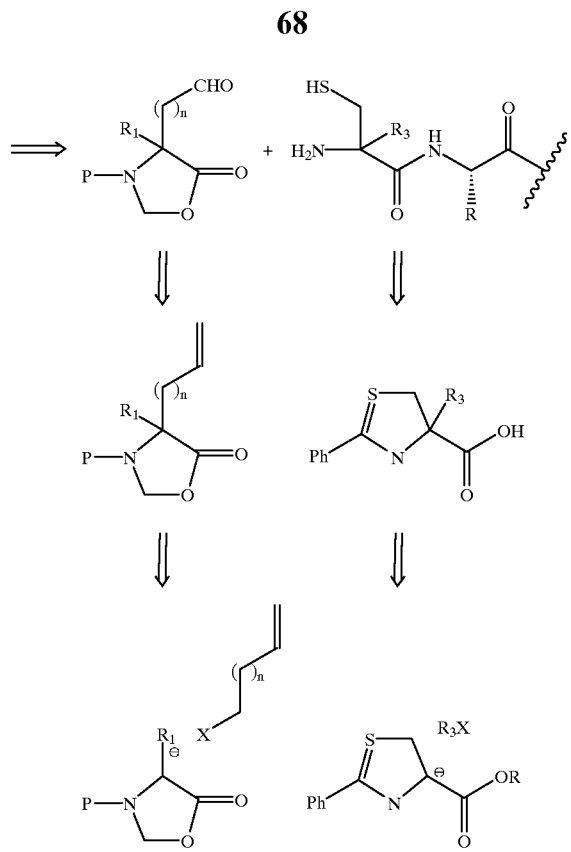

The complexity of the library generated by this technique is ($R_1$) ($R_3$) (R) (Y). Assuming $R_1$, $R_3$ and R are selected from naturally occurring amino acid side chains moieties, n is constant, and Y is H, Ac or —$SO_2R$ as defined above, a library having on the order of 24,000 members [(20) (20) (20) (3)] is generated.

After screening the library against a specific target (e.g., enzyme), the library may then recovered and screened with a second target, and so on.

In addition, a library of inhibitors can be constructed and screened in a standard chromogenic assay. For example, the library may be constructed as follows, where the following example is merely representative of the inhibitor libraries that may be prepared in an analogous manner to the specific example provided below.

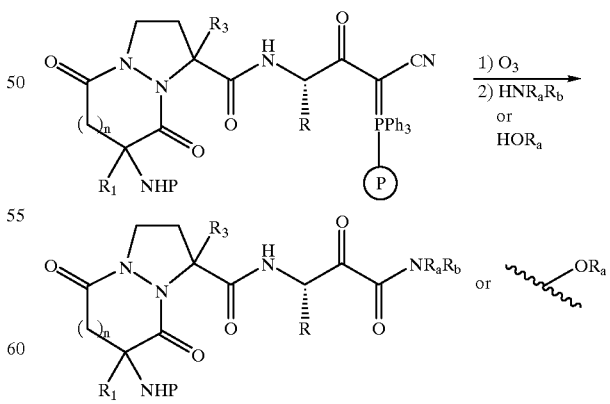

inhibitors of serine or cysteinyl proteases (See Wasserman et al., *J. Org. Chem.* 59:4364–6, 1994.)

A further alternative strategy is to link the library through the sidechain R group as shown below.

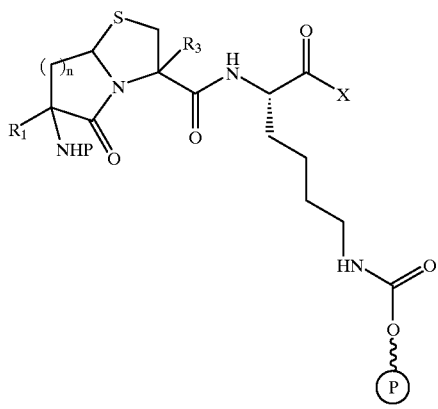

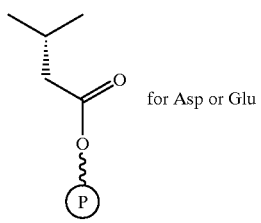

for Asp or Glu

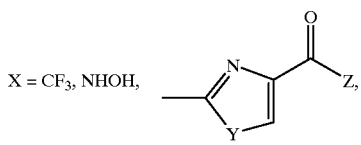

X = CF₃, NHOH,

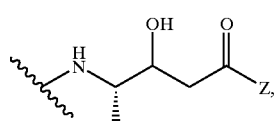

Z = OR, NHR, or amino acids

A library of aspartic protease inhibitors may be constructed having the following exemplary structure, and then cleaved from the resin and screened:

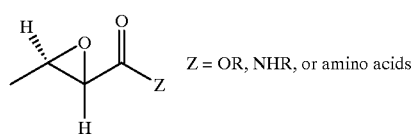

Similarly, for metalloproteases, a library having the exemplary structure shown below may be constructed and then cleaved from the resin to provide a library of hydroxamic acids:

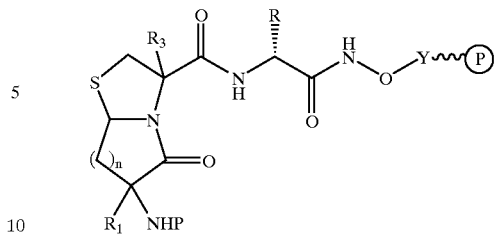

The activity of the β-sheet mimetics of this invention may be further illustrated by reference to Table 2 which lists a number of biologically active peptides. In particular, the peptides of Table 2 are known to have biological activity as substrates or inhibitors.

TABLE 2

Biologically Active Peptides

Protease Inhibitors:

(a) (D)FPR (Thrombin)
    Enzyme 40:144–48, 1988
(b) (D)IEGR (Factor X)
    Handbook of Synthetic Substrates for the Coagulation and Fibronlytic Systems, H.C. Hemker, pp. 1–175, 1983, Martinus Nijhoff Publishers, The Hague.

Protein Kinase Substrates and Inhibitors:

(c) LRRASLG (Serine Kinase)
    Biochem. Biophys. Res. Commun. 61:559, 1974
(d) LPYA (Tyrosine Kinase)
    J. Bio. Chem. 263:5024, 1988
(e) PKI (Serine Kinase)
    Science 253:1414–20, 1991

CAAX Inhibitors:

(f) (H)-CVIM-(OH)
    Proc. Natl. Acad. Sci. USA 88:732–36, 1991
(g) (H)-CVFM-(OH)
    Bioorg. Med. Chem. Letters 4:887–92, 1994
(h) (H)-CIT-(homoserine lactone)
    Science 260:1934–37, 1993

SH2 Peptide Analogs:

(i) ᴾYZPZSᴾYZPZS (IRS 1 analogue)
    Biochemistry 33:9376–81, 1994
(j) EPQᴾYEEIPIYL (Src SH₂ binding motif)
    Cell 72:767–68, 1993

Class MHC I peptides:

(k) TYQRTRALV (Influenza nucleoprotein)
    J. Exp. Med. 175:481–87, 1991
(l) RGYVYQGL (VSV)
    Ann. Rev. Imm. 11:211–44, 1993

ᴾY = phosphorylated Y
Z = norleucine

More generally, the β-sheet mimetics of this invention can be synthesized to mimic any number of biologically active peptides by appropriate choice of the R₂, R₂', R₃, F, Y and Z moieties (as well as the A, B, C, D and E moieties of structure (I) itself). This is further illustrated by Table 3 which discloses various modifications which may be made to the β-sheet mimetics of structure (I) to yield biologically active compounds. In Table 3, R₂ and R₃ are independently chosen from among the atoms or groups shown under the "R₂/R₃" column.

TABLE 3
Modifications to Structure (I) to Yield Biologically Active Compounds
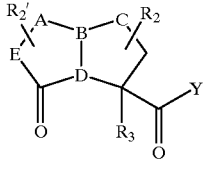
(I)
| R₁ | R₂/R₃ | Y | Z |
|----|-------|---|---|
I. PROTEASE INHIBITORS
A. Serine
| | | | |
|---|---|---|---|
| 1. Thrombin | $C_6$–$C_{10}$ aromatic (e.g., phenyl, benzyl, naphthyl), $C_1$–$C_{10}$ aliphatic or cycloaliphatic, substituted $C_6$–$C_{10}$ aromatic, —$SiR_3$, —$CO_2H$, —$CO_2R$ | hydrogen 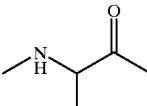 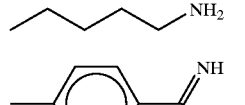 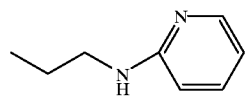 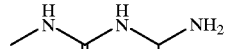  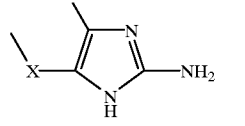 X = $CH_2$, NH, S, O  R = H, $CH_3$ 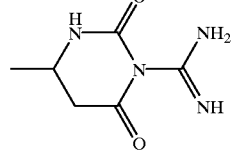 | hydrogen, alkyl, aryl, <br> R = aliphatic |

-continued
| R₁ | R₂/R₃ | Y | Z |
|---|---|---|---|
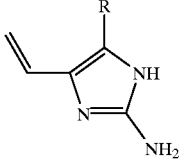
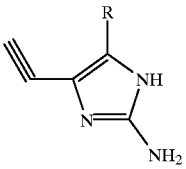
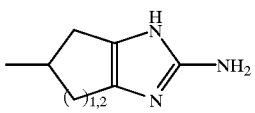
②  = CH₂Cl
     CF₃
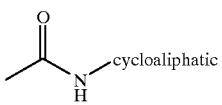
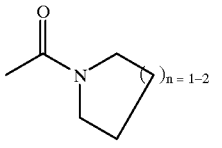
X = O, S, NH
R = CO₂H, CO₂R,
    SO₂R, COCF₃
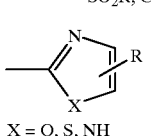
X = O, S, NH
R = CO₂H, SO₂R,
    CO₂R
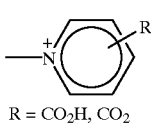
R = CO₂H, CO₂
    SO₂R, COCF₃
| 2. Elastase | C₁–C₁₀ aliphatic | hydrogen or C₁–C₁₀ heterocyclic | | acyl |
(Y structure: MeNH-CH(①)-C(=O)-CF₃)
① = —CH₃
    —CH(CH₃)₂
    or -continued

| | R₁ | R₂/R₃ | Y | Z |
|---|---|---|---|---|
| | | | ![pyruvamide aromatic or aliphatic] | |
| 3. Factor X | C₁–C₁₀ aliphatic carboxylic aromatic carboxylate C₁–C₁₀ acidic heterocyclic | hydrogen | (structure with ① and ②) ① = ethyl-guanidine pentylamine p-methylbenzamidine propyl-2-aminopyridine methylurea-guanidine 2-aminoimidazole (X = CH₂, NH) dihydropyrimidinone-guanidine p-methylbenzamidine ② = —CH₂Cl, —CF₃ acetamide—③ acetyl-pyrrolidine (n = 1–2) | D(Ile) Acyl Dansyl |

-continued

| | $R_1$ | $R_2/R_3$ | Y | Z |
|---|---|---|---|---|

Y structures:

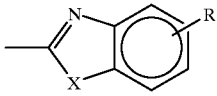

X = O, S, NH
R = $CO_2H$, $CO_2R$, $SO_2R$, $COCF_3$

X = O, S, NH
R = $CO_2H$, $SO_2R$, $CO_2R$

R = $CO_2H$, $CO_2$, $SO_2R$, $COCF_3$

③ = aliphatic
    cycloaliphatic
    peptide

B. Aspartic

1. HIV1    $C_1$–$C_{10}$ aliphatic or arginine    $C_1$–$C_{10}$ aliphatic arginine or

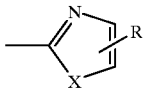

Z = acyl

① = $C_1$–$C_{10}$ aliphatic
    arginine
    or

① = $C_1$–$C_{10}$ aliphatic
    $C_1$–$C_{10}$ aromatic

② = amino acid
    $C_1$–$C_{10}$ alkyl
    $C_1$–$C_{10}$ aryl
    acyl
    hydrogen

C. Cysteine

1. Cathepsin B    $C_6$–$C_{10}$ aromatic $C_1$–$C_{10}$ aliphatic hydrogen    $C_1$–$C_{10}$ basic aromatic hydrophobic

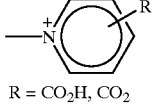

Z = benzyl
    acyl

-continued

| | $R_1$ | $R_2/R_3$ | Y | Z |
|---|---|---|---|---|
| | | | ① = —CH$_2$O(C=O)Ar<br>—CH$_2$OAc<br>—CH$_2$N$_2^+$<br>—H<br><br>[epoxide-C(=O)-CH$_2$-NH—②]<br><br>② = C1–C10 aliphatic | |
| 2. Calpain | C$_6$–C$_{10}$ aromatic, C$_1$–C$_{10}$ aliphatic, hydrophobic | C$_1$–C$_{10}$ aliphatic | [NH-CH(①)-C(=O)-②]<br><br>① = C$_1$–C$_{10}$ aromatic, hydrophobic<br><br>② = —CH$_2$F<br>—CH$_2$N$_2$<br>—CH$_2$OAc<br>—H | benzyl acyl |
| 3. ICE | C$_1$–C$_{10}$ aliphatic | hydrogen | [NH-CH(CH$_2$CO$_2$H)-C(=O)-①]<br><br>① = —H<br>—CH$_2$F<br>—CH$_2$N$_2^+$<br>—CH$_2$O(C=O)Ar<br>—CH$_2$OAc<br><br>[CH$_3$-C(=O)-CF$_2$-②]<br><br>② = C$_1$–C$_{10}$ aliphatic<br>C$_1$–C$_{10}$ aromatic | dihydro-cinnamic, aromatic, aliphatic, acetyl |
| D. Metallo | | | | |
| 1. ACE | C$_1$–C$_{10}$ aliphatic | indoyl<br>C$_1$–C$_{10}$ aromatic | —OH | [CH(①)(CH$_3$)-P(=O)(OH)(OH)]<br><br>① = C$_1$–C$_{10}$ alkyl<br>C$_1$–C$_{10}$ aryl |

-continued

| | R$_1$ | R$_2$/R$_3$ | Y | Z |
|---|---|---|---|---|
| 2. Collagenase | C$_1$–C$_{10}$ alkyl hydrogen | C$_1$–C$_{10}$ aromatic, C$_1$–C$_{10}$ aliphatic, C$_1$–C$_{10}$ basic |  ①= alkyl | hydroxyl 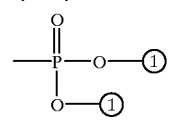 ①= hydrogen C$_1$–C$_{10}$ alkyl |
| | or | | | |
| | C$_6$–C$_{10}$ aromatic | C$_1$–C$_{10}$ alkyl C$_1$–C$_{10}$ aliphatic | —NHOH | hydroxyl 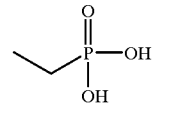 ①= hydrogen C$_1$–C$_{10}$ alkyl, or |

II. KINASE INHIBITORS

| | | | | |
|---|---|---|---|---|
| A. Serine/ Threonine | amino acid side chain | amino acid side chain | Serine, Threonine | amino acid |
| B. Tyrosine | amino acid side chain | amino acid side chain | Tyrosine | amino acid |
| C. Histidine | amino acid side chain | amino acid side chain | Histidine | amino acid |

III. MHC II INHIBITORS

A. Class I

| | | | | |
|---|---|---|---|---|
| 1. HIV gp120 | hydrogen | hydrogen | 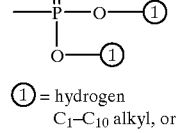 | |

B. Class II

| | | | | |
|---|---|---|---|---|
| 1. HA(306–18) | hydrogen | 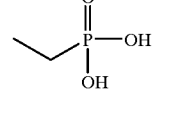 | —YVKQNTLKLAT | hydrogen |
| 2. HSP 65(3–13) | Cl-hydrophobic | hydrogen | —YDEEARR | —TK |

When the β-sheet mimetics of this invention are substituted for one or more amino acids of a biologically active peptide, the β-sheet modified peptides, wherein each β-sheet modified peptide has a variety of amino acid substitutions in combination with a variety of different β-sheet mimetics. In addition, it should also be recognized that, following cleavage of the β-sheet modified peptide from the solid support, the Z moiety is $AA_3$ and the Y moiety is $AA_2$ and $AA_1$ in the above diagram. (While this diagram is presented for illustration, additional or fewer amino acids may be linked to the β-sheet mimetic—that is, $AA_3$ may be absent or additional amino acids my be joined thereto; and $AA_2$ and/or $AA_1$ may be omitted or additional amino acids may be joined thereto).

Once a preferred substrate is identified by the procedures disclosed above, the substrate may be readily converted to an inhibitor by known techniques. For example, the C-terminal amino acid (in this case $AA_1$) may be modified by addition of a number of moieties known to impart inhibitor activity to a substrate, including (but not limited to) —$CF_3$ (a known reversible serine protease inhibitor), —$CH_2Cl$ (a known irreversible serine protease inhibitor), —$CHN_2$ and —$CH_2S(CH_3)_2^+$ (known cysteinyl protease inhibitors), —NHOH (a known metalloprotease inhibitor),

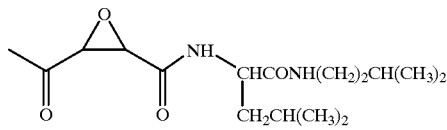

(a known cysteinyl protease inhibitor), and

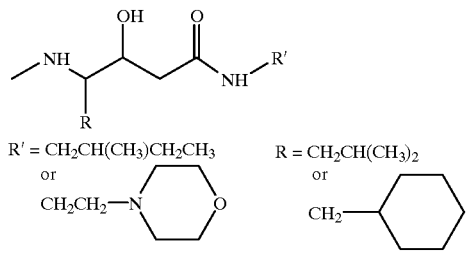

(a known aspartyl protease inhibitor).

While the utility of the β-sheet mimetics of this invention have been disclosed with regard to certain embodiments, it will be understood that a wide variety and type of compounds can be made which includes the β-sheet mimetics of the present invention. For example, a β-sheet mimetic of this invention may be substituted for two or more amino acids of a peptide or protein. In addition to improving and/or modifying the β-sheet structure of a peptide or protein, especially with regard to conformational stability, the β-sheet mimetics of this invention also serve to inhibit proteolytic breakdown. This results in the added advantage of peptides or proteins which are less prone to proteolytic breakdown due to incorporation of the β-sheet mimetics of this invention.

More specifically, the β-sheet mimetics of this invention have broad utility in naturally occurring or synthetic peptides, proteins and molecules. For example, peptides, proteins and molecules. For example, the β-sheet mimetics disclosed herein have activity as inhibitors of kinases and proteases, as well as having utility as MHC II inhibitors. For example, the β-sheet mimetics of this invention have activity as inhibitors of the large family oL trypsin-like serine proteases, including those preferring arginine or lysine as a P' substituent. These enzymes are involved in hemostasis and include (but are not limited to) Factor VIIa, Factor IXa, Factor Xa, Factor XIa, thrombin, kallikrein, urokinase (which is also involved in cancer metastasis) and plasmin. A related enzyme, tryptase, is involved in inflammatory responses. Thus, the ability to selectively inhibit these enzymes has wide utility in therapeutic applications involving cardiovascular disease, inflammatory diseases, and oncology.

For example, compounds of the following structures represent further embodiments of this invention in the context of Factor VIIa and thrombin inhibitors.

Factor VIIa Inhibitors

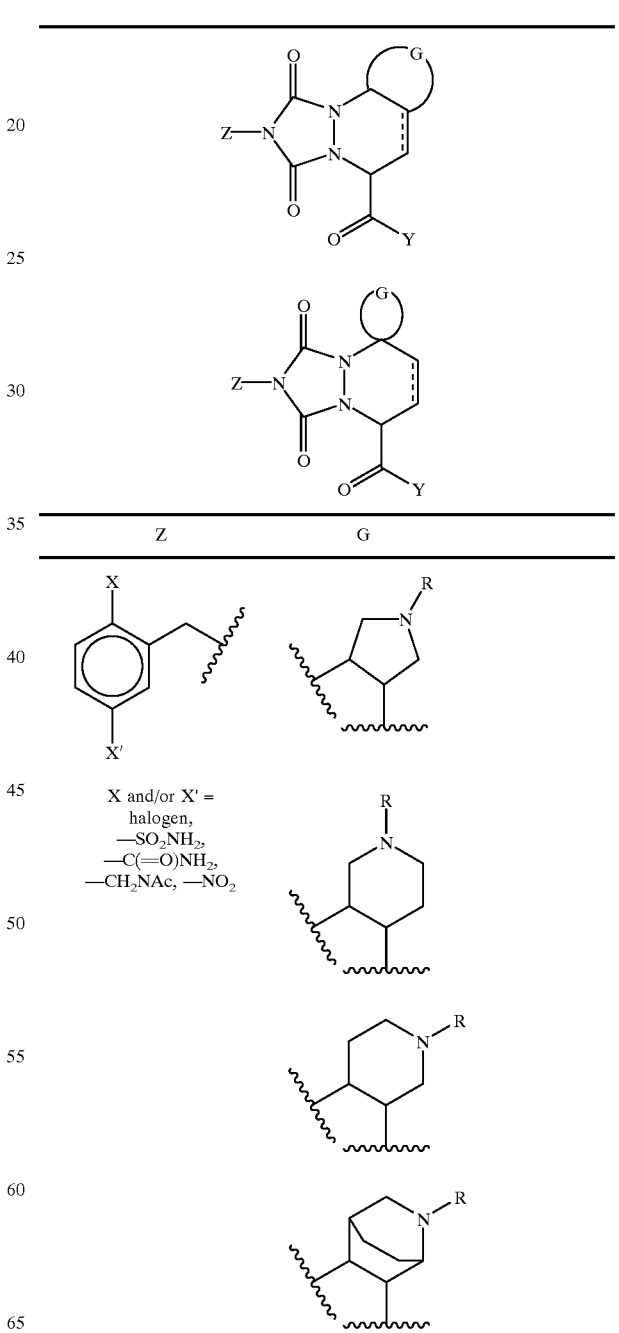

-continued
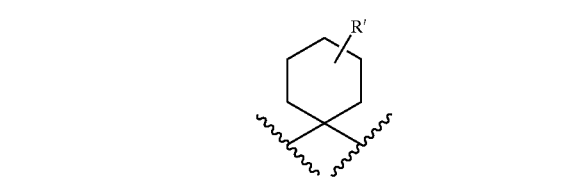
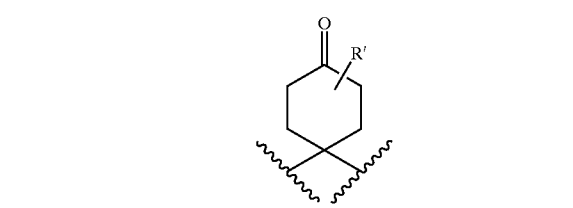
R = —SO₂NH₂, —SO₂CH₃, —SO₂Ar,
—CH₂aryl,
—CH₂heteroaryl, —C(=O)CH₂aryl,
—C(=O)CH₂heteroaryl
R' = ring substituent
Y
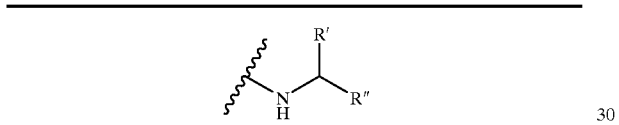
R'
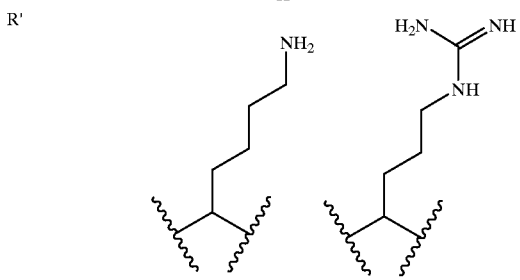
R"
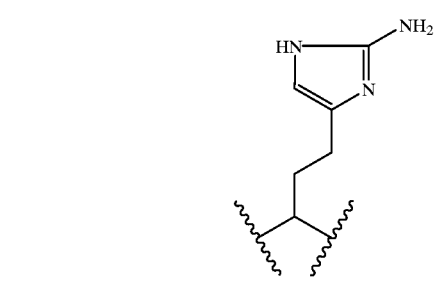
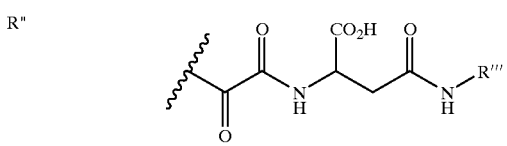
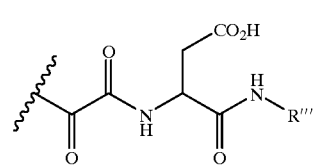
-continued
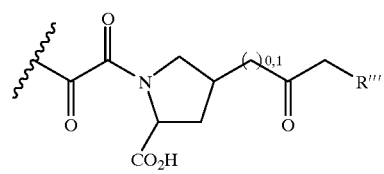
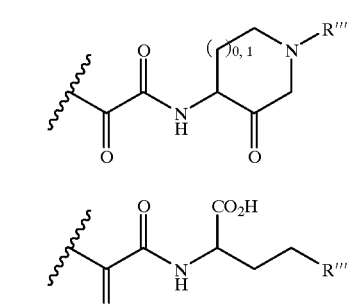
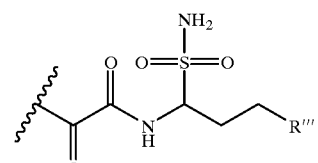
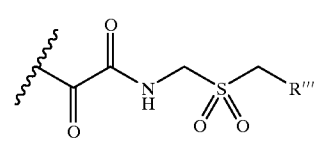
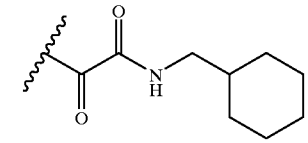
R'" = alkyl, aryl
Thrombin Inhibitors
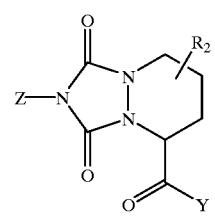
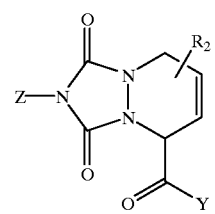

-continued

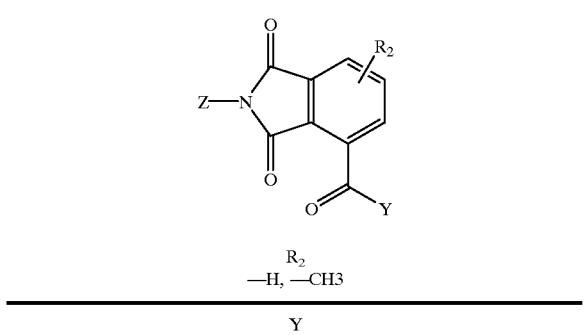

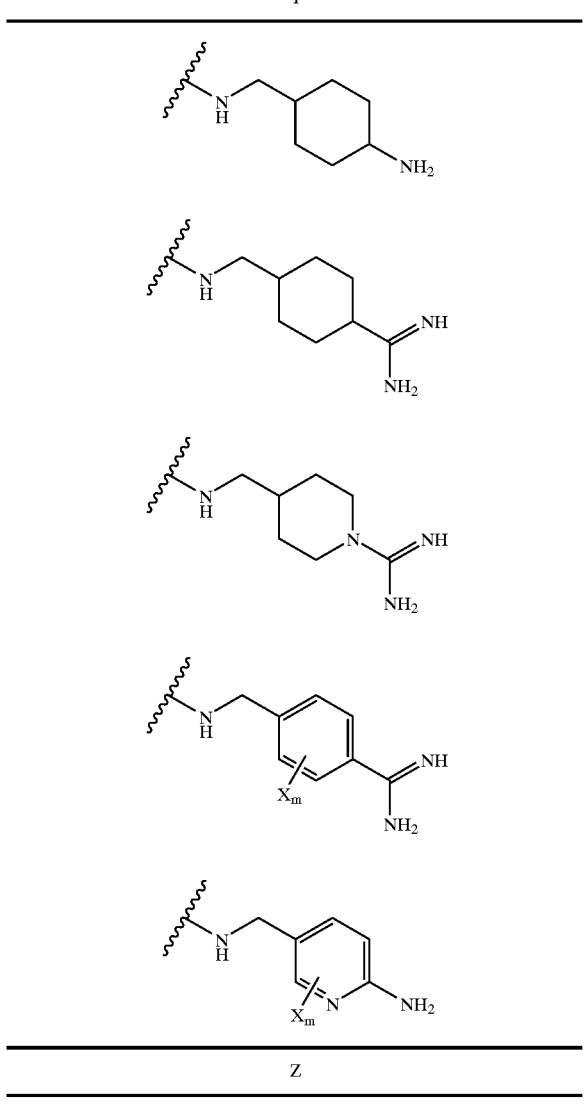

-continued

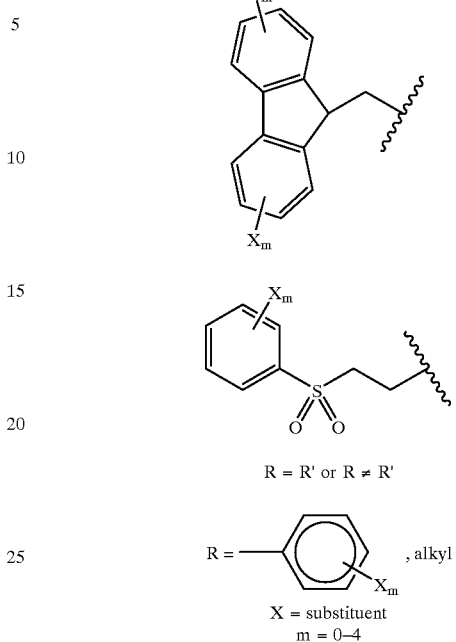

In another aspect, the present invention encompasses pharmaceutical compositions prepared for storage or administration which comprise a therapeutically effective amount of a β-sheet mimetic or compound of the present invention in a pharmaceutically acceptable carrier. Anticoagulant therapy is indicated for the treatment and prevention of a variety of thrombotic conditions, particularly coronary artery and cerebrovascular disease. Those experienced in this field are readily aware of the circumstances requiring anticoagulant therapy.

The "therapeutically effective amount" of a compound of the present invention will depend on the route of administration, the type of warm-blooded animal being treated, and the physical characteristics of the specific animal under consideration. These factors and their relationship to determining this amount are well known to skilled practitioners in the medical arts. This amount and the method of administration can be tailored to achieve optimal efficacy but will depend on such factors as weight, diet, concurrent medication and other factors which as noted those skilled in the medical arts will recognize.

The "therapeutically effective amount" of the compound of the present invention can range broadly depending upon the desired affects and the therapeutic indication. Typically, dosages will be between about 0.01 mg/kg and 100 mg/kg body weight, preferably between about 0.01 and 10 mg/kg, body weight.

"Pharmaceutically acceptable carriers" for therapeutic use are well known in the pharmaceutical art, and are described, for example, in Remingtons Pharmaceutical Sciences, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. In addition, antioxidants and suspending agents may be used.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited (e.g., when contacting the mammal's blood with material selected from the group consisting of vascular grafts, stems, orthopedic prosthesis, cardiac prosthesis, and extracorporeal circulation systems).

The thrombin inhibitors can be co-administered with suitable anti-coagulation agents or thrombolytic agents such as plasminogen activators or streptokinase to achieve synergistic effects in the treatment of various vascular pathologies. For example, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter. They may also be combined with heparin, aspirin, or warfarin.

The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent or treating ocular build up of fibrin. The compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carriers to which the compound molecules are coupled. The thrombin inhibitors may also be coupled with soluble polymers as targetable drug carriers. Such polymers can include polyvinlypyrrolidone, pyran copolymer, polyhydroxypropyl-methacrylamide-phenol, polyhydroxyethyl-aspartamide-phenol, polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydibydropyrans, polycyanoacrylates and cross linked or amphipathic block copolymers of hydrogels.

The dose and method of administration can be tailored to achieve optimal efficacy but will depend on such factors as weight, diet, concurrent medication and other factors which those skilled in the medical arts will recognize. When administration is to be parenteral, such as intravenous on a daily basis, injectable pharmaceutical compositions can be prepared in conventional forms, either as liquid solutions or suspensions, solid forms suitable for solution or suspension in liquid prior to injection, or as emulsions.

Tablets suitable for oral administration of active compounds of the invention can be prepared as follows:

|  | Amount-mg | | |
| --- | --- | --- | --- |
| Active Compound | 25.0 | 50.0 | 100.0 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

An intravenous dosage form of the above-indicated active compounds may be prepared as follows:

| Active Compound | 0.5–10.0 mg |
| --- | --- |
| Sodium Citrate | 5–50 mg |
| Citric Acid | 1–15 mg |
| Sodium Chloride | 1–8 mg |
| Water for Injection (USP) | g.s. to 1 ml |

Utilizing the above quantities, the active compound is dissolved at room temperature in a previously prepared solution of sodium chloride, citric acid, and sodium citrate in Water for Injection (USP, see page 1636 of United States Pharmacopoeia/National Formulary for 1995, published by United States Pharmacopoeia Convention, Inc., Rockville, Md., copyright 1994).

Compounds of the present invention when made and selected as disclosed are useful as potent inhibitors of thrombin in vitro and in vivo. As such, these compounds are useful as in vitro diagnostic reagents to prevent the clotting of blood and as in vivo pharmaceutical agents to prevent thrombosis in mammals suspected of having a condition characterized by abnormal thrombosis.

The compounds of the present invention are useful as in vitro diagnostic reagents for inhibiting clotting in blood drawing tubes. The use of stoppered test tubes having a vacuum therein as a means to draw blood obtained by venipuncture into the tube is well known in the medical arts (Kasten, B. L., "Specimen Collection," *Laboratory Test Handbook*, 2nd Edition, Lexi-Comp Inc., Cleveland pp. 16–17, Edits. Jacobs, D. S. et al. 1990). Such vacuum tubes may be free of clot-inhibiting additives, in which case, they are useful for the isolation of mammalian serum from the blood they may alternatively contain clot-inhibiting additives (such as heparin salts, EDTA salts, citrate salts or oxalate salts), in which case, they are useful for the isolation of mammalian plasma from the blood. The compounds of the present invention are potent inhibitors of factor Xa or thrombin, and as such, can be incorporated into blood collection tubes to prevent clotting of the mammalian blood drawn into them.

The compounds of the present invention may be used alone, in combination of other compounds of the present invention, or in combination with other known inhibitors of clotting, in the blood collection tubes. The amount to be added to such tubes is that amount sufficient to inhibit the formation of a clot when mammalian blood is drawn into the tube. The addition of the compounds to such tubes may be accomplished by methods well known in the art, such as by introduction of a liquid composition thereof, as a solid composition thereof, or liquid composition which is lyophilized to a solid. The compounds of the present invention are added to blood collection tubes in such amounts that, when combined with 2 to 10 mL of mammalian blood, the concentration of such compounds will be sufficient to inhibit clot formation. Typically, the required concentration will be about 1 to 10,000 nM, with 10 to 1000 nM being preferred.

With respect to regulation of transcription factors, the compounds of this invention regulate transcription factors whose ability to bind to DNA is controlled by reduction of a cysteine residue by a cellular oxidoreductase. In one embodiment, the transcription factor is NF-κB. In this embodiment, the compounds of this invention have activity as mediators of immune and/or inflammatory responses, or serve to control cell growth. In another embodiment, the transcription factor is AP-1, and the cellular oxidoreductase is Ref-1. In this embodiment, the compounds of this invention have activity as anti-inflammatory and/or anticancer agents. In yet further embodiments, the transcription factor is selected from Myb and glucocorticoid receptor. Other transcription factors that may be regulated within the context of this invention also include: those of the NFkB family, such as Rel-A, c-Rel, Rel-B, p50 and p52; those of the AP-1 family, such as Fos, FosB, Fra-1, Fra-2, Jun, JunB and JunD; ATF; CREB; STAT-1, -2, -3, -4, -5 and -6; NFAT-1, -2 and -4; MAF; Thyroid Factor; IRF; Oct-1 and -2; NF-Y; Egr-1; and USF-43.

In the practice of the methods of this invention, a therapeutically effective amount of a compound of this invention is administered to a warm-blooded animal in need thereof. For example, the compounds of this invention may be administered to a warm-blooded animal that has been diagnosed with, or is at risk of developing, a condition selected from Chrohns disease, asthma, rheumatoid arthritis, ischemia, reperfusion injury, graft versus host disease (GVHD), amyotrophic lateral sclerosis (ALS), Alzheimer's disease, allograft rejection and adult T-cell leukemia.

The following examples are offered by way of illustration, not limitation.

EXAMPLES

Example 1

Synthesis of Representative β-Sheet Mimetic

This example illustrates the synthesis of a representative β-sheet mimetic of this invention.

Synthesis of Structure (1)

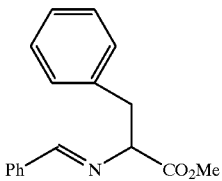

(1)

Phenylalanine benzaldimine, structure (1), was synthesized as follows. To a mixture of L-phenylalanine methyl ester hydrochloride (7.19 g, 33.3 mmol) and benzaldehyde (3.4 ml, 33.5 mmol) stirred in $CH_2Cl_2$ (150 ml) at room temperature was added triethylamine (7.0 ml, 50 mmol). Anhydrous magnesium sulfate (2 g) was added to the resulting solution and the mixture was stirred for 14 h then filtered through a 1 inch pad of Celite with $CH_2Cl_2$. The filtrate was concentrated under reduced pressure to ca. one half of its initial volume then diluted with an equal volume of hexanes. The mixture was extracted twice with saturated aqueous $NaHCO_3$, $H_2O$ and brine then dried over anhydrous $Na_2SO_4$ and filtered. Concentration of the filtrate under vacuum yielded 8.32 g (93% yield) of colorless oil. $^1H$ NMR analysis indicated nearly pure (>95%) phenylalanine benzaldimine. The crude product was used without further purification.

Synthesis of Structure (2)

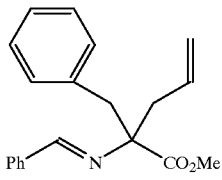

(2)

α-Allylphenylalanine benzaldimine, structure (2), was synthesized as follows. To a solution of diisopropylamine (4.3 ml, 33 mmol) stirred in THF (150 ml) at −78° C. was added dropwise a solution of n-butyllithium (13 ml of a 2.5 M hexane solution, 33 mmol). The resulting solution was stirred for 20 min. then a solution of phenylalanine benzaldimine (7.97 g, 29.8 mmol) in THF (30 ml) was slowly added. The resulting dark red-orange solution was stirred for 15 min. then allyl bromide (3.1 ml, 36 mmol) was added. The pale yellow solution was stirred for 30 min. at −78° C. then allowed to warm to room temperature and stirred an additional 1 h. Saturated aqueous ammonium chloride was added and the mixture was poured into ethyl acetate. The organic phase was separated and washed with water and brine then dried over anhydrous sodium sulfate and filtered. Concentration of the filtrate under vacuum yielded 8.54 g of a viscous yellow oil. Purification by column chromatography yielded 7.93 g (87%) of α-allylphenylalanine benzaldimine as a viscous colorless oil.

Synthesis of Structure (3)

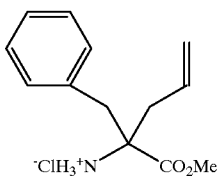

(3)

α-Allylphenylalanine hydrochloride, structure (3), was synthesized as follows. To a solution of α-allylphenylalanine benzaldimine (5.94 g, 19.3 mmol) stirred in methanol (50 ml) was added 5% aqueous hydrochloric acid (10 ml). The solution was stirred at room temperature for 2 h then concentrated under vacuum to an orange-brown caramel. The crude product was dissolved in $CHCl_3$ (10 ml) and the solution was heated to boiling. Hexanes (~150 ml) were added and the slightly cloudy mixture was allowed to cool. The liquid was decanted away from the crystallized solid then the solid was rinsed with hexanes and collected. Removal of residual solvents under vacuum yielded 3.56 g (72%) of pure (α-allylphenylalanine hydrochloride as a white crystalline solid.

$^1$H NMR (500 MHz, $CDCl_3$) δ8.86 (3H, br s), 7.32–7.26 (5H, m), 6.06 (1H, dddd, J=17.5, 10.5, 7.6, 7.3 Hz), 5.33 (1H, d, J=17.5 Hz), 5.30 (1H, d, J=10.5 Hz), 3.70 (3H, s), 3.41 (1H, d, J=14.1 Hz), 3.35 (1H, d, J=14.1 Hz), 2.98 (1H, dd, J=14.5, 7.3 Hz), 2.88 (1H, dd, J=14.5, 7.6 Hz)

Synthesis of Structure (4)

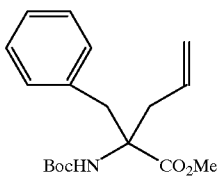

(4)

N-tert-butyloxycarbonyl-α-allylphenylalanine, structure (4) was synthesized as follows. To a solution of D,L α-allylphenylalanine hydrochloride (565 mg, 2.21 mmol) stirred in a mixture of THF (15 ml) and water (5 ml) was added di-tert-butyl dicarbonate followed by careful addition of solid sodium bicarbonate in small portions. The resulting two phase mixture was vigorously stirred at room temperature for 2 days then diluted with ethyl acetate. The organic phase was separated and washed with water and brine then dried over anhydrous sodium sulfate and filtered. Concentration of the filtrate under vacuum yielded a colorless oil that was purified by column chromatography (5 to 10% EtOAc in hexanes gradient elution) to yield 596 mg (86%) of N-tert-butyloxycarbonyl-α-allylphenylalanine.

TLC $R_f$=0.70 (silica, 20% EtOAc in hexanes); $^1$H NMR (500 MHz, $CDCl_3$) δ7.26–7.21 (3H, m), 7.05 (2H, d, J=6.1 Hz), 5.64 (1H, dddd, J=14.8, 7.6, 7.2, 7.2 Hz), 5.33 (1H, br s), 5.12–5.08 (2H, m), 3.75 (3H, s), 3.61 (1H, d, J=13.5 Hz), 3.21 (1H, dd, J=13.7, 7.2 Hz), 3.11 (1H, d, J=13.5 Hz), 2.59 (1H, dd, J=13.7, 7.6 Hz), 1.47 (9H, s).

Synthesis of Structure (5)

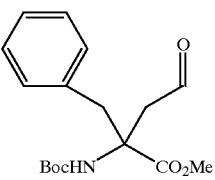

(5)

An aldehyde of structure (5) was synthesized as follows. Ozone was bubbled through a solution of 2.10 g (6.57 mmol) of the structure (4) olefin stirred at −78° C. in a mixture of $CH_2Cl_2$ (50 ml) and methanol (15 ml) until the solution was distinctly blue in color. The solution was stirred an additional 15 min. then dimethyl sulfide was slowly added. The resulting colorless solution was stirred at −78° C. for 10 min. then allowed to warm to room temperature and stirred for 6 h. The solution was concentrated under vacuum to 2.72 g of viscous pale yellow oil which was purified by column chromatography (10 to 20% EtOAc in hexanes gradient elution) to yield 1.63 g of pure aldehyde as a viscous colorless oil.

TLC $R_f$=0.3 (silica, 20% EtOAc in hexanes); $^1$H NMR (500 MHz, $CDCl_3$) δ9.69 (1H, br s), 7.30–7.25 (3H, m,), 7.02 (2H, m,), 5.56 (1H, br s), 3.87 (1H, d, J=17.7 Hz,), 3.75 (3H, s,), 3.63 (1H, d, J=13.2 Hz), 3.08 (1H, d, J=17.7 Hz), 2.98 (1H, d, J=13.2 Hz,), 1.46 (9H, s,).

Synthesis of Structure (6)

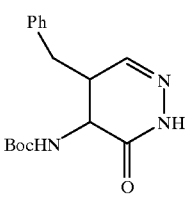

(6)

A hydrazone of structure (6) was synthesized as follows. To a solution of the aldehyde of structure (5) (1.62 g, 5.03 mmol) stirred in THF (50 ml) at room temperature was added hydrazine hydrate (0.32 ml, 6.5 mmol). The resulting solution was stirred at room temperature for 10 min. then heated to reflux for 3 days. The solution was allowed to cool to room temperature then concentrated under vacuum to 1.59 g (105% crude yield) of colorless foam. The crude hydrazone product, structure (6), was used without purification.

TLC $R_f$=0.7 (50% EtOAc in hexanes); $^1$H NMR (500 MHz, $CDCl_3$) δ8.55 (1H, br s), 7.32–7.26 (3H, m), 7.17 (1H, br s), 7.09 (2H, m), 5.55 (1H, br s), 3.45 (1H, d, J=17.7 Hz), 3.29 (1H, d, J=13.5 Hz), 2.90 (1H, d, J=13.5 Hz), 2.88 (1H, dd, J=17.7, 1.3 Hz), 1.46 (9H, s); MS (CI+, $NH_3$) m/z 304.1 ($M+H^+$).

Synthesis of Structure (7)

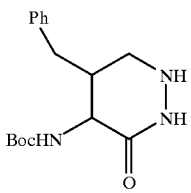
(7)

A cyclic hydrazide of structure (7) was synthesized as follows. The crude hydrazone of structure (6) (55 mg, 0.18 mmol) and platinum oxide (5 mg, 0.02 mmol) were taken up in methanol and the flask was fitted with a three-way stopcock attached to a rubber balloon. The flask was flushed with hydrogen gas three times, the balloon was inflated with hydrogen, and the mixture was stirred vigorously under a hydrogen atmosphere for 17 hours. The mixture was filtered through Celite with ethyl acetate and the filtrate was concentrated under vacuum to a white form. Purification of the white foam by flash chromatography yielded 44 mg of the pure cyclic hydrazide of structure (7) (80%).

$^1$H NMR (500 MHz, CDCl$_3$) δ7.34–7.28 (3H, m), 7.21 (2H, m), 6.95 (1H, br s), 5.29 (1H, br s), 3.91 (1H, br s), 3.35 (1H, d, J=12.9 Hz), 3.00 (1H, ddd, J=13.9, 5.3, 5.0 Hz), 2.96 (1H, d, J=12.9 Hz), 2.67 (1H, br m), 2.38 (1H, br m), 2.30 (1H, ddd, J=13.9, 5.4, 5.0 Hz), 1.45 (9H, s); MS (CI+, NH$_3$) m/z 306.2 (M+H$^+$).

Synthesis of Structure (8)

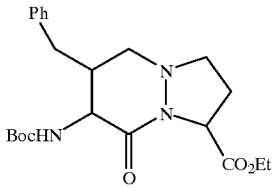
(8)

Structure (8) was synthesized as follows. To a solution of the cyclic hydrazide of structure (7) (4.07 g, 13.32 mmol) stirred in ethyl acrylate (200 ml) at 90° C. was added formaldehyde (1.2 mL of a 37% aqueous solution). The mixture was heated to reflux for 15 h then allowed to cool to room temperature and concentrated under vacuum to a white foam. The products were separated by column chromatography (5% then 10% acetone/chloroform) to yield 0.851 g of the least polar diastereomer of the bicyclic ester, structure (8b), and a more polar diastereomer (8a). The impure fractions were subjected to a second chromatography to afford more pure structure (8b), 25% combined yield.

$^1$H NMR (500 MHz, CDCl$_3$) δ7.27–7.21 (3H, m), 7.09 (2H, d, J=6.5 Hz), 5.59 (1H, br s), 4.52 (1H, dd, J=9.1, 3.4 Hz), 4.21 (2H, m), 3.40 (1H, d, J=12.5 Hz), 3.32 (1H, d, J=12.5 Hz), 3.10 (2H, m), 2.79 (1H, br m), 2.66 (1H, br m), 2.79 (1H, br m), 2.66 (1H, br m), 2.54 (1H, br m), 2.4 (1H, m), 2.18 (1H, m), 1.44 (9H, s), 1.28 (3H, t, J=7.0 Hz); MS (CI+, NH$_3$) 418.4 (M+H$^+$).

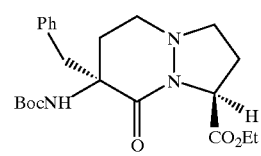
(8b)

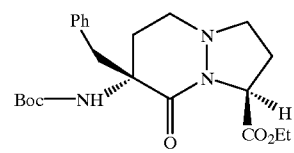
(8a)

Synthesis of Structure (9b)

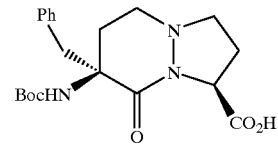
(9b)

Structure (9b) was synthesized as follows. To a solution of the least polar ethyl ester (i.e., structure (8b)) (31 mg, 0.074 mmol) stirred in THF (1 ml) was added aqueous lithium hydroxide (1 M, 0.15 ml). The resulting mixture was stirred at room temperature for 2 h then the reaction was quenched with 5% aqueous citric acid. The mixture was extracted with ethyl acetate (2×) then the combined extracts were washed with water and brine. The organic layer was dried over anhydrous sodium sulfate, filtered and concentrated under vacuum to a colorless glass. The crude acid, structure (9b), was used in subsequent experiments without further purification.

Synthesis of Structure (10b)

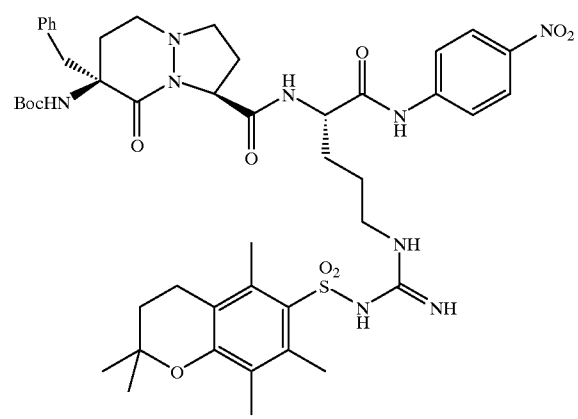
(10b)

Structure (10b) was synthesized as follows. The crude acid of structure (9b) (30 mg, 0.074 mmol), HArg(PMC) pNA (41 mg, 0.074 mmol), and HOBt (15 mg, 0.098 mmol) were dissolved in THF (1 ml) then diisopropylethylamine (0.026 ml, 0.15 mmol) was added followed by EDC (16 mg, 0.084 mmol). The resulting mixture was stirred at room temperature for 4 h then diluted with ethyl acetate and extracted with 5% aqueous citric acid, saturated aqueous sodium bicarbonate, water and brine. The organic layer was dried over anhydrous sodium sulfate, filtered and concentrated under vacuum to 54 mg of pale yellow glass. The products were separated by column chromatography to yield 33 mg (50%) of a mixture of diastereomers of the coupled (i.e., protected) product, structure (10b). MS (CI+, NH$^3$) m/z 566.6 (M+H$^+$).

Synthesis of Structure (11b)

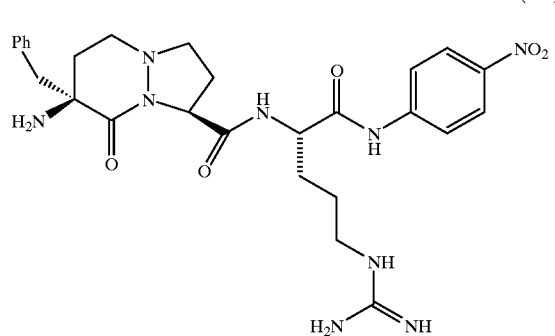

(11b)

A β-sheet mimetic of structure (11b) was synthesized as follows. A solution of 0.25 ml of H$_2$O, 0.125 ml of 1,2-ethanedithiol and 360 mg of phenol in 5 ml of TFA was prepared and the protected product of structure (10b) (33 mg, 0.035 mmol) was dissolved in 2 ml of this solution. The resulting solution was stirred at room temperature for 3 h then concentrated under reduced pressure. Ether was added to the concentrate and the resulting precipitate was collected by centrifugation. The precipitate was triturated with ether and centrifuged two more times then dried in a vacuum desiccator for 14 h. The crude product (14 mg) was purified by HPLC chromatography to yield the β-sheet mimetic of structure (11b). MS (CI+, NH$_3$) m/z 954.8 (M+Na$^+$).

Synthesis of Structure (12b)

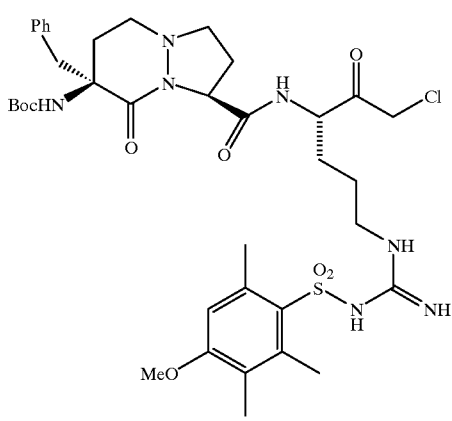

(12b)

Structure (12b) was synthesized as follows. To a solution of the crude acid of structure (9b) (24 mg, 0.062 mmol) and N-methylmorpholine (0.008 ml), stirred in THF (1 ml) at −50° C. was added isobutyl chloroformate. The resulting cloudy mixture was stirred for 10 min. then 0.016 ml (0.14 mmol) of N-methylmorpholine was added followed by a solution of HArg(Mtr)CH$_2$Cl (50 mg, 0.068 mmol) in THF (0.5 ml). The mixture was kept at −50° C. for 20 min. then was allowed to warm to room temperature during 1 h. The mixture was diluted with ethyl acetate and extracted with 5% aqueous citric acid, saturated aqueous sodium bicarbonate and brine. The organic layer was dried over anhydrous sodium sulfate, filtered and concentrated under vacuum to yield 49 mg of colorless glass, structure (12). Separation by column chromatography yielded 12 mg of a less polar diastereomer and 16 mg of a more polar diastereomer.

$^1$H NMR (500 MHz, CDCl$_3$) δ7.93 (1H, br s), 7.39–7.31 (3H, m), 7.16 (2H, d, J=6.9 Hz), 6.52 (1H, s), 6.30 (1H, br s), 5.27 (1H, s), 4.74 (1H, dd, J=9.1, 6.9 Hz), 4.42 (1H, br d, J=6.8 Hz), 4.33 (1H, d, J=6.8 Hz), 3.82 (3H, s), 3.28 (1H, d, J=13.3 Hz), 3.26–3.12 (4H, m), 2.98 (1H, d, J=13.3 Hz), 2.69 (3H, s), 2.60 (3H, s), 2.59–2.33 (4H, m), 2.25–2.10 (3H, m), 2.11 (3H, s), 1.77 (1H, br m), 1.70–1.55 (3H, br m), 1.32 (9H, s).

Synthesis of Structure (13b)

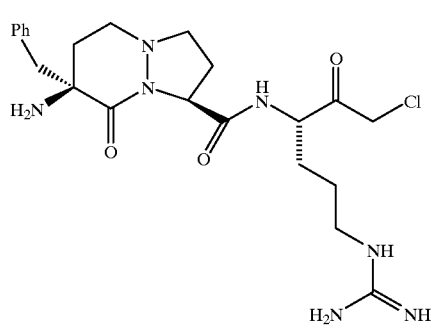

(13b)

A β-sheet mimetic of structure (13b) was synthesized as follows. The more polar diastereomer of structure (12b) (16 mg, 0.021 mmol) was dissolved in 95% TFA/H$_2$O (1 ml) and the resulting solution was stirred at room temperature for 6 h then concentrated under vacuum to 11 mg of crude material. The crude product was triturated with ether and the precipitate was washed twice with ether then dried under high vacuum for 14 h. $^1$H NMR analysis indicated a 1:1 mixture of fully deprotected product and product containing the Mtr protecting group. The mixture was dissolved in 95% TFA/H$_2$O and stirred for 2 days and the product was recovered as above. Purification of the product by HPLC yielded 5 mg of the pure compound of structure (13b). MS (EI+) m/z 477.9 (M$^+$).

Example 2

Synthesis of Representative β-Sheet Mimetic

This example illustrates the synthesis of a further representative β-sheet mimetic of this invention.

Synthesis of Structure (14)

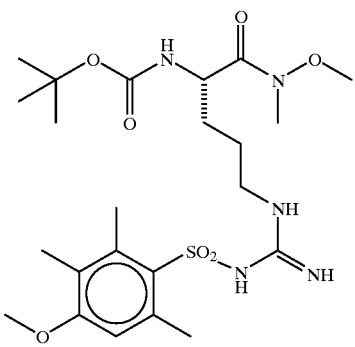

(14)

N,O-Dimethyl hydroxamate, structure (14) was synthesized as follows. To a mixture of Boc-N$^g$-4-methoxy-2,3,6trimethylbenzenesulfonyl-L-arginine (8.26 g, 14.38 mmol), N-O-dimethylhydroxylamine hydrochloride (2.78 g, 28.5 mymol) and 1-hydroxybenzotriazole hydrate (2.45 g, 16.0 mmol) stirred in THF (150 ml) at ambient temperature was added N,N-diisopropylethylamine (7.5 ml, 43 mmol) followed by solid EDC (3.01 g, 15.7 mmol). The resulting solution was stirred for 16 h then diluted with ethyl acetate (200 ml) and extracted sequentially with 5% aqueous citric acid, saturated aqueous sodium bicarbonate, water and brine. The organic solution was dried over anhydrous sodium sulfate and filtered. Concentration of the filtrate under vacuum yielded 7.412 g of white foam.

$^1$H NMR (500 Mhz, CDCl$_3$): δ6.52 (1H, s), 6.17 (1H, br s), 5.49 (1H, d, J=8.8Hz), 4.64 (1H, br t), 3.82 (3H, s), 3.72 (3H, s), 3.36 (1H, br m), 3.18 (3H, s) 3.17 (1H, br m), 2.69 (3H, s), 2.61 (3H, s), 2.12 (3H, 2), 1.85–1.55 (5H, m), 1.41 (9H, s); MS (FB+): m/z 530.5 (M+H$^+$).

Synthesis of Structure (15)

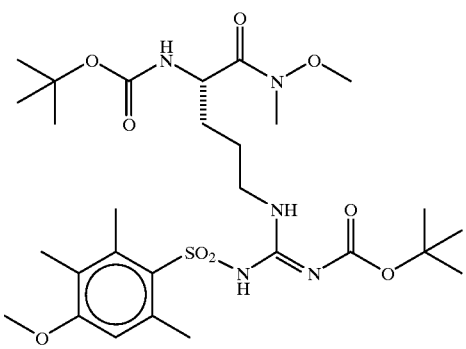

(15)

Structure (15) was synthesized as follows. To a solution of the arginine amide (7.412 g, 13.99 mmol) stirred in dichloromethane (150 ml) at room temperature was added N,N-diisopropylethylamine (2.9 ml, 17 mmol) followed by di-tert-butyldicarbonate (3.5 ml, 15.4 mmol) and N,N-dimethylaminopyridine (0.175 g, 1.43 mmol). The resulting solution was stirred for 1.5 h then poured into water. The aqueous layer was separated and extracted with two 100 ml portions of dichloromethane. The combine extracts were shaken with brine then dried over anhydrous sodium sulfate and filtered. Concentration of the filtrate under vacuum yielded a white foam that was purified by flash chromatography to yield 8.372 g of white foam.

$^1$H NMR (500 MHz, CDCl$_3$): δ9.79 (1H, s), 8.30 (1H, t, J=4.96), 6.54 (1H, s), 5.18 (1H, d, J=9.16 Hz), 4.64 (1H, m), 3.83 (3H, s), 3.74 (3H, s), 3.28 (2H, dd, J=12.6, 6.9 Hz), 3.18 (3H, s), 2.70 (3H, s), 2.62 (3H, s), 2.14 (3H, s), 1.73–1.50 (5H, m), 1.48 (9H, s) 1.42 (9H, s); MS (FB+): m/z 630.6 (M+H$^+$).

Synthesis of Structure (16)

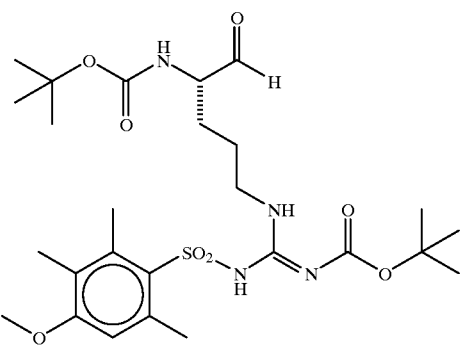

(16)

The arginal, structure (16), was synthesized as follows. To a solution of the arginine amide structure (15) stirred in toluene at −78° C. under a dry argon atmosphere was added a solution of diisobutylaluminum hydride in toluene (1.0 M, 7.3 ml ) dropwise over a period of 15 minutes. The resulting solution was stirred for 30 minutes then a second portion of diisobutylaluminum hydride (3.5 ml) was added and stirring was continued for 15 minutes. Methanol (3 ml) was added dropwise and the solution was stirred at −78° C. for 10 minutes then allowed to warm to room temperature. The mixture was diluted with ethyl acetate (100 ml) and stirred vigorously with 50 ml of saturated aqueous potassium sodium tartrate for 2.5 h. The aqueous phase was separated and extracted with ethyl acetate (2×100 ml). The extracts were combined with the original organic solution and shaken with brine then dried over anhydrous sodium sulfate and filtered. Concentration of the filtrate under vacuum yielded a white foam that was separated by flash chromatography to yield 1.617 g of the aldehyde as a white foam.

$^1$H NMR (500 MHz, CDCl$_3$): δ9.82 (1H, s), 9.47 (1H, s), 8.35 (1H, br t), 6.55 (1H, s), 5.07 (1H, d, J=6.9 Hz), 4.18 (1H, br m), 3.84 (3H, s), 3.25 (2H, m), 2.70 (3H, s), 2.62 (3H, s), 2.14 (3H, s), 1.89 (1H, m), 1.63–1.55 (4H, m), 1.49 (9H, s), 1.44 (9H, s); MS (FB+): m/z 571.6 (M+H$^+$).

Synthesis of Structure (17)

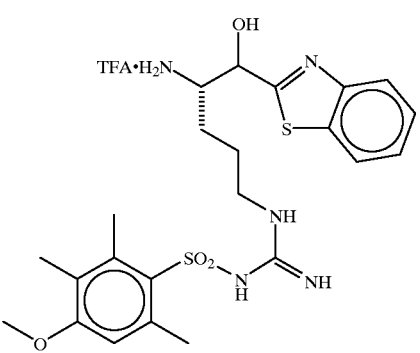

(17)

Hydroxybenzothiazole, structure (17), was synthesized as follows. To a solution of benzothiazole (1.55 ml, 14 mmol)

stirred in anhydrous diethyl ether (60 ml) at −78° C. under a dry argon atmosphere was added a solution of n-butyllithium (2.5 M in hexane, 5.6 ml, 14 mmol) dropwise over a period of 10 minutes. The resulting orange solution was stirred for 45 minutes then a solution of the arginal structure (16) (1.609 g, 2.819 mmol) in diethyl ether (5 ml) was slowly added. The solution was stirred for 1.5 h then saturated aqueous ammonium chloride solution was added and the mixture was allowed to warm to room temperature. The mixture was extracted with ethyl acetate (3×100 ml) and the combined extracts were extracted with water and brine then dried over anhydrous sodium sulfate and filtered. Concentration of the filtrate under vacuum yielded a yellow oil that was purified by flash chromatography (30% then 40% ethyl acetate/hexanes eluent) to yield 1.22 g of the hydroxybenzothiazoles (ca. 2:1 mixture of diastereomers) as a white foam.

The mixture of hydroxybenzothiazoles (1.003 g, 1.414 mmol) was stirred in $CH_2Cl_2$ (12 ml) at room temperature and trifluoroacetic acid (3 ml) was added. The resulting solution was stirred for 1.5 h then concentrated under reduced pressure to yield 1.22 g of the benzothiazolylarginol trifluoroacetic acid salt as a yellow foam.

MS (EI+): m/z 506.2 (M+H$^+$).

Synthesis of Structure (18b)

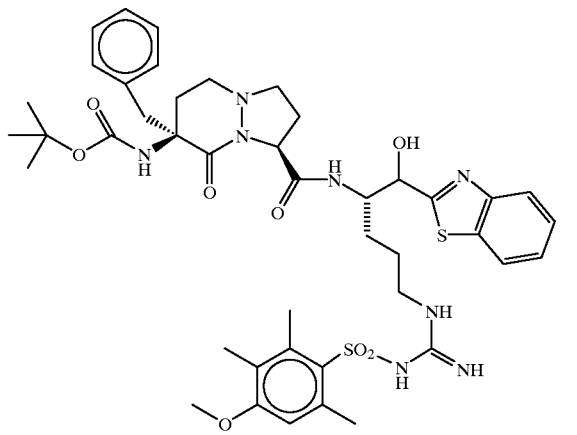

(18b)

The bicyclic compound, structure (18b) was synthesized as follows. The bicyclic acid of structure (9b) from Example 1 (151 mg, 0.387 mmol) and HOBt hydrate (71 mg, 0.46 mmol) were dissolved in THF (5 ml) and diisopropylethylamine (0.34 ml, 1.9 mmol) was added followed by EDC (89 mg, 0.46 mmol). After stirring for ten minutes a solution of the benzothiazolylarginol trifluoroacetic acid salt (structure (17) 273 mg, 0.372 mmol) in THF (1 ml) was added along with a THF (0.5 ml) rinse. The mixture was stirred at room temperature for 15 h then diluted with ethyl acetate and extracted sequentially with 5% aqueous citric acid, saturated aqueous sodium bicarbonate, water and brine. The organic solution was dried over anhydrous sodium sulfate, filtered and concentrated under vacuum to 297 mg of a yellow glass. $^1$H NMR analysis indicated a mixture of four diastereomeric amides which included structure (18b).

MS (ES+):m/z 877 (M$^+$).

Synthesis of Structure (19b)

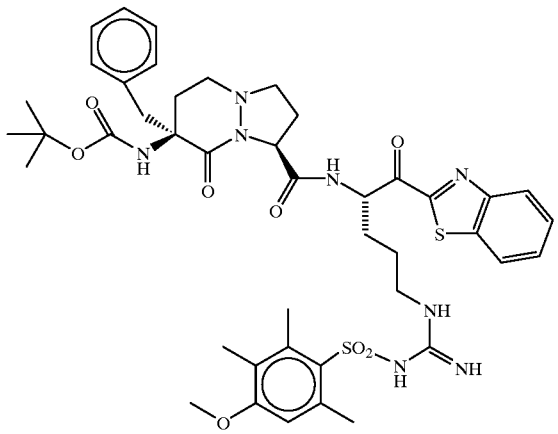

(19b)

Structure (19b) was synthesized as follows. The crude hydroxybenzothiazole (247 mg, 0.282 mmol) was dissolved in $CH_2Cl_2$ (5 ml) and Dess-Martin periodinane (241 mg, 0.588 mmol) was added. The mixture was stirred at room temperature for 6 h then diluted with ethyl acetate and stirred vigorously with 10% aqueous sodium thiosulfate for 10 minutes. The organic solution was separated and extracted with saturated aqueous sodium bicarbonate, water and brine then dried over anhydrous sodium sulfate and filtered. Concentration of the filtrate under vacuum yielded 252 mg of yellow glass. $^1$H NMR analysis indicated a mixture of two diastereomeric ketobenzothiazoles which included structure (19b).

Synthesis of Structure (20b)

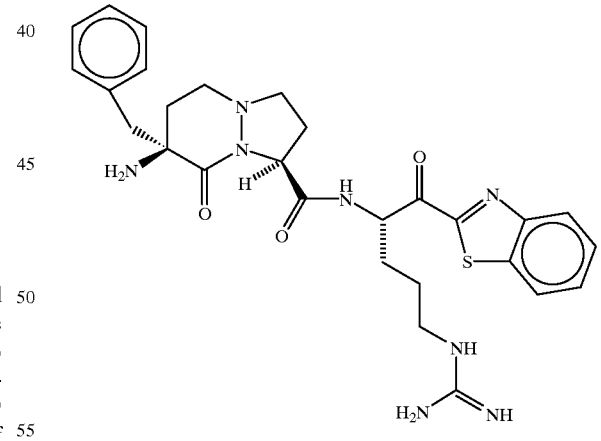

(20b)

The ketobenzothiazole, structure (20), was synthesized as follows. Ketobenzothiazole (19) (41 mg, 0.047 mmol) was dissolved in 95% aqueous trifluoroacetic (0.95 ml) acid and thioanisole (0.05 ml) was added. The resulting dark solution was stirred for 30 hours at room temperature then concentrated under vacuum to a dark brown gum. The gum was triturated with diethyl ether and centrifuged. The solution was removed and the solid remaining was triturated and collected as above two more times. The yellow solid was dried in a vacuum desiccator for 2 hours then purified by HPLC (Vydac reverse phase C-4 column (22×250 mm ID).

Mobile phase: A=0.05% TFA in water; B=0.05% TFA in acetonitrile. The flow rate was 10.0 mL/min. The gradient used was 8% B to 22% B over 25 min, and isochratic at 22% thereafter. The peak of interest (structure (20b)) eluted at 42 minutes) to give 2.5 mg of the deprotected product, structure (20b).

MS (ES+): 563.5 (M+H$^+$).

Example 3

Activity of a Representative β-Sheet Mimetic as a Proteolytic Substrate

This example illustrates the ability of a representative β-sheet mimetic of this invention to selectively serve as a substrate for thrombin and Factor VII. The β-sheet mimetic of structure (11b) above was synthesized according the procedures disclosed in Example 1, and used in this experiment without further modification.

Both the thrombin and Factor VII assays of this experiment were carried out at 37° C. using a Hitachi UV/Vis spectrophotometer (model U-3000) Structure (11b) was dissolved in deionized water. The concentration was determined from the absorbance at 342 nm. Extinction coefficient of 8270 liters/mol/cm was employed. The rate of structure (11b) hydrolysis was determined from the change in absorbance at 405 nm using an extinction coefficient for p-nitroaniline of 9920 liters/mol/cm for reaction buffers. Initial velocities were calculated from the initial linear portion of the reaction progress curve. Kinetic parameters were determined by unweighted nonlinear least-squares fitting of the simple Michaelis-Menten equation to the experimental data using GraFit (Version 3.0, Erithacus Software Limited).

For the thrombin assay, experiments were performed in pH 8.4 Tris buffer (Tris, 0.05M; NaCl, 0.15M). 6.4 NIH units of bovine thrombin (from Sigma) were dissolved into 10 ml of the assay buffer to yield 10 nM thrombin solution. In a UV cuvette, 130 to 148 μl of the buffer and 100 μl of the thrombin solutions were added, preincubated at 37° C. for 2 minutes, and finally 2 to 20 microliters (to make the final volume at 250 μl) of 0.24 mM structure (11b) solution was added to initiate the reaction. The first two minutes of the reactions were recorded for initial velocity determination. Eight structure (11b) concentration points were collected to obtain the kinetic parameters. $k_{cat}$ and $K_M$ were calculated to be 50 s$^{-1}$ and 3 μM, respectively. $k_{cat}/K_M$ was found to be $1.67 \times 10^7$ M$^{-1}$ s$^{-1}$.

For the Factor VII assay, pH 8.0 Tris buffer (0.05 M Tris, 5 mM CaCl$_2$, 0.15 M NaCl, 0.1% TWEEN 20, 0.1% BSA) was used. 10 μl of 20 μM human Factor VIIa (FVIIa) and 22 μM of human tissue factor (TF) was brought to assay buffer to make 160 nM FVIIa and TF solutions, respectively. 40 to 48 μl of buffer, 25 μl of FVIIa and 25 μl TF solution were added to a cuvette, and incubated at 37° C. for 5 minutes, then 2 to 10 μl of 2.4 mM structure (11b) solution was added to the cuvette to initiate reaction (final volume was 100 ml). The initial 3 minutes reaction progress curves were recorded. Five structure (11b) concentration points were collected. The initial rates were linear least-square fitted against the concentrations of structure (11b) with GraFit. The $k_{cat}/K_M$ was calculated from the slope and found to be 17,500 M$^{-1}$s$^{-1}$.

In both the thrombin and Factor VII assay of this experiment, (D)FPR-PNA was run as a control. Activity of structure (11b) compared to the control was 0.76 and 1.38 for thrombin and Factor VII, respectively (Factor VII: $K_{cat}/K_M=1.27 \times 10^4$ M$^{-1}$ S$^{-1}$; thrombin: $K_{cat}/K_M=2.20 \times 10^7$ M$^{-1}$ S$^{-1}$).

Example 4

Activity of a Representative β-Sheet Mimetic as a Protease Inhibitor

This example illustrates the ability of a representative β-sheet mimetic of this invention to function as a protease inhibitor for thrombin, Factor VII, Factor X, urokinase, tissue plasminogen activator (t-PA), protein C, plasmin and trypsin. The β-sheet mimetic of structure (13b) above was synthesized according to the procedures disclosed in Example 1, and used in this experiment.

All inhibition assays of this experiment were performed at room temperature in 96 well microplates using a Bio-Rad microplate reader (Model 3550). 0.29 mg of structure (13b) was dissolved into 200 ml of 0.02 N hydrochloric acid deionized water solution. This solution (2.05 mM) served as the stock solution for all the inhibition assays. The hydrolysis of chromogenic substrates was monitored at 405 nm. The reaction progress curves were recorded by reading the plates typically 90 times with 30 seconds to 2 minute intervals. The initial rate were determined by unweighted nonlinear least-squares fitting to a first order reaction in GraFit. The determined initial velocities were then nonlinear least-square fitted against the concentrations of structure (13b) using GraFit to obtain IC$_{50}$. Typically, eight structure (13b) concentration points were employed for IC$_{50}$ determination.

For the thrombin assay, N-p-tosyl-Gly-Pro-Arg-pNA (from Sigma) was used at 0.5 mM concentration in 1% DMSO (v/v) pH 8.4 Tris buffer as substrate. From structure (13b) stock solution two steps of dilution were made. First, 1:2000 dilution into 0.02 N hydrochloride solution, then 1:100 dilution into pH 8.4 Tris buffer. The final dilution of structure (13b) served as the first point (10 nM). Seven sequential dilutions were made from the first point with a dilution factor of 2. Into each reaction well, 100 μl of 10 nM thrombin solution and 50 μl of structure (13b) solution was added. The mixture of the enzyme and inhibitor was incubated for 20 minutes, then 100 μl of 0.5 mM substrate solution was added to initiate the reaction. The IC$_{50}$ of structure (13b) against thrombin was found to be 1.2±0.2 nM.

In the Factor VII assay, S-2288 (from Pharmacia), D-Ile-Pro-Arg-pNA was used at 20 μM in deionized water as substrate. From the stock of structure (13b), a 1:100 dilution was made into pH 8.0 Tris buffer. This dilution served as the first point of the inhibitor (20 μM). From this concentration point 6 more sequential dilutions were made with a dilution factor of 2. 50 μl of 16 nM FVIIa and TF complex solution and 40 μl of the inhibitor solutions were added into each well, the mixtures were incubated for 20 minutes before 10 μl of 20 mM S-2288 was added. IC$_{50}$ of structure (13b) against factor VII was found to be 140±3 nM.

In the Factor X assay, buffer and substrate are the same as used for thrombin assay. A 1:100 dilution was made into pH 8.4 Tris buffer to serve as the first point. Seven dilutions with a dilution factor of 2 were made. The assay protocol is the same as for thrombin except 25 nM of bovine factor Xa (from Sigma) in pH 8.4 Tris buffer was used instead of thrombin. IC$_{50}$ of structure (13b) against factor X was found to be 385±17 nM.

In the urokinase assay, buffer was pH 8.8 0.05 M Tris and 0.05 M NaCl in deionized water. S-2444 (from Sigma), pyroGlu-Gly-Arg-pNA at 0.5 mM in water was utilized as substrate. The same dilution procedure was used as for Factor VII and Factor X. Assay protocol is the same as for thrombin except 18.5 nM of human urokinase (from Sigma) was utilized. IC$_{50}$ was found to be 927±138 nM.

Tissue Plasminogen Activator (t-PA)

Buffer, substrate and the dilution scheme of structure (13b) were the same as utilized for Factor VII assay.

Activated Protein C (aPC)

Buffer was the same as used in thrombin assay. 1.25 mM S-2366 in the assay buffer was utilized as substrate. Dilutions of structure (13b) were the same as in urokinase assay.

Plasmin

Buffer (see thrombin assay); S-2551 (from Pharmacia), D-Val-Leu-Lys-pNA at 1.25 mM in assay buffer was utilized as substrate. For dilutions of structure (13b) (see urokinase assay).

In the trypsin assay, pH 7.8 Tris (0.10 M Tris and 0.02 M $CaCl_2$) was utilized as the buffer. BAPNA (from Sigma) was used at 1 mg/ml in 1% DMSO (v/v) deionized water solution as substrate. The same dilutions of structure (13b) were made as for Factor VII assay. 40 µl of 50 µg/ml bovine trypsin (from Sigma) and 20 µl of structure (13b) solution were added to a reaction well, the mixture was incubated for 5 minutes before 40 µl of 1 mg/ml BAPNA was added to initiate the reaction. The $IC_{50}$ of structure (13b) against trypsin was found to be 160±8 nM.

In the above assays, (D)FPR-$CH_2$Cl ("PPACK") was run as a control. Activity of structure (13b) compared to the control was enhanced (see Table 4).

TABLE 4

| Enzymes | PPACK | Structure (13b) |
| --- | --- | --- |
| Thrombin | 1.5 | 1.2 |
| Factor VII | 200 | 140 |
| Factor X | 165 | 385 |
| Protein C | 281 | 528 |
| Plasmin | 699 | 978 |
| Trypsin | 212 | 16 |
| Urokinase | 508 | 927 |
| t-PA | 106 | 632 |

With respect to prothrombin time (PT), this was determined by incubating (30 minutes at 37° C.) 100 µl of control plasma (from Sigma) with 1–5 µl of buffer (0.05 M Tris, 0.15 M NaCl, pH=8.4) or test compound (i.e., PPACK or structure (13b)) in buffer. Then 200 µl of prewarmed (at 37° C. for ~10 minutes) thromboplastin with calcium (from Sigma) was rapidly added into the plasmia sample. The time required to form clot was manually recorded with a stop watch (see Table 5), and was found to be comparable with PPACK.

TABLE 5

| | PT (second) | |
| --- | --- | --- |
| Concentration | PPACK | Structure (13b) |
| 0 (Control) | 13 | 13 |
| 1 pM | — | 13 |
| 10 pM | — | 17 |
| 50 pM | — | 18 |
| 100 pM | — | 23 |
| 200 pM | — | 24 |
| 500 pM | 15 | 27 |
| 1 nM | 18 | 30 |
| 10 nM | 22 | 31 |
| 20 nM | 25 | — |
| 30 nM | — | 31 |
| 40 nM | 28 | — |
| 50 nM | — | 30 |
| 60 nM | 30 | — |
| 80 nM | 31 | 33 |

Example 5

Activity of a Representative β-Sheet Mimetic as a Protease Inhibitor

This example illustrates the ability of a further representative β-sheet mimetic of this invention to function as an inhibitor for thrombin, Factor VII, Factor X, urokinase, Tissue Plasminogen Activator, Activated Protein C, plasmin, tryptase and trypsin. The β-sheet mimetic of structure (20b) above was synthesized according to the procedures disclosed in Example 2, and used in this experiment.

All inhibition assays were performed at room temperature in 96 well microplates using Bio-Rad microplate reader (Model 3550). A 1 mM solution of structure (20b) in water served as the stock solution for all the inhibition assays. The hydrolysis of chromogenic substrates was monitored at 405 nm. The reaction progress curves were recorded by reading the plates, typically 60 times with 30 second to 2 minute intervals. Initial rates were determined by unweighted non-linear least-squares fitting to a first order reaction in GraFit (Erithacus Software Limited, London, England). The determined initial velocities were then nonlinear least-square fitted against the concentrations of structure (20b) using GraFit to obtain Ki. The general format of these assays are: 100 ml of a substrate solution and 100 ml of structure (20b) solution were added in a microplate well, then 50 ml of enzyme solution was added to initiate the reaction. Typically, eight structure (20b) concentration points were employed for Ki determination. The values of Ki of structure (20b) against nine serine proteases are tabulated in Table 6.

Thrombin

N-p-tosyl-Gly-Pro-Arg-pNA (from Sigma) was used at 0.5 mM concentration in 1% DMSO (v/v) pH8.0 tris buffer (tris, 50 mM, TWEEN 20, 0.1%, BSA, 0.1%, NaCl, 0.15 M, $CaCl_2$, 5 mM) as substrate. From structure (20b) stock solution two steps of dilution were made, first, 1:100 dilution in water, then 1:50 dilution in the pH8.0 tris buffer to serve as the first point (200 nM). Seven sequential dilutions were made from the first point for the assay.

Factor VII

S-2288 (from Pharmacia), D-Ile-Pro-Arg-pNA was used at 2.05 mM in the pH 8.0 tris buffer (see thrombin assay). From the stock of structure (20b), a 1:100 dilution was made in the tris buffer. From this concentration point seven more sequential dilutions were made for the assay.

Factor X

Buffer and substrate were the same as used for thrombin assay. A 1:100 dilution was made in the pH8.0 tris buffer to serve as the first point. Seven more dilutions from the first were made for the assay.

Urokinase

Buffer, 50 mM tris, 50 mM NaCl, pH=8.8. S-2444 (from Sigma), pyroGlu-Gly-Arg-pNA at 0.25 mM in buffer was utilized as substrate. 1:10 dilution in buffer was made from the stock of structure (20b) as the first point, then seven more dilutions from the first point were made for the assay.

Tissue Plasminogen Activator (t-PA)

Buffer, substrate and the dilution scheme of structure (20b) were the same as utilized for Factor VII assay.

Activated Protein C (aPC)

Buffer was the same as used in thrombin assay. 1.25 mM S-2366 in the assay buffer was utilized as substrate. Dilutions of structure (20b) were the same as in urokinase assay.

Plasmin

Buffer (see thrombin assay); S-2251 (from Pharmacia), D-Val-Leu-Lys-pNA at 1.25 mM in assay buffer was utilized as substrate. For dilutions of structure (20b) (see urokinase assay).

Tryptase 0.1 M tris, 0.2 M NaCl, 0.1 mg/ml heparin, pH=8.0 was utilized as buffer. 0.5 mM S-2366 (from Pharmacia), L-pyroGlu-Pro-Arg-pNA in buffer was used as substrate. From the 1 mM stock of structure (20b), 10 mM solution was made in water, then 1 mM solution was made in buffer from the 10 mM solution to serve as the first concentration point. From this point seven more dilutions were made for the assay.

Trypsin

Buffer, substrate and the dilution Scheme of structure (20b) were the same as used for thrombin.

TABLE 6

| Enzyme | Source | Assay Conc. (nM) | Structure (20b) $K_i$ (nM) |
|---|---|---|---|
| thrombin | bovine plasma | 2 | 0.66 |
| factor VII | human | 4 | 270 |
| factor X | bovine plasma | 8 | 966 |
| urokinase | human kidney | 3.7 | 600 |
| t-PA | human | 10 | 495 |
| APC | human plasma | 1 | 3320 |
| plasmin | bovine plasma | 4 | 415 |
| tryptase | human lung | 2 | 12.4 |
| trypsin | bovine pancreas | 5 | 0.64 |

As illustrated by the data presented in Table 6 above, structure (20b) functioned as a good thrombin inhibitor, with good specificity against fibrinolytic enzymes.

Example 6
Synthesis of Representative β-Sheet Mimetic

This example illustrates the synthesis of a representative β-sheet mimetic of this invention having the following structure (21):

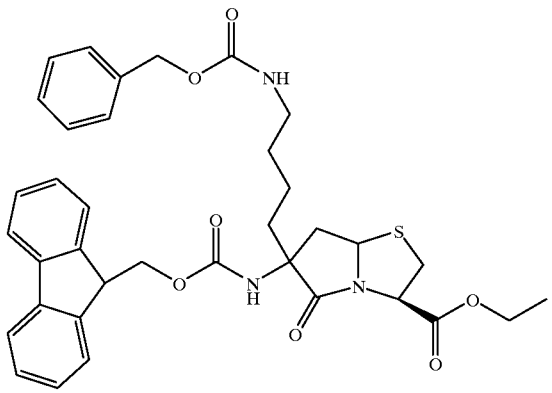

Structure (21) was synthesized as follows. A solution of 48 mg (0.859 mmol) $N^a$-FMOC-$N^e$-Cbz-a-ethanal-Lys-Ome [synthesized from $N^e$-Cbz-Lys-OMe by the same method used for the preparation of structure (5) from Phe-OMe], 15.9 mg (0.0859 mmol) Cys-OEt.HCl, and 13.2 μL (0.0945 mmol) TEA were in 0.43 mL $CH_2Cl_2$ were stirred under Ar for 2 hr at room temperature. Bis(bis(trimethylsilyl)amino) tin(II) (39.8 μL) was added and the reaction stirred overnight. The reaction solution was diluted with 10 mL EtOAc and washed with 6 mL each 10% citrate, water, and brine. The organic layer was dried over $Na_2SO_4$, filtered, and concentrated. The resulting residue was purified by flash chromatography on silica gel using 40% EtOAc/hexanes to give, after drying in vacuo, 12.9 mg of colorless oil (23%) as a mixture of diastereomers by $^1$H NMR ($CDCl_3$). MS ES(+) m/z 658.2 (MH$^+$, 30), 675.3 (M+Na$^+$, 100), 696.1 (M+K$^+$, 45).

Example 7
Synthesis of Representative β-Sheet Mimetic

This example illustrates the synthesis of a further representative β-sheet mimetic of this invention.

Synthesis of Structure (22)

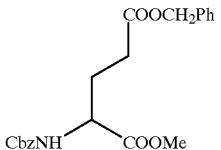

Structure (22) was synthesized as follows. To a stirred solution of Cbz-Glu(OBn) —OH (5 g, 13.5 mmol) with DMAP (270 mg) and methanol (3 ml) in dichloromethane (100 ml) was added EDCI (3g) at 0° C. After stirring at 0° C. for 3 h, the solution was stirred at room temperature (rt) overnight. After concentration, the residue was taken up into EtOAc (100 ml) and 1N HCl (100 ml). The aqueous phase was separated and extracted with EtOAc (100 ml). The combined organic extracts were washed with sat. $NaHCO_3$ (100 ml), brine (100 ml), dried ($MgSO_4$), passed through a short pad of silica gel, and concentrated to provide 4.95 g an oil (95%). The product was pure enough to use for the next reaction without any further purification. $^1$H NMR ($CDCl_3$) δ2.00 (m, 1H), 2.25 (m, 1H), 2.50 (m, 2H), 3.74 (s, 3H, $OCH_3$), 4.42 (m, 1H, CHNH), 5.10 and 5.11 (two s, 4H, $CH_2$Ph), 5.40 (d, 1H, NH), 7.35 (s, 10H, phenyls); MS CI(isobutane) m/z 386 (M+H$^+$).

Synthesis of Structure (23)

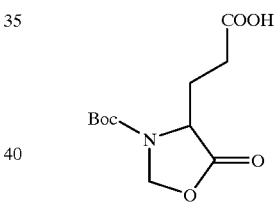

Structure (23) was synthesized as follows: To a stirred solution of L-Glu-OH (4.41g, 30 mmol) with triethylamine (8.4 ml, 60 mmol) in 1,4-dioxane (40 ml) and $H_2O$ (20 ml) was added $Boc_2O$ (7 g, 32 mmol) at rt. After stirring for 1.5 h, the solution was acidified with 6N HCl (pH 2), and extracted with EtOAc (3×100 ml). The combined organic extracts were washed with $H_2O$ (100 ml), brine (50 ml), dried ($Na_2SO_4$), and concentrated to provide an oil (9.5 g). Without further purification, the oil was used in the next reaction.

A mixture of above oil (9.5 g) with paraformaldehyde (5 g) and p-TsOH.$H_2O$ (400 mg) in 1,2-dichloroethane (200 ml) was heated at reflux with a Dean-Stark condenser, which was filled with molecular sieve 4A, for 6 h. After addition of EtOAc (100 ml) and sat. $NaHCO_3$ (50 ml), the solution was extracted with sat. $NaHCO_3$ (3×50 ml). The combined aqueous extracts were acidified with 6N HCl (pH 2), and extracted with EtOAc (3×100 ml). The combined organic extracts were washed with brine (100 ml), dried ($Na_2SO_4$), and concentrated to provide an oil. The crude oil was purified by flash chromatography (hexane:EtOAc=80:20 to 70:30 to 60:40) to provide an oil (4.04 g, 52%) which solidified slowly upon standing. $^1$H NMR ($CDCl_3$) δ1.49 (s, 9H, C($CH_3$)$_3$), 2.18 (m, 1H, —$CH_2CH_2$), 2.29 (m, 1H, CH$_2$CH$_2$), 2.52 (m, 2H, —CH$_2$CH$_2$—), 4.33 (m, 1H, NHCHCH$_2$), 5.16 (d, 1H, J=4.5 Hz, NCH$_2$O), 5.50 (br, 1H, NCH$_2$O); $^{13}$C NMR (CDCl$_3$) δ25.85, 28.29, 29.33, 54.16, 79.10, 82.69, 152.47, 172.37, 178.13; MS (ES+) m/z 260 (M+H$^+$), 282 (M+Na$^+$), 298 (M+K$^+$).

Synthesis of Structure (24)

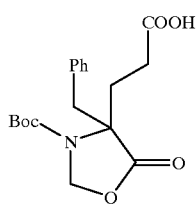

(24)

Structure (24) was synthesized as follows. To a stirred solution of 1,1,1,3,3,3-hexamethyldisilazane (2.1 ml, 10 mmol) in THF (10 ml) was added n-BuLi (4 ml of 2.5M in hexane, 10 mmol) at 0° C. The resulting solution was stirred at the same temperature for 30 min. After cooling to −78° C., to this stirred solution was added a solution of carboxylic acid (23) (1.02 g, 3.94 mmol) in THF (10 ml) followed by rinsings of the addition syringe with 5 ml THF. The resulting solution was stirred at −78° C. for 1 h, and PhCH$_2$Br (0.46 ml, 3.9 mmol) was added. After stirring at −30° C. for 3 h, to this solution was added 1N HCl (50 ml) and the resulting solution was extracted with EtOAc (100 ml). The organic extract was washed with brine (50 ml), dried (Na$_2$SO$_4$), and concentrated to provide an oil. The crude product was purified by flash chromatography (hexane:EtOAc=80:20 to 60:40 to 50:50) to provide a foamy solid (1.35 g, 98%): $^1$H NMR (CDCl$_3$) δ1.55 and 1.63 (two s, 9H, ratio 1.5:1 by rotamer, OC(CH$_3$)$_3$), 2.2–2.4 (m, 3H, —CH$_2$CH$_2$—), 2.6–2.9 (set of m, 1H, —CH$_2$CH$_2$—), 3.04 (d, 1H, J=13.5 Hz, —CH$_2$Ph), 3.33 and 3.58 (two d, 1H, J=13 Hz, ratio 2:1, —CH$_2$Ph), 4.03 (two d, 1H, J=4 Hz, A of ABq, —NCH$_2$O—), 4.96 (two d, 1H, J=4Hz, B of ABq, —NCH$_2$O—); MS (ES-) m/z 348 (M−H$^+$).

Synthesis of Structure (25)

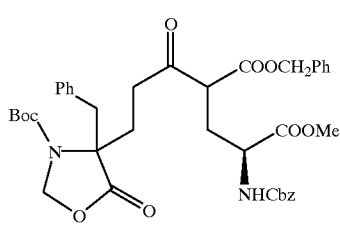

(25)

Synthesis of structure (25) was carried out as follows. To a stirred solution of carboxylic acid (24) (1.05 g, 3.0 mmol) in dry THF (5 ml) was added 1,1'-carbonyldiimidazole (500 mg, 3.1 mmol) at rt. The resulting solution was stirred at rt for 30 min. The solution of acyl imidazole was used for the next reaction without purification.

Meanwhile, to a stirred solution of 1,1,1,3,3,3-hexamethyldisilazane (1.6 ml, 7.5 mmol) in THF (5 ml) was added n-BuLi (3 ml of 2.5 M solution in hexane, 7.5 mmol) at 0° C. After stirring at the same temperature for 30 min, the solution was cooled to −78° C. To the stirred solution was added a solution of Cbz-Glu(OBn) —OMe (1.16 g, 3 mmol) in THF (5 ml) followed by rinsings of the addition syringe with 2 ml THF. The resulting solution was stirred at the same temperature for 15 min. To this stirred solution was added the above acyl imidazole in 3 ml THF. After stirring 30 min. at −78° C., to this solution was added sat. NH$_4$Cl (50 ml) and extracted with EtOAc (2×75 ml). The combined organic extracts were washed with sat. NaHCO, (50 ml), brine (50 ml), dried (Na$_2$SO$_4$), passed through a short pad of silica gel, and concentrated to provide an oil. The crude product was purified by flash chromatography (hexane: EtOAc=90:10 to 80:20 to 70:30 to 60:40) to provide an oil (1.48 g, 69w): MS (ES+) m/z 734.4 (M+NH$_4$$^+$).

Synthesis of Structure (26a)

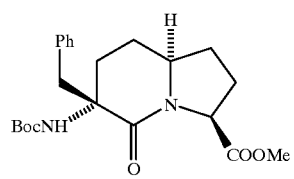

(26a)

Structure (26a) was synthesized as follows. A stirred solution of above starting keto ester (25) (530 mg, 0.7mmol) in EtOH/AcOH (10/1 ml) was treated with 10% Pd/C (ca. 100 mg) under 20 atm pressure of H$_2$ for 2 days. After filtration through a short pad of Celite, the filtrate was concentrated and dissolved in EtOAc (50 ml). The solution was washed with 1N HCl (30 ml), sat. NaHCO$_3$ (30 ml), brine (30 ml), dried (Na$_2$SO$_4$), and concentrated to provide an oil. The crude product was purified by flash chromatography (hexane: EtOAc=80:20 to 60:40 to 50:50 to 20:80 to 0:100) to provide a foamy solid (95 mg, 34%). TLC (EtOAc) R$_f$ 0.68; NMR (CDCl$_3$) δ1.38 (two s, 9H, OC(CH$_3$)$_3$), 1.63 (s, 1H), 1.75 (m, 2H), 2.05 (m, 5H), 2.1–2.3 (set of m, 1H), 3.00 (d, 1H, J=14 Hz, CH$_2$Ph), 3.21 (d, 1H, J=13.5 Hz, CH$_2$Ph), 3.74 (collapsed two s, 4H, OCH$_3$ and NCH), 4.53 (d, 1H, J=9.5 Hz), 5.01 (br, 1H, NH); MS (ES+) m/z 403 (M+H$^+$), 425 (M+Na$^+$). Stereochemistry was assigned by 2D NMR.

Synthesis of Structure (27a)

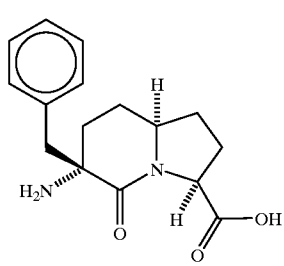

(27a)

Structure (27a) was synthesized as follows. To a solution of 28 mg (0.070 mmol) of the bicyclic ester (26a) stirred in 1 ml THF at room temperature was added 0.14 ml 1.0 M aqueous lithium hydroxide solution. The mixture was stirred vigorously for 20 h then quenched with 5% aqueous citric acid (1 ml). The mixture was extracted with ethyl acetate (3×25 ml) then the combined extracts were washed with water and brine and dried over anhydrous sodium sulfate. Filtration and concentration of the filtrate under vacuum gave 26 mg of white foam, used without further purification.

Synthesis of Structure (28a)

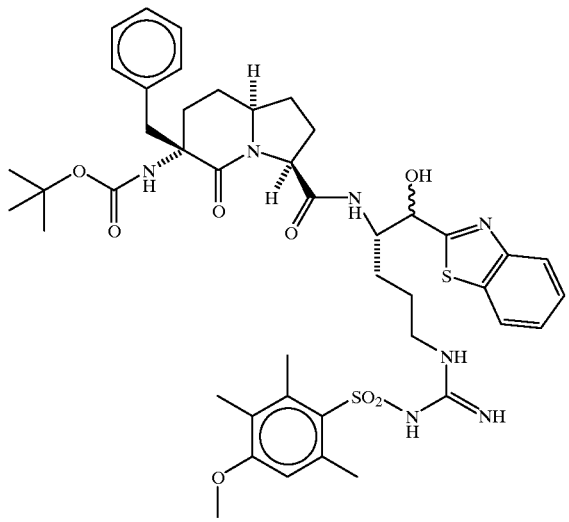

(28a)

Structure (28a) was synthesized as follows. The bicyclic acid (27a) (26 mg, 0.067 mmol), benzothiazolylarginol trifluoroacetic acid salt (structure (17) 61 mg, 0.083 mmol) EDC (21 mg, 0.11 mmol) and HOBt hydrate (16 mg, 0.10 mmol) were dissolved in THF (5 ml) and diisopropylethylamine (0.34 ml, 1.9 mmol) was added. The mixture was stirred at room temperature for 15 h then diluted with ethyl acetate and extracted sequentially with 5% aqueous citric acid, saturated aqueous sodium bicarbonate, water and brine. The organic solution was dried over anhydrous sodium sulfate, filtered and concentrated under vacuum to 60 mg of a yellow glass. $^1$H NMR analysis indicated a mixture of four diastereomeric amides. MS (ES+): m/z 898 (M+Na$^+$).

Synthesis of Structure (29a)

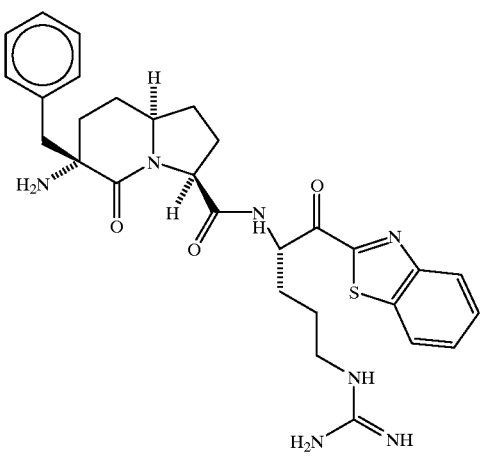

(29a)

A β-sheet mimetic of structure (29a) was synthesized as follows. The crude hydroxybenzothiazole (28a) (60 mg, 0.068 mmol) was dissolved in CH$_2$Cl$_2$ (2 ml) and Dess-Martin periodinane (58 mg, 0.14 mmol) was added. The mixture was stirred at room temperature for 6 h then diluted with ethyl acetate and stirred vigorously with 10% aqueous sodium thiosulfate for 10 minutes. The organic solution was separated and extracted with saturated aqueous sodium bicarbonate, water and brine then dried over anhydrous sodium sulfate and filtered. Concentration of the filtrate under vacuum yielded 42 mg of yellow glass. $^1$H NMR analysis indicated a mixture of two diastereomeric ketobenzothiazoles.

The ketobenzothiazole (42 mg, 0.048 mmol) was dissolved in 95% aqueous trifluoroacetic (0.95 ml) acid and thioanisole (0.05 ml) was added. The resulting dark solution was stirred for 18 hours at room temperature then concentrated under vacuum to a dark brown gum. The gum was triturated with diethyl ether and centrifuged. The solution was removed and the solid remaining was triturated and collected as above two more times. The yellow solid was dried in a vacuum desiccator for 2 hours then purified by HPLC to give 1.4 mg of the deprotected product. MS (ES+): 562.4 (M+H$^+$). HPLC: (t$_R$=21.17 min.)

Synthesis of Structure (26b)

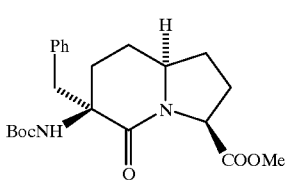

(26b)

Structure (26b) was synthesized as follows. A stirred solution of above starting keto ester (25) (615 mg, 0.86 mmol) in MeOH/AcOH (10/1 ml) was treated with 10% Pd/C (ca. 60 mg) under 20 atm pressure of H$_2$ for 3 days. After filtration through a short pad of Celite, the filtrate was concentrated to provide an oil. The crude product was purified by flash chromatography (hexane:EtOAc=80:20 to 60:40 to 50:50 to 0:100) to collect the more polar fraction (50 mg). Rf 0.12 (hexane: EtOAc=60:40); MS (ES+) m/z 433 (M+H$^+$).

Above oil was treated with p-TsOH.H$_2$O (5 mg) in 1,2-dichloroethane (10 ml) at reflux temperature for 2 days. After concentration, the oily product was purified by preparative TLC (hexane:EtOAc=80:20 to 60:40) to give an oil (10 mg). TLC Rf 0.36 (hexane:EtOAc=60:40); $^1$H NMR (CDCl$_3$) δ1.43 (s, 9H), 1.66 (m, 3H), 1.89 (m, 3H), 2.14 (m, 1H), 2.75 (m, 1H), 2.98 (m, 1H, CHN), 3.72 (s, 3H, Me), 4.30 (m, 1H), 5.59 (d, 1H, NH), 7.1–7.3 (m, 5H, phenyl); MS CI (NH$_3$) 403.2 (M+H$^+$). Stereochemistry was assigned by 2D NMR.

Synthesis of Structure (28b)

(28b)

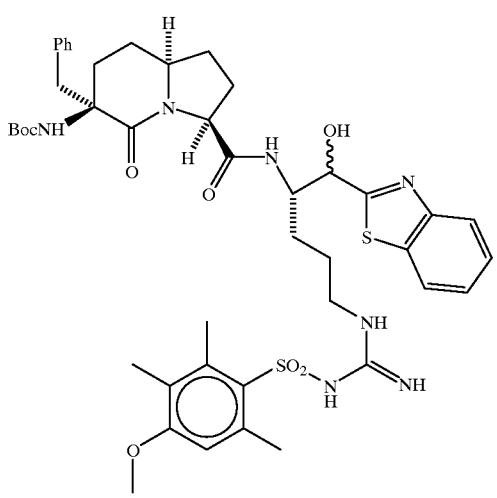

Structure (28b) was synthesized as follows. To a solution of 12 mg (0.030 mmol) of the bicyclic ester (26b) stirred in THF 1 ml at room temperature was added 0.060 ml 1.0 M aqueous lithium hydroxide solution. The mixture was stirred vigorously for 25 h then quenched with 5% aqueous citric acid (1 ml). The mixture was extracted with ethyl acetate (3×25 ml) then the combined extracts were washed with water and brine and dried over anhydrous sodium sulfate. Filtration and concentration of the filtrate under vacuum gave 19 mg of white foam.

The foam, benzothiazolylarginol trifluoroacetic acid salt (30 mg, 0.041 mmol) EDC (10 mg, 0.052 mmol) and HOBt hydrate (9 mg, 0.059 mmol) were dissolved in THF (2 ml) and diisopropylethylamine (0.026 ml, 0.15 mmol) was added. The mixture was stirred at room temperature for 30 h then diluted with ethyl acetate and extracted sequentially with 5% aqueous citric acid, saturated aqueous sodium bicarbonate, water and brine. The organic solution was dried over anhydrous sodium sulfate, filtered and concentrated under vacuum to 28 mg of a yellow glass. $^1$H NMR analysis Indicated a mixture of four diastereomeric amides. MS (ES+): m/z 898 (M+Na$^+$)

Synthesis of Structure (29b)

(29b)

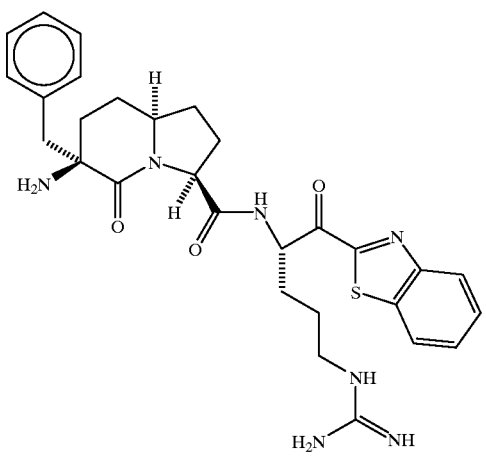

Structure (29b) was synthesized as follows. The crude hydroxybenzothiazole (28b) (28 mg) was dissolved in CH$_2$Cl$_2$ (2 ml) and Dess-Martin periodinane (29 mg, 0.071 mmol) was added. The mixture was stirred at room temperature for 18 h then diluted with ethyl acetate and stirred vigorously with 10% aqueous sodium thiosulfate for 10 minutes. The organic solution was separated and extracted with saturated aqueous sodium bicarbonate, water and brine then dried over anhydrous sodium sulfate and filtered. Concentration of the filtrate under vacuum yielded 32 mg of yellow glass. $^1$H NMR analysis indicated a mixture of two diastereomeric ketobenzothiazoles.

The ketobenzothiazole (32 mg) was dissolved in 95% aqueous trifluoroacetic (0.95 ml) acid and thioanisole (0.05 ml) was added. The resulting dark solution was stirred for 20 hours at room temperature then concentrated under vacuum to a dark brown gum. The gum was triturated with diethyl ether and centrifuged. The solution was removed and the remaining solid was triturated and collected as above two more times. The yellow solid was dried in a vacuum desiccator for 2 hours then purified by HPLC to give 1.3 mg of the deprotected product. MS (FB+): 562.36 (M+H$^+$); HPLC: $t_R$=21.51 min. (Gradient 0 to 90% 0.1% TFA in CH$_3$CN/0.1% TFA in H$_2$O over 40 min.)

Example 8

Activity of Representative β-Sheet Mimetic as a Protease Inhibitor

This example illustrates the ability of a further representative β-sheet mimetic of this invention to function as an inhibitor for thrombin, Factor VII, Factor X, Factor XI, and trypsin. The β-sheet mimetics of structures (29a) and (29b) above were synthesized according to the procedures disclosed in Example 7, and used in this experiment.

The proteinase inhibitor assays were performed as described in Example 5 except as described below for Factor XI. The results are presented in Table 7.

Factor XI. The same buffer was utilized in this assay as in the thrombin assay. 1 mM S-2366 (from Pharmacia), L-pyroGlu-Pro-Arg-pNA, solution in water was used as substrate. From a 1 mM stock solution of structure (29a) or (29b) in water, a 1:10 dilution was made in buffer. From this 100 μM solution, seven serial 1:5 dilutions were made in buffer for assay.

TABLE 7

| Enzymes | Structure (29a) | Structure (29b) |
|---|---|---|
| Thrombin | 10.4 | 0.085 |
| Trypsin | 0.54 | 0.20 |
| Factor VII | 1800 | — |
| Factor X | 4600 | 17 |
| Factor XI | 391 | — |

Example 9

Activities of Representative β-Sheet Mimetics as a Protease Inhibitor

This example illustrates the ability of further representative β-sheet mimetics of this invention to function as an inhibitor for thrombin, Factor VII, Factor X, Factor XI, tryptase, aPC, plasmin, tPA, urokinase and trypsin. The β-sheet mimetics of structures (20) and (29b) above were synthesized according to the procedures disclosed in Examples 2 and 7, respectively, and used in this experiment.

The proteinase inhibitor assays were performed as described in Example 5 except as described in Example 8 for Factor XI. The results are presented in Table 8.

TABLE 8

| | Structure (20b) | | Structure (29b) | |
|---|---|---|---|---|
| | Ki (nM) | Selectivity* | Ki (nM) | Selectivity* |
| Thrombin | 0.65 | 1 | 0.085 | 1 |
| Trypsin | 0.62 | 0.95 | 0.23 | 2.7 |
| Factor VII | 270 | 415 | 200 | 2353 |
| Factor X | 222 | 342 | 19.3 | 227 |
| Factor XI | 27.0 | 42 | 75.3 | 886 |
| Tryptase | 12.3 | 18.9 | 9.0 | 106 |
| aPC | 3320 | 5108 | 1250 | 14706 |
| Plasmin | 415 | 638 | 251 | 2953 |
| tPA | 495 | 762 | 92.9 | 1093 |
| Urokinase | 600 | 923 | 335 | 3941 |

*selectivity is the ratio of Ki of an enzyme to the Ki of thrombin

Example 10
Synthesis of Representative β-Sheet Mimetics

This example illustrates the synthesis of a further representative β-sheet mimetic of this invention.

Synthesis of Structure (30)

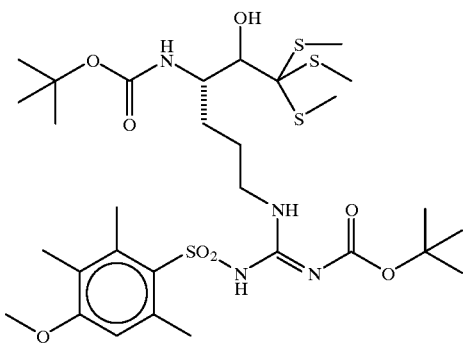

(30)

Structure (30) was synthesized as follows. n-Butyllithium (700 μL, 1.75 mmol, 2.5M in hexanes) was added over 5 min to a solution of tris(methylthio)methane (256 μL, 1.95 mmol) in THF (1 ml) at –78° C. The mixture was stirred for 40 min then treated with a solution of bis-Boc-argininal (structure (16) from Example 2) (100 mg, 1.75 mmol) in 2 ml THF, dropwise, over a period of 5 min. After stirring for 1.5 h, the reaction was quenched with saturated NH$_4$Cl solution and allowed to warm to room temperature. The layers were separated and the aqueous layer extracted with EtOAc (3x), washed with brine (1x), dried (Na$_2$SO$_4$) and concentrated. Purification by flash chromatography (EtOAc:Hexane 1:4) yielded 93 mg (73%) of the orthothiomethyl ester (structure (30)) and 8 mg of recovered aldehyde (structure (16)). $^1$H NMR (500 MHz, CDCl$_3$.) δ9.80 (s, 1H), 8.32 (t, J=5.0 Hz, 1H), 6.54 (s, 1H), 5.23 (d, J=9.0 Hz, 1H), 4.0 (m, 1H), 3.84 (s, 3H), 3.64 (br s, 1H), 3.38 (br s, 1H), 3.31 (m, 2H), 2.70 (s, 3H), 2.62 (s, 3H), 2.19 (s, 9H), 2.14 (s, 3H), 1.68–1.50 (m, 4H), 1.49 (s, 9H), 1.43 (s, 9H)

Synthesis of Structure (31)

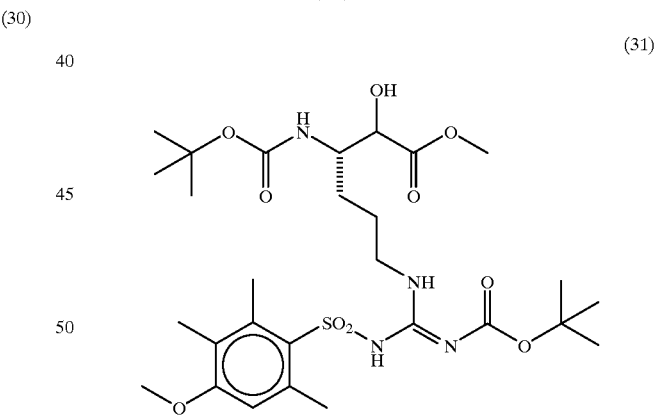

(31)

Structure (31) was synthesized as follows. A mixture of 77 mg (0.11 mmol) of the orthothiomethyl ester (structure (30)), 117 mg (0.43 mmol) of mercuric chloride, and 39 mg (0.18 mmol) of mercuric oxide in 2.5 ml of 12:1 methanol/water was stirred at rt for 4 h. The mixture was filtered through Celite and the residue washed with EtOAc (3x). The filtrate was diluted with water and extracted with EtOAc (3x). The organic layer was washed twice with 75% NH$_4$OAc/NH$_4$Cl, then with NH$_4$Cl and dried (Na$_2$SO$_4$). The solvent was removed in vacuo and the residue purified by flash chromatography (EtCAc/Hex, 1:3) to give 48 mg (72%) of the two diastereomers of structure (31) in a 1:2.7 ratio. $^1$H NMR (500 MHz, CDCl$_3$) (major diastereomer)

δ 9.80 (s, 1H), 8.33 (t, J=5.0 Hz, 1H), 6.54 (s, 1H), 4.66 (d, J=10.5 Hz, 1H), 4.08 (dd, J=5.0, 2.0 Hz, 1H), 3.97 (m, 1H), 3.84 (s, 3H), 3.77 (s, 3H), 3.30 (m, 2H), 3.06 (d, J=5.0 Hz, 1H), 2.70 (s, 3H), 2.63 (s, 3H), 2.14 (s, 3H), 1.68–1.50 (m, 4H), 1.49 (s, 9H), 1.40 (s, 9H); MS (ES+) m/z 631.5 (M+H$^{30}$).

Synthesis of Structure (32)

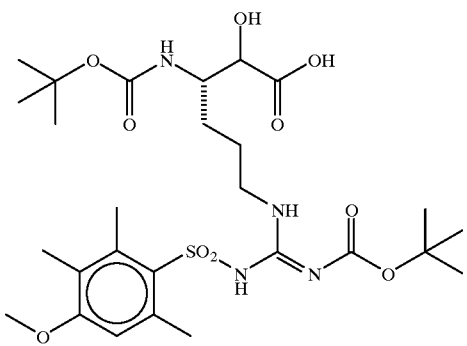

(32)

Structure (32) was synthesized as follows. A solution of 32 mg of the methyl ester (structure (31)) (0.051 mmol) in THF/water (4 ml, 1:3) was treated with 5 mg (0.119 mmol) of LiOH.H$_2$O; After stirring for 45 min, the reaction was diluted with 5% citric acid and extracted with ethyl acetate (3×). The combined extracts were washed with brine, dried over Na$_2$SO$_4$ and concentrated to give 30 mg (96%) of structure (32) as a white solid. The product was used without further purification. $^1$H NMR 500 MHz, CDCl$_3$) δ 9.80 (br s, 1H), 8.29 (br s, 1H), 6.54 (s, 1H), 5.62 (br s, 1H), 4.08 (m, 1H), 3.82 (s, 3H), 3.27 (br s, 3H), 2.69 (s, 3H), 2.62 (s, 3H), 2.13 (s, 3H), 1.65–1.50 (m, 4H), 1.48 (s, 9H), 1.37 (s, 9H); MS (ES−) m/z 615.5 (M−H$^+$)

Synthesis of Structure (33)

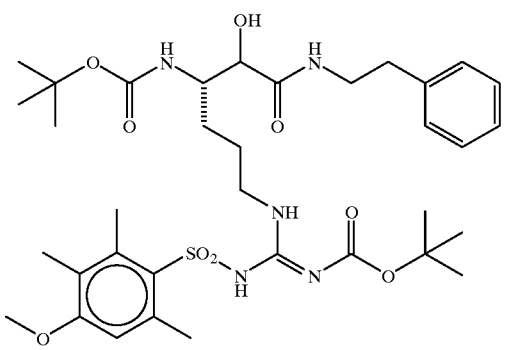

(33)

Structure (33) was synthesized as follows. To a solution of the compound of structure (32) (29 mg, 0.047 mmol), HOBt (8 mg, 0.056 mmol) and EDC (11 mg, 0.056 mmol) in THF (5 ml), phenethylamine (7 ml, 0.056 mmol) was added followed by diisopropylethylamine (12 μL, 0.071 mmol). The reaction mixture was stirred at rt overnight and diluted with 5% citric acid. The organic layer was separated and the aqueous phase extracted with EtOAc (3×). The combined extracts were washed with a saturated solution of NaHCO$_3$, brine, dried over Na$_2$SO$_4$, and filtered. After concentration the crude product was purified by chromatography (EtOAc/Hex, 1:1) to give 26 mg (77%) of structure (33) over two steps. $^1$H NMR (500 MHz, CDCl$_3$) δ 9.84 (s, 1H), 8.34 (t, J=5 Hz, 1H), 7.28 (m, 3H), 7.21 (m, 2H), 7.04 (m, 1H), 6.55 (s, 1H), 5.16 (d, J=8.5 Hz, 1H), 4.56 (d, J=5 Hz, 1H), 4.11 (dd, J=5.0, 3.0 Hz, 1H), 3.98 (m, 1H), 3.84 (s, 3H), 3.66 (m, 1H), 3.51 (m, 2H), 3.17 (m, 1H), 2.81 (t, J=7.5 Hz, 2H), 2.71 (s, 3H), 2.65 (s, 3H), 2.14 (s, 3H), 1.68–1.52 (m, 4H), 1.49 (s, 9H), 1.39 (s, 9H); MS (FAB+) m/z 720.6 (M+H$^+$) (FAB−) m/z 718.5 (M−H$^+$).

Synthesis of Structure (34)

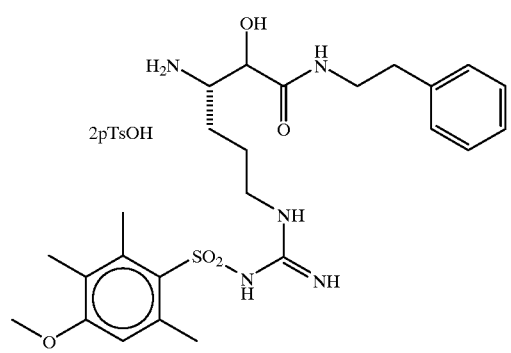

(34)

Structure (34) was synthesized as follows. To a solution of phenethylamide (structure (33), 25 mg, 0.035 mmol) in THF (5 ml) was added 18 mg of p-toluenesulfonic acid monohydrate (0.093 mmol). The reaction mixture was stirred at rt overnight to give a baseline spot by TLC. The solution was concentrated in vacuo, and the residue washed twice with ether removing excess pTsOH to give structure (34) as a yellowish-white solid, which was used without further purification. $^1$H NMR (500 MHz, CDCl$_3$) was consistent with the expected product, however, individual peak assignment was difficult due to broadening. MS (ES+) m/z 520.4 (M+H$^+$).

Structure (34) was reacted with structure (9a) of Example 1 (in an analogous manner to the procedure described in Example 2 for the synthesis of structure (18)), followed by oxidation and deprotection (in an analogous manner as described with respect to the oxidation and deprotection of structures (18) and (19), respectively) to provide structure (35) as identified in Table 9 below.

Example 11

Synthesis of Representative β-Sheet Mimetics

This example illustrates the synthesis of a further representative β-sheet mimetic of this invention.

Synthesis of Structure (36)

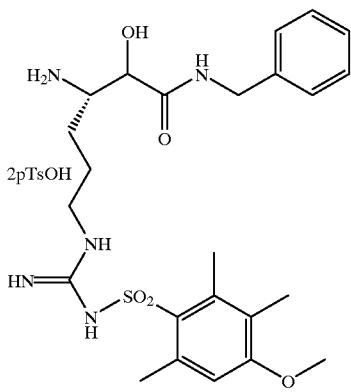

(36)

Structure (36) was synthesized in an analogous fashion to compound (34) starting with benzylamine and structure (32). $^1$H NMR (500 MHz, CDCl$_3$) was consistent with the expected product, however, individual peak assignment was difficult due to broadening. MS (FAB+) m/z 506.4 (M+H$^+$).

Structure (36) was reacted with structure (9a) of Example 1 (in an analogous manner to the procedure described in Example 2 for the synthesis of structure (18)), followed by oxidation and deprotection (in an analogous manner as described with respect to the oxidation and deprotection of structures (18) and (19), respectively) to provide structure (37) as identified in Table 9 below.

Example 12
Synthesis of Representative β-Sheet Mimetics

This example illustrates the synthesis of a further representative β-sheet mimetic of this invention.
Synthesis of Structure (38)

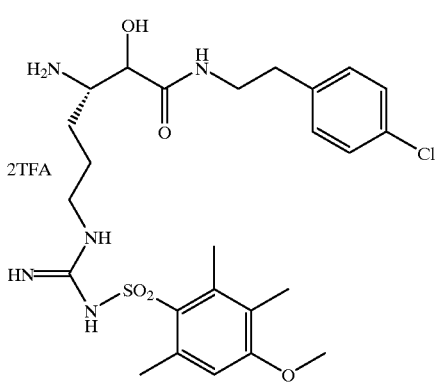

(38)

Structure (38) was synthesized in an analogous fashion to structure (34) starting with p-chlorophenethylamine and structure (32). $^1$H NMR (500 MHz, CDCl$_3$) was consistent with the expected product, individual peak assignment was difficult due to broadening. MS (ES+) m/z 554.5 (M+H$^+$).

Structure (38) was reacted with structure (9a) of Example 1 (in an analogous manner to the procedure described in Example 2 for the synthesis of structure (18)), followed by oxidation and deprotection (in an analogous manner as described with respect to the oxidation and deprotection of structures (18) and (19), respectively) to provide structure (39) as identified in Table 9 below.

Example 13
Synthesis of Representative β-Sheet Mimetics

This example illustrates the synthesis of a further representative β-sheet mimetic of this invention.
Synthesis of Structure (40)

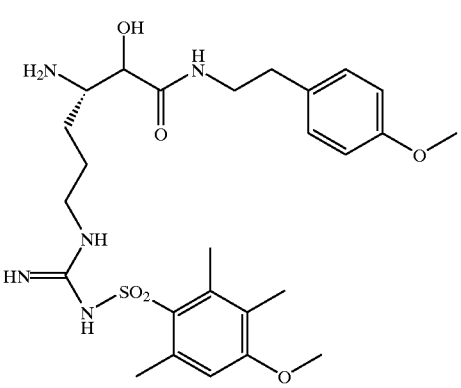

(40)

Structure (40) was synthesized in an analogous fashion to compound (34) using p-methoxyphenethylamine and structure (32). $^1$H NMR (500 MHz, CDCl$_3$) was consistent with the expected product, however, individual assignment was difficult due to broadening. MS (ES+) m/z 550.5 (M+H$^+$).

Structure (40) was reacted with structure (9a) of Example 1 (in an analogous manner to the procedure described in Example 2 for the synthesis of structure (18)), followed by oxidation and deprotection (in an analogous manner as described with respect to the oxidation and deprotection of structures (18) and (19), respectively) to provide structure (41) as identified in Table 9 below.

Example 14
Synthesis of Representative β-Sheet Mimetics

This example illustrates the synthesis of a further representative β-sheet mimetic of this invention.
Synthesis of Structure (42)

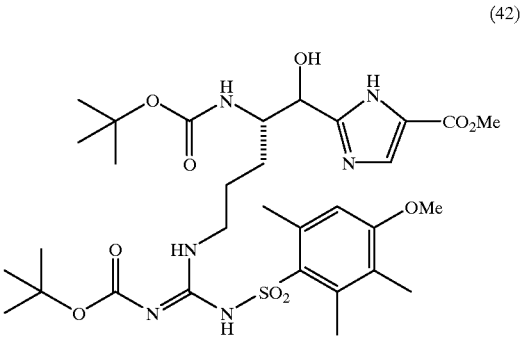

(42)

Structure (42) was prepared as follows. In a 10 ml round-bottomed flask were added CH$_2$Cl$_2$ (10 ml), methyl 2,3-dimethylaminopropionate dihydrochloride (19.9 mg, 0.103 mmol, 1.5 eq), and diisopropylethylamine (53 ml, 0.304 mmol, 4.4 eq). This suspension was stirred magnetically at room temperature for 1 h at which time was added the compound of structure (30) (50 mg, 0.068 mmol, 1 eq), mercury(II)chloride (82.4 mg, 0.304 mmol, 4.4 eq), and mercury(II)oxide (25.7 mg, 0.120 mmol, 1.7 eq). The result ing yellow suspension was stirred for 16.5 h during which time the suspension turned gray. The reaction was diluted with $CH_2Cl_2$ (50 ml), washed with saturated aqueous $NH_4Cl$ (5 ml), saturated aqueous NaCl (5 ml) and dried over $Na_2SO_4$. The cloudy suspension was filtered and the solvent removed in vacuo. The white solid was purified on preparative thin-layer chromatography to produce the imidazoline structure (42) (25.3 mg, 52% yield) as a clear amorphous solid.: $R_f$ 0.11 (10% $MeOH/CHCl_3$); $^1H$ NMR (500 MHz, $CDCl_3$) δ9.82 (s, 0.6H, N'H, mixture of tautomers), 9.78 (s, 0.4H, N"H), 8.35 (dd, J=4.3, 11 Hz, $^1H$, N-5), 6.54 (s, 1H, ArH), 5.08 (d, J=11 Hz, 1H, CHOH), 4.52 (m, 1H, imidazoline $CH_2$), 4.38 (d, J=21 Hz, 1H), 3.8–4.0 (m, 2H), 3.86 (s, 3H, $CO_2CH_3$), 3.767 (s, 3H, $ArOCH_3$), 3.5–3.7 (m, 2H, C-5 $CH_2$), 3.16–3.27 (m, C-5 $CH_2$), 2.70 (s, 3H, $ArCH_3$), 2.63 (s, 3H, $ArCH_3$), 2.14 (s, 3H, $ArCH_3$), 1.5–1.7 (m, 4H, C-3 and C-4 CH2), 1.49 (s, 9H, Boc), 1.46 (s, 9H, Boc); IR (film) 1725.56, 1685.68, 1618.36, 1585.45, 1207.09, 1148.85 $cm^{-1}$; MS (ES+) m/e 699.4 ($M+H^+$).

Synthesis of Structure (43)

(43)

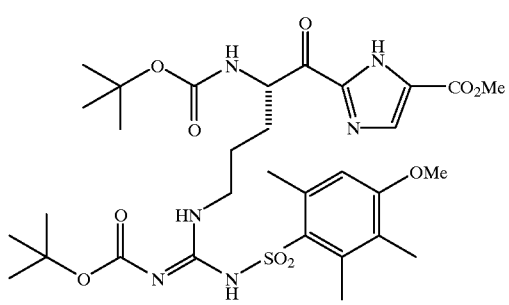

Structure (43) was synthesized as follows. In a 25 ml round-bottomed flask was placed the compound of structure (42) (230 mg, 0.33 mmol), $CHCl_3$ (5 ml) and $MnO_2$ (500 mg, 5.75 mmol, 17.4 eq). After stirring for 5 h the suspension was filtered and the solid washed with methanol. The solvent was removed in vacuo and the residue was dissolved in ethyl acetate (5 ml) and methanol (1 ml) and a fresh portion of $MnO_2$ (500 mg) was introduced and the reaction stirred for 15 h at room temperature. The solid was filtered and the solvent removed in vacua. The residue was purified via column chromatography on silica gel, eluting with 1:1 ethyl acetate:hexane, then pure ethyl acetate, then 1:9 methanol:ethyl acetate to obtain the desired product (structure (43), 190 mg, 83% yield) as an amorphous solid.: $R_f$ 0.64 (70:30-ethyl acetate:hexane); $^1H$ NMR (500 MHz, $CDCl_3$) δ10.70 (bs, 1H, imidazole NH), 9.70 (s, 1H), 8.28 (s, 1H), 7.84 (s, 1H), 6.54 (s, 1H, ArH), 5.35 (m, 1H, aH), 5.25 (s, 1H, BocNH), 3.926 (s, 3H), 3.840 (s, 3H), 3.15–3.40 (m, 2H), 2.682 (s, 3H), 2.133 (s, 3H), 1.52–1.70 (m, 4H), 1.470 (s, 9H), 1.424 (s, 9H); IR (film) 1724.68, 1619.03, 1277.72, 1151.93, 1120.61 $cm^{-1}$; MS (ES+) m/e 695.2 ($M+H^+$, 22), 717.2 ($M+Na^+$, 100).

Synthesis of Structure (44)

(44)

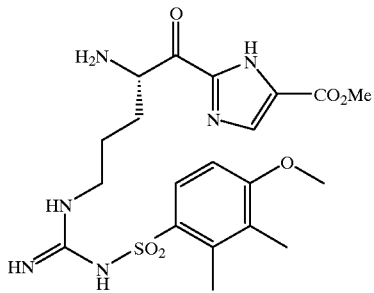

Structure (44) was synthesized by the same method used to construct structure (33) to structure (34). The product was used in the coupling without further purification.

Structure (44) was reacted with structure (9a) of Example 1 (in an analogous manner to the procedure described in Example 2 for the synthesis of structure (18)), followed by deprotection (in an analogous manner as described with respect to the deprotection of structure (19) respectively) to provide structure (45) as identified in Table 9 below. In the preparation of structure (45), the coupling step was performed with the carbonyl compound of structure (44), rather than with the analogous hydroxy compound.

Example 15

Synthesis of Representative β-Sheet Mimetics

This example illustrates the synthesis of a further representative β-sheet mimetic of this invention.

Synthesis of Structure (46)

(46)

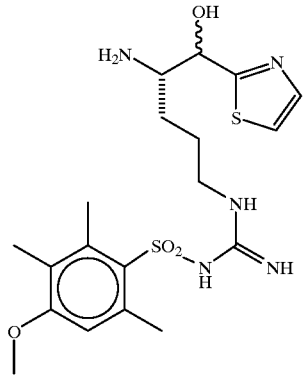

Structure (46) was synthesized in an analogous fashion to structure (17) starting from structure (16) and thiazole. This compound was used in the coupling step without further purification.

Structure (46) was reacted with structure (9a) of Example 1 (in an analogous manner to the procedure described in Example 2 for the synthesis of structure (18)), followed by oxidation and deprotection (in an analogous manner as described with respect to the oxidation and deprotection of structures (18) and (19), respectively) to provide structure (47) as identified in Table 9 below.

Example 16

Synthesis of Representative β-Sheet Mimetics

This example illustrates the synthesis of a further representative β-sheet mimetic of this invention.

Synthesis of Structure (48)

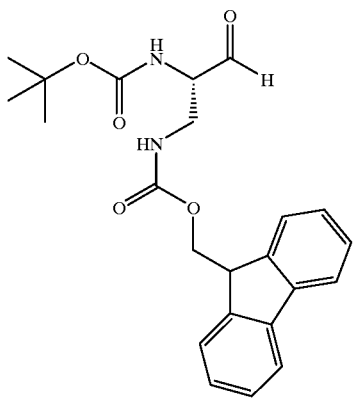

(48)

To a solution of α-Boc-β-Fmoc-2,3-diaminopropionic acid (818 mg, 1.92 mmol) stirred in THF (5 ml) at −25° C. was added 4-methylmorpholine (0.23 ml, 2.1 mmol) followed by isobutylchloroformate (0.25 ml, 1.9 mmol). The resulting suspension was stirred for 5 minutes and then filtered with the aid of 5 ml of THF. The filtrate was cooled in an ice/water bath then sodium borohydride (152 mg, 0.40 mmol) dissolved in water (2.5 ml) was added dropwise. The mixture was stirred for 15 minutes then water (50 ml) was added and the mixture was extracted with $CH_2Cl_2$ (3×50 ml). The combined extracts were washed with brine, dried over anhydrous sodium sulfate and filtered. Concentration of the filtrate under vacuum yielded a pale yellow solid that was purified by flash chromatography (50% ethyl acetate/hexanes eluent) to give 596 mg of the alcohol as a white solid.

The alcohol (224 mg, 0.543 mmol) was dissolved in methylene chloride and Dess-Martin periodinane (262 mg, 0.64 mmol) was added. The mixture was stirred at room temperature for 1 h then diluted with ethyl acetate (50 ml) and extracted sequentially with 10% aqueous $Na_2S_2O_3$, saturated aqueous $NaHCO_3$, and brine. The organic solution was dried over anhydrous sodium sulfate, filtered and concentrated under vacuum to a white solid. Purification of the solid by flash chromatography yielded 169 mg of the aldehyde structure (48) as a white solid.

Synthesis of Structure (49)

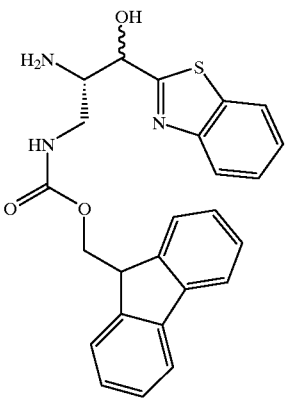

(49)

Structure (49) was synthesized in an analogous fashion to structure (17) starting from structure (48) and benzothiazole. This compound was used as a 1:1 mixture of diastereomers in the coupling step (described below) without further purification. MS (EI+): m/z 446.4 (M+H$^+$).

Synthesis of Structure (50)

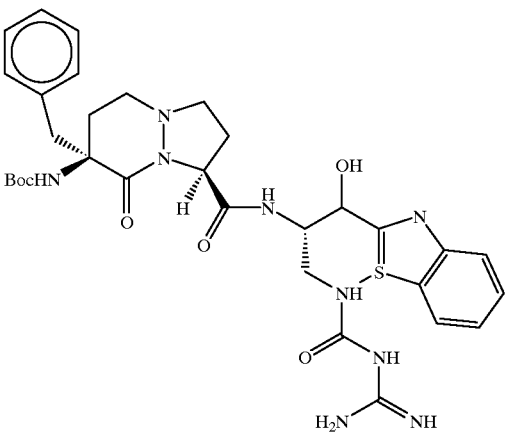

(50)

Structure (49) and bicyclic acid structure (9a) (27 mg, 0.069 mmol) and HOBt hydrate (71 mg, 0.46 mmol) were dissolved in THF (1 ml) and diisopropylethylamine (0.0.059 ml, 0.34 mmol) was added followed by EDC (19 mg, 0.099 mmol). The mixture was stirred at room temperature for 20 h then diluted with ethyl acetate and extracted sequentially with 5% aqueous citric acid, saturated aqueous sodium bicarbonate, water and brine. The organic solution was dried over anhydrous sodium sulfate, filtered and concentrated under vacuum to 61 mg of a yellow foam. $^1$H NMR analysis indicated a mixture of diastereomeric amides.

The foam was dissolved in $CH_3CN$ and diethylamine was added. The solution was stirred at room temperature for 30 minutes then concentrated under vacuum to a yellow foam. The foam was rinsed with hexanes and dissolved in DMF (0.5 ml). In a separate flask, carbonyldiimidazole (16 mg, 0.99 mmol) and guanidine hydrochloride (10 mg, 0.10 mmol) were dissolved in DMF (1 ml) and diisopropylethylamine (0.035 ml, 0.20 mmol) was added followed by DMAP (1 mg). The solution was stirred for 1.5 h at room temperature then the solution of amine was added and stirring was continued for 16 h. The solution was concentrated under vacuum then water was added to the residue and the mixture was extracted with ethyl acetate (3×25 ml) The combined extracts were washed with brine, dried over anhydrous sodium sulfate and filtered. Concentration of the filtrate under vacuum yielded 58 mg of structure (50) as a yellow foam. MS (ES+): m/z 680.6 (M+H$^+$).

Structure (50) was oxidized to provide the corresponding ketone of structure (51).

Example 17

Activities of Representative β-Sheet Mimetics as a Protease Inhibitor

This example illustrates the ability of further representative δ-sheet mimetics of this invention to function as an inhibitor for thrombin, Factor VII, Factor X, Factor XI, tryptase, aPC, plasmin, tPA, urokinase thrombin thrombomodulin complex and trypsin. The β-sheet mimetics of the structures listed in Table 9 had the inhibition activities shown in Table 10.

The proteinase inhibitor assays were performed as described in Example 9. The assay for thrombin-thrombomodulin complex was conducted as for thrombin except that prior to the addition of inhibitor and substrate, thrombin was preincubated with 4 nM thrombomodulin for 20 minutes at room temperature.

TABLE 9

Structures, Synthetic Precursors, and Physical Data for Various Serine Protease Inhibitors

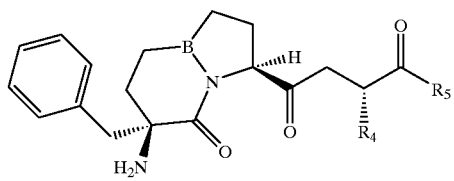

| Structure Number | B$^δ$ | R$_4$ | R$_5$ | Precursor | M.S (ES+) | HPLC* R.T. (min) |
|---|---|---|---|---|---|---|
| (47) | N | 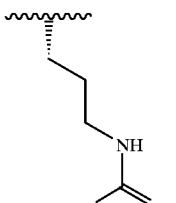 | 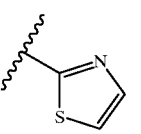 | (46) | 513.5 (M + H$^+$) | 15.9 |
| (20b) | N | 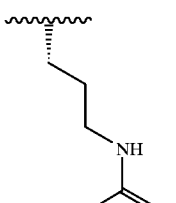 | 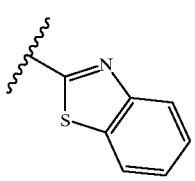 | (17) | 563.5 (M + H$^+$) | 17.9 |
| (37) | N | 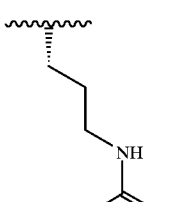 | 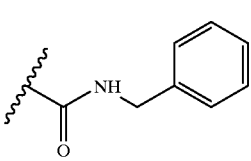 | (36) | 563.6 (M + H$^+$) | 16.9 |

TABLE 9-continued

Structures, Synthetic Precursors, and Physical Data for
Various Serine Protease Inhibitors

| Structure Number | B[b] | R₄ | R₅ | Precursor | M.S (ES+) | HPLC* R.T. (min) |
|---|---|---|---|---|---|---|
| (39) | N | –(CH₂)₃–NH–C(=NH)–NH₂ | –C(=O)–NH–CH₂CH₂–(4-Cl-C₆H₄) | (38) | 611.3 (M + H⁺) | 19.8 |
| (29a)[e] | CH | –(CH₂)₃–NH–C(=NH)–NH₂ | 2-benzothiazolyl | (17) | 562.4 (M + H⁺) | 21.2 |
| (35) | N | –(CH₂)₃–NH–C(=NH)–NH₂ | –C(=O)–NH–CH₂CH₂–C₆H₅ | (34) | 577.4 (M + H⁺) | 18.1 |
| (45) | N | –(CH₂)₃–NH–C(=NH)–NH₂ | methyl imidazole-carboxylate | (44) | 554.2 (M + H⁺) | 15.7 |
| (51) | N | –CH₂–NH–C(=O)–NH–C(=NH)–NH₂ | 2-benzothiazolyl | (49) | 578.3 (M + H⁺) | 22.3 |

TABLE 9-continued

Structures, Synthetic Precursors, and Physical Data for Various Serine Protease Inhibitors

| Structure Number | B[b] | R₄ | R₅ | Precursor R₄, R₅ | M.S (ES+) | HPLC* R.T. (min) |
|---|---|---|---|---|---|---|
| (29b) | CH | (guanidino-propyl) | (benzothiazol-2-yl) | (17) | FAB 562.4 (M + H⁺) | 21.5 |
| (41) | N | (guanidino-propyl) | (N-(4-methoxyphenethyl)acetamide) | (40) | 607.4 (M + H⁺) | 18.2 |
| (13) | N | (guanidino-propyl) | CH₂Cl | Arg(Mtr)—CH₂Cl | 477.9 (M + H⁺) | 14.9 |

[b]The stereochemistry of the template for B = CH is (3R, 6R, 9S) except where noted (see footnote e).
[e]Template stereochemistry is (3S, 6R, 9S).
*HPLC was performed on a reverse phase C-18 column using a gradient of 0–90% acetonitrile/water, 0.1% TFA.

TABLE 10

Ki (M) Inhibition Activity of Various Compounds Against Serine Proteases

| Structure Number | Thrombin | Factor VII | Factor X | Factor XI | Urokinase | T.T.C.[a] | aPC[b] | Plasmin | tPA[c] | Trypsin | Tryptase |
|---|---|---|---|---|---|---|---|---|---|---|---|
| 35 | 7.10E−11 | 1.64E−08 | 3.45E−07[e] | | | | | | | 2.70E−11 | |
| 37 | 7.32E−11 | | | | | | | | | 7.73E−11 | |
| 29b | 8.50E−11 | 2.00E−07 | 1.93E−08 | 7.53E−08 | 3.35E−07 | 8.80E−11 | 1.25E−06 | 2.51E−07 | 9.29E−08 | 2.30E−10 | 9.00E−09 |
| 39 | 3.10E−10 | | | | | | | | | | |
| 41 | 4.50E−10 | | | | | | | | | | |
| 20b | 6.50E−10 | 2.70E−07 | 2.22E−07 | 2.70E−08 | 6.00E−07 | | 3.32E−06 | 4.15E−07 | 4.95E−07 | 6.20E−10 | 1.24E−08 |
| 47 | 2.40E−09 | 9.68E−07 | 1.50E−06[e] | | | | | | | 1.90E−09 | |
| 45 | 5.40E−09 | 2.96E−05 | 3.80E−05 | 1.24E−06 | | 6.90E−09 | 2.56E−05 | 2.38E−05 | 1.72E−05 | 5.24E−08 | 1.65E−06 |
| 51 | 7.25E−09 | 4.26E−06 | 5.70E−05 | 1.73E−06 | | | | | | 3.79E−08 | |

TABLE 10-continued

Ki (M) Inhibition Activity of Various Compounds Against Serine Proteases

| Structure Number | Thrombin | Factor VII | Factor X | Factor XI | Urokinase | T.T.C.[a] | aPC[b] | Plasmin | tPA[c] | Trypsin | Tryptase |
|---|---|---|---|---|---|---|---|---|---|---|---|
| 29a | 1.04E−08 | 1.77E−06 | 4.65E−06[e] | 3.91E−07 | | | | | | 5.40E−10 | |
| 13[d] | 1.20E−09 | 1.40E−07 | 3.86E−07[e] | | 9.27E−07 | | 5.28E−07 | 9.78E−07 | 6.32E−07 | 1.60E−07 | |

[a]Thrombin thrombomodulin complex,
[b]activated Protein C,
[c]tissue Plasminogen Activator,
[d]IC50,
[e]bovine plasma

Example 18

Figure 2:
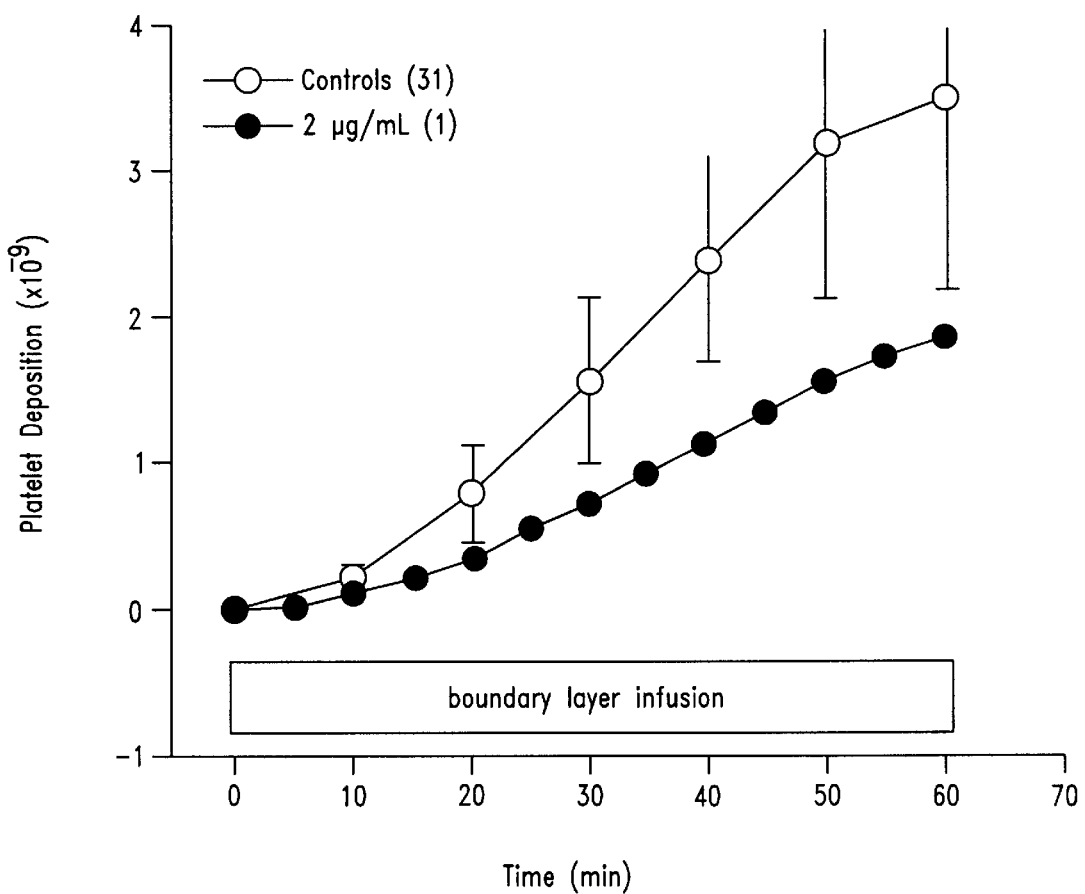
FIG. 2 is a plot showing the effect of various concentrations of structure (39) on platelet deposition in a vascular graft.
Figure 3:
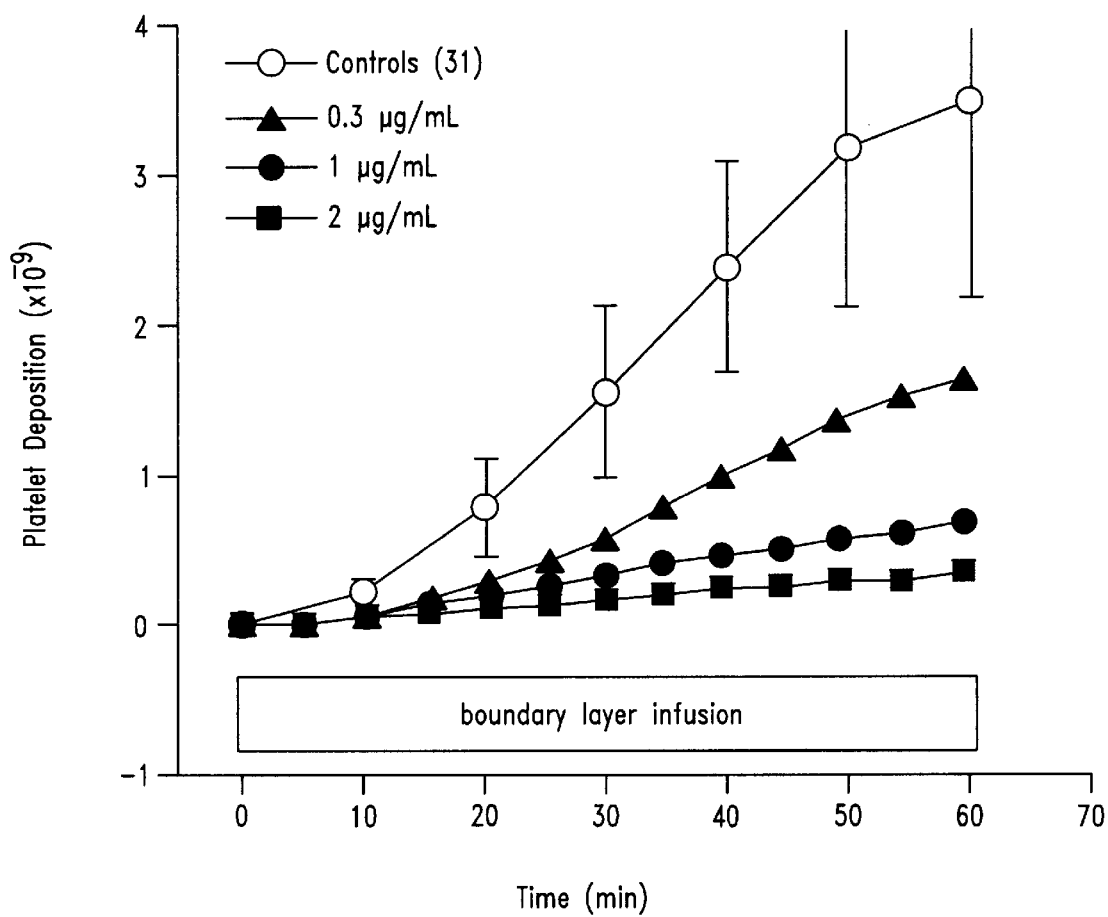
FIG. 3 is a plot showing the effect of various concentrations of structure (29b) on platelet deposition in a vascular graft.

Effect of Representative β-Sheet Mimetics on Platelet Deposition in a Vascular Graft The effect of compounds of the invention on platelet deposition in a vascular graft, was measured according to the procedure of Hanson et al. "Interruption of acute platelet-dependent thrombosis by synthetic antithrombin D-phenylalanyl-L-prolyl-L-arginyl chloromethylketone" *Proc. Natl. Acad. Sci., USA* 85:3148–3188, (1988), except that the compound was introduced proximal to the shunt as described in Kelly et al., *Proc. Natl. Acad. Sci., USA* 89:6040–6044 (1992). The results are shown in FIGS. 1, 2 and 3 for structures (20b), (39) and (29b), respectively.

Example 19

Synthesis of Representative β-Sheet Mimetics

This example illustrates the synthesis of a further representative β-sheet mimetic of this invention having the structure shown below.

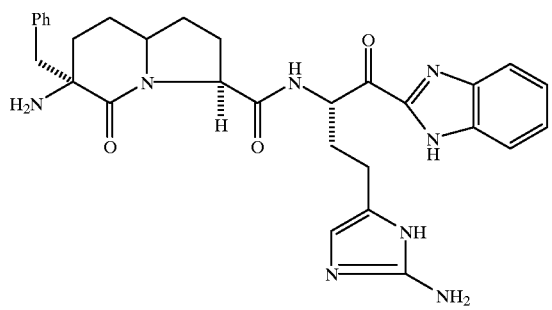

(52)

Structure (52) may be synthesized employing the following intermediate (53) in place of intermediate (16) in Example 2:

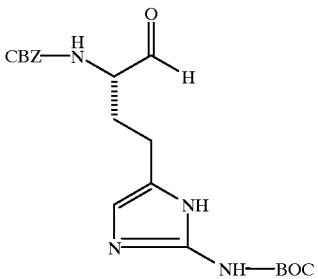

(53)

Intermediate (53) may be synthesized by the following reaction scheme:

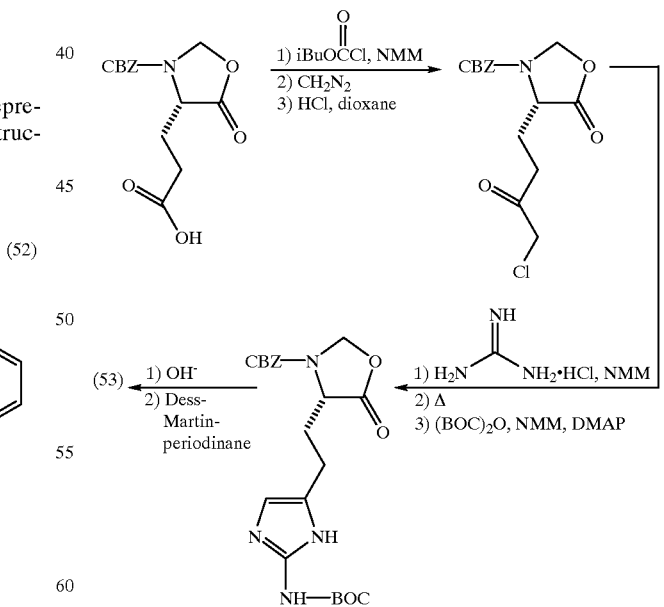

Alternatively, intermediate (53) may be synthesized by the following reaction scheme:

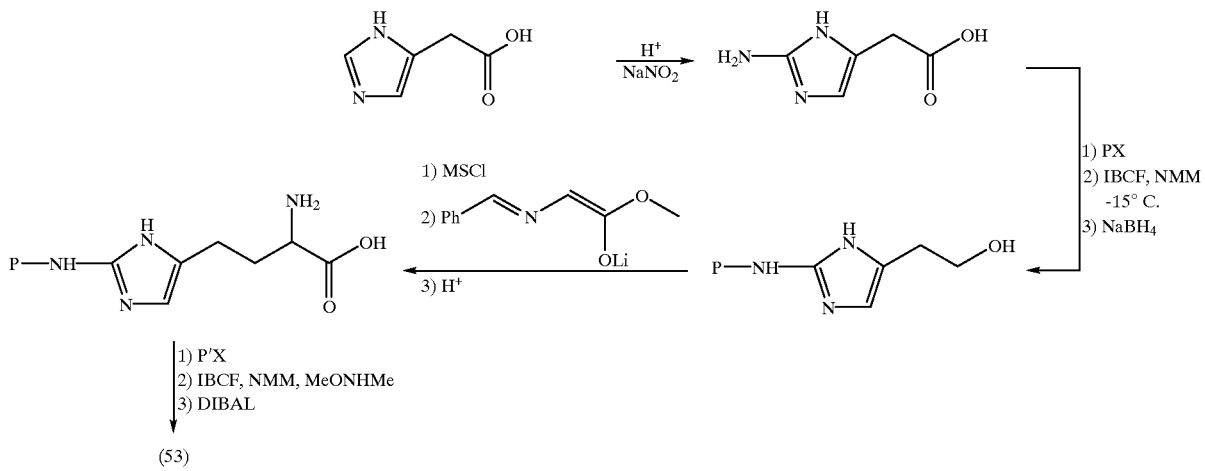

(53)

Example 20

Representative β-Sheet Mimetics Which Bind to MHC I and MHC II

The following structures (54), (55) and (56) were synthesized by the techniques disclosed herein.

The ability of structures (54) and (55) to bind to MHC I molecules can be demonstrated essentially as described by Elliot et al. (*Nature* 351:402–406, 1991). Similarly, the ability of structure (56) to bind to MHC II molecules can be demonstrated by the procedure of Kwok et al. (*J. Immunol.* 155:2468–2476, 1995).

(54)

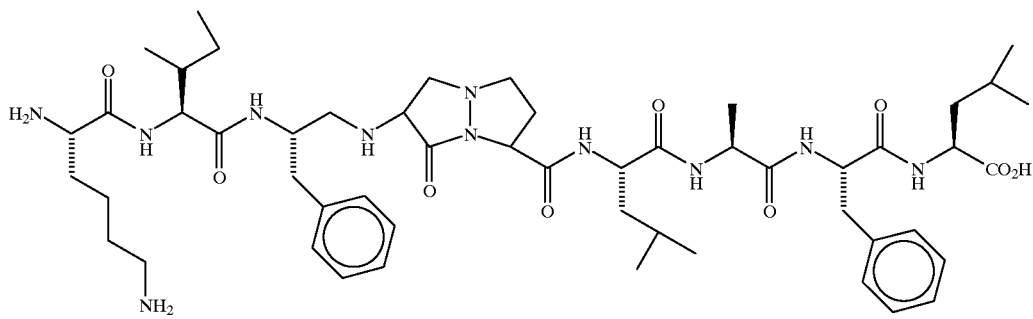

MS ES (+) 510 (M + 2H$^+$)$^{2+}$; HPLC R$_t$ 22.10' (0–90% acetonitrile/H$_2$O, 0.1% TFA)

(55)

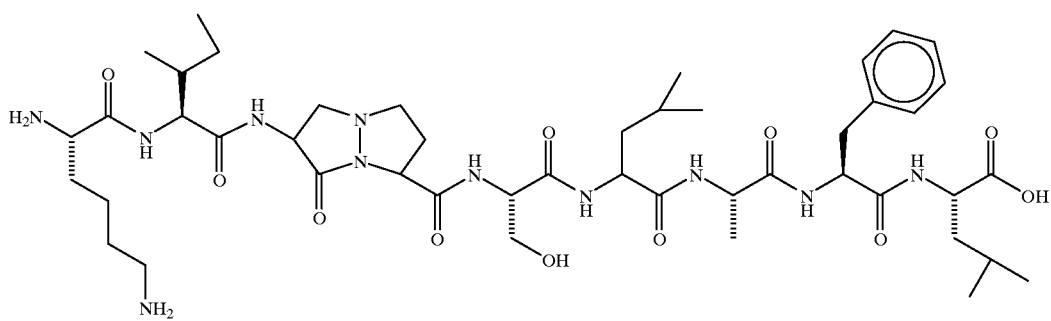

MS ES (+) 510 (MH$^+$)$^+$; HPLC R$_t$ 22.37' (0–90% acetonitrile/H$_2$O, 0.1% TFA)

-continued
(56)
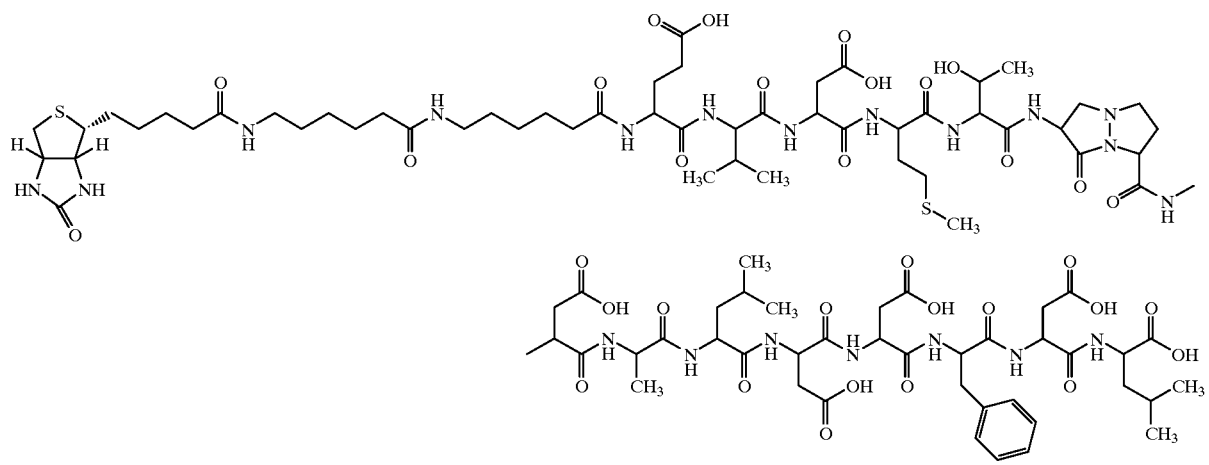
MS ES (-) 704.9 (M-3H⁺)³⁻; HPLC $R_t$ 22.39' (0–90% acetonitrile/H$_2$O, 0.1% TFA)
Example 21
Representative β-Sheet Mimetics Which Bind The SH2 Domain
The following structure (57) was synthesized, and structure (58) may be synthesized, by the techniques disclosed herein.
SH-PTP1
(57)
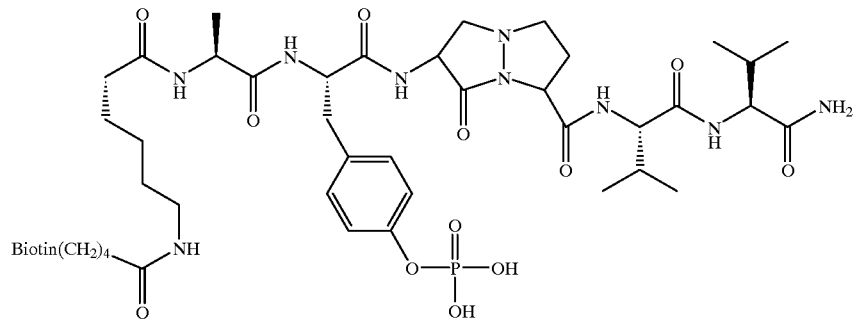
MS ES (-) 104.3 (M - H⁺)⁻; HPLC $R_t$ 17.28' (0–90% acetonitrile/H$_2$O, 0.1 TFA)
(58)
STAT6
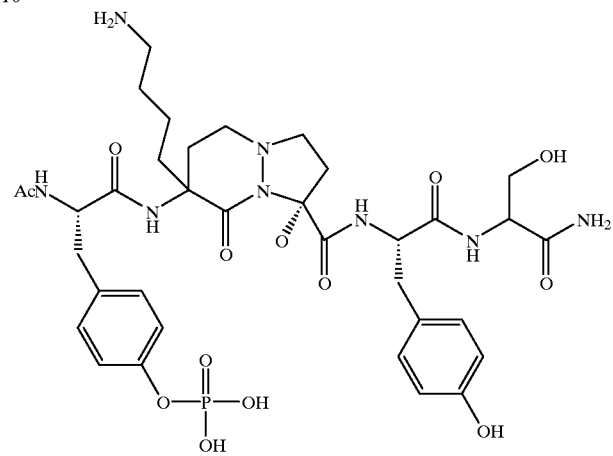

The ability of structure (58) to bind to the SH2 domain of STAT6, or of structure (57) to bind the SH2 domain of the protein tyrosine phosphatase SH-PTP1 can be demonstrated by the procedures disclosed by Payne et al. (*PNAS* 90:4902–4906, 1993). Libraries of SH2 binding mimetics may be screened by the procedure of Songyang et al. (*Cell* 72:767–778, 1993).

Example 22
Representative β-Sheet Mimetics Which Bind Protein Kinases

The following structure (59) may be synthesized by the techniques disclosed herein.

(59)

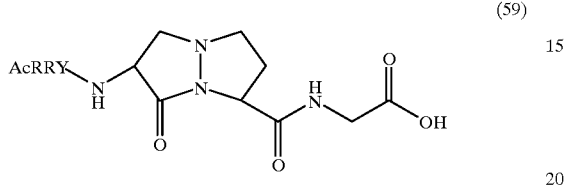

The ability of structure (59) to act as a substrate or inhibitor of protein kinases may be demonstrated by the procedure of Songyang et al. (*Current Biology* 4:973–982, 1994).

Example 23
Synthesis of Representative β-Sheet Mimetics

This example illustrates the synthesis of representative β-sheet mimetics of this invention having the following structures (60) through (63), wherein B is N or CH:

(60)

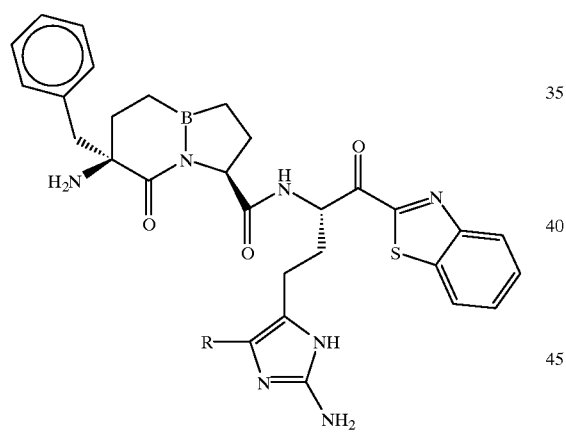

(61)

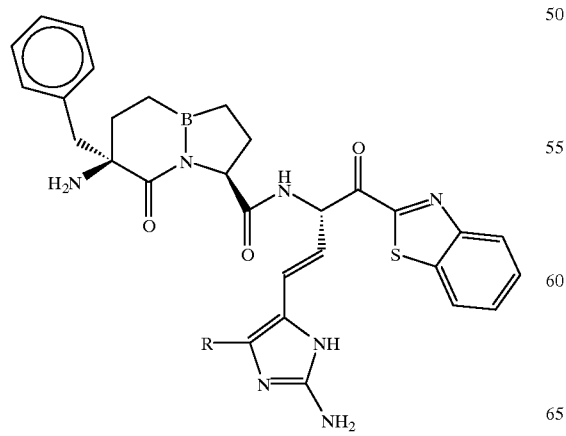

(62)

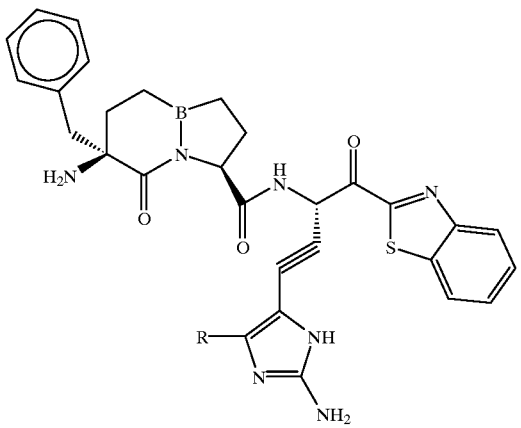

(63)

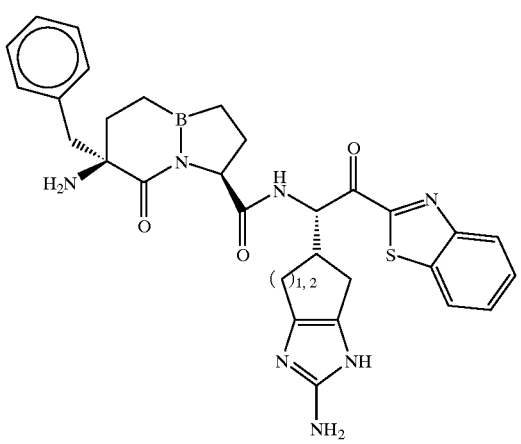

Synthesis of structure (60)

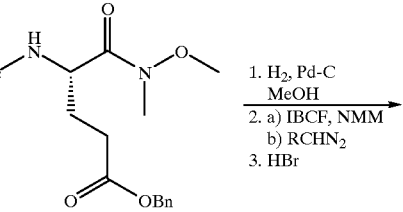

1. H$_2$, Pd-C
   MeOH
2. a) IBCF, NMM
   b) RCHN$_2$
3. HBr

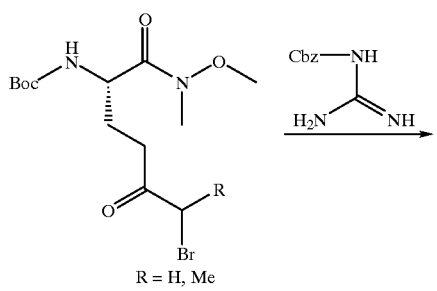

R = H, Me

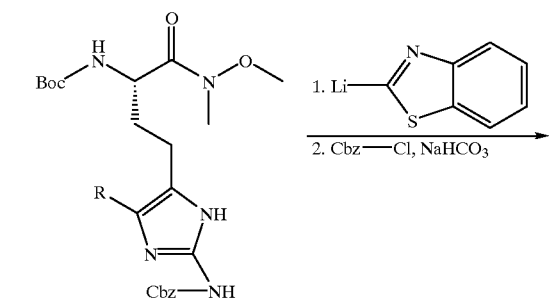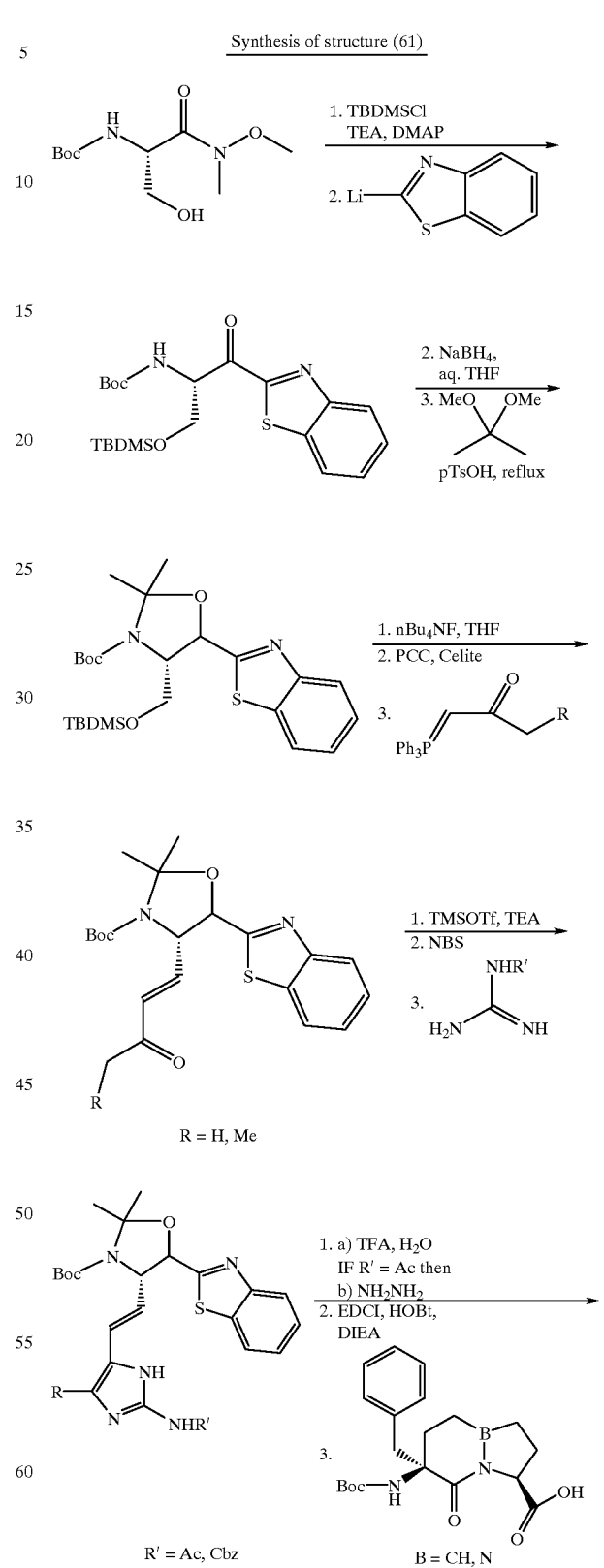

141
-continued
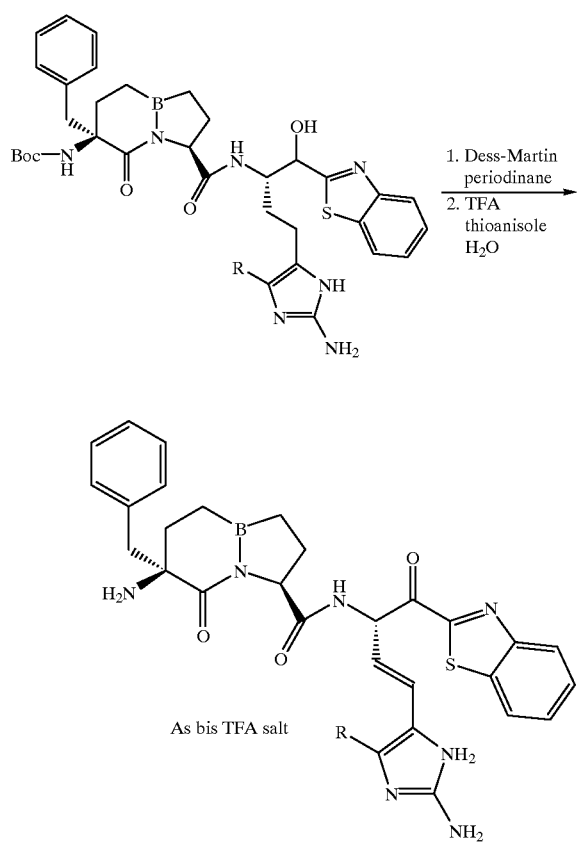
Alternative synthesis of structure (61)
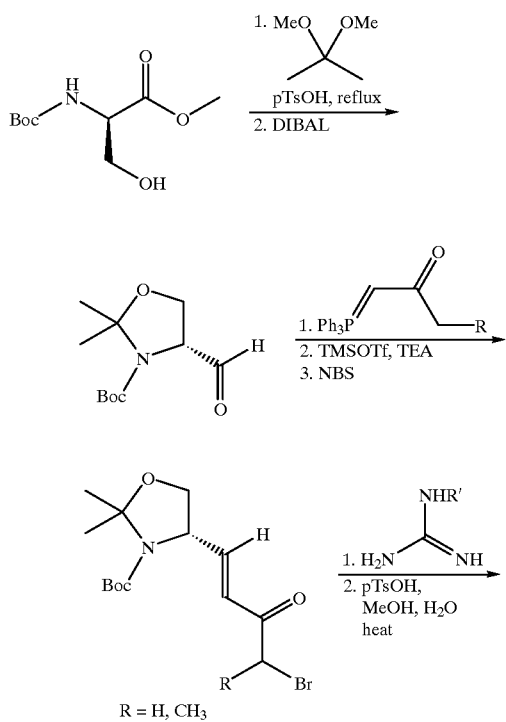
142
-continued
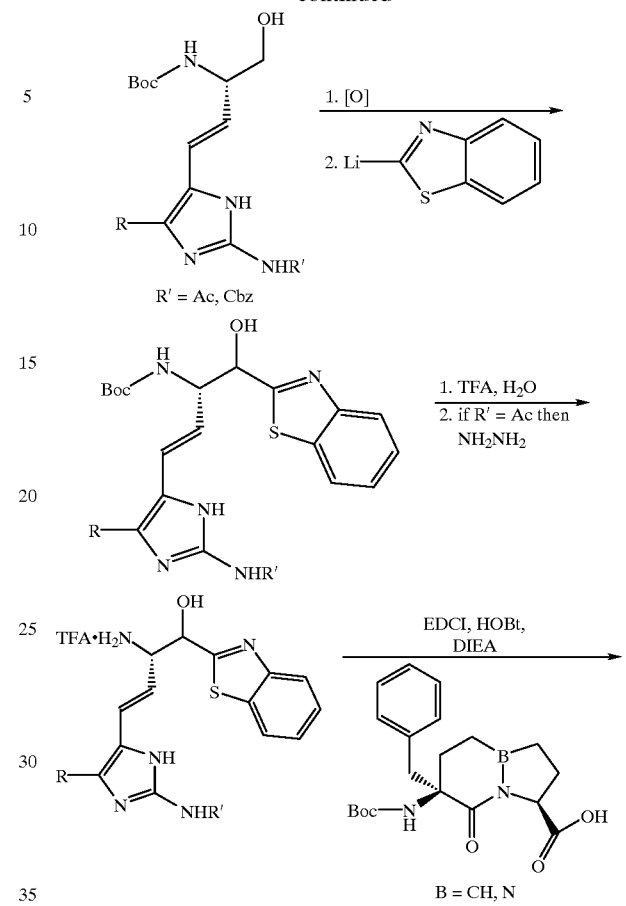
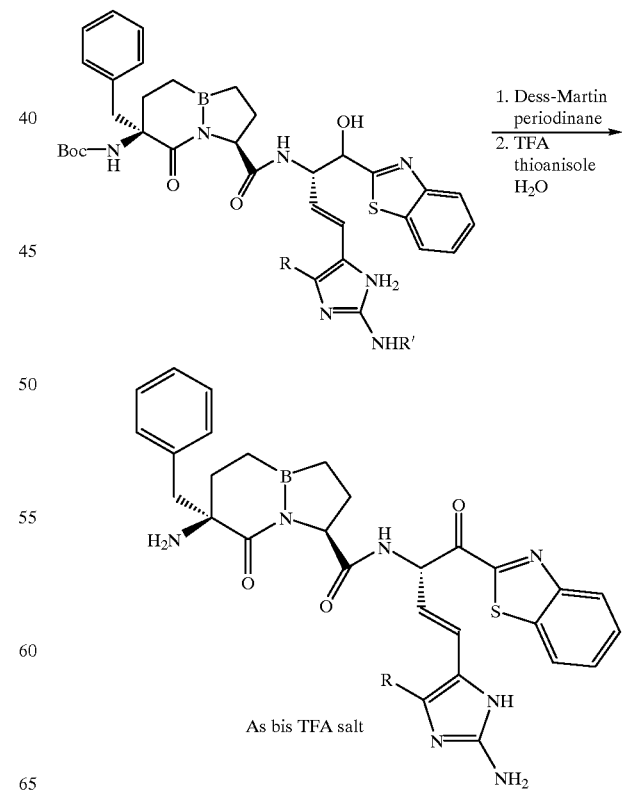

Synthesis of structure (62)
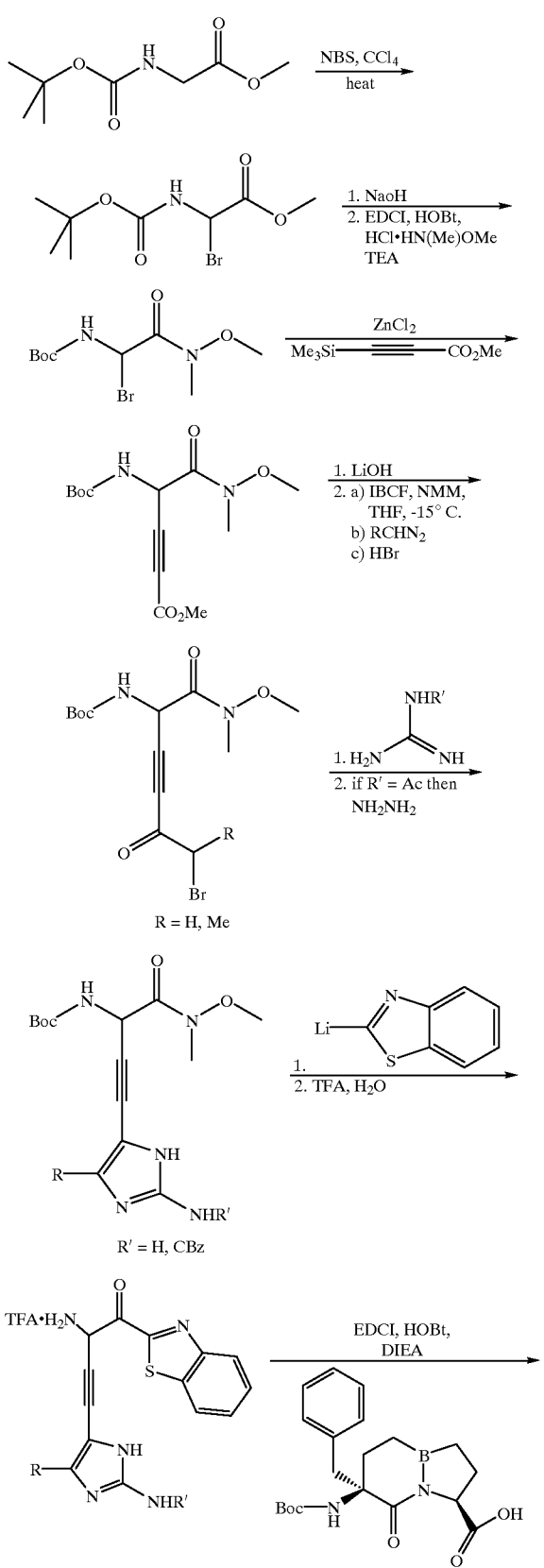
Alternative synthesis of structure (62)
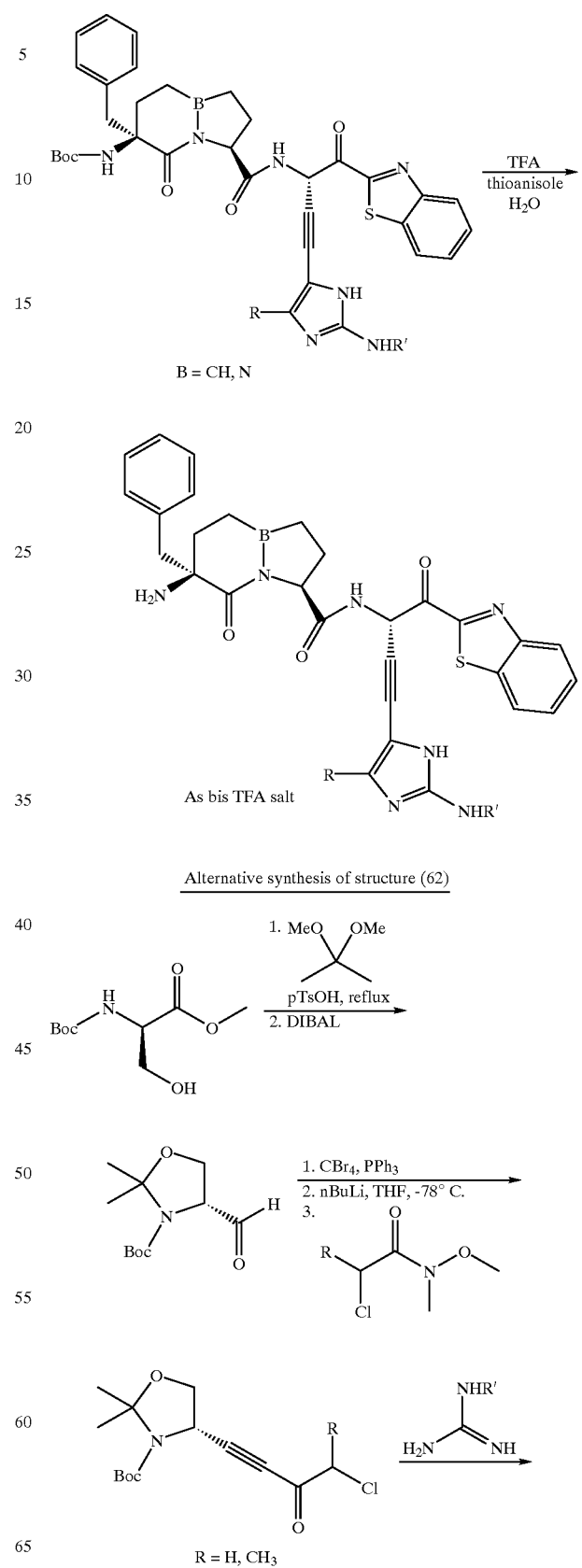

145
-continued
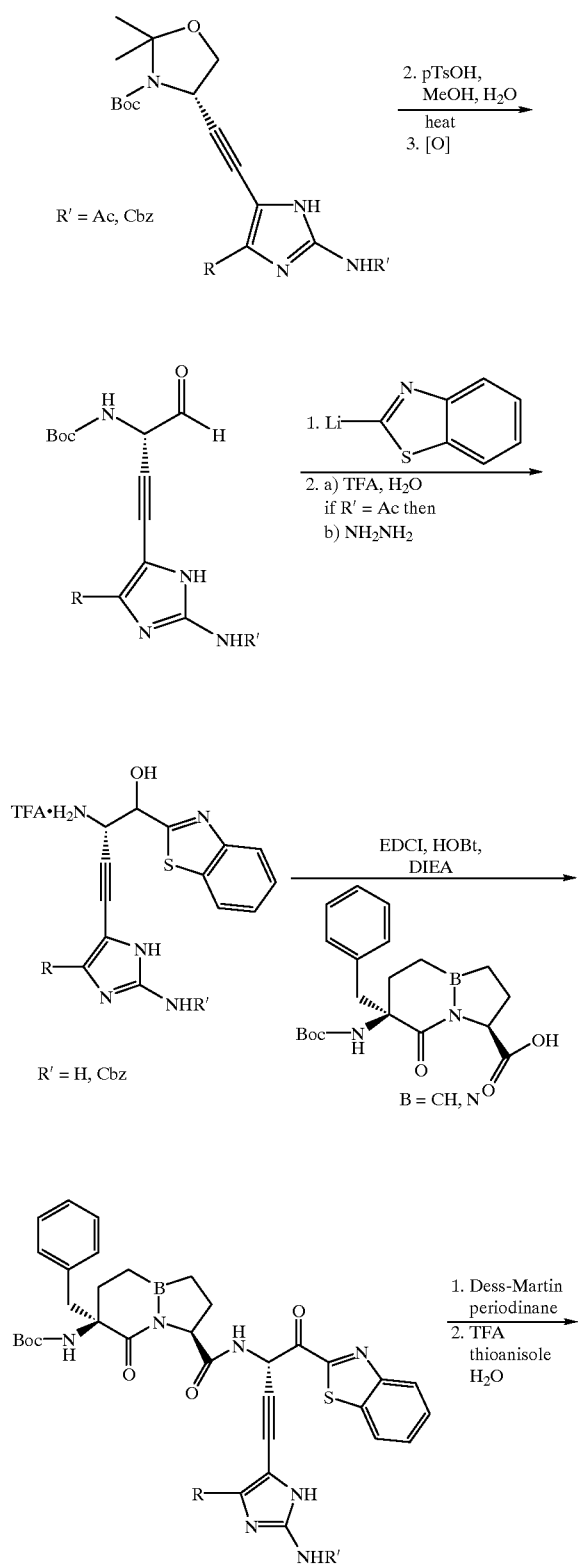
146
-continued
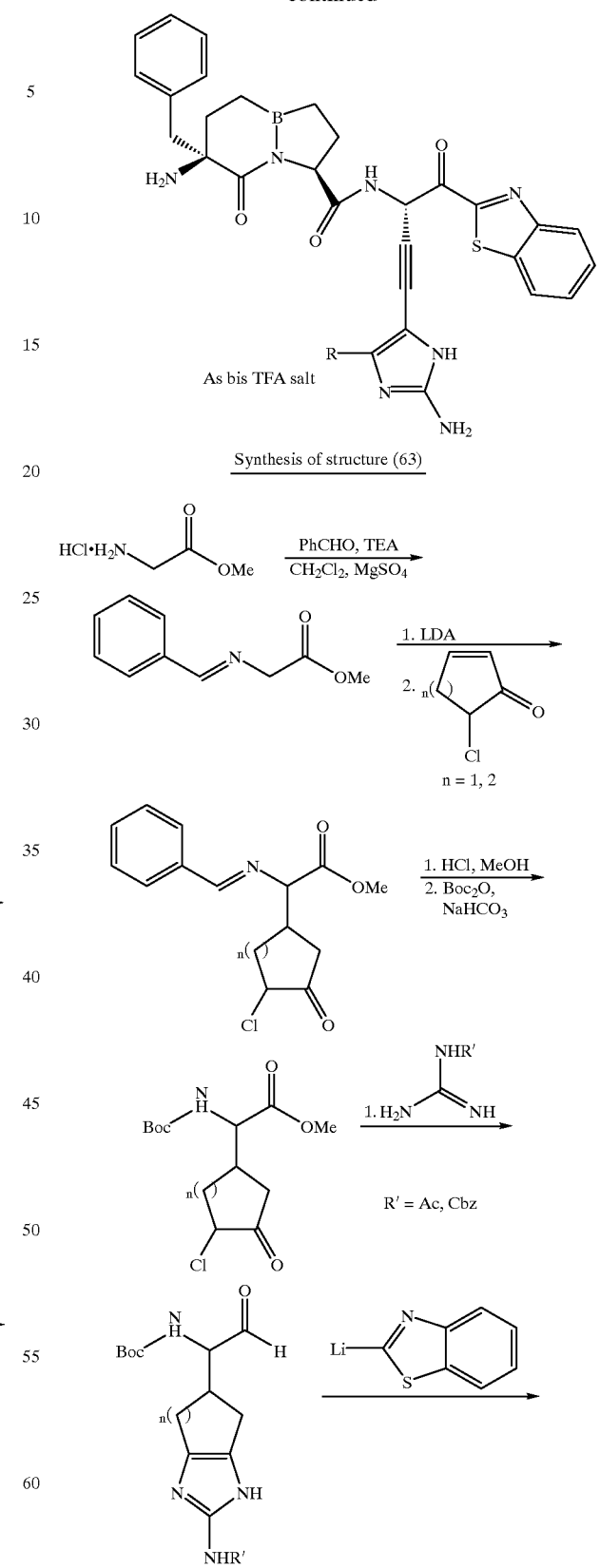
Synthesis of structure (63)

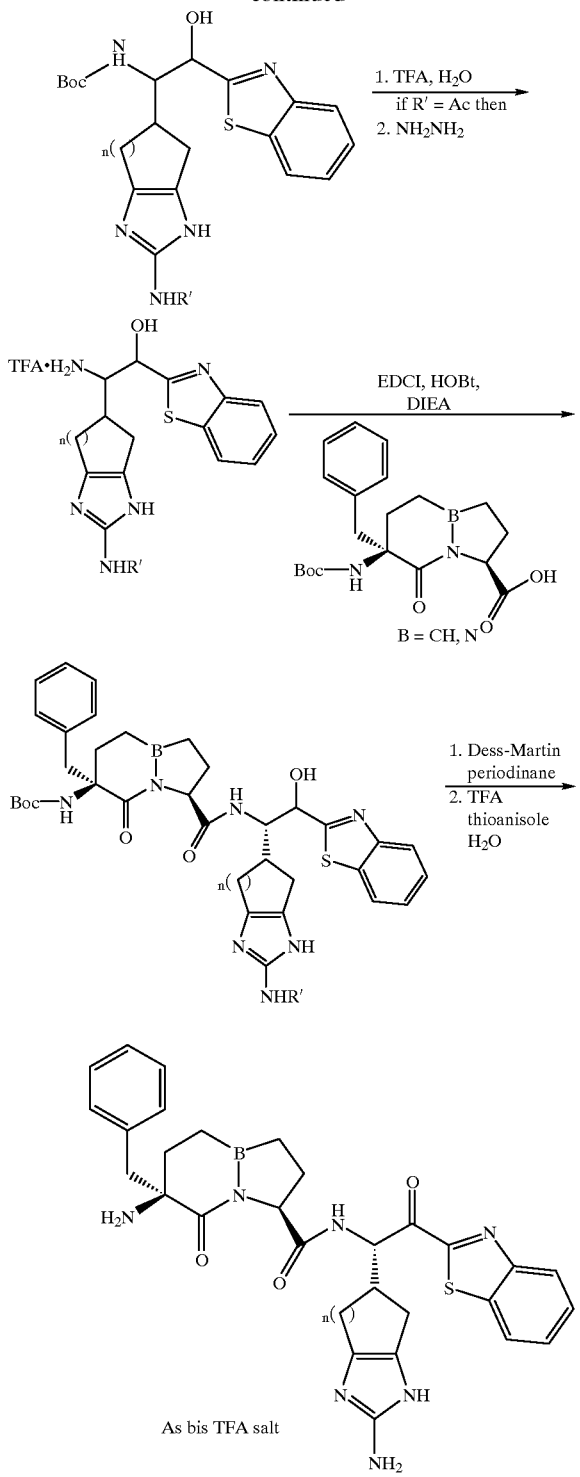

Figure 4A:
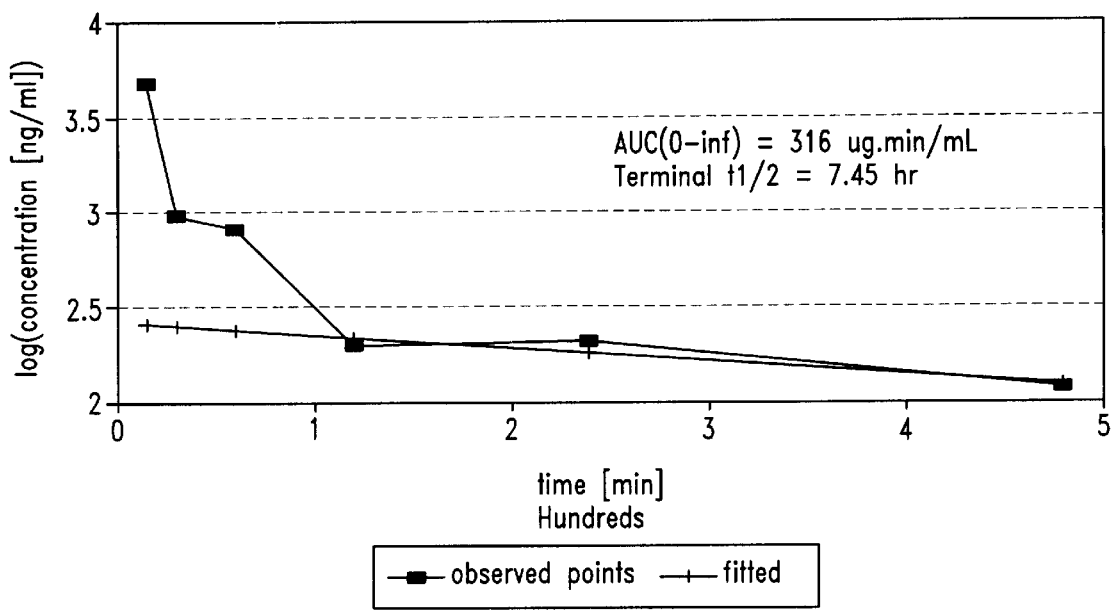
FIGS. 4A and 4B illustrate the bioavailability of structure (20b) via both IV and PO administration.
Figure 4B:
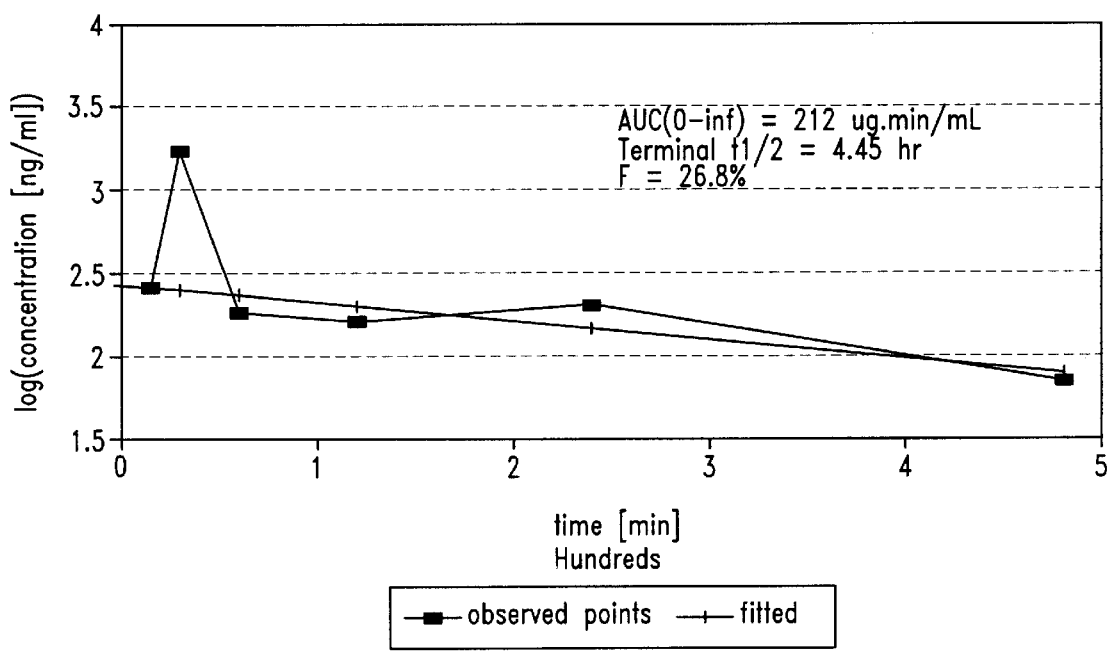

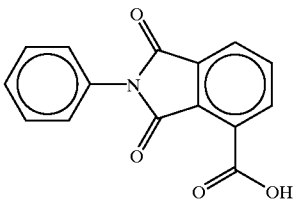

structure (20b) at 4 mg/kg intravenously (IV) or 10 mg/kg orally (PO). Groups of rats (n=3 or 4) were sacrificed and exsanguinated at 0.25, 0.5, 1, 2, 4 and 8 hours following dosing. Efficacy parameters, aPTT and TT, were measured for each plasma sample. Concentrations of structure (20b) in plasma were determined by a trypsin inhibition assay. The results of this experiment are presented in FIGS. 4A and 4B for dosing of 4 mg/kg IV and 10 mg/kg PO, respectively. The data presented in FIGS. 4A and 4B illustrate in vivo efficacy of structure (20b) via both IV and PO administration. Non-compartmental pharmacokinetic analysis of mean structure (20b) concentration values demonstrate terminal halflives of 7.5 hr (IV) and 4.5 hr (PO). The bioavailability of orally administered structure (20b) is approximately 27%.

Example 25

Synthesis of Representative β-Sheet Mimetics

This example illustrates the synthesis of a further representative β-sheet mimetics of this invention having the structure shown below.

Synthesis of Structure (64)

(64)

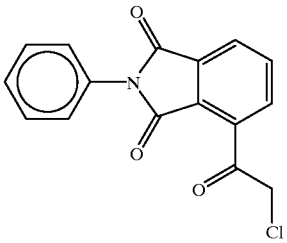

Structure (64) was synthesized as follows. A 150 ml round bottom flask was charged with 5.19 grams (24.7 mmol) of 1,2,3-benzene tricarboxylic acid, 75 ml of toluene, and 3.3 mL (24.7 mmol) of triethyl amine. The reaction was heated at reflux for 3 hours with the azeotropic removal water. At this time 2.07 ml of aniline was added, and the reaction again refluxed for six hours with the azeotropic removal of water. Upon cooling the reaction solution a crystalline product formed and was filtered off (4.68 g). The solution was then extracted with $NaHCO_3$ and ethyl acetate, and the bicarbonate layer acidified and reextracted with a second EtOAc wash. The organic layer was dried over $NaSO_4$, filtered, and the solvent removed to give an additional 1.24 grams of product. The total yield was 5.92 g (82%). $^1$H NMR (CDCl$_3$) δ7.41, (d, 2H, J=10 Hz), 7.48 (t, 1H, J=10 Hz), 7.55 (t, 2H, J=10 Hz), 7.98 (t, 1H, J=10 Hz ), 8.20 (d, 1H, J=10 Hz), 8.70 (d, 1H, J=10 Hz); MS (ES-): 266 (M-H$^+$).

Synthesis of Structure (65)

(65)

Example 24

Bioavailability of Representative β-Sheet Mimetics

This example illustrates the bioavailability of the compound of structure (20b) as synthesized in Example 2 above, and having the biological activity reported in Example 9 above.

Specifically, a pharmacodynamic and pharmacokinetic study of structure (20b) was conducted in male Sprague Dawley rats. Rats were administered a saline solution of Structure (65) was synthesized as follows. The imide-acid of structure (64) (53.4 mg, 0.2 mmol) in THF (2 ml) was cooled to −40° C. and treated with 24.2 μl (0.22 mmol) of NMM and 28.2 μl IBCF (0.22 mmol). The reaction was stirred for 3 minutes and then 0.69 ml (0.69 mmol) of a 1 M solution of diazomethane in ether was added. The temperature was slowly raised to −20 degrees, and the reaction stirred for 2 h at this temperature. The reaction was warmed to 0° C. and stirred for 3 h more.

The reaction was diluted with EtOAc (30 ml) and the organic phase washed with 5% citric acid, NaHCO$_3$, and saturated NaCl. It was then dried over Na$_2$SO$_4$ and concentrated to give 62.4 mg of residue. This crude product was dissolved in THF, cooled to −40° C., and treated with 74 ul of a 4 M solution of HCl in dioxane. The reaction was warmed to −20° C. and stirred for 1 h. Subsequently the reaction was stirred for 2 h at 0° C. TLC of the reaction mixture at this pointed showed disappearance of the starting diazoketone. The solvent was removed, and the product purified by preparative TLC (EtOAc/hexanes, 7/3) to give 22.6 mg (38%) of pure chloromethylketone. $^1$H NMR (CDCl$_3$) δ4.93 (s, 2H), 7.35–7.60 (m, 5H), 7.9 (m, 2H), 8.12 (dd, 1H, J=9, 1.8 Hz); MS (EI): 299.1 (M$^+$), 264.0 (M$^+$−Cl), 250.2 (M$^+$−CH$_2$Cl).

Synthesis of Structure (66)

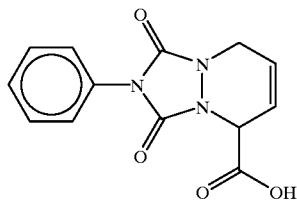

(66)

Structure (66) was synthesized as follows. To a stirred suspension of 910 mg (5.14 mmol) of 4-phenyl urazole in 50 ml of methylene chloride, was added 1.654 g (5.14 mmol) of iodobenzene diacetate. A deep red color developed, and with stirring, all material went into solution. After stirring for 15 minutes at room temperature, 560 mg of 90% pure 2,4-penatdienoic acid was added and the color gradually faded as a white solid formed. After fifteen minutes an additional 70 mg of pentadienoic acid was added. After stirring for 2 h at room temperature, the methylene chloride was removed under reduced pressure. Ether was added (25 ml) and the resulting suspension was cooled to −20° C. and solid material (1.41 g, 100%) filtered off. The product could be recrystallized from EtOAc/cyclohexane. $^1$H NMR (CDCl$_3$) δ4.04, (d, 1H, J=20 Hz), 4.40 (d, 1H, J=20 Hz), 5.17 (s, 1H), 6.13 (m, 2H) 7.4–7.5 (m, 5H); MS (ES−): 271.9 (M−H$^+$), 228.1 (M−CO$_2$H).

Synthesis of Structure (67)

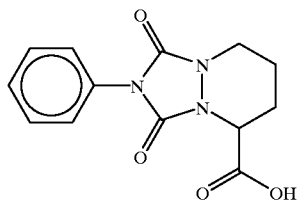

(67)

Structure (67) was synthesized as follows. The Diels-Alder adduct of structure (66) (432 mg, 1.57 mmol) was mixed with 150 mg 10% Pd/C in 50 ml MeOH. The reaction was stirred overnight under a hydrogen atmosphere (hydrogen balloon). After 18 h, an aliquot (1 ml) was removed and the solvent evaporated under reduced pressure. $^1$H NMR of the residue showed greater than 95% conversion to the saturated product. The reaction mixture was filtered through celite, and the solvent removed via rotary evaporator, to give 424 mg of crystalline product. $^1$H NMR (CDCl$_3$) δ1.72 (m, 1H), 1.91 (m, 1H), 2.02 (m, 1H), 2.31 (m, 1H) 3.18 (m, 1H), 4.18 (d, 1H, J=10 Hz), 4.88 (d, 1H, J=12 Hz), 7.35–7.5 (m, 5H); MS (ES−) 274 (M−H$^+$).

Synthesis of Structure (68)

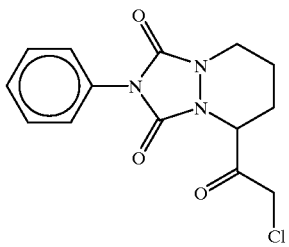

(68)

Structure (68) was synthesized as follows. To a solution of 450 mg (1.64 mmol) of (67) in 40 ml of methylene chloride was added 142 μL of oxalyl chloride (1.64 mmol) and a drop of DMF. The reaction was stirred at room temperature overnight under Ar. The methylene chloride was removed via rotary evaporator and 30 ml of THF added. This solution was cooled to −20 degrees and 2 ml of a 1 M solution of diazomethane in ether added. This was stirred 4 h, while gradually warming to room temperature. The reaction was then cooled to −78 degrees, and 500 uL of 4 M HCl in dioxane added. The reaction was again stirred under Ar while gradually warming to room temperature. Solvents were removed under reduced pressure to give a mixture (by $^1$H NMR analysis) of chloromethylketone and methyl ester. This was chromatographed on silica gel (EtOAc) to give 185 mg (36%) of chloromethylketone. $^1$H NMR (CDCl$_3$) δ1.62 (m, 1H), 1.86 (m, 1H), 2.08 (m, 1H), 2.39 (m, 1H), 3.26 (m, 1H), 3.97 (m, 1H), 4.20 (½ of AB quartet, 1H, J=15 Hz), 4.26 (½ of AB quartet, 1H, J=15 Hz), 4.94 (m, 1H), 7.35–7.55 (m, 5H); MS (ES+): 308 (M+H$^+$), 330 (M+Na$^+$).

Synthesis of Structure (69)

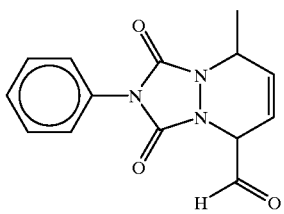

(69)

Structure (69) was synthesized as follows. To 4-phenyl urazole (1.179 g, 6.65 mmol) in 60 ml methylene chloride 2.14 g of iodobenzene diacetate (6.64 mmol) was added and the reaction mixture stirred at room temperature. A deep red color developed as all the solids gradually dissolved. After about 15 minutes, 640 mg of sorbinal (6.66 mmol) in 10 ml methylene chloride was added to the reaction flask, and the red color slowly faded. After two hours, the methylene chloride was removed under reduced pressure. Ether (30 ml) was added to the resulting residue, and cooled to −20 degrees overnight. The solid material (1.55 g, 86% yield) formed was collected on filter paper. $^1$H NMR (CDCl$_3$) δ1.54 (d, 3H, J=7.5 Hz), 4.57 (m, 1H), 4.90 (m, 1H) 5.86 (m, 1H), 6.09 (m, 1H), 7.38 (m, 1H), 7.50 (t, 2H), 7.58, (m, 2H), 9.6 (s, 1H); MS (CI, NH$_3$): 272 (M+H$^+$), 289 (M+NH$_4$$^+$).

Synthesis of Structure (70)

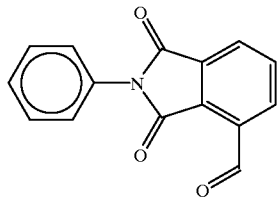

(70)

To 0.78 grams (3.0 mmol) of the acid of structure (64) in a 100 ml round-bottomed flask was added 20 ml THF and the reaction mixture was cooled to −20° C. 4-Methyl morpholine (0.34 ml, 3.0 mmol) was added and was followed by the addition of 0.42 ml (3.3 mmol) isobutylchloroformate. The resultant suspension was stirred for 5 min, and then a suspension of 0.34 grams (9.0 mmol) of sodiumborohydride in 0.9 ml water was added rapidly. After 4–5 min, 40 ml of water were added and the suspension was extracted with 125 ml of ethylacetate. The EtOAc layer was then washed with water and brine and dried over MgSO$_4$. Filtration and solvent evaporation provided the crude alcohol.

The crude alcohol was dissolved in 40 ml dichloromethane and 2.0 grams (4.7 mmol) of Dess-Martin periodinane reagent were added at room temperature. The reaction was stirred for 2 h, diluted with 40 ml dichloromethane and washed with 3×20 ml 1:1 (by volume) solution of 10% sodiumbicarbonate and 10% sodiumthiosulfate, 1×40 ml water, 1×40 ml brine and dried over magnesium sulfate. Filtration, solvent evaporation, and flash chromatography using 30% EtOAc/hexanes afforded the pure aldehyde (0.5 g, 67% 2 steps). $^1$H NMR (CDCl$_3$, 500 Mhz) d 11.09 (s, 1H), 8.33 (dd, 1H, J=8, 1 Hz), 8.20 (dd, 1H, J=8, 1 Hz), 7.93 (t, 1H, J=8 Hz), 7.54 (m, 2H), 7.45 (m, 3H).

Synthesis of Structure (71)

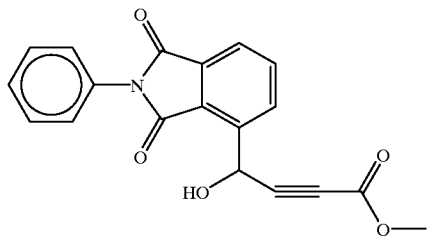

(71)

To 3 ml tetrahydrofuran in a 25 ml round-bottomed flask was added 0.066 ml (0.69 mmol) of methyl propiolate and the solution was cooled to −78° C. n-Butyl lithium (0.28 ml, 0.69 mmol) was added dropwise and the reaction allowed to stir for 7–10 min at which point a 3 ml dichloromethane solution of 0.15 g (0.6 mmol) of the aldehyde of structure (70) was rapidly added. The reaction was stirred at −78° C. for 35–45 min then it was quenched with 1.5 ml of saturated ammonium chloride solution. The organic solvents were removed under reduced pressure and the aqueous layer was extracted with 24 ml of EtOAc which in turn was washed with brine. The organic layer was dried over sodium sulfate, filtered, and the solvent evaporated under reduced pressure to afford the crude product. Preparative TLC purification using 40% EtOAc/hexanes afforded product (107 mg, 47%). $^1$H NMR (CDCl$_3$, 500 MHz) d 7.98 (dd, 1H, J=7.0, 1.0 Hz), 7.88 (dd, 1H, J=7.5, 1 Hz), 7.83 (d, 1H, J=7.0 Hz), 7.54 (m, 2H), 7.45 (m, 3H), 6.01 (d, 1H, J=9 Hz), 5.02 (d, 1H, J=9 Hz), 3.78 (s, 3H). MS (EI) 335 (M+), 275.

Example 26

Activity of Representative β-Sheet Mimetics

In this example, the compounds of Example 25 were assayed for inhibition of TNF induced V-CAM expression in human umbilical vein entothelial cells (HUVEC). Upon stimulation with inflammatory cytokines, HUVEC express cell surface adhesion molecules, including E-selectin, V-CAM, and I-CAM. Proteasome antagonists inhibit TNFα induced expression of these adhesion molecules, thereby providing a mechanism for regulating leucocyte adhesion and the inflammatory response.

More specifically, compounds (65), (68), (69) and (71) were assayed by the procedures set forth by Deisher, Kaushansky and Harlan ("Inhibitors of Topoisomerase II Prevent Cytokine-Induced Expression of Vascular Cell Adhesion Molecule-1, While Augmenting the Expression of Endothelial Leukocyte Adhesion Molecule-1 on Human Umbilical Vein Endothelial Cells," *Cell Adhesion Commun.* 1:133–42, 1993) (incorporated herein by reference), with the exception that tetramethyl benzidine was used in place of o-phenylenediamine-peroxide.

The results of this experiment are as follows: compound (65), 9.6±0.1 μM; compound (68), 14.2±0.8 μM; compound (69), 32.4±1.7 μM; and compound (71) 4.9±0.18 μM.

Example 27

Synthesis of Representative Linkers Used in the Solid Phase Synthesis of β-Sheet Mimetics This example illustrates the synthesis of linkers used in the solid-phase synthesis of β-sheet mimetics.

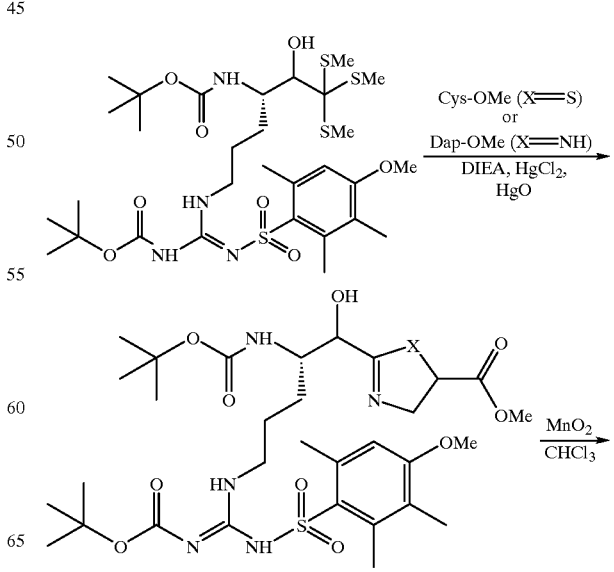

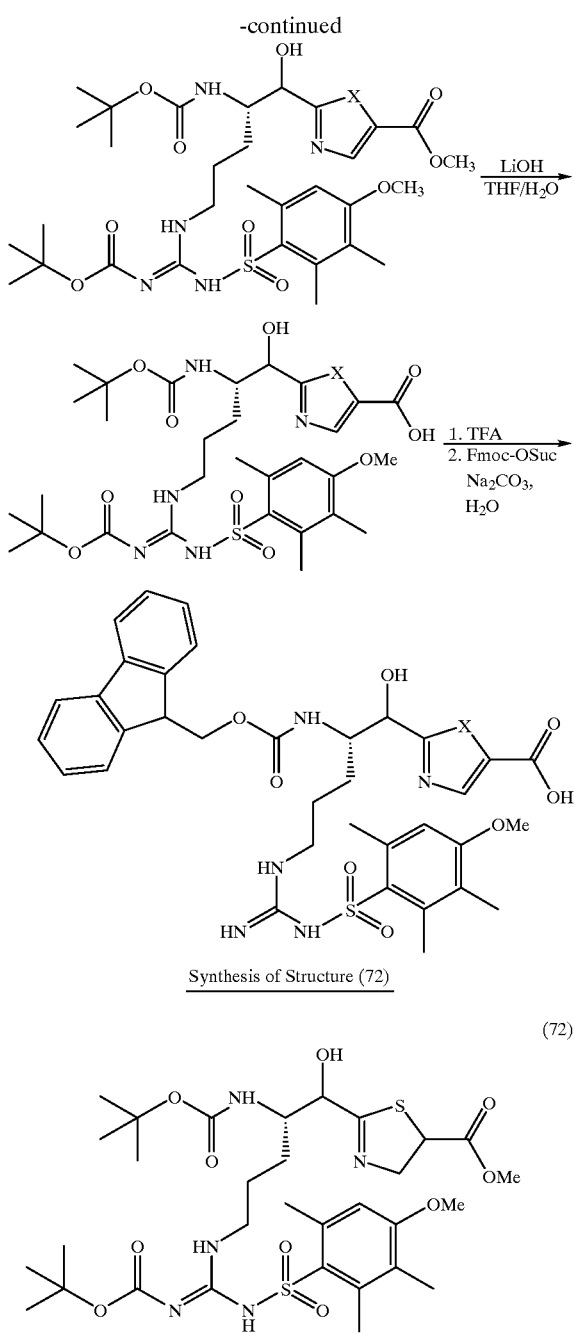

Synthesis of Structure (72)

In a 500 mL round-bottomed flask were placed tris(methylthio)methyl arginol (30) (10.70 g, 14.8 mmol) and CH$_2$Cl$_2$ (20 mL) with magnetic stirring. In a 125 mL Erlenmeyer flask were placed cysteine methyl ester hydrochloride (3.81 g, 22.2 mmol), CH$_2$Cl$_2$ (50 mL), and diisopropylethylamine (8.5 mL, 6.3 g, 48.7 mmol). This mixture was stirred until the cysteine methyl ester had dissolved (25 min), and the solution appeared as a faintly cloudy suspension of diisopropylethylamine hydrochloride. This suspension was added to the flask containing the arginol and additional CH$_2$Cl$_2$ (100 mL) was added to the reaction. HgCl$_2$ (17.7 g, 65.1 mmol) and HgO (5.46 g, 25.2 mmol) were added to the reaction mixture and the suspension was stirred rapidly enough so that the mercury salts remained suspended. The flask was lightly capped and stirred at room temperature for 22 h, by which time the starting material had been consumed. The yellow solution was quenched with saturated ammonium chloride and diluted with CH$_2$Cl$_2$. The layers were separated and the aqueous layer extracted 2× with CH$_2$Cl$_2$. The combined organic layers were dried over Na$_2$SO$_4$/MgSO$_4$ and filtered through a pad of silica gel. The solvents were removed in vacuo and the residue purified two successive times on silica gel, the first time eluting with 7:3 ethyl acetate/hexane, and the second time eluting with 1:1 ethyl acetate/hexane, then 7:3 ethyl acetate/hexane. The combined purifications afforded 7.97 g (75% yield) of the N$_\alpha$, N$_G$-bisBoc-N$_G$'-Mtr-1-[(4'-carboxymethyl)thiazolin-2-yl] arginol as a pale yellow foam.: $^1$H NMR (500 MHz, CDCl$_3$) δ9.81 (s, 1H, N$_G$-H), 8.30 (t, J=5.5 Hz, 1H, N$_d$-H), 6.54 (s, 1H, ArH), 5.12 (t, J=8.5 Hz, 1H, C$\underline{H}$OH), 4.95 (d, J=8.0 Hz, 1H, BocN$\underline{H}$), 4.45 (bs, 1H, NCHCO2Me), 3.83 (s, 3H, ArOCH$_3$), 3.80 (s, 3H, CO$_2$CH$_3$), 3.64 (dd, J=11.5, 9.0 Hz, 1H, CH$_2$S), 3.58 (t, J=8.5 Hz, 1H, CH$_2$S), 3.37–3.31 (m, 1H, CH$_2$-guanidine), 3.31–3.25 (m, 1H, CH$_2$-guanidine), 2.70 (s, 3H, ArCH$_3$), 2.63 (s, 3H, ArCH$_3$), 2.14 (s, 3H, ArCH$_3$), 1.54–1.70 (m, 4H, C$_\beta$H and C$_\gamma$ H), 1.49 (s, 9H, N$_G$ Boc) 1.40 (s, 9H, N$_\alpha$ Boc), C$_\alpha$H not observed.

Synthesis of Structure (73)

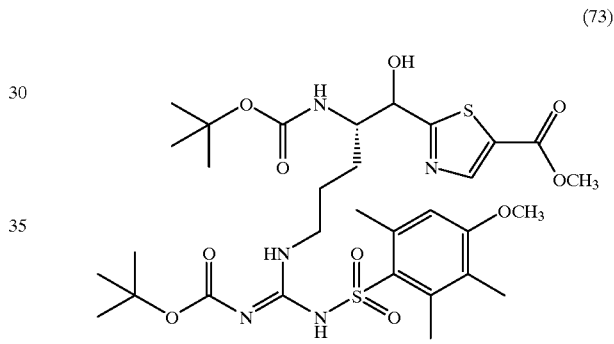

(73)

A 300 mL round-bottomed flask was charged with chloroform (20 mL) and arginol (72) (7.97 g, 11.1 mmol), and equipped for magnetic stirring. Manganese(IV)dioxlde (9.65 g, 111 mmol, 10 eq.) was added, and the flask was stoppered. Additional chloroform (10 mL) was added, and the suspension was vigorously stirred for 8 h at room temperature after which time it was filtered through silica gel, rinsing with ethyl acetate. The solvent was removed in vacuo and the residue was purified by column chromatography on silica gel, (45:55 EtOAc/hexane) to give N$_\alpha$, N$_G$-bisBoc-N$_G$'-Mtr-1-[(4'-carboxymethyl)thiazol-2-yl]arginol (4.83 g, 61% yield) as a pale yellow amorphous solid, and 1.89 g (24%) of recovered starting material.: $^1$H NMR (500 MHz, CDCl$_3$) d 9.84 (s, 1H, N$_G$-H), 8.36 (bs, 1H, N$_\delta$-H), 8.15 (s, 1H, SCH=C), 6.54 (s, 1H, ArH), 5.10 (d, J=8.5 Hz, 1H, BocN$_\alpha$H), 3.95 (s, 3H, ArOCH$_3$), 3.95–3.87 (m, 1H, C$_\alpha$H), 3.83 (s, 3H, CO$_2$CH$_3$), 3.43–3.33 (m, 1H, CH$_2$-guanidine), 3.33–3.25 (m, 1H, CH$_2$-guanidine), 2.70 (s, 3H, ArCH$_3$), 2.63 (s, 3H, ArCH$_3$), 2.14 (s, 3H, ArCH$_3$), 1.80–1.55 (m, 4H, C$_\beta$H and C$_\gamma$ H), 1.50 (s, 9H, N$_G$Boc), 1.35 (s, 9H, N$_\alpha$Boc); IR (neat) 3328, 1727, 1619, 1566, 1278, 1242, 1152, 1121 cm$^{-1}$; MS (ES+) m/z 714 (M+H$^+$, 100)736 (M+Na$^+$, 9), 716 (35), 715 (45).

Synthesis of Structure (74)

(74)

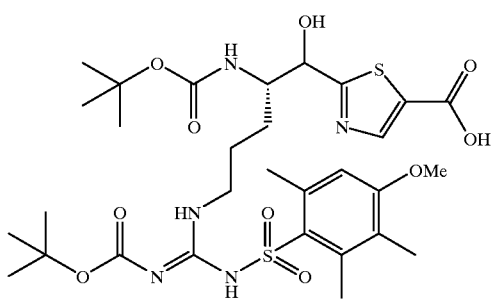

To a 25 mL conical flask containing H₂O (1 mL) was added 2.0N LiOH (0.25 mL, 0.50 mmol, 1.5 eq.) and $N_\alpha$, $N_G$-bisBoc-$N_G$'-Mtr-1-[(4'-carboxymethyl)thiazol-2-yl] arginol (238 mg, 0.33 mmol) as a solution in THF (1 mL). A second portion of THF (1 mL) was used to rinse the flask containing the arginol and added to the reaction. The homogeneous mixture was magnetically stirred at room temperature for 6.5 h at which time 5% HCl (0.34 mL, 0.55 mmol) and ethyl acetate (10 mL) were added. The organic layer was separated and the aqueous layer extracted with 2×10 mL ethyl acetate. The combined organic layers were washed with saturated NaCl and dried over Na₂SO₄. The solvent was removed to afford 212 mg (92% yield) of $N_\alpha$, $N_G$-bisBoc-$N_G$'-Mtr-1-[(4'-carboxylic acid)thiazol-2-yl] arginol as a pale yellow foam.: ¹H NMR (500 MHz, CDCl₃) δ9.84 (s, 1H, $N_G$-H), 8.39 (t, J=5.0 Hz, 1H, $N_\delta$-H), 8.22 (s, 1H, SCH=C), 6.54 (s, 1H, ArH), 5.11 (d, J=8.0 Hz, 1H, $BocN_\alpha H$), 4.02–3.95 (m, 1H, $C_\alpha H$), 3.95 (s, 3H, ArOCH₃), 3.45–3.36 (m, 1H, CH₂-guanidine), 3.36–3.27 (m, 1H, CH₂-guanidine), 2.69 (s, 3H, ArCH₃), 2.63 (s, 3H, ArCH₃), 2.14 (s, 3H, ArCH₃), 1.83–1.62 (m, 4H, $C_\beta H$ and $C_\gamma H$), 1.50 (s, 9H, $N_G$Boc), 1.34 (s, 9H, $N_\alpha$Boc); MS (ES+) m/z 700.3 (M+H⁺, 100), 722.3 (M+Na⁺, 10), 702.3 (20), 701.3 (38).

Synthesis of Structure (75)

(75)

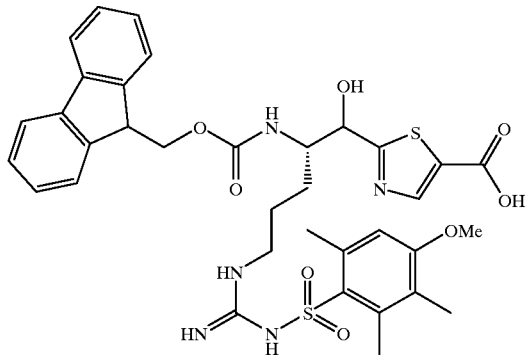

A 250 mL round-bottomed flask equipped for magnetic stirring was charged with CH₂Cl₂ (10 mL), the acid (74) (3.40 g, 4.86 mmol), and trifluoroacetic acid (2 mL). After 1.5 h the reaction was incomplete. Additional trifluoroacetic acid (5 mL) was added and the solution was stirred 4 h more. The solvent was removed in vacuo and the residue taken up in THF (50 mL). Saturated NaHCO₃ solution (50 mL) was added (pH~7–8) followed by 9-fluorenylmethyl-N-succinimidyl carbonate (1.97 g, 5.83 mmol, 1.2 eq.) in THF (20 mL). After 16 h stirring at room temperature, starting material was still present and the pH=7.0. A 2 M Na₂CO₃ solution (~3 mL) was added (pH=8.5) followed by a second portion of FmocONSu (328 mg, 0.97 mmol, 0.2 eq.). The solution was stirred for 2 h more at room temperature. The reaction mixture was washed 2×100 mL hexane. Ethyl acetate (100 mL) was added and the reaction mixture acidified to pH=0 with 6 N HCl. The organic layer was separated and the aqueous layer extracted 2×100 mL ethyl acetate. The combined organic layers were washed with saturated NaCl and dried over Na₂SO₄. The solvent was removed to afford the crude Fmoc acid as a brown foam. This foam was dissolved in a minimum of ethyl acetate and pipetted into ethyl ether (250 mL). The precipitate was centrifuged and collected. The supernatant was concentrated and dropped into ethyl ether (50 mL). The white precipitate was centrifuged and the combined precipitates dried in vacuo to afford 3.42 g (98% yield) of the $N_\alpha$-Fmoc-$N_G$'-Mtr-1-[(4'-carboxylic acid)thiazol-2-yl]arginol as a white powder.: ¹H NMR (500 MHz, CDCl₃) δ8.07 (s, 1H, SCH=C), 7.70 (d, J=7.0 Hz, 2H, Fmoc ArH), 7.46 (dd, J=5.0, 7.5 Hz, 2H, Fmoc ArH), 7.34 (dd, J=4.0, 7.5 Hz, 2H, Fmoc ArH), 7.23 (d, J=7.5 Hz, 2H, Fmoc ArH), 6.49 (s, 1H, ArH), 4.94 (s, 1H, $FmocN_\alpha H$), 4.32–4.23 (m, 2H, FmocCH₂), 4.07 (t, J=5.5 Hz, 1H, FmocCH), 4.02–3.95 (m, 1H, $C_\alpha H$), 3.78 (s, 3H, ArOCH₃), 3.27–3.17 (m, 1H, CH₂-guanidine), 3.17–3.10 (m, 1H, CH₂-guanidine), 2.64 (s, 3H, ArCH₃), 2.57 (s, 3H, ArCH₃), 2.08 (s, 3H, ArCH₃), 1.74–1.49 (m, 4H, $C_\beta H$ and $C_\gamma H$); MS (ES+) m/z 722.3 (M+H⁺, 85), 736.3 (M+Na⁺, 21), 723.2 (35).

Synthesis of Structure (76)

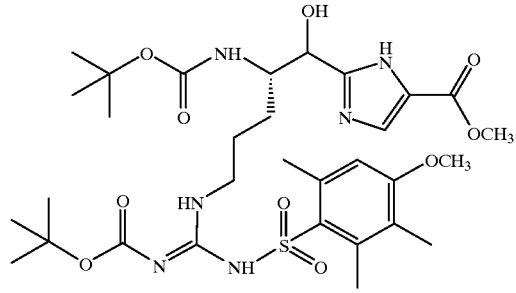

The arginol ester derivative (42) (1.35 g, 1.93 mmol) was dissolved in 70 mL of EtOAc at room temperature. To the solution was added manganese (IV) dioxide (5 g, 89.2 mmol) and the suspension was stirred vigorously for 5 h at room temperature after which time it was filtered through silica gel. The solvent was removed and the residue was purified by flash chromatography (30% hexane/EtOAc) to give the desired alcohol (76) (0.23 g, 18%) and the ketone (0.153 g, 11.5%). ¹H NMR (500 MHz, CDCl₃) δ9.80 (s, 1H, $N_G$-H), 8.34 (bs, 1H, $N_\delta$-H), 7.65 (s, 1H, NCH=C), 6.54 (s, 1H, ArH), 5.20 (b, 1H, $BocN_\alpha H$), 4.89(s, 1H, CHOH), 4.15 (b, 1H, $c_\alpha H$), 3.84 (s, 3H, ArOCH₃), 3.83 (s, 3H, CO₂CH₃), 3.70–3.6 (b, 1H, CH₂-guanidine), 3.25–3.15 (m, 1H, CH₂-guanidine), 2.70 (s, 3H, ArCH₃), 2.63 (s, 3H, ArCH₃), 2.14 (s, 3H, ArCH₃), 1.80–1.55 (m, 4H, $C_\beta H$ and $C_\gamma H$), 1.50 (s, 9H, $N_G$Boc), 1.35 (s, 9H, $N_\alpha$Boc); MS (ES+) m/e 697 (M+H⁺, 100).

Synthesis of Structure (77)

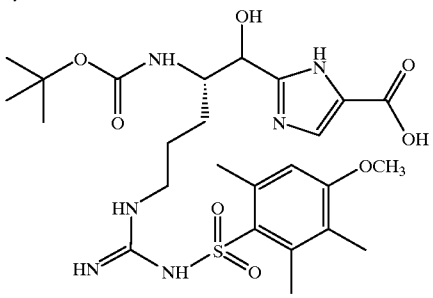

The ester (76) (70 mg, 0.1 mmol) was dissolved in a mixture of THF (10 mL) and water (10 mL). To the solution was added LiOH (18 mg, 4.3 mmol) and the solution was heated to reflux for 7 h. The resulting solution was evaporated. The residue was dissolved in water and extracted with ether. The aqueous layer was evaporated. The resulting residue was dissolved in MeOH, and Dowex resin (50W×8, H$^+$ form) was added to acidify the solution. The resin was filtered off, and the filtrate was evaporated to furnish the acid (35 mg, 60%). $^1$H NMR (500 MHz, CD$_3$OD) δ7.7(s, 1H, NCH=C), 6.70 (s, 1H, ArH), 4.3 (m, 1H, C$_\alpha$H), 3.87 (s, 3H, ArOCH$_3$), 3.34 (m, 1H, CH$_2$-guanidine), 3.3–3.2 (m, 1H, CH$_2$-guanidine), 2.69 (s, 3H, ArCH$_3$), 2.61 (s, 3H, ArCH$_3$), 2.14 (s, 3H, ArCH$_3$), 1.73–1.62 (m, 4H, C$_\beta$H and C$_\gamma$H), 1.34 (s, 9H, N$_\alpha$Boc); MS (ES+) m/z 583.3 (M+H$^+$, 100).

Synthesis of Structure (78)

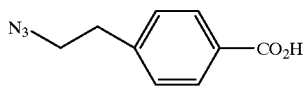

To 4-(chloroethyl)benzoic acid (8.0 g, 0.046 mol) in CH$_3$CN/DMF (80 mL:80 mL) were added NaN$_3$ (6.0 g, 0.092 mol), tetra-n-butylammonium azide (cat.), tetra-n-butylammonium iodide (cat.) and the reaction was heated at gentle reflux for 7–9 h at which point the reaction mixture transformed into one solid block. Water (350 mL) and EtOAc (500 mL) were added and the aqueous layer was extracted with EtOAc(2×400 mL). The organic layer was washed with H$_2$O (250 mL), brine (300 mL) and dried over Na$_2$SO$_4$. Filtration and solvent evaporation afforded a yellowish solid (9.4 g) which was pure enough to use in the next step. IR (CDCl3) v$^{-1}$ 2111.

Synthesis of Structure (79)

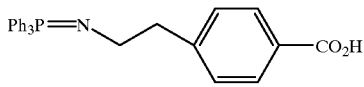

To a solution of (78) (9.4 g, 0.053 mol) in THF/DME (175 mL:60 mL) was added triphenylphosphine (15.2 g, 0.058 mol) and the reaction was stirred for 10 m. H$_2$O (1.2 mL) was added and the reaction was vigorously stirred at rt for 22–24 h at which point the solution turned into a thick suspension. The off-white solid was filtered and washed with THF (3×40 mL) to afford, after drying, 16.4 g of pure iminophosphorane. MS (ES+) (M+H$^+$) 426.1.

Synthesis of Structure (80)

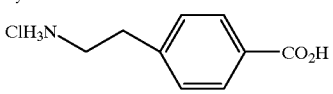

The iminophosphorane (79) was suspended in THF/H$_2$O (320 mL:190 mL) and 2N HCl (64 mL) was added and the reaction was heated at reflux for 5 h. Concentrated HCl (11 mL) was added and reflux continued for an additional 20 h. The solvents were removed under vacuo and the resultant off-white solid was dried under high vacuum for 2 h (18.0 g) and used in the next step without further purification.

Synthesis of Structure (81)

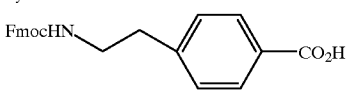

To a suspension of 4-(aminoethyl)benzoic acid .HCl (80) (9.0 g, 0.019 mol, theoretical) in CH$_3$CN (320 mL) was added TEA (7.7 mL, 0.053 mol) and the suspension was cooled to 0° C. Fmoc-ONSu (9.3 g, 0.026 mol) was added in one portion and the reaction was allowed to warm to rt over 1 h and stirred an additional 1 h. The solvent was removed under reduced pressure and the residue was dissolved in EtOAc (1200 mL), washed with 10% citric acid (220 mL) and brine (220 mL) and dried over Na$_2$SO$_4$. Filtration and solvent evaporation afforded the crude product which was purified by flash chromatography using 8% MeOH/CHCl$_3$ to afford pure product (2.4 g). $^1$H NMR (CDCl$_3$) δ2.81 (t, 2H, J=7.0 Hz), 3.36 (m, 2H), 4.15 (t, 1H, J=6.5 Hz), 4.36 (d, 2H, J=7.0 Hz), 5.24 (br s, 1H), 7.18 (d, 2H, J=8.0 Hz), 7.26 (m, 2H), 7.35 (t, 2H, J=7.5 Hz), 7.52 (d, 2H, J=7.5 Hz), 7.71(d, 2H, J7.5 Hz), 7.92 (d, 2H, J=8.0 Hz). MS (ES+) (M+H$^+$) 387.7.

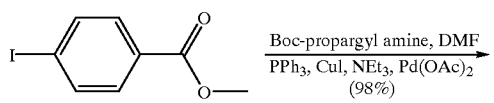
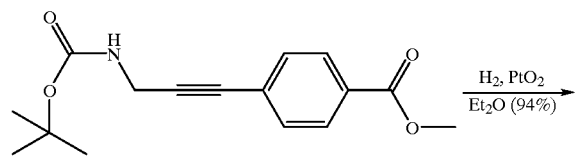
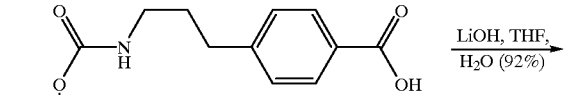
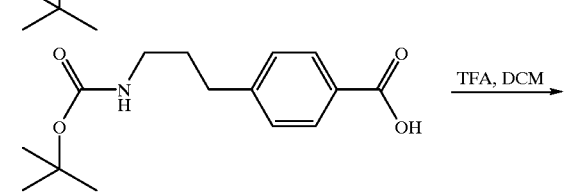

-continued

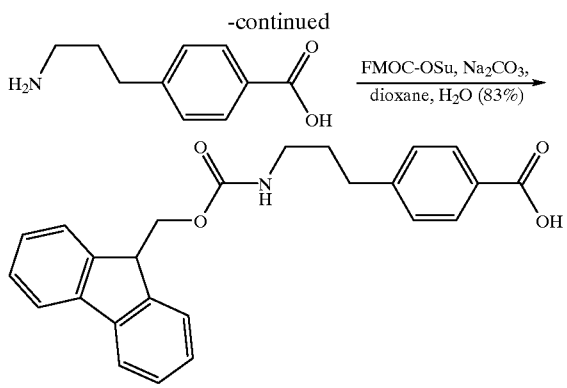

Synthesis of Structure (82)

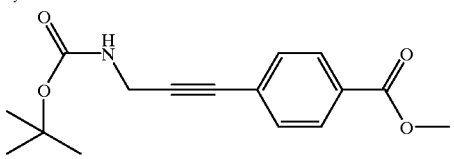

To 2.20 g (8.4 mmol) of 4-iodo-methylbenzoate under nitrogen was added 1.95 g (12.26 mmol) of Boc-propargyl amine, 0.33 g (1.26 mmol) of triphenylphosphine, 0.08 g (0.42 mmol) of copper(I) iodide, 2.11 mL (15.1 mmol) of triethylamine, and 250 mL of DMF. The solution was stirred and degassed with nitrogen for 15 min followed by the addition of 0.10 g (0.42 mmol) of palladium(II) acetate and stirring at room temperature for 18 h. The solution was diluted with EtOAc and washed with 5% citric acid(4×), brine (2×) and dried over MgSO$_4$. Purification by column chromatography (silica gel, 9:1 hexanes/EtOAc) afforded ester (82) (2.37 g, 98%) as an orange solid: $^1$H NMR (CDCl$_3$, 500 MHz) δ1.47 (s, 9H), 3.91 (s, 3H), 4.17 (m, 2H), 4.80 (broad s, 1H), 7.46 (d, J=8.5 Hz, 2H), 7.97 (d, J=8.5 Hz, 2H).

Synthesis of Structure (83)

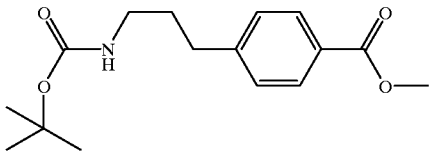

To 2.86 g (9.88 mmol) of alkyne (82) under 1 atm of H$_2$ was added 40 mL of anhydrous diethyl ether and a catalytic amount of platinum(IV) oxide. The reaction was monitored by TLC and complete after 13 h. The mixture was filtered through a pad of Celite, washed with diethyl ether and the solvent was removed in vacuo to give ester (83) (2.72 g 94%) as an orange oil: $^1$H NMR (CDCl$_3$, 500 MHz) δ1.44 (s, 9H), 1.82 (m, 2H), 2.69 (m, 2H), 3.15 (m, 2H), 3.89 (s, 3H), 4.55 (broad s, 1H), 7.23 (d, J=8.0 Hz, 2H), 7.94 (d, J=8.0 Hz, 2H); MS (ES+) m/z 294 (M+H$^+$).

Synthesis of Structure (84)

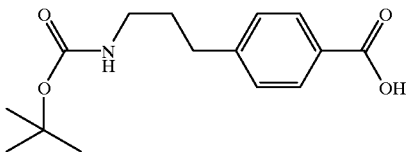

To 2.72 g (9.27 mmol) of ester (83) was added 1.17 g (27.18 mmol) of lithium hydroxide monohydrate, 50 mL of THF and 50 mL of H$_2$O. The solution was stirred at room temperature for 16 h and quenched with 5% citric acid. The reaction was extracted with EtOAc (4×) and the combined extracts were washed with brine and dried over MgSO$_4$. Removal of the solvent afforded acid (84) (2.38 g, 92%) as a pale yellow solid: $^1$H NMR (CD$_3$OD, 500 MHz) δ1.44 (s, 9H), 1.80 (m, 2H), 2.70(m, 2H), 3.07 (m, 2H), 7.30 (d, J=8.0 Hz), 7.92 (d, J=8.0 Hz).

Synthesis of Structure (85)

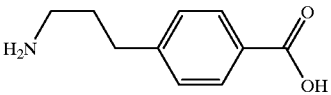

To 2.38 g of acid (84) was added 20 mL of dichloromethane and 20 mL of TFA. The solution was stirred for 2 h at room temperature and the solvent removed in vacuo to give amino acid (85) (3.57 g) as a pale orange solid: $^1$H NMR (CD$_3$OD, 500 MHz) δ1.98 (m, 2H), 2.79 (m, 2H), 2.95 (m, 2H), 7.35 (d, J=8.0 Hz), 7.97 (d, J=8.0 Hz)

Synthesis of Structure (86)

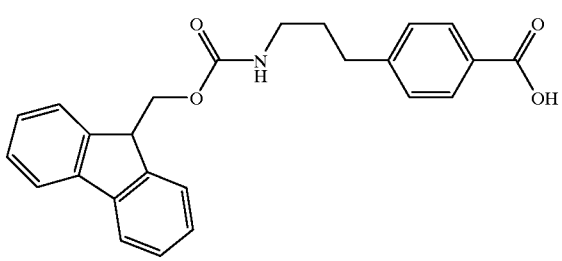

To 3.57 g (12.20 mmol)of amino acid (85) was added 70 mL of 1,4 dioxane, 70 of H$_2$O, 1.29 g (12.20 mmol), and 4.93 g (14.6 mmol) of N-(9-fluorenylmethoxycarbonyloxy) succinimide. The cloudy mixture was stirred for 48 h, diluted with a large volume of EtOAc and washed with saturated ammonium chloride. The mixture was extracted with EtOAc (3×) and the combined organics were washed with saturated bicarbonate, brine and dried over sodium sulfate. Removal of the solvent in vacuo gave a pale yellow solid which was washed with ether to afford acid (86) (2.85 g 58%; 83% based on (75) as a white powder: $^1$H NMR (CD$_3$OD, 500 MHz) δ1.81 (m, 2H), 2.68 (m, 2H), 3.12 (m, 2H), 4.37 (m, 2H),7.30 (m, 4H), 7.38 (m, 2H), 7.65 (d, J=8.0 Hz, 2H), 7.79 (d, J=7.5 Hz, 2H), 7.92 (d, J=8.0 Hz, 2H); MS (ES+) m/z 402 (M+H$^+$).

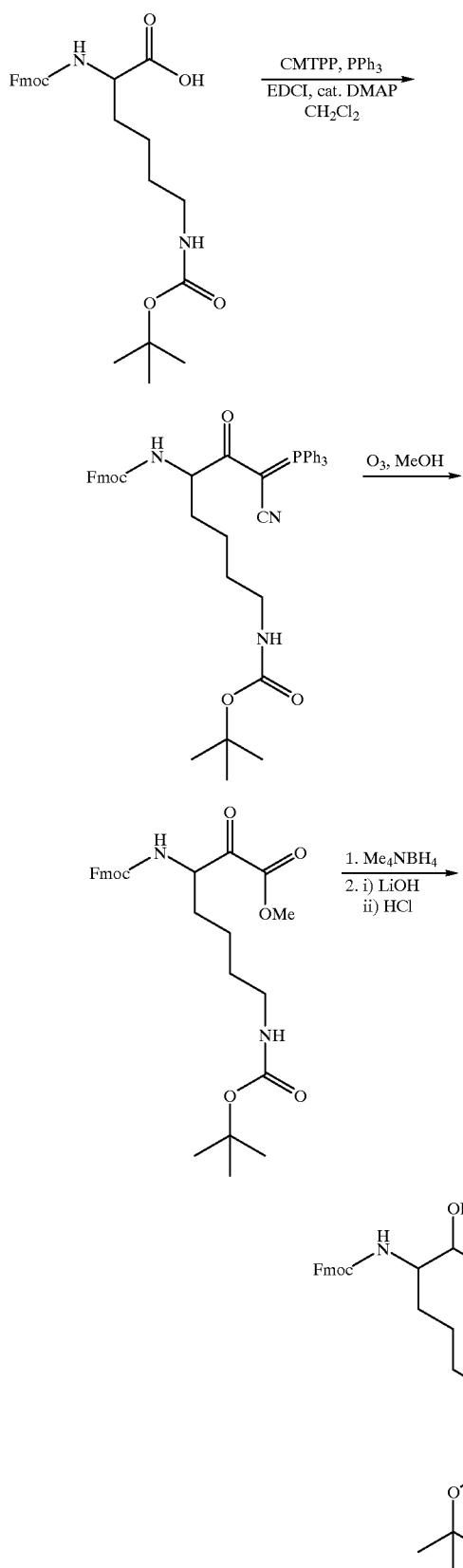

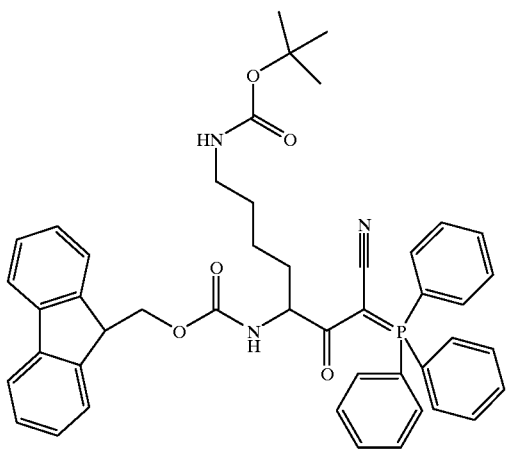

Synthesis of Structure (87)

A solution of cyanomethyl triphenylphosphonium chloride (CMTPP) (8.2 g, 24 mmol) was prepared in 75 mL of dichloromethane and stirred for 10 m. With the addition of Fmoc-Lys(Boc) (10 g, 21.3 mmol), 1-(dimethylaminopropyl)-3-ethyl carbodiimide hydrochloride (EDCI) (4.9 g, 25.6 mmol) and 4-Dimethylaminopyridine (DMAP) (2.2 mmol), the reaction vessel was sealed and stirred for twelve hours at room temperature. The solvent was concentrated in vacuo to an oil which was dissolved in 300 mL of ethyl acetate and 100 mL 1N HCl with stirring. The layers were separated and the organic phase was extracted 2×50 mL of brine. The ethyl acetate was dried over magnesium sulfate and concentrated to a solid. This material was used without further purification. MS (ES+) 752 (M+H+)

Synthesis of Structure (88)

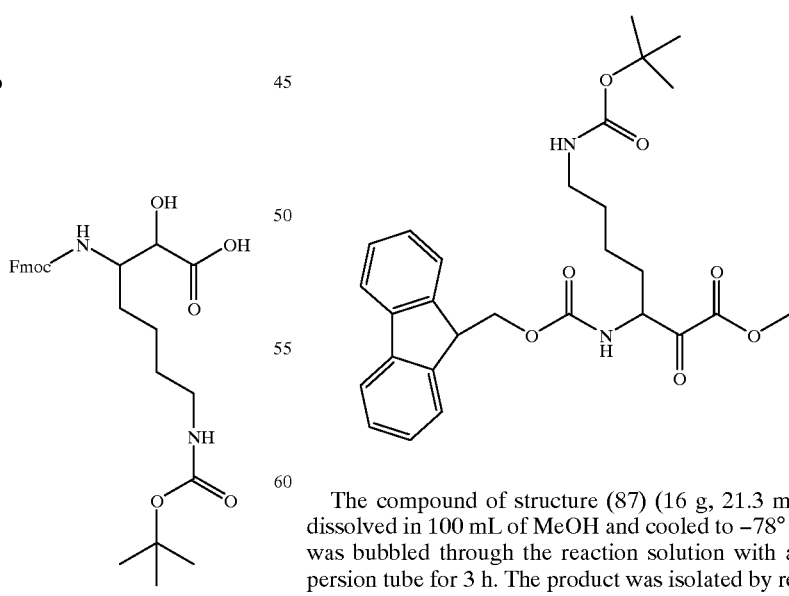

The compound of structure (87) (16 g, 21.3 mmol) was dissolved in 100 mL of MeOH and cooled to −78° C. Ozone was bubbled through the reaction solution with a gas dispersion tube for 3 h. The product was isolated by removal of MeOH under reduced pressure and was purified on a silica gel column (200 g dry weight) equilibrated in a mobile phase of ethyl acetate/hexane (3:7). The product was eluted with ethyl acetate/hexane (4:6), and gave after drying 5.1 g (47% for the two steps). MS (ES+) 511 (M+H⁺).

Synthesis of Structure (89)

(89)

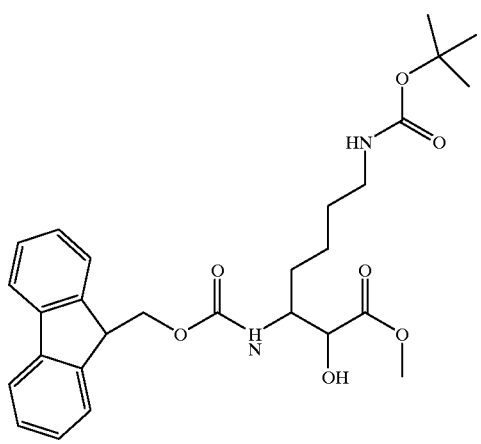

The keto ester (88) (5.1 g, 9.8 mmol) was dissolved in 100 mL of THF. After the addition of tetramethylammonium borohydride (1.4 g, 11.8 mmol) to the solution, the vessel was sealed and stirred for 4 h. The reaction was incomplete at this point and more borohydride (0.21 g, 2.4 mmol) was added and stirring was continued for an additional h. The reaction mixture was concentrated to an oil in vacuo and applied to a silica gel column (150 g dry weight) equilibrated and eluted with ethyl acetate/hexane (4:6) to give 2.7 g (53%) of product. MS (ES+) 513 (M+H⁺).

Synthesis of Structure (90)

(90)

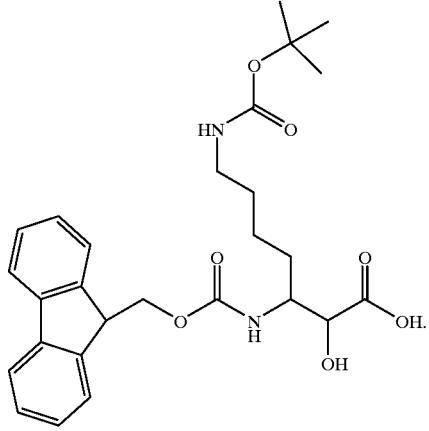

The hydroxy ester (89) (2.7 g, 5.3 mmol) was dissolved in 100 mL of THF and cooled to 0°–5° C. 0.2N LiOH (66.5 mL, 13.3 mmol) was added to the chilled solution and stirred for thirty minutes. The reaction was incomplete at that time and more 0.2N LiOH (10.4 mL, 2.1 mmol) was added. The reaction was stirred of another thirty minutes and then quenched with 300 mL of ethyl acetate/0.2N HCl (2:1). The aqueous phase was separated, washed with 100 mL of ethyl acetate and the combined organic extracts were dried over magnesium sulfate and filtered. The filtrate was evaporated in vacuo to an oil and dried to a solid (2.0 g, 78%) CDCl₃ δ1.2–1.8 (m,15H), 3.1 (m,2H), 4.1–4.5 (m,5H), 4.6 (m,1H), 5.4 (m,1H), 7.2 (m,2H), 7.4 (m,2H) 7.6 (m,2H), 7.8 (m,2H); MS (ES+) 501 (M+H⁺).

(91)

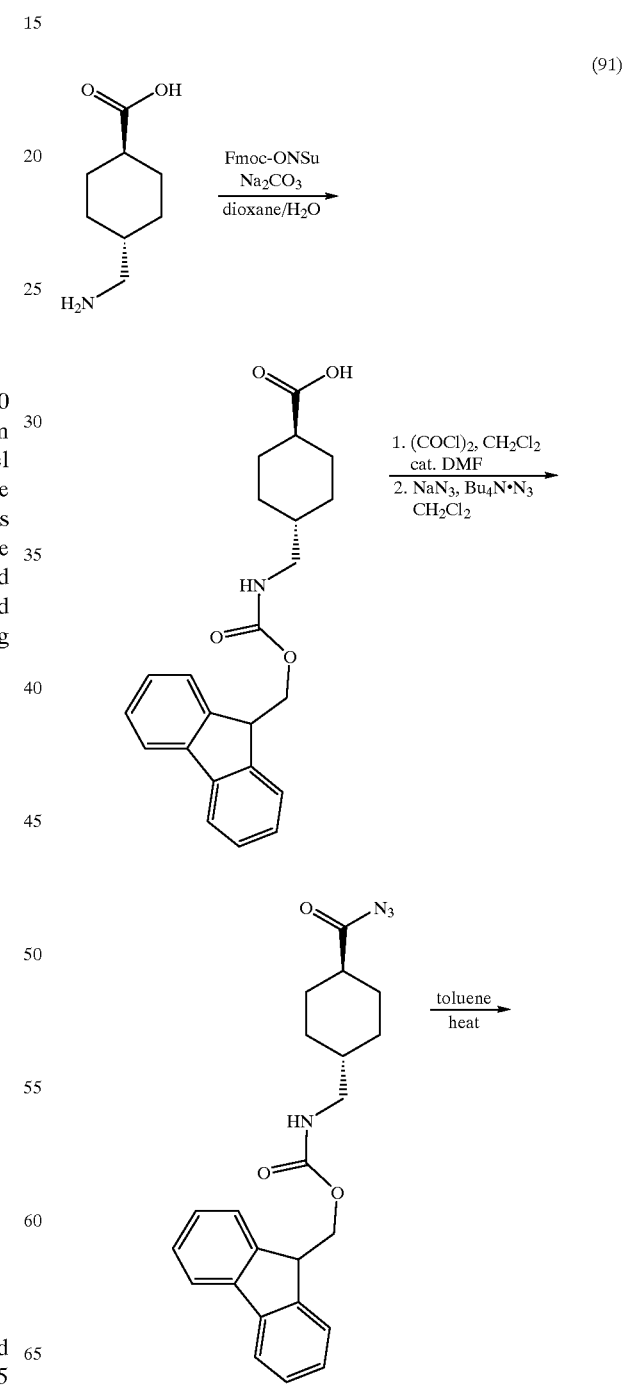

-continued

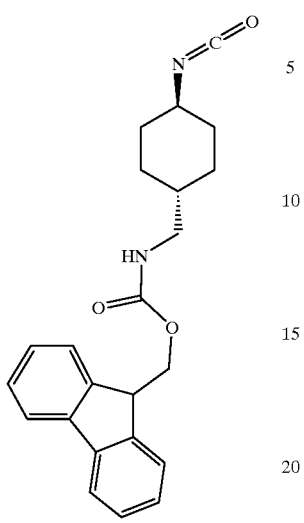

Example 28
Synthesis of Representative Components for the Solid Phase Synthesis of β-Sheet Mimetics
Urazole Synthesis The following syntheses are representative of the procedures used to prepare the urazole components used in the solid phase synthesis of β-sheet mimetics of this invention.

Synthesis of Structure (92)

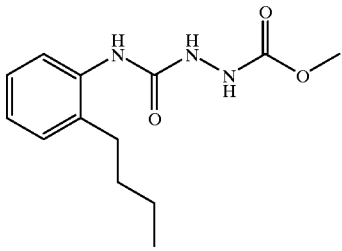

(92)

Structure (92) was synthesized by a minor modification of the method of Cookson and Gupte (*Org. Syntheses*, Vol. VI (1988), 936). 2-n-Butylaniline (12.0 mL, 76.6 mmol) in 160 mL of EtOAc was added via addition funnel to 324 mL of 20% phosgene in toluene at rt over 30 min. The solution was refluxed 30 min, and the solvent removed by distillation. The residual oil was dissolved in 75 mL of chloroform and was added via addition funnel over 15 min to a suspension of methyl hydrazinocarboxylate (6.90 g, 76.6 mmol) in toluene at rt. The mixture was refluxed for 1.5 h during which time all the solids dissolved. Upon cooling to rt, a precipitate formed and was collected by vacuum filtration. It was washed with toluene and dried in vacuo to give 18.17 g of off-white powder (89%). The product was used in the next step without further purification. TLC ($CH_2Cl_2$/MeOH, 95/5) $R_f$ 0.12; $^1$H NMR ($CD_3OD$) δ0.94 (t, 3H, J=7.4 Hz), 1.39 (m, 2H), 1.56 (m, 2H), 2.61 (m, 2H), 3.74 (s, 3H), 7.09–7.21 (m, 4H); MS (ES+) m/z 265.8 (M+H$^+$, 100).

Synthesis of Structure (93)

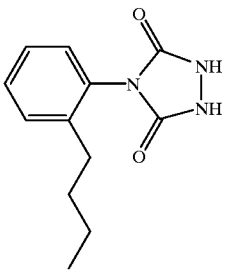

(93)

The compound of structure (92) (18.03 g, 68.0 mmol) was suspended in 190 mL of 4 N KOH and heated to reflux for 2 hours. Upon cooling, the now clear pink solution was extracted with ether (6×) and acidified with concentrated HCl. The precipitate was collected by vacuum filtration, washed with water and EtOAc, and dried in vacuo overnight to yield 14.00 g of white solid (88%). [If necessary, urazoles may be recrystallized from MeOH or another suitable solvent system.] TLC ($CH_2Cl_2$/MeOH/AcOH, 94/4/2) $R_f$ 0.63; Purity* by UV: $^3$97%; $^1$H NMR ($CD_3OD$) δ0.89 (t, 3H, J=7.3 Hz), 1.32 (m, 2H), 1.51 (m, 2H), 7.18–7.42 (m, 4H); MS (ES−) m/z 232 (M−H$^+$). Note: urazoles generally give poor mass spectra.

*A rough check of purity may be obtained by measuring the UV absorbance of the triazoline derived from oxidation of the urazole as follows. Urazole (5–10 mg) and bis(trifluoroacetoxy)iodobenzene (40 mg) are dissolved in DMF to 5 mL in a volumetric flask. The absorbance of this pink solution is measured at 520 nm (ϵ≈177) in a cuvette with a 1 cm path length against a DMF blank. Under these conditions, the purity of the parent urazole is obtained by the following equation: Purity=2.82(A)(MW)/(m), where A is the absorbance, MW is the molecular weight of the urazole, and m is the weight in mg of the sample urazole.

Synthesis of Structure (94)

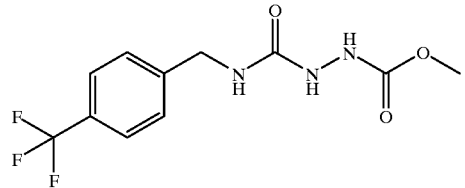

(94)

4-(Fluoromethyl)-benzylamine (4.1 mL, 28.5 mmol) was added to a stirring solution of methyl hydrazinocarboxylate (2.56 g, 28.5 mmol) and 1,1'-carbonyldiimidazole (4.62 g, 28.5 mmol) in THF (25 mL). The solution was stirred at room temperature for 18 hours. A white precipitate formed that was collected by vacuum filtration, washed with cold THF, and dried in vacuo to yield 3.22 g of (94) (39%). $^1$H NMR (DMSO-d$_6$) δ3.57 (s, 3H), 4.26 (d, 2H, J=6.0 Hz), 7.44 (d, 2H, J=8.0 Hz), 7.64 (d, 2H, J=8.0 Hz); MS (ES+) m/z 292 (M+H$^+$, 100).

Synthesis of Structure (95)

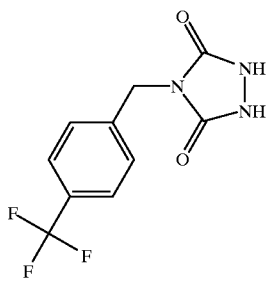

(95)

The compound of structure (94) (3.22 g, 11.0 mmol) was suspended in 20 mL of 4 N KOH and heated to reflux for 3 hours. Upon cooling the solution was acidified with concentrated HCl. A white precipitate formed and was collected by vacuum filtration, washed with cold water, and dried in vacuo overnight to yield 2.45 g of white solid (86%). Purity by UV: $^3$83%; $^1$H NMR (DMSO) δ4.62 (s, 2H), 7.46 (d, 2H, J=8.0 Hz), 7.70 (d, 2H, J=8.0 Hz), 10. 29 (bs, 2H); MS (ES–) m/z 258 (M–H$^+$, 100).

Diene Synthesis

The following syntheses are representative of the procedures used to prepare the diene components used in the solid phase synthesis of β-sheet mimetics of this invention.

Synthesis of Structure (95)

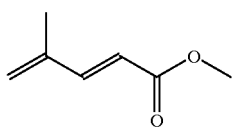

(95)

A solution of methacrolein (7.01 g, 100 mmol) and methyl (triphenylphosphoranilidene)acetate (35.11 g, 105 mmol) in 150 mL of dry dichloromethane was refluxed for 2 h under a nitrogen atmosphere. The solvent was evaporated under reduced pressure, and the product was purified by chromatography on a short silica gel column (EtOAc-hexanes, 1:9). After evaporation of the product-containing fractions, compound (95) was obtained as a clear oil (8.71 g, 69%). TLC (EtOAc-hexanes, 1:4) R$_f$ 0.59 $^1$H NMR (CDCl$_3$) δ1.89 (s, 3H), 3.76 (s, 3H), 5.33–5.37 (m, 2H), 5.87 (d, J=16 Hz, 1H), 7.37 (d, J=16 Hz, 1H).

Synthesis of Structure (96)

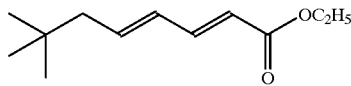

(96)

Compound (96) was synthesized by a modification of the procedure of K. Sato et al. (*J. Org. Chem.* 32:177, 1967). To a suspension of NaH (60% in mineral oil, 0.40 g, 10 mmol) in 25 mL of dry THF, cooled to 0° under a nitrogen atmosphere, triethyl phosphonocrotonate (2.50 g, 10 mmol) was added dropwise with stirring. After the addition, the solution was stirred at 0° C. for 1.5 h. To the brown-red solution, maintained at 0° C., 3,3-dimethylbutyraldehyde (1.00 g, 10 mmol) was added dropwise. The solution was allowed to warm up to room temperature, and stirred for 1 h at room temperature. The mixture was diluted with ethyl acetate (75 mL) and water (75 mL), and the two layers were separated. The organic layer was washed with water (2×50 mL) and brine (75 mL), and dried over sodium sulfate. The solvent was removed under reduced pressure, and flash chromatography on silica (EtOAc/hexanes, 1:9) yielded 1.00 g (51%) of (96) as a pale yellow solid. TLC (EtOAc/hexanes, 1:9) R$_f$ 0.60 $^1$H NMR (CDCl$_3$) δ0.90 (s, 9H), 1.29 (t, J=7 Hz, 3H), 2.04 (d, J=6 Hz, 2H), 4.19 (q, J=7 Hz, 2H), 5.80 (d, J=15.5 Hz, 1H), 6.13–6.17 (m, 2H), 7.24–7.39 (m, 2H).

Synthesis of Structure (97)

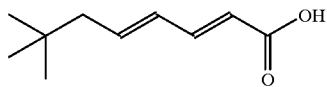

(97)

A solution of methyl 7,7-dimethyl-2,4-octadienoate (96) (0.99 g, 5 mmol) and sodium hydroxide (0.60 g, 15 mmol) in methanol (15 mL) and water (5 mL) was refluxed for 30 min. After cooling to room temperature, the solvent was removed in vacuo, and the residue was dissolved in water (30 mL). The resulting solution was acidified with conc. HCl to pH 2, and the precipitate was collected by filtration, washed with water (10 mL), and dried in vacuo to yield 0.84 (99%) of the acid as a white solid. $^1$H NMR (CDCl$_3$) δ0.92 (s, 3H), 2.07 (d, J=6.5 Hz, 2H), 5.80 (d, J=15.5 Hz, 1H), 6.19–6.23 (m, 2H) 7.34–7.40 (m, 2H).

Example 29
Solid Phase Synthesis of Representative β-Sheet Mimetics

This example illustrates the solid phase synthesis of representative β-sheet mimetics (100) through (227) (Tables 11–15). The compounds of this example were synthesized according to the following reaction scheme:

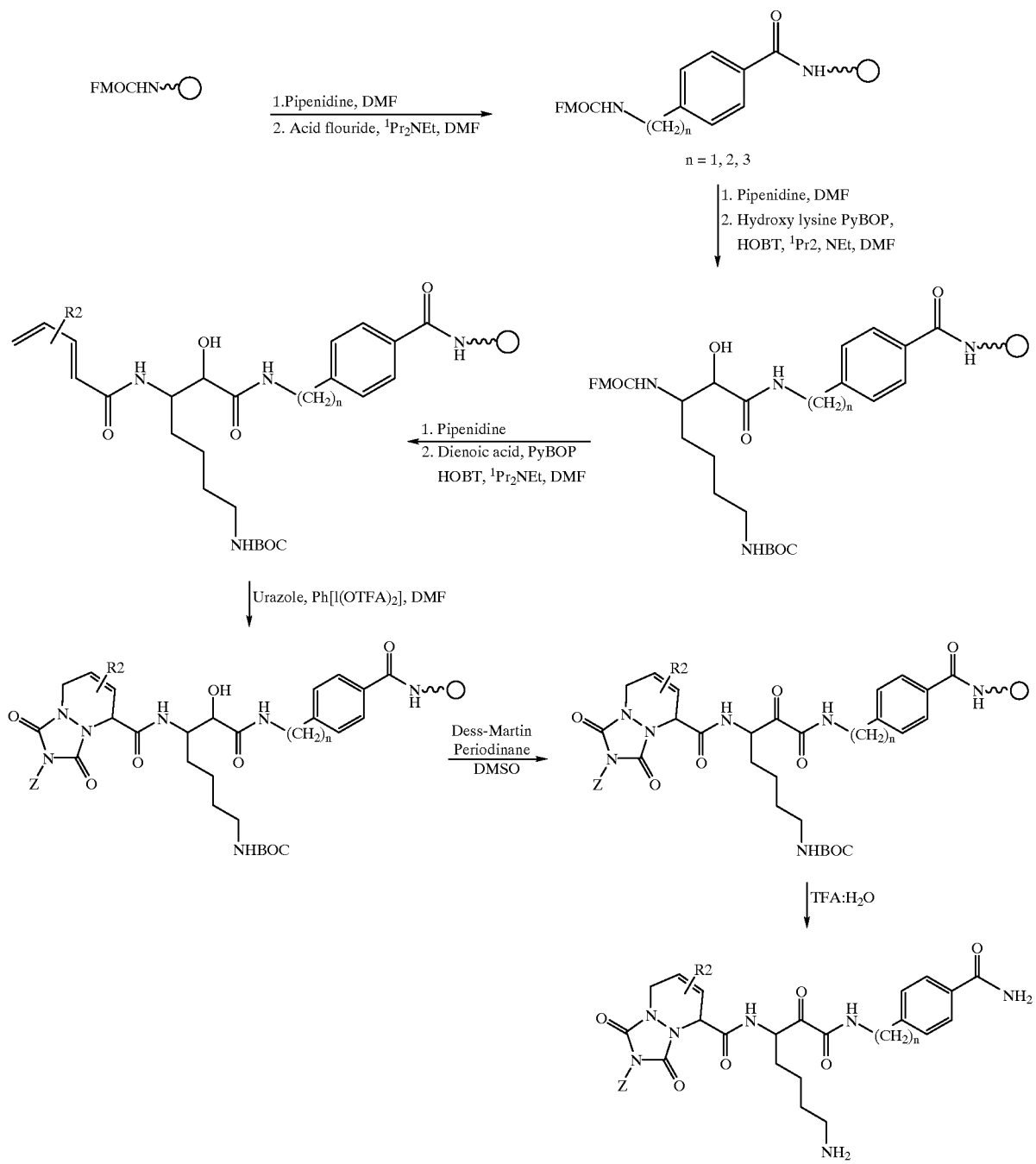

General Procedure: The synthesis of β-strand mimetics was initiated by deprotection of Fmoc PAL resin using 25% piperidine in DMF. Following extensive washing with DMF, the resin was treated with the acid fluoride of N-Fmoc-4-aminomethylbenzoic acid, or (81), or (86) and Hunigs' base in DMF until the Kaiser test was negative. Alternatively, the Fmoc-protected thiazole- (75) or imidazole-based (77) linkers were coupled to the resin using BOP, HOBt and DIEA. In some instances Fmoc-Leu or another amino acid was attached to the resin prior to the thiazole- (75) or imidazole-based (77) linkers via the same methodology. In the case of structures (217)–(221), the isocyanate (91) was coupled to Wang resin overnight in the presence of catalytic HCl in dichloromethane. Deprotection of all Fmoc-protected linkers was effected by treatment with 25% piperidine in DMF, and deprotection the Boc-protected linker (77) was effected by TMS-Cl (1 M) and phenol (3 M) in dichloromethane for 30 min. The lysinol derivative (90) was coupled to resin-bound linkers N-Fmoc-4-aminomethylbenzoic acid, (81), or (86) using PyBOP, HOBt and Hunigs' base in DMF until a negative Kaiser test was achieved. Treatment of the resin with 25% piperidine in DMF then cleaved the FMOC group. Following washing with DMF a dienoic acid was coupled to the resin-bound linkers using PyBOP, HOBt and Hunigs' base in DMF until the result of a Kaiser test was negative. The cycloaddition was performed by pretreatment of a solution of a pyrazolidinedione (not shown) or urazole in DMF with a solution of [bis(trifluoroacetoxy)iodo]benzene in DMF. The polymer-supported diene was treated with the resulting solution for 2–16 hours. The resin was then washed with DMF and $CH_2Cl_2$. Oxidation to the ketoamide was effected by treatment of the resin with a solution of Dess-Martin periodinane in DMSO for 60 min. The resin was washed with $CH_2Cl_2$ and the product was cleaved from the resin by treatment of the resin with 95:5 TFA:$H_2O$ for 1–12 h. The supernatant was collected and the resin was washed with additional TFA. The combined filtrates were concentrated in vacuo. The residue was precipitated with diethyl ether and the ether was decanted. The resulting solid was reconstituted in 1:1 $CH_3CN:H_2O$ and lyophilized. Compounds (100) through (227) in Tables 11–15 each gave the expected (M+H$^+$) peak when submitted to LCMS (ES+). The compounds were assayed for inhibition of coagulation enzymes as mixtures of diastereomers.

All of the compounds listed in Tables 11–15 had Ki<100 nM as thrombin inhibitors, or had activity as Factor VIIa inhibitors (Table 15). The compounds noted with an "*" in Tables 11–15 had a Ki<10 nM as thrombin inhibitors and represent preferred embodiments.

TABLE 11

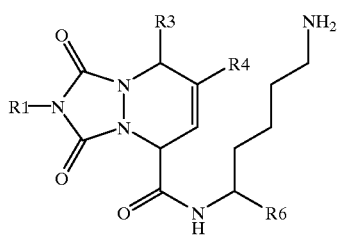

| Cpd. No. | R1 | R3 | R4 | F6 |
|---|---|---|---|---|
| 100* | 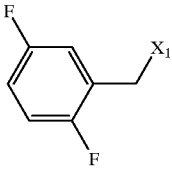 | |  | 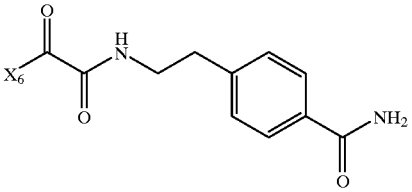 |
| 101* | 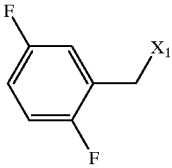 | 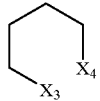 | | 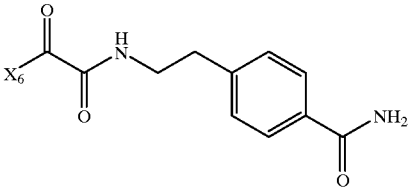 |
| 102* | 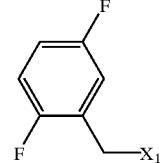 | |  | 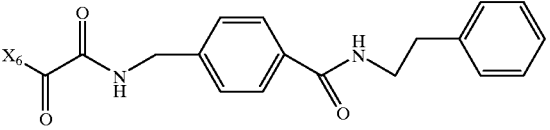 |
| 103* | 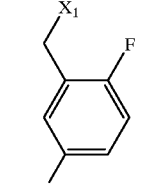 | 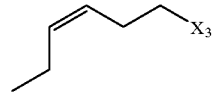 | | 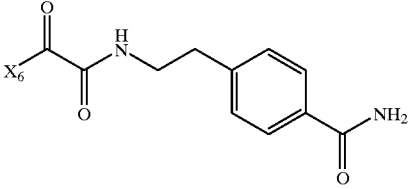 |

TABLE 11-continued
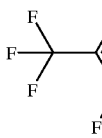
| Cpd. No. | R1 | R3 | R4 | F6 |
|---|---|---|---|---|
| 104* | 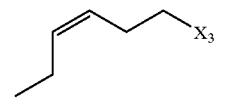 | 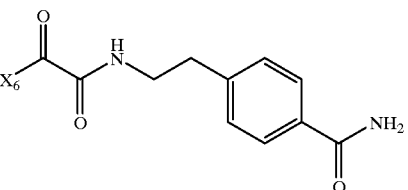 | | 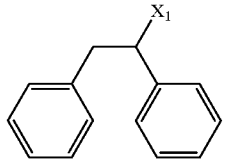 |
| 105* | 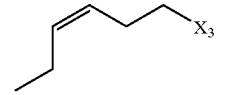 | 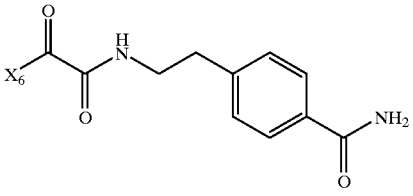 | | 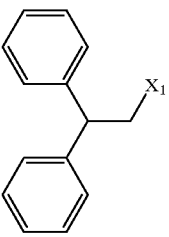 |
| 106* | 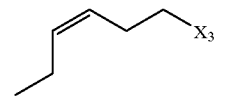 | 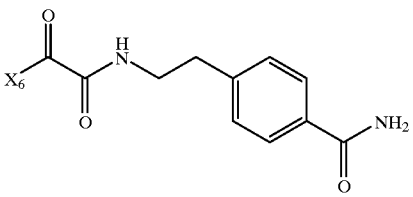 | | 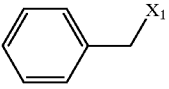 |
| 107* | 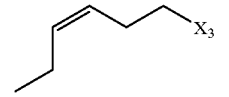 | 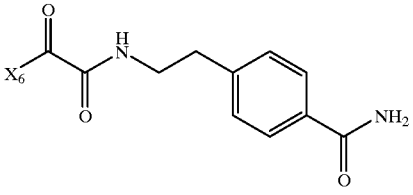 | | 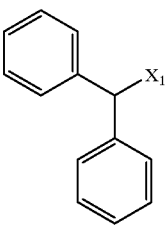 |
| 108* | 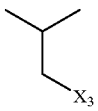 | 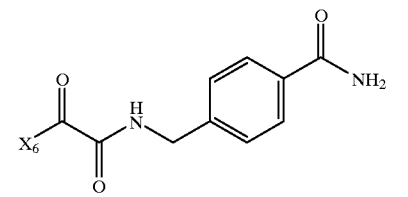 | | |

TABLE 11-continued
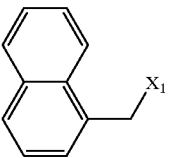
| Cpd. No. | R1 | R3 | R4 | F6 |
|---|---|---|---|---|
| 109* | 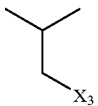 | 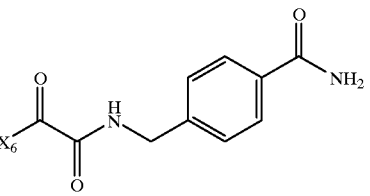 | | 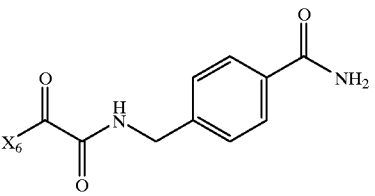 |
| 110* | 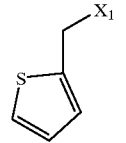 | 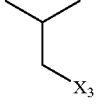 | | 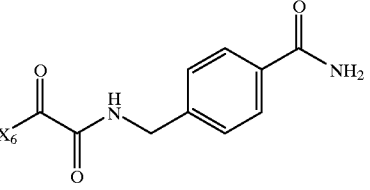 |
| 111* | 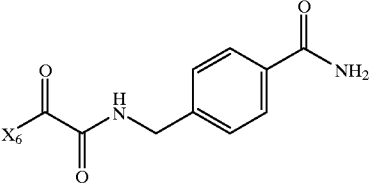 | 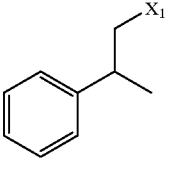 | | 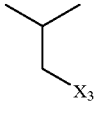 |
| 112* | 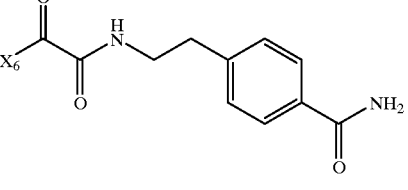 | 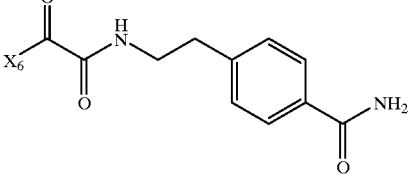 | | 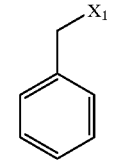 |
| 113* | 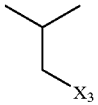 | 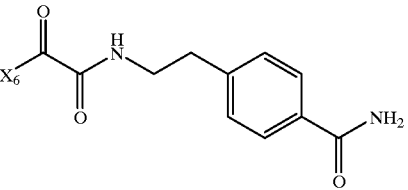 | | 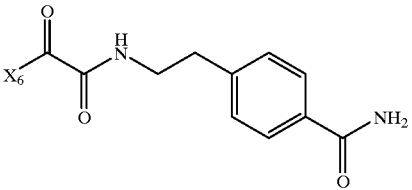 |
| 114* | 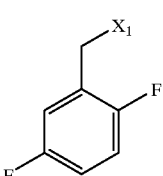 | 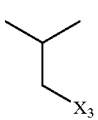 | | 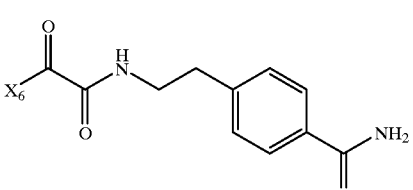 |

TABLE 11-continued
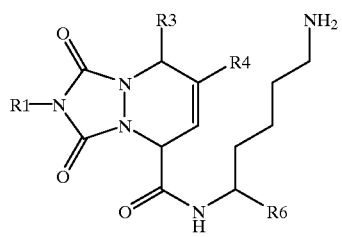
| Cpd. No. | R1 | R3 | R4 | F6 |
| --- | --- | --- | --- | --- |
| 115* | thiophene-2-CH2-X1 | isobutyl-X3 | | X6-C(O)-C(O)-NH-CH2CH2-C6H4-C(O)NH2 |
| 116* | thiophene-2-CH2-X1 | isobutyl-X3 | | X6-C(O)-C(O)-NH-CH2CH2-C6H4-C(O)NH2 |
| 117* | naphthalen-1-yl-CH2-X1 | isobutyl-X3 | | X6-C(O)-C(O)-NH-CH2CH2-C6H4-C(O)NH2 |
| 118* | (diphenyl)CH-X1 | isobutyl-X3 | | X6-C(O)-C(O)-NH-CH2CH2-C6H4-C(O)NH2 |
| 119* | thiophene-2-CH2CH2-X1 | | butylene X3-X4 | X6-C(O)-C(O)-NH-CH2CH2-C6H4-C(O)NH2 |
| 120* | 2,5-difluorobenzyl-X1 | | butylene X3-X4 | X6-C(O)-C(O)-NH-CH2CH2-C6H4-C(O)NH2 |

TABLE 11-continued
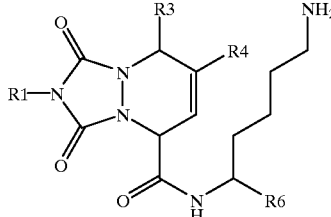
| Cpd. No. | R1 | R3 | R4 | F6 |
|---|---|---|---|---|
| 121* | 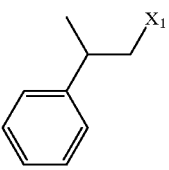 |  | |  |
| 122* | 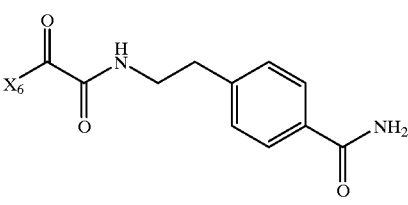 | 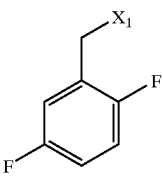 | 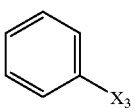 |  |
| 123* | 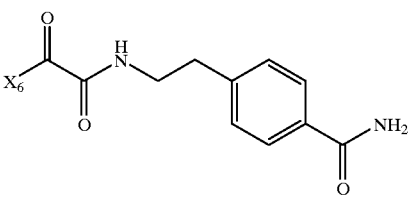 | 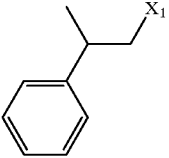 | 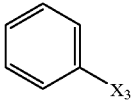 |  |
| 124* | 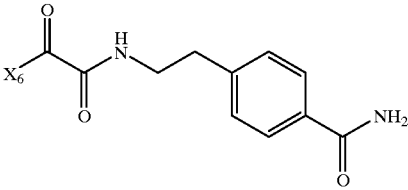 | 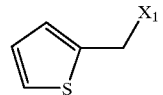 | 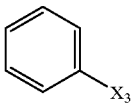 |  |
| 125* | 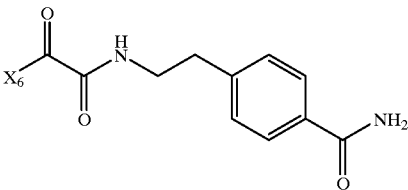 | 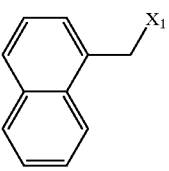 | 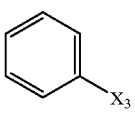 |  |
| 126* | 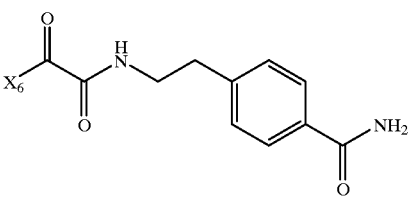 | 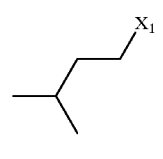 | | 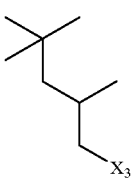 |

TABLE 11-continued
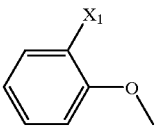
| Cpd. No. | R1 | R3 | R4 | F6 |
|---|---|---|---|---|
| 127* | 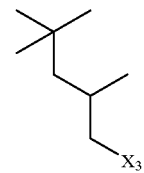 | 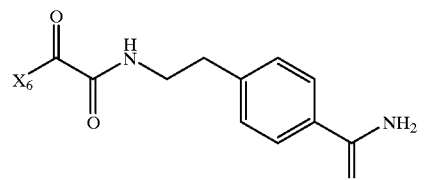 | | 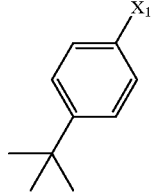 |
| 128* | 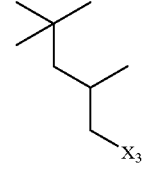 | 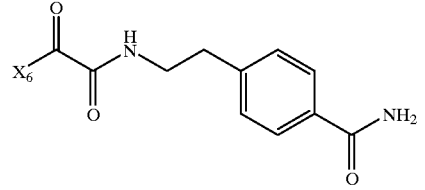 | | 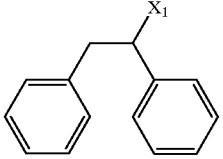 |
| 129* | 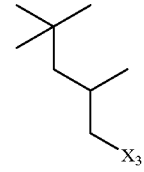 | 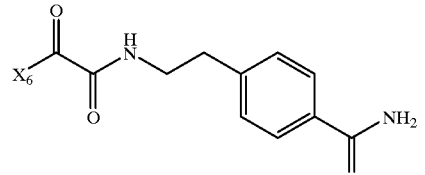 | | 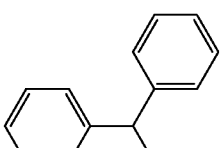 |
| 130* | 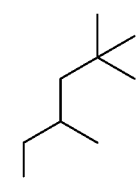 | 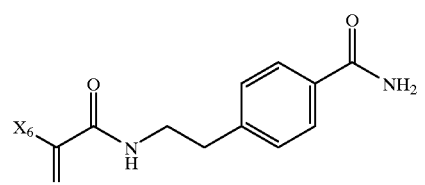 | | 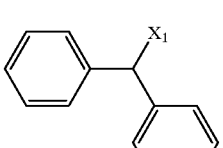 |
| 131* | 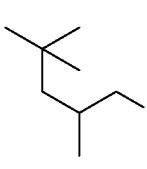 | 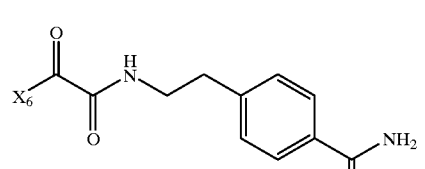 | | 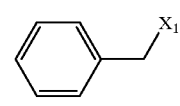 |
| 132* | 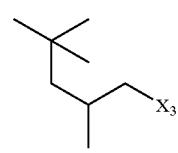 | 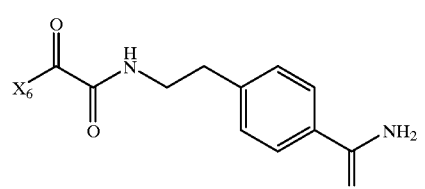 | | |

TABLE 11-continued
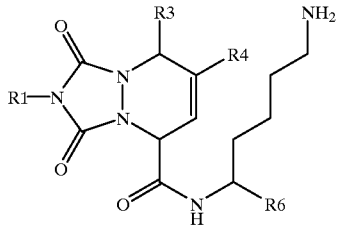
| Cpd. No. | R1 | R3 | R4 | F6 |
|---|---|---|---|---|
| 133* | 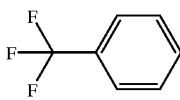 | 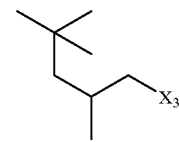 | | 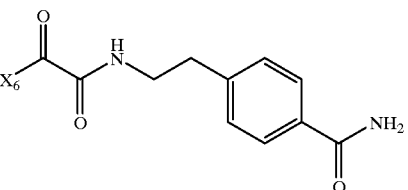 |
| 134* | 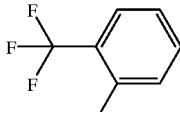 | 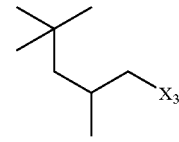 | | 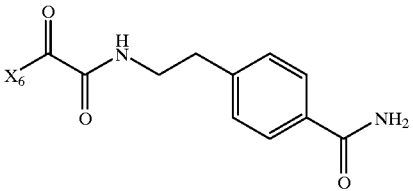 |
| 135* | 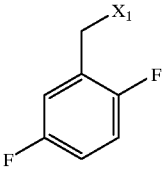 | 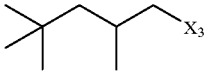 | | 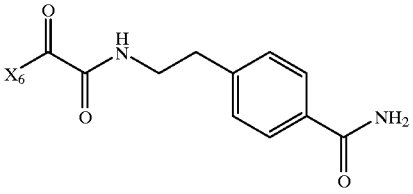 |
| 136* | 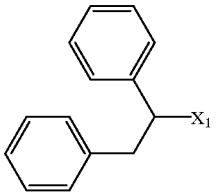 | |  | 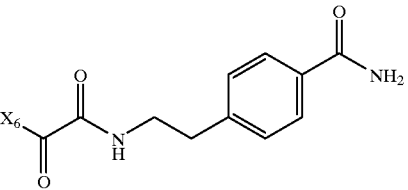 |
| 137* | 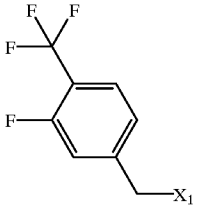 | |  | 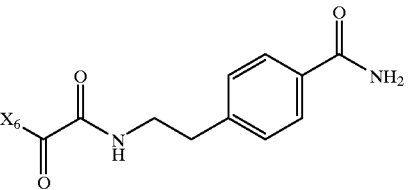 |

TABLE 11-continued
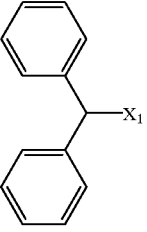
| Cpd. No. | R1 | R3 | R4 | F6 |
|---|---|---|---|---|
| 138* |  | | 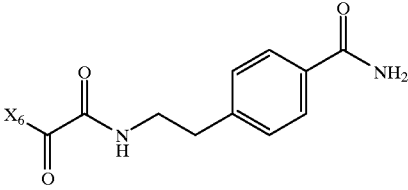 | 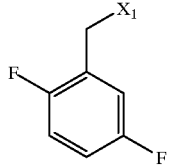 |
| 139* | 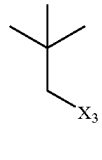 | | 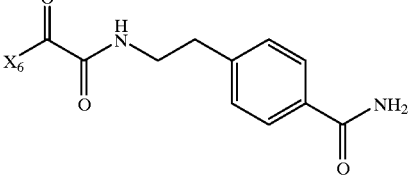 | 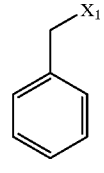 |
| 140* | 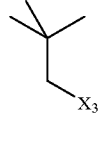 | | 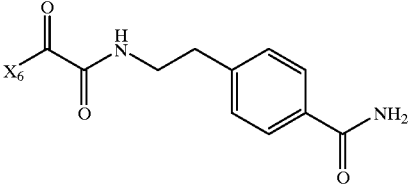 | 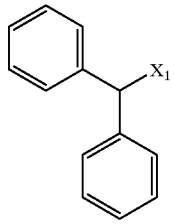 |
| 141* | 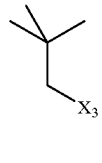 | | 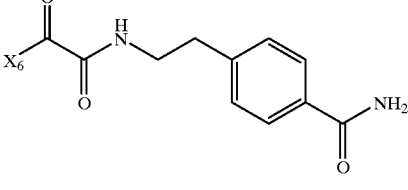 | 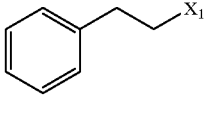 |
| 142* | 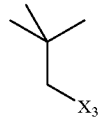 | | 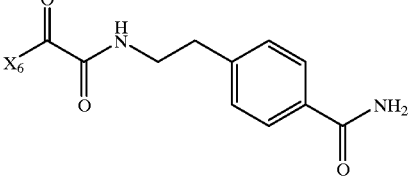 | |

TABLE 11-continued
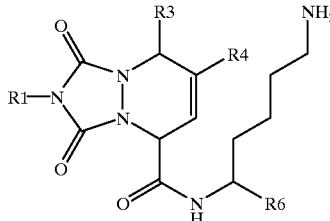
| Cpd. No. | R1 | R3 | R4 | F6 |
|---|---|---|---|---|
| 143* | 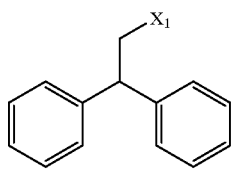 | 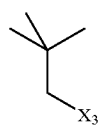 | | 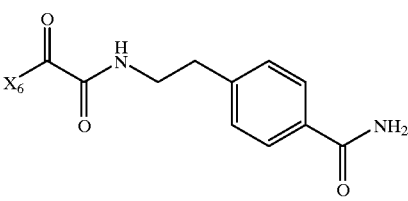 |
| 144* | 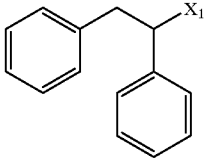 | 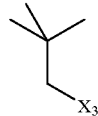 | | 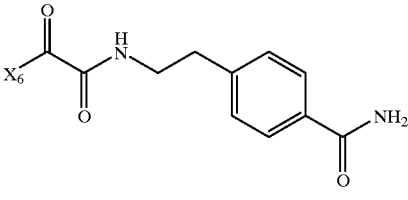 |
| 145* | 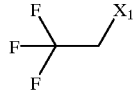 | |  | 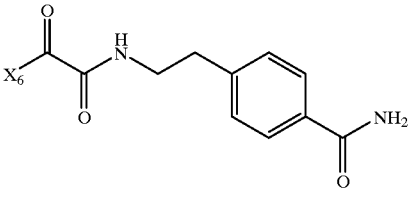 |
| 146* | 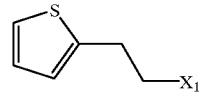 |  | | 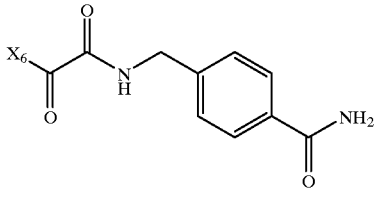 |
| 147* | 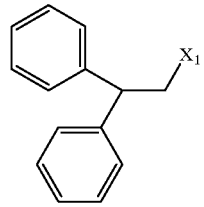 | |  | 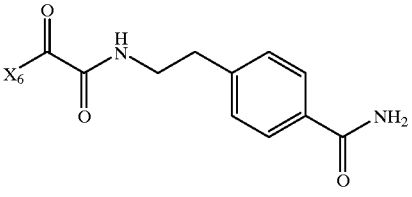 |
| 148 | 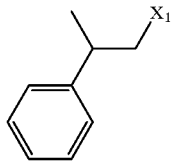 | |  | 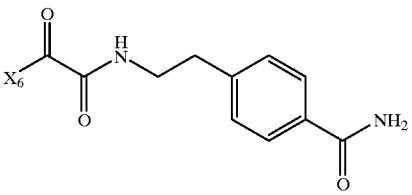 |

TABLE 11-continued
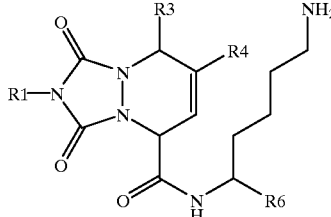
| Cpd. No. | R1 | R3 | R4 | F6 |
|---|---|---|---|---|
| 149 | 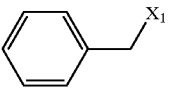 | 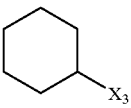 | | 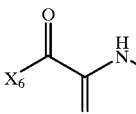 |
| 150 | 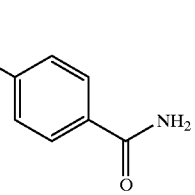 | 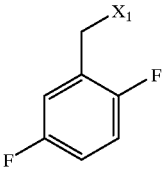 | | 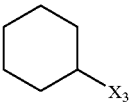 |
| 151 | 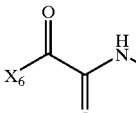 | 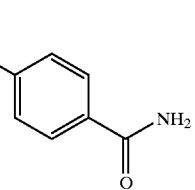 | | 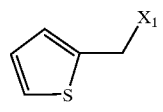 |
| 152 | 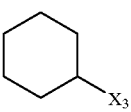 | 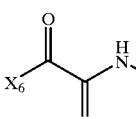 | | 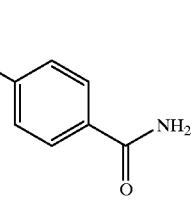 |
| 153 | 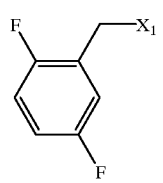 | 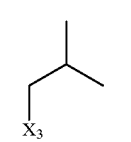 | | 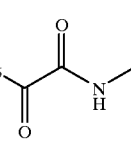 |
| 154 | 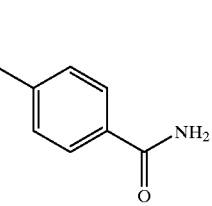 | 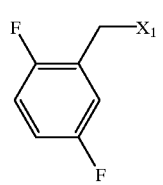 | | 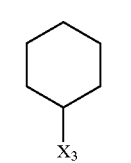 |

US 6,372,744 B1
191                                                                                     192
TABLE 11-continued
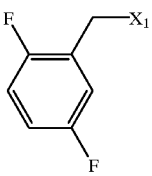
| Cpd. No. | R1 | R3 | R4 | F6 |
|---|---|---|---|---|
| 155 |  | | 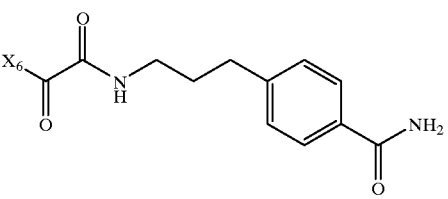 | 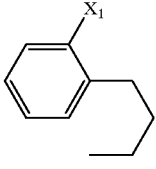 |
| 156 |  | | 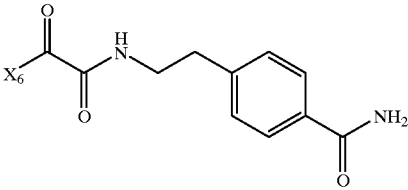 | 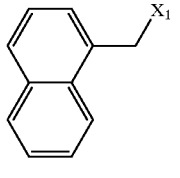 |
| 157 |  | | 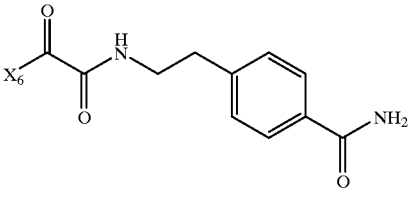 | 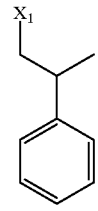 |
| 158 |  | | 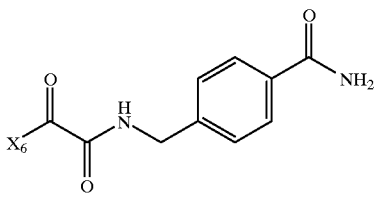 | 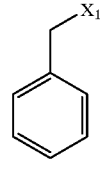 |
| 159 |  | | 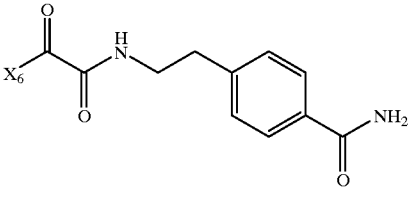 | 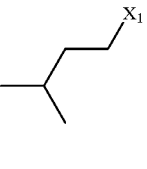 |
| 160 |  | | 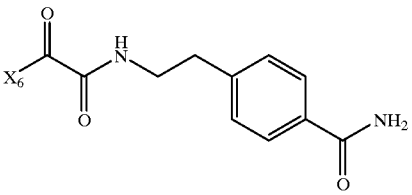 | |

TABLE 11-continued
| Cpd. No. | R1 | R3 | R4 | F6 |
|---|---|---|---|---|
| 161 | 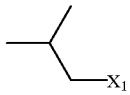 | 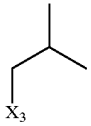 | | 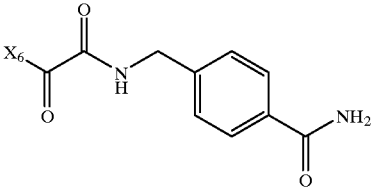 |
| 162 | 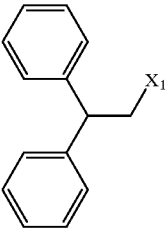 | 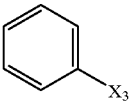 | 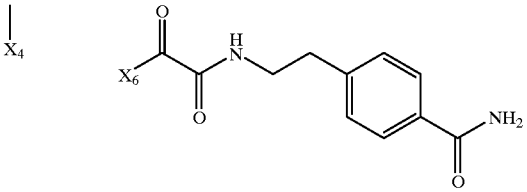 | 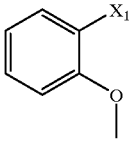 |
| 163 | 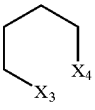 | 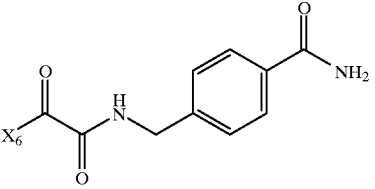 | | 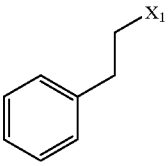 |
| 164 | 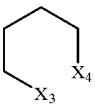 | 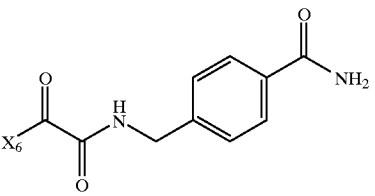 | | 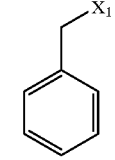 |
| 165 | 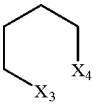 | 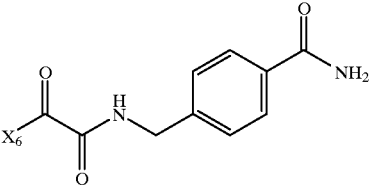 | | 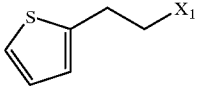 |
| 166 | 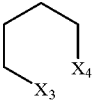 | 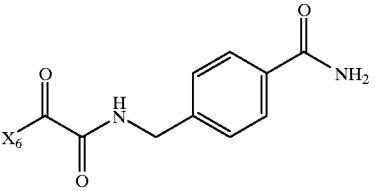 | | |

TABLE 11-continued

| Cpd. No. | R1 | R3 | R4 | F6 |
|---|---|---|---|---|
| 167 | 2-(pyridin-2-yl)ethyl-X₁ | cyclohexyl X₃-X₄ | | X₆-C(O)C(O)NH-CH₂-C₆H₄-C(O)NH₂ |
| 168 | 2-methoxyphenyl-X₁ | | X₄ | X₆-C(O)C(O)NH-CH₂CH₂-C₆H₄-C(O)NH₂ |
| 169 | isopentyl-X₁ | cyclohexyl X₃-X₄ | | X₆-C(O)C(O)NH-CH₂-C₆H₄-C(O)NH₂ |
| 170 | 3-methylbutyl-X₁ | | X₄ | X₆-C(O)C(O)NH-CH₂-C₆H₄-C(O)NH₂ |
| 171 | isobutyl-X₁ | | X₄ | X₆-C(O)C(O)NH-CH₂-C₆H₄-C(O)NH₂ |
| 172 | 2,5-difluorobenzyl-X₁ | cyclohexyl X₃-X₄ | | X₆-C(O)C(O)NH-CH₂-C₆H₄-C(O)NH₂ |

TABLE 11-continued
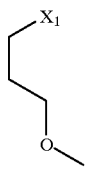
| Cpd. No. | R1 | R3 | R4 | F6 |
|---|---|---|---|---|
| 173 |  | | X₄ | 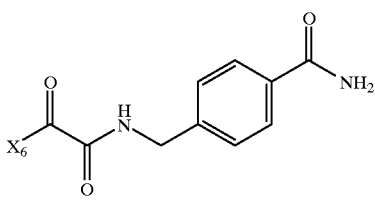 |
| 174 |  | | X₄ |  |
| 175 | 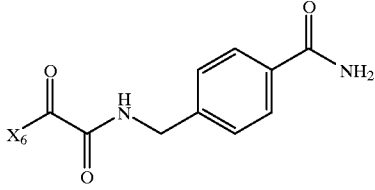 | 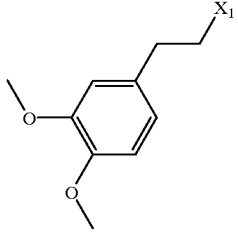 | | 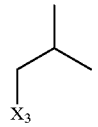 |
| 176 | 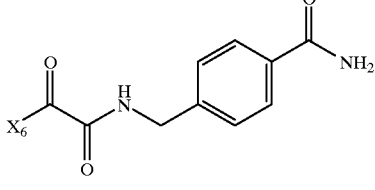 | | X₄ | 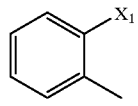 |
| 177 |  | 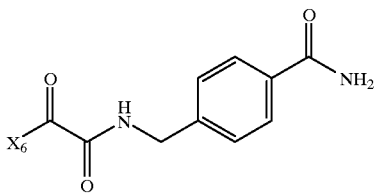 | | 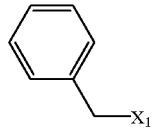 |
| 178 | 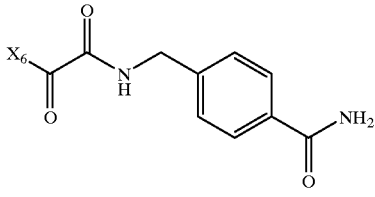 | | X₄ | 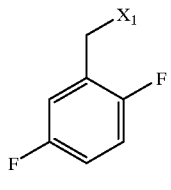 |

TABLE 11-continued
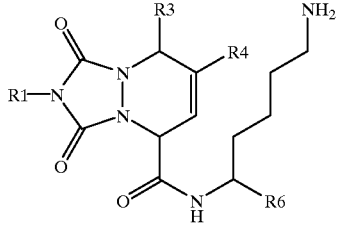
| Cpd. No. | R1 | R3 | R4 | F6 |
|---|---|---|---|---|
| 179 | 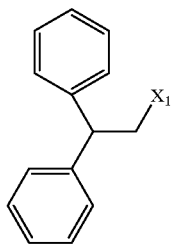 | | 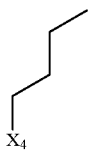 | 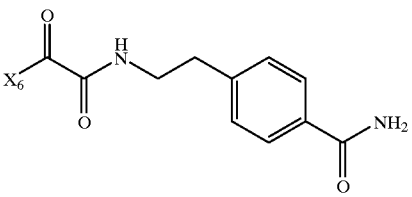 |
| 180 | 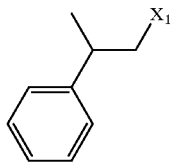 | 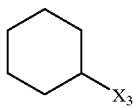 | | 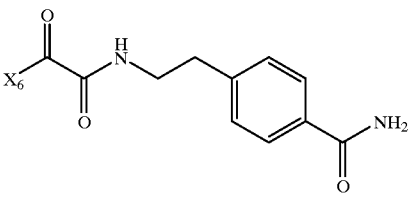 |
| 181 | 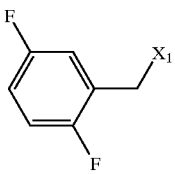 | 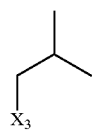 | | 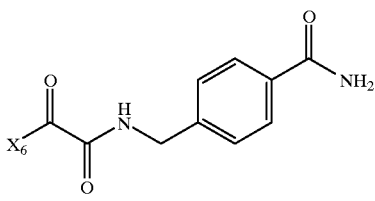 |
| 182 | 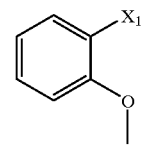 | |  | 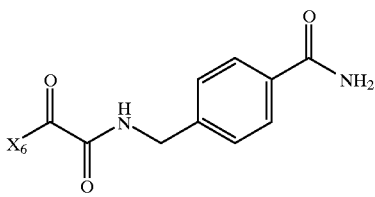 |
| 183 | 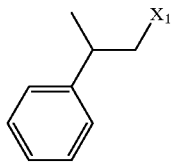 | 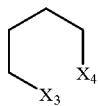 | | 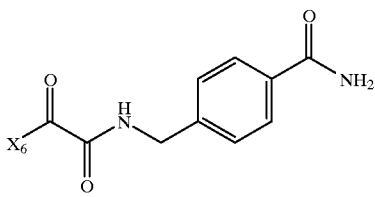 |

TABLE 11-continued
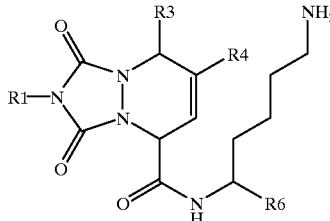
| Cpd. No. | R1 | R3 | R4 | F6 |
|---|---|---|---|---|
| 184 | 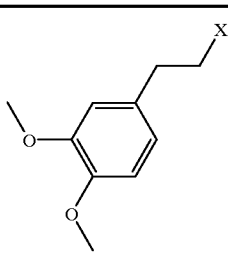 | 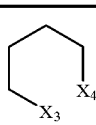 | | 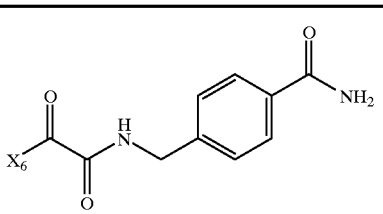 |
| 185 | 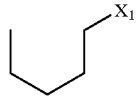 | | 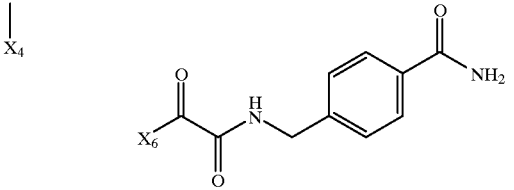 | 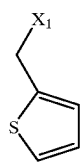 |
| 186 | 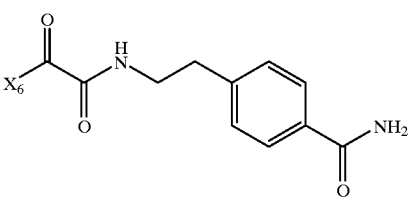 | | | |

TABLE 12

| Cpd. No. | R1 | R2 | R3 | R4 | R5 | R6 | MS ES+ (M + H+) |
|---|---|---|---|---|---|---|---|
| 187* | benzyl-X1 | benzyl-X2 | | X4-ethyl | H2N-(CH2)4-X5 | X6-C(O)-C(O)-NH-CH2CH2-C6H4-C(O)NH2 | 694 |
| 188* | isobutyl-X1 | isobutyl-X2 | | X4-ethyl | H2N-(CH2)4-X5 | X6-C(O)-C(O)-NH-CH2CH2-C6H4-C(O)NH2 | 626 |
| 189* | H2N-X1 | benzyl-X2 | | X4-ethyl | H2N-(CH2)4-X5 | X6-C(O)-C(O)-NH-CH2-C6H4-C(O)NH2 | 605 |

TABLE 12-continued

| Cpd. No. | R1 | R2 | R3 | R4 | R5 | R6 | MS ES+ (M + H+) |
|---|---|---|---|---|---|---|---|
| 190* | H2N–X1 | ethyl–X2 | benzyl–X3 | | H2N(CH2)4–X5 | X6–C(O)C(O)NH2 | 486 |
| 191 | H2N–X1 | allyl-O-C(O)-NH-(CH2)3–X2 | –X3 | | H2N(CH2)4–X5 | X6–C(O)C(O)NH-CH2-C6H4-C(O)NH2 | 656 |
| 192 | H2N–X1 | ethyl–X2 | benzyl–X3 | | H2N(CH2)4–X5 | X6–C(O)C(O)NH-CH2-C6H4-C(O)NH2 | 619 |

TABLE 12-continued

| Cpd. No. | R1 | R2 | R3 | R4 | R5 | R6 | MS ES+ (M + H+) |
|---|---|---|---|---|---|---|---|
| 193 | H2N-X1 | isobutyl-X2 | benzyl-X3 | | 4-aminobutyl-X5 | 4-carbamoylbenzyl-NH-C(O)-C(O)-X6 | 647 |
| 194 | H2N-X1 | isopropyl-X2 | | methyl-X4 | 4-aminobutyl-X5 | 4-carbamoylbenzyl-NH-C(O)-C(O)-X6 | 557 |
| 195 | H2N-X1 | 4-nitrobenzyl-X2 | methyl-X3 | | 3-guanidinopropyl-X5 | benzothiazol-2-yl-C(O)-X6 | 635 |

TABLE 12-continued
| Cpd. No. | R1 | R2 | R3 | R4 | R5 | R6 | MS ES+ (M + H+) |
|---|---|---|---|---|---|---|---|
| 196 | 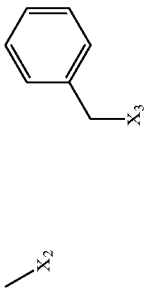 | 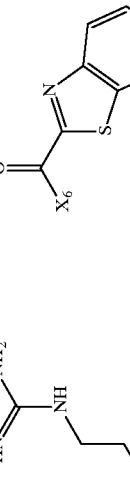 | 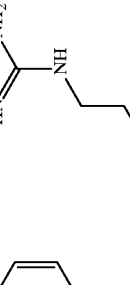 | |  | | 590 |

TABLE 13

| Cpd. No. | R1 | R3 | R4 | R6 | MS (ES+) (M + H+) |
|---|---|---|---|---|---|
| 197 | 2-pyridyl-ethyl-X₁ | | X₄-methyl | thiazole-4-carboxamide, X₆-C(O)- | 584 |
| 198* | diphenylmethyl-CH₂-X₁ | | X₄-methyl | thiazole-4-carboxamide, X₆-C(O)- | 659 |
| 199 | diphenylmethyl (with two X₁) | phenyl-X₃ | X₄-methyl | thiazole-4-carboxamide-NH-CH(CH₂CH(CH₃)₂)-C(O)NH₂, X₆-C(O)- | 848 |
| 200 | diphenylmethyl-CH₂-X₁ | | X₄-butyl | thiazole-4-carboxamide-NH-CH(CH₂CH(CH₃)₂)-C(O)NH₂, X₆-C(O)- | 814 |
| 201* | diphenylmethyl-CH₂-X₁ | | X₄-methyl | imidazole-4-carboxamide, X₆-C(O)- | 642 |
| 202 | 2-pyridyl-ethyl-X₁ | | X₄-methyl | imidazole-4-carboxamide, X₆-C(O)- | 567 |

TABLE 13-continued

| Cpd. No. | R1 | R3 | R4 | R6 | MS (ES+) (M + H+) |
|---|---|---|---|---|---|
| 203 | 3-methoxypropyl-X1 | | X4-methyl | 2-acyl-1H-imidazole-4-carboxamide | 534 |
| 204 | 3-(2-oxopyrrolidin-1-yl)propyl-X1 | | X4-methyl | 2-acyl-1H-imidazole-4-carboxamide | 587 |
| 205 | 2,2-diphenylethyl-X1 | tetrahydropyran X3,X4 | | thiazole-leucinamide | 812 |
| 206 | 2,5-difluorobenzyl-X1 | cyclohexyl-X3 | | 2-acyl-1H-imidazole-4-carboxamide | 656 |
| 207 | 2,5-difluorobenzyl-X1 | phenyl-X3 | X4-methyl | 2-acyl-1H-imidazole-4-carboxamide | 664 |
| 208 | 2,5-difluorobenzyl-X1 | isobutyl-X3 | | 2-acyl-1H-imidazole-4-carboxamide | 630 |

TABLE 13-continued
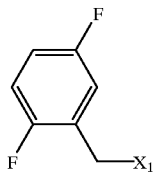
| Cpd. No. | R1 | R3 | R4 | R6 | MS (ES+) (M + H+) |
|---|---|---|---|---|---|
| 209 | 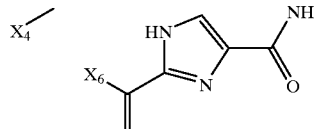 | | 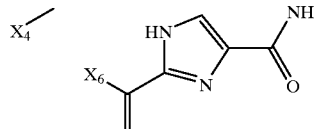 | 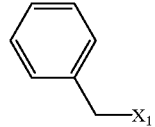 | 588 |
| 210 | 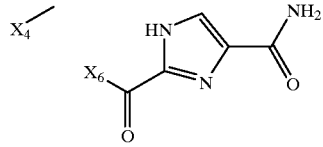 | | 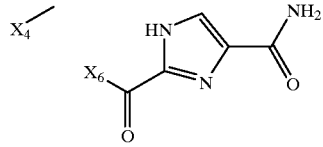 | 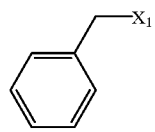 | 552 |
| 211* | 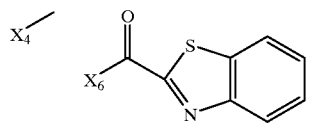 | | 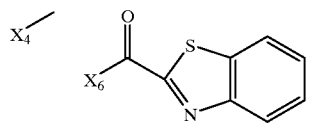 | 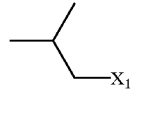 | 576 |
| 212 |  |  | |  | 705 |
| 213 | 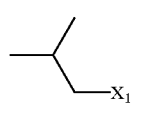 |  | |  | 648 |
| 214 |  | 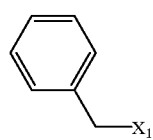 | |  | 724 |

TABLE 13-continued
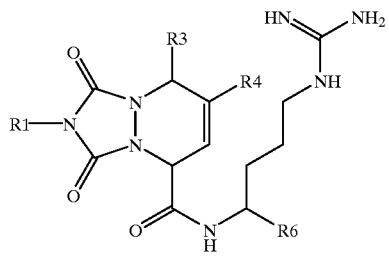
| Cpd. No. | R1 | R3 | R4 | R6 | MS (ES+) (M + H+) |
|---|---|---|---|---|---|
| 215* | (diphenylethyl-X1) | | X4–CH3 | X6–C(O)-benzothiazol-2-yl | 666 |
| 216 | benzyl-X1 | | 2,4,4-trimethylpentyl-X3 | X6–C(O)-thiazol-2-yl-C(O)NH-CH(CH2CH(CH3)2)-C(O)NH2 | 780 |
TABLE 14
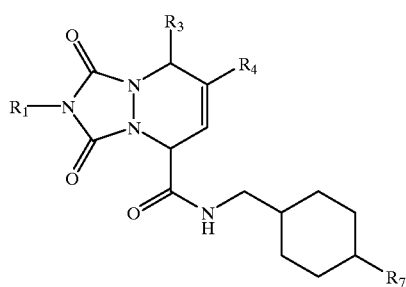
| Cpd. No. | R1 | R3 | R4 | R7 | MS (ES+) (M + H+) |
|---|---|---|---|---|---|
| 217* | (diphenylethyl-X1) | | X4–CH3 | X7–NH2 | 503 |
| 218 | phenethyl-X1 | | X4–CH3 | X7–NH2 | 426 |

TABLE 14-continued
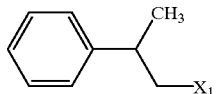
| Cpd. No. | R1 | R3 | R4 | R7 | MS (ES+) (M + H+) |
|---|---|---|---|---|---|
| 219* |  | | X₄—CH₃ | X₇—NH₂ | 441 |
| 220 |  | | X₄—CH₃ | X₇—NH₂ | 503 |
| 221 | 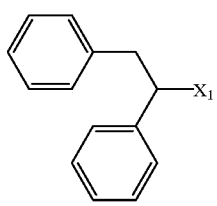 | | X₄—CH₃ | X₇—NH₂ | 455 |
| 221-1 |  | | X₄—CH₃ |  | 545 |
| 221-2 | 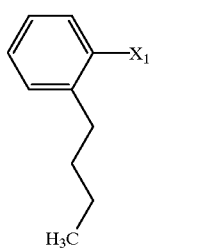 | | X₄—CH₃ | X₇—NH₂ | 456 |
| 221-3 |  | | X₄—CH₃ | X₇—NH₂ | 545 |

TABLE 14-continued
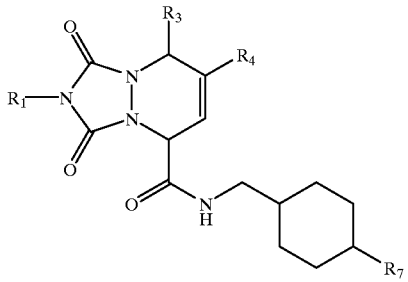
| Cpd. No. | R1 | R3 | R4 | R7 | MS (ES+) (M + H+) |
|---|---|---|---|---|---|
| 221-4 |  | | $X_4$—CH$_3$ | $X_7$—NH$_2$ | 581 |
| 221-5* |  | | $X_4$—CH$_3$ | $X_7$—NH$_2$ | 490 |
| 221-6* | 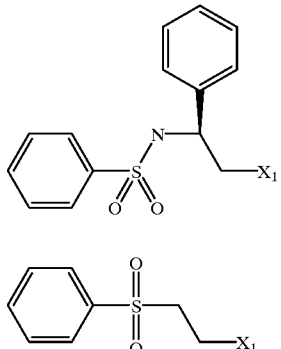 | | $X_4$—CH$_3$ | $X_7$—C(=NH)NH$_2$ | 518 |
| 221-7 |  | | $X_4$—CH$_3$ | $X_7$—NH$_2$ | 486 |
| 221-8 |  | | $X_4$—CH$_3$ | $X_7$—NH$_2$ | 465 |
| 221-9 | 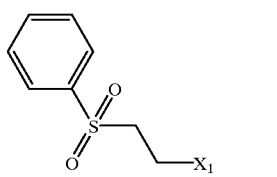 | | $X_4$—CH$_3$ | $X_7$—NH$_2$ | 441 |
| 221-10 |  | | $X_4$—CH$_3$ | $X_7$—NH$_2$ | 432 |

TABLE 14-continued

| Cpd. No. | R1 | R3 | R4 | R7 | MS (ES+) (M + H+) |
|---|---|---|---|---|---|
| 221-11 | 4-nitrophenyl-CH₂CH₂-X₁ | | X₄-CH₃ | X₇-NH₂ | 471 |
| 221-12* | phenyl-CH₂CH₂-X₁ | | X₄-CH₃ | X₇-C(=NH)NH₂ | 454 |
| 221-13* | (phenyl)₂CH-CH₂-X₁ | X₃-CH₃ | | X₇-NH₂ | 503 |
| 221-14* | PhSO₂-CH₂CH₂-X₁ | | | X₇-NH₂ | 477 |
| 221-15* | (phenyl)₂CH-CH₂-X₁ | | | X₇-NH₂ | 489 |
| 221-16 | PhSO₂-CH₂CH₂-X₁ | | X₄-CH₂OH | X₇-NH₂ | 506 |
| 221-17* | 3,4-dimethoxyphenyl-CH₂CH₂-X₁ | | X₄-CH₃ | X₇-C(=NH)NH₂ | 514 |

TABLE 14-continued
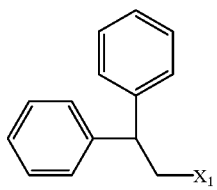
| Cpd. No. | R1 | R3 | R4 | R7 | MS (ES+) (M + H+) |
|---|---|---|---|---|---|
| 221-18* |  | | $X_4$—CH$_3$ | 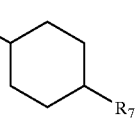 | 530 |
| 221-19* |  | | | $X_7$—NH$_2$ | 491 |
| 221-20* | 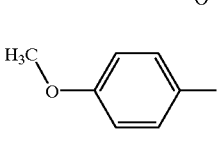 | | | $X_7$—NH$_2$ | 507 |
| 221-21 |  | | | 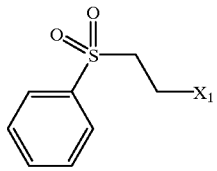 | 503 |

TABLE 15
| Cpd. No. | R1 | R3 | R4 | R5 | R6 | MS (ES+) (M + H⁺) |
|---|---|---|---|---|---|---|
| 222* | 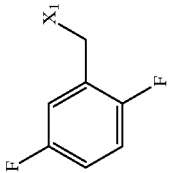 | | CH₃—X₄ | 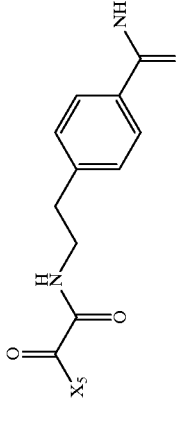 | 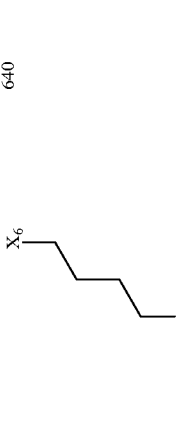 | 640 |
| 223* | 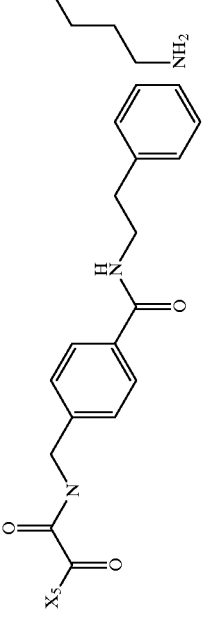 | | CH₃—X₄ | 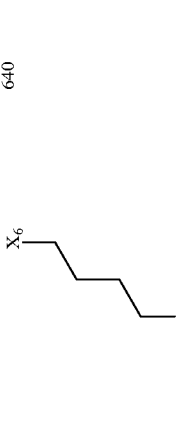 | 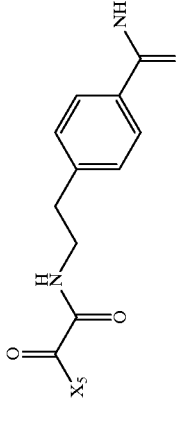 | 730 |
| 224* | 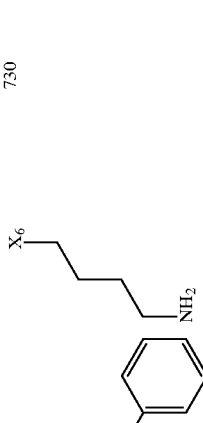 | | CH₃—X₄ | 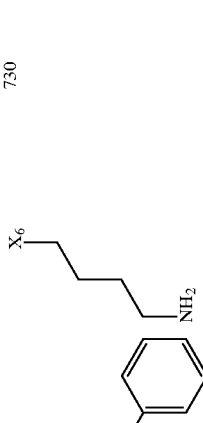 | | 575 |

TABLE 15-continued

| Cpd. No. | R1 | R3 | R4 | R5 | R6 | MS (ES+) (M + H+) |
|---|---|---|---|---|---|---|
| 225* | 2,5-difluorobenzyl-X1 | neopentyl-X3 | | X5-C(O)C(O)N-CH2CH2-(4-carbamoylphenyl) | X6-(CH2)4-NH2 | 697 |
| 226* | 2,5-difluorobenzyl-X1 | piperidinyl-X3,X4 | | X5-C(O)C(O)N-CH2CH2CH2-(4-carbamoylphenyl) | X6-(CH2)4-NH2 | 694 |
| 227 | 2,5-difluorobenzyl-X1 | | CH3-X4 | X5-C(O)C(O)N-CH2-(4-carbamoylphenyl) | X6-(CH2)4-NH2 | 626 |

TABLE 15-continued
| Cpd. No. | R1 | R3 | R4 | R5 | R6 | MS (ES+) (M + H+) |
|---|---|---|---|---|---|---|
| 227-1 |  |  | | 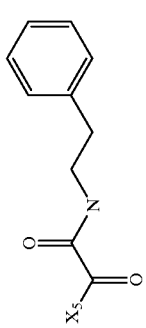 | 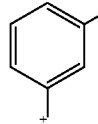 | 647 |
| 227-2 |  |  | | 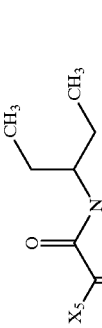 | 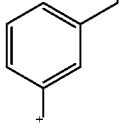 | 613 |
| 227-3 |  | 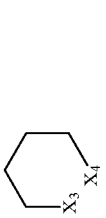 | | 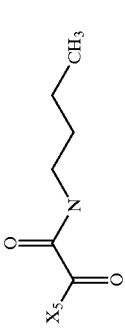 | 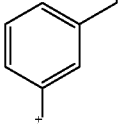 | 599 |

TABLE 15-continued

| Cpd. No. | R1 | R3 | R4 | R5 | R6 | MS (ES+) (M + H+) |
|---|---|---|---|---|---|---|
| 227-4 | 3-nitrobenzyl (X1) | cyclohexyl (X3, X4) | | thiophene-ethyl-N-C(O)C(O)-X5 | X6-(CH2)4-NH2 | 654 |
| 227-5 | 3-nitrobenzyl (X1) | cyclohexyl (X3, X4) | | CH3C(O)CH2-N-C(O)C(O)-X5 | X6-(CH2)4-NH2 | 599 |
| 227-6 | 3-nitrobenzyl (X1) | 4-(ethoxycarbonyl)cyclohexyl (X3, X4) | | H2N-(CH2)4-X5 | X6-C(O)C(O)OH | 615 |

TABLE 15-continued

| Cpd. No. | R1 | R3 | R4 | R5 | R6 | MS (ES+) (M + H+) |
|---|---|---|---|---|---|---|
| 227-7 | 3-nitrobenzyl-X1 | cyclohexyl-X3,X4 | | 4-methylphenethyl-N(C(O)C(O)X5)- | -X6(CH2)4NH2 | 660 |
| 227-8 | 3-nitrobenzyl-X1 | cyclohexyl-X3,X4 | | 4-nitrophenethyl-N(C(O)C(O)X5)- | -X6(CH2)4NH2 | 691 |
| 227-9 | 3-nitrobenzyl-X1 | cyclohexyl-X3,X4 | | cyclohexylmethyl-N(C(O)C(O)X5)- | -X6(CH2)4NH2 | 638 |

TABLE 15-continued

| Cpd. No. | R1 | R3 | R4 | R5 | R6 | MS (ES+) (M + H⁺) |
|---|---|---|---|---|---|---|
| 227-10 | 3-nitrobenzyl-X1 | cyclohexyl-X3,X4 | cyclohexyl-N(C(O)C(O)X5) | | X6-(CH2)4-NH2 | 624 |
| 227-11 | 3-nitrobenzyl-X1 | 1-(piperidine-4-carbonyl)piperidin-3-yl-X3 | phenethyl-N(C(O)C(O)X5) | | X6-(CH2)4-NH2 | 786 |
| 227-12 | 3-nitrobenzyl-X1 | 4-oxo-butyl-X3,X4 | cyclohexylmethyl-N(C(O)C(O)X5) | | X6-(CH2)4-NH2 | 653 |

TABLE 15-continued

| Cpd. No. | R1 | R3 | R4 | R5 | R6 | MS (ES+) (M + H+) |
|---|---|---|---|---|---|---|
| 227-13 | 3-nitrobenzyl-X1 | cyclohexyl (X4, X3) | | pyridin-3-ylmethyl-N-C(O)-C(O)-X5 | X6-(CH2)4-NH2 | 633 |
| 227-14 | 3-nitrobenzyl-X1 | cyclohexyl (X4, X3) | | CH3-O-N-C(O)-C(O)-X5 | X6-(CH2)4-NH2 | 573 |
| 227-15 | 3-nitrobenzyl-X1 | 3-(acetyl)phenyl-N-C(O)-piperidin-4-yl-X3 | | X6-(CH2)4-NH2 | HO-C(O)-C(O)-X6 | 733 |

TABLE 15-continued

| Cpd. No. | R1 | R3 | R4 | R5 | R6 | MS (ES+) (M + H+) |
|---|---|---|---|---|---|---|
| 227-16 | 3-nitrobenzyl (X1) | piperazine (X3) | | cyclohexylmethyl-N-C(O)-C(O)-X5 | X6-(CH2)4-NH2 | 654 |
| 227-17 | 3-nitrobenzyl (X1) | 2-(carboxymethyl)piperidine (X3) | | cyclohexylmethyl-N-C(O)-C(O)-X5 | X6-(CH2)4-NH2 | 711 |
| 227-18 | 3-nitrobenzyl (X1) | 4-hydroxy-tetrahydropyran (X3) | | cyclohexylmethyl-N-C(O)-C(O)-X5 | X6-(CH2)4-NH2 | 669 |

TABLE 15-continued

| Cpd. No. | R1 | R3 | R4 | R5 | R6 | MS (ES+) (M + H⁺) |
|---|---|---|---|---|---|---|
| 227-19 | 3-nitrobenzyl (X₁) | 4-oxo-piperidinyl-acetic acid (X₃) | | cyclohexylmethyl-N-C(O)-C(O)-X₅ | X₆-(CH₂)₄-NH₂ | 724 |
| 227-20 | 3-nitrobenzyl (X₁) | piperidin-2-yl-propanoic acid (X₃) | | cyclohexylmethyl-N-C(O)-C(O)-X₅ | X₆-(CH₂)₄-NH₂ | 725 |
| 227-30 | 3-nitrobenzyl (X₁) | 4-oxo-piperidinyl-acetonitrile (X₃) | | cyclohexylmethyl-N-C(O)-C(O)-X₅ | X₆-(CH₂)₄-NH₂ | 705 |

Example 30
Synthesis of Representative β-Sheet Mimetics

This example further illustrates the synthesis of representative β-sheet mimetics of this invention.

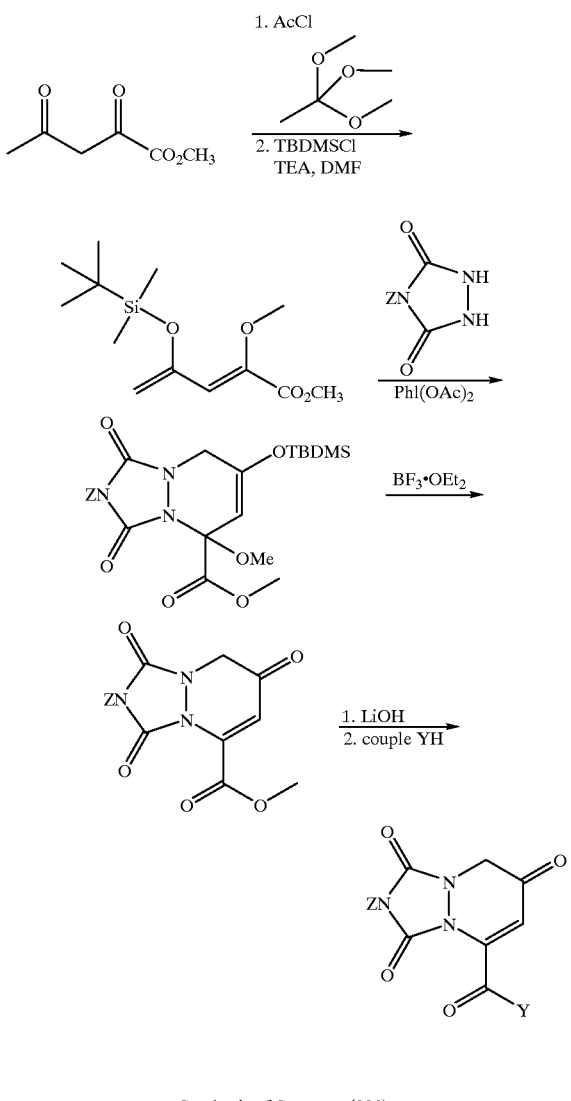

Synthesis of Structure (228)

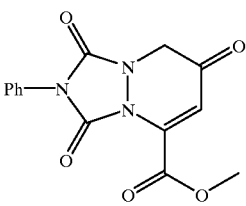

(228)

Methyl-2,4-dioxo-pentanoate (14.4 g, 0.10 mol) and 10.6 g of trimethyl orthoacetate were dissolved in 100 mL of methanol followed by the addition of 300 μL of acetyl chloride. This solution was then stirred at room temperature for 6 h. An aliquot was then taken and the solvent removed using a rotary evaporator. ¹H NMR analysis of the residue suggested a complete conversion to the methyl enol ether. The reaction solution was evaporated in vacuo. By ¹H NMR, purity was 90%, and the material was used for the next step without purification.

2-Methoxy-4-oxo-2-pentenone (1.58 g, 10 mmol) and 1.63 g of t-butyldimethylsilyl chloride (11 mmol) were dissolved in 15 mL of DMF. Triethylamine (1.553 mL, 12 mmol) was added and the reaction stirred overnight under argon at rt. The next morning 50 mL of hexane was added and the reaction was extracted with cold $NaHCO_3$ solution. The hexane layer was dried over $Na_2SO_4$ and hexane removed under vacuum to give 2.01 g of the diene as an oil (78%), which was used without further purification. NMR ($CDCl_3$) δ0.16 (s, 6H), 0.94 (s, 9H), 3.53 (s, 3H),3.73 (s, 3H),4.32 (bs, 1H), 4.6 (bs,1H), 6.21 (s,1H).

Synthesis of Structure (229)

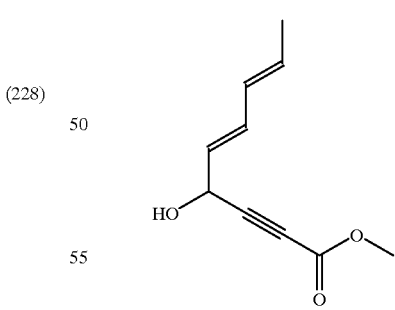

(229)

To a mixture of 4-phenyl urazole (177 mg, 1 mmol) and iodobenzene diacetate(322 mg, 1 mmol) in $CH_2Cl_2$ (5 mL) was added a solution of the diene (228) (269 mg, 1.05 mmol) in $CH_2Cl_2$. The reaction mixture was stirred 30 min, and then cooled to 0° C. $BF_3.OEt_2$ (141 mg, 1 mmol) was added dropwise and the reaction stirred for 30 min, diluted with $CH_2Cl_2$ (50 mL), washed with $NaHCO_3$ solution (2×15 mL), water (15 mL) and brine, dried and evaporated. Crude product was purified by column chromatography on silica gel (EtOAc/hexane, 1:3, v/v) to afford pure product (97 mg,32%). ¹H NMR (500 MHz, $CDCl_3$) δ7.53–7.42 (m, 5H),6.30 (s, 1H), 4.47 (s, 2H), 3.97 (s, 3H); MS (EI, 12 eV) 301 ($M^+$, 100), 273.4, 246.3, 154.4, 119.5.

Example 31
Synthesis of Representative β-Sheet Mimetics

This example further illustrates the synthesis of representative β-sheet mimetics of this invention.

Synthesis of Structure (24)

(230)

To a 250 mL flame-dried round bottom flask was added 130 mL of dry THF. The flask was cooled to –78° C. under an argon atmosphere, and 10 mL of 2.5 M n-BuLi were added followed by 5.3 mL of hexamethyldisilazane. This solution was stirred at –78° C. for 30 min., and then 2.2 mL of methyl propiolate were added. After stirring at –78° C. for 50 min., 2.5 mL (22 mmol) of hexadienal were added. The reaction was then slowly warmed to –30° C. over a period of 4 h. After an hour at –30° C., it was quenched by addition of aqueous tartaric acid solution. The reaction mixture was then partitioned between EtOAc and water, and the aqueous layer was washed with additional ethyl acetate. The combined organic layers were then washed with saturated sodium chloride, dried over sodium sulfate, and concentrated to give about 4.1 g of a reddish oil. Flash chromatography via silica gel (20% ethyl acetate/80% hexane) gave 3.1 g of a yellowish oil (78%). $^1$H NRM (CDCl$_3$) δ1.78 (d, 3H, J=9), 3.79, (s, 3H), 5.01 (bs, 1H), 5.63 (dd, 1H, J=9, 16), 5.84 (m, 1H), 6.06 (m, 1H), 6.38 (dd, 1H, J=16, 9).

Synthesis of Structure (25)

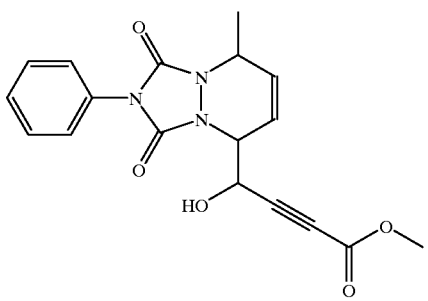

(231)

A 500 mL roundbottom flask was charged with phenyl urazole (4.91 g) and 150 mL of methylene chloride. Iodobenzene diacetate (8.94 g) was added to the flask and the reaction stirred for 10 min. as a deep red color developed. A solution of 5.0 g of compound (230) dissolved in 50 mL of methylene chloride was then added, and the reaction instantaneously decolorized. The reaction was stirred at room temperature for 3 additional hours. The solvent was removed on rotary evaporator and the residue placed under high vacuum overnight. The residue was purified via flash chromatography on silica gel (40% EtOAc/hexane) to give 8.3 g of a ~60/40 diastereomeric mixture of epimeric alcohols (84%). $^1$H NMR (CDCl$_3$) (isomer 1): δ1.474 (d, 3H, J=7), 3.773 (s, 3H), 4.66 (m, 2H), 4.83 (s, 1H), 5.73 (d, 1H, J=10), 6.19 (bd, 1H, J=10), 7.4=7.56 (m, 5H); (isomer 2): δ1.53 (d, 3H, J=7), 3.77 (s, 3H), 4.64 (m, 1H, 4.72 (m, 1H), 5.18 (bs, 1H), 6.1 (s, 2H) 7.36–7.56 (m, 5H); MS (ES+): 356 (M+1), 378 (M+Na).

Synthesis of Structure (26)

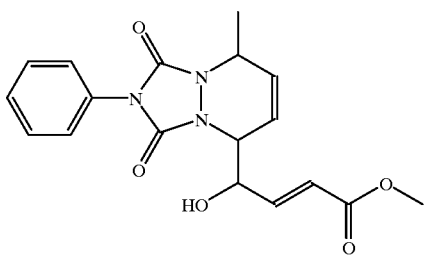

(232)

A solution of 1.0 9 of (231) as a diastereomeric mixture of acetylene alcohols was dissolved in 40 mL of MeOH and cooled to 0° C. in an ice bath. To the reaction mixture 80 mg (~3 equivalents of hydride) of powdered sodium borohydride was added with stirring. After an hour at 0° C., the reaction was warmed to room temperature and stirred for an additional hour. It was quenched by addition of 100 mL EtOAc and 60 mL of water. The layers were separated in a separatory funnel, and the aqueous phase extracted twice with additional EtOAc. The combined organic phases were then washed with saturated sodium chloride and dried over sodium sulfate. The organic solvent was removed by rotary evaporator and the residue purified by flash chromatography (40/60 EtOAc/hexanes) to give 630 mg of a mixture of diastereomerlc alcohols (~63%). $^1$H NMR (CDCl$_3$) isomer 1: δ1.39 (d, 3H, J=11) 3.78 (s, 3H), 4.68 (m, 1H), 4.71 (m, 1H), 4.75 (m, 1H), 5.81 (d, 1H, J=10), 6.16 (dm, 1H, J=10), 6.26 (d, 1H, J=9), 7.01 (d, J=9), 7.01 (d, J=9), 7.35=7.5 (m, 5H). Isomer 2: 1.43 (d, 3H, J=10), 3.72 (s, 3H), 4.5 (m, 2H), 5.53 (d, 1H, J=12), 5.86 (m, 2H), 6.12 (d, 1H, J=10) 6.89 (d, 1H, J=10), 7.35–7.5 (m, 5H). MS (ES+) 358 (M+1).

Synthesis of Structure (27)

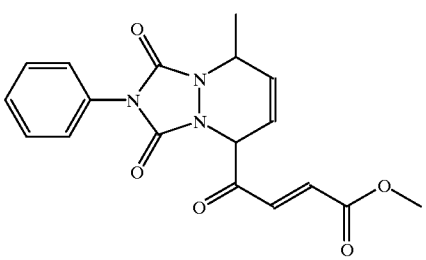

(233)

To a solution of 357 mg of compound (231) as a diastereomeric mixture in 50 mL of methylene chloride was added 424 mg of powdered Dess-Martin reagent. The reaction stirred at room temperature for 6 h. It was then stirred for five minutes with a sodium thiosulfate solution and extracted with aqueous bicarbonate solution. The organic phase was washed with saturated sodium chloride and dried over anhydrous sodium sulfate. The methylene chloride was removed by rotary evaporation to give 348 mg of a solid residue (97%). δ1.61 (d, 3H, J=9 Hz), 3.82 (s, 3H), 4.52 (bm, 1H), 5.16 (s, 1H), 5.93 (bd, 1H, J=10 Hz), 6.01 (bd, 1H, J=10 Hz), 6.88 (d, 1H, J=15 Hz), 7.29 (d, 1H, J=15 Hz), 7.3–7.55 (m, 5H); MS (EI) 355 (M°).

Synthesis of Structure (28)

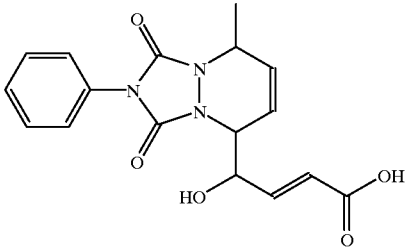

(234)

A 100 mL roundbottom flask was charged with 357 mg of compound (232) as an isomeric mixture of alcohols and 25 mL of THF. The reaction solution was cooled to 0° C., the reaction was allowed to warm up to room temperature, and stirred for an additional hour. It was then extracted with 40 mL of EtOAc and 30 mL of water. The aqueous phase was acidified with 1 mmol of tartaric acid, and reextracted with 40 mL of fresh EtOAc. The organic phase was dried over anhydrous NaSO$_4$, filtered and the solvent removed via rotary evaporator to give 328 mg of a solid residue. $^1$H NMR (CDCl$^3$) isomer 1: δ1.37 (d, 3H, J=6.5), 4.61 (m, 1H), 4.65 (m, 1H), 4.68 (m, 1H), 5.77 (d, 1H, J=11), 6.12 (d, 1H, J=11), 6.23 (d, 1H, J=15), 7.083 (d, 1H, J=15), 7.35–7.54 (m, 5H); isomer 2: 1.47 (d, 3H, J=6.5), 4.5 (m, 1H), 4.58 (m, 1H), 4.96 (m, 1H), 5.9 (m, 2H), 6.12 (d, 1H, J=16), 6.98 (d, 1H, J=16) 7.35=7.54 (m, 5H).

Example 32

In this example, compounds (231) and (233) of Example 31 were assayed for their ability to block insulin disulfide reduction by thioredoxin. Thioredoxin has been shown to up-regulate NF-kB for DNA binding by reduction of a disulfide bond involving Cys62 of the p50 subunit of NF-kB. Thioredoxin is also known to reduce the disulfide bonds in insulin $10^4$ times faster than low molecular weight thiols (Holmgren, *J. Biol. Chem.* 254:9627–9632, 1979) (incorporated herein by reference). Therefore, if an inhibitor of NF-kB activation is acting via inhibition of thioredoxin, it should also be able to block reduction of insulin by thioredoxin. The following assay measures spectrophotometrically the increasing turbidity of insulin at 650 nm as its disulfide bonds are reduced in the presence of thioredoxin.

A slight modification of the method of Holmgren was used. On a 96 well microtiter plate solutions of thioredoxin in 0.1 M potassium phosphate pH 6.5 buffer were preactivated for 15 minutes in the presence of 0.33 mM dithiothreitol (DTT) and 2 mM EDTA. Solutions of substrate and inhibitor were added to a final concentration of 8 $\mu$M thioredoxin, 0.13 mM insulin, and 0–100 $\mu$M of either compound (231) or (233). The turbidity of the solutions was measured at 650 nM over the course of 60 minutes on a Spectra Max 250 absorbance plate reader (Molecular Devices). The results demonstrate that turbidity decreases with increasing concentration of compounds (231) or (233).

As a negative control, inhibitor in the presence of DTT and EDTA, but without thiorfedoxin present did not display turbidity (DTT did not reduce thioredoxin over the time period examined). As a positive control, the structurally related natural products parthenolide and santonin were tested in the above assay in place of the inhibitors. Parthenolide, which contains an unsaturated exomethylene lactone and is known to inhibit NF-KB activation in a concentration dependent fashion (Bork et al., *FEBS Lett.* 402: 85–90, 1997), similarly blocked thioredoxin-induced turbidity of insulin. Santonin, which contains a saturated lactone group and does not inhibit NF-kB activation, did not block thioredoxin-induced turbidity of insulin. Taken together, these results are evidence that compounds (231) and (233) prevent NF-kB activation by inhibition of thioredoxin.

Example 33
Activity of a Representative β-Sheet Mimetic as a Protease Inhibitor

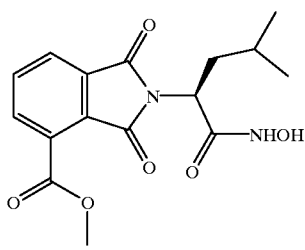

(234)

This example further illustrates the activity of a β-sheet mimetic of structure (234) (prepared by methods disclosed in reaction scheme 20) as an inhibitor of the metalloproteinases leucine aminopeptidase M and thermolysin. The method is a modification of that of Spungin-Bialik et al., *FEBS Lett.* (1996) 380, 79–82.

The following protocol was used: A buffer solution containing 50 mM Tris-Cl, 100 mM NaCl, 1 mM $CaCl_2$, 0.005% Triton X-100 (pH=7.5) is prepared. A second buffer solution, 40 mM in EDTA, is prepared from the first. A 750 $\mu$M solution of substrate, Suc-Ala-Ala-Phe-pNA, is prepared in water from a 50 mM stock solution DMSO. A 15 nM solution of thermolysin is prepared by diluting with buffer a 200 $\mu$M thermolysin stock solution in 20% glycerol/$H_2O$. Dilute the commercially available solution of Leucine Aminopeptidase M (Sigma, 2.6 mg/ml stock in $H_2O$) down to 50 $\mu$g/ml with buffer. The inhibitor in 50% EtOH/$H_2O$ was diluted with water to 3x the desired concentration levels. Add 50 $\mu$l of enzyme, substrate, and inhibitor per well (96 well microtiter plate) to the desired number of microtiter strips. This will yield final concentrations of 5 nM for thermolysin and 250 $\mu$M for the substrate. The wells should then be incubated at rt for 20 minutes. After 20 minutes, add the EDTA in buffer solution to all wells at 50 $\mu$L per well. and add simultaneously to the wells at 50 $\mu$l per well. This will yield a final concentration of 10 $\mu$g/ml. The plate should be read 100x at 405 nm with 21 second intervals. $K_i$ values were calculated as before (Example 5). The values of $K_i$ obtained for compound (234) were 6 and 11 $\mu$M for thermolysln and leucine aminopeptidase M, respectively. These results demonstrate that a β-sheet mimetic of this invention can function as a metalloproteinase inhibitor.

Example 34
Activity of a Representative β-Sheet Mimetic as a Protease Inhibitor

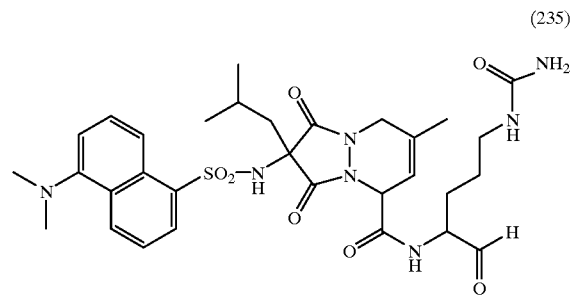

(235)

This example further illustrates the activity of a β-sheet mimetic of structure (235) (prepared by methods disclosed in reaction scheme 15) as an inhibitor of the cysteine proteinase, papain. The assay method is a modification of that of Mellor et al., *Biochem. J.* (1993) 290, 289.

The assay was conducted in a microtiter plate as in Example 4. The following protocol was used: Prepare a buffer containing 0.05 M sodium citrate, 0.15 M NaCl, 2 mM DTT, 1 mM EDTA (pH=6.5). A 2 mM stock solution of substrate (Ac-Phe-Gly-pNA) is diluted to 200 $\mu$M in buffer. A 5 mM stock solution (in 50% EtOH/$H_2O$) of the inhibitor is diluted to 500 $\mu$M in buffer, and six serial 1:5 dilutions are made. Aliquots of 100 $\mu$L each of buffer, substrate, and inhibitor (at the appropriate concentrations) are added per well to an eight well microtiter strip. A 1.0 mM stock solution of papain is diluted to 200 $\mu$M in buffer and incubated for 5 min prior to addition of a 100 $\mu$L aliquot to the assay wells. The plate should be read 100x at 405 nm with 21 second intervals. $IC_{50}$ values were calculated as before (Example 4). Compound (234) exhibited an $IC_{50}$ value of 8 $\mu$M. This result demonstrates that a β-sheet mimetic of this invention can function as a cysteine proteinase inhibitor.

Example 35
Activity of Representative β-Sheet Mimetics as Antithrombotic Agents

This example illustrates the activity of β-sheet mimetics of structures (221-14) and (221-21) of Table 14 as antithrombotic agents. Rats (Splague Dawley) were fasted overnight and used under pentobarbital anesthesia. A polyethylene tube containing a 5 cm silk thread was placed between the right cartid artery and the left junglar vein. Thirty minutes after oral administration of 100 mg.kg of one of the above compounds (dissolved with 50% propylene glycol at 20 mg/ml, and orally administered 5 ml/kg), or one minute after intravenous administration of the Argatroban (0.3 mg/kg), blood was circulated through the tube for seven minutes. At the end of circulation, the tube was removed and the thrombus wet weight and thrombus protein content were measured. Blood was also withdrawn from the abdominal artery and APTT was measured.

Figure 5A:
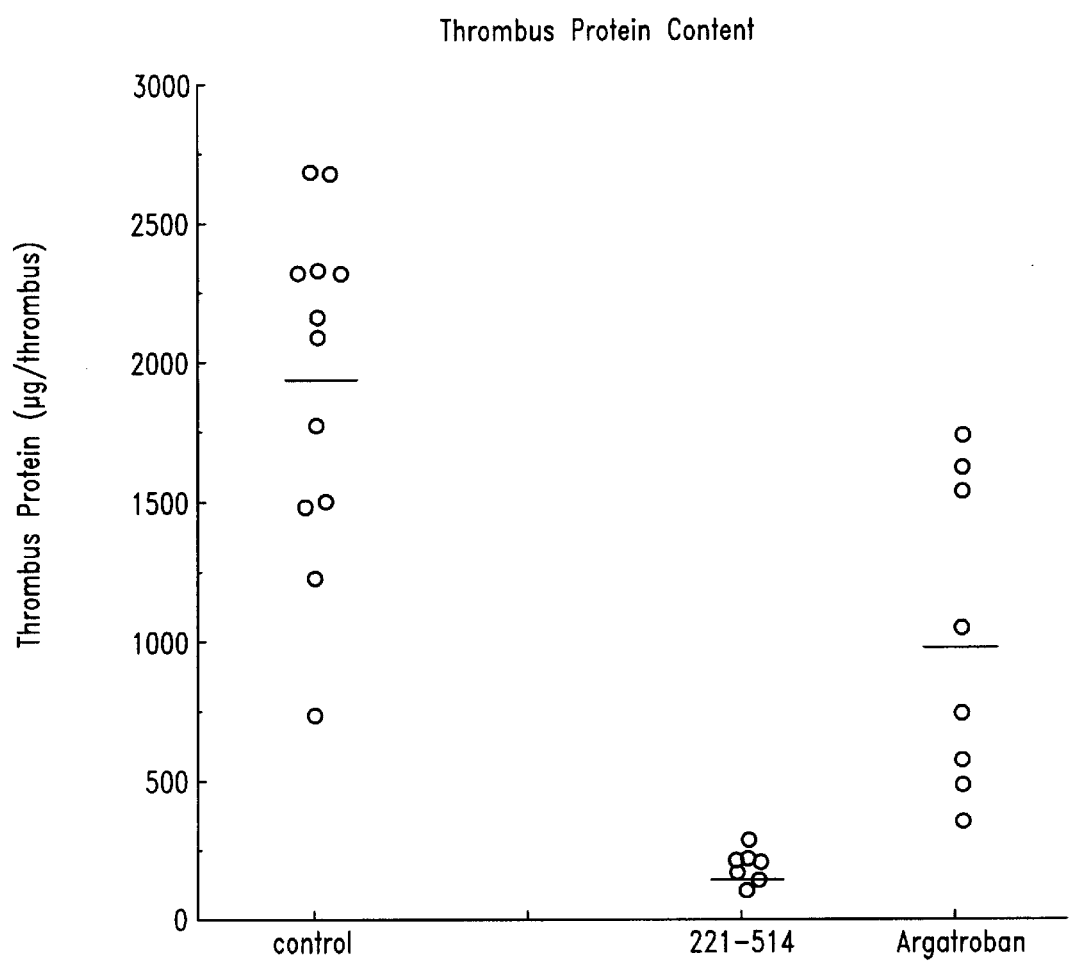
FIGS. 5A and 5B illustrate the ability of structures (221-5) and (221-6) to serve as antithrombotic agents.
Figure 5B:
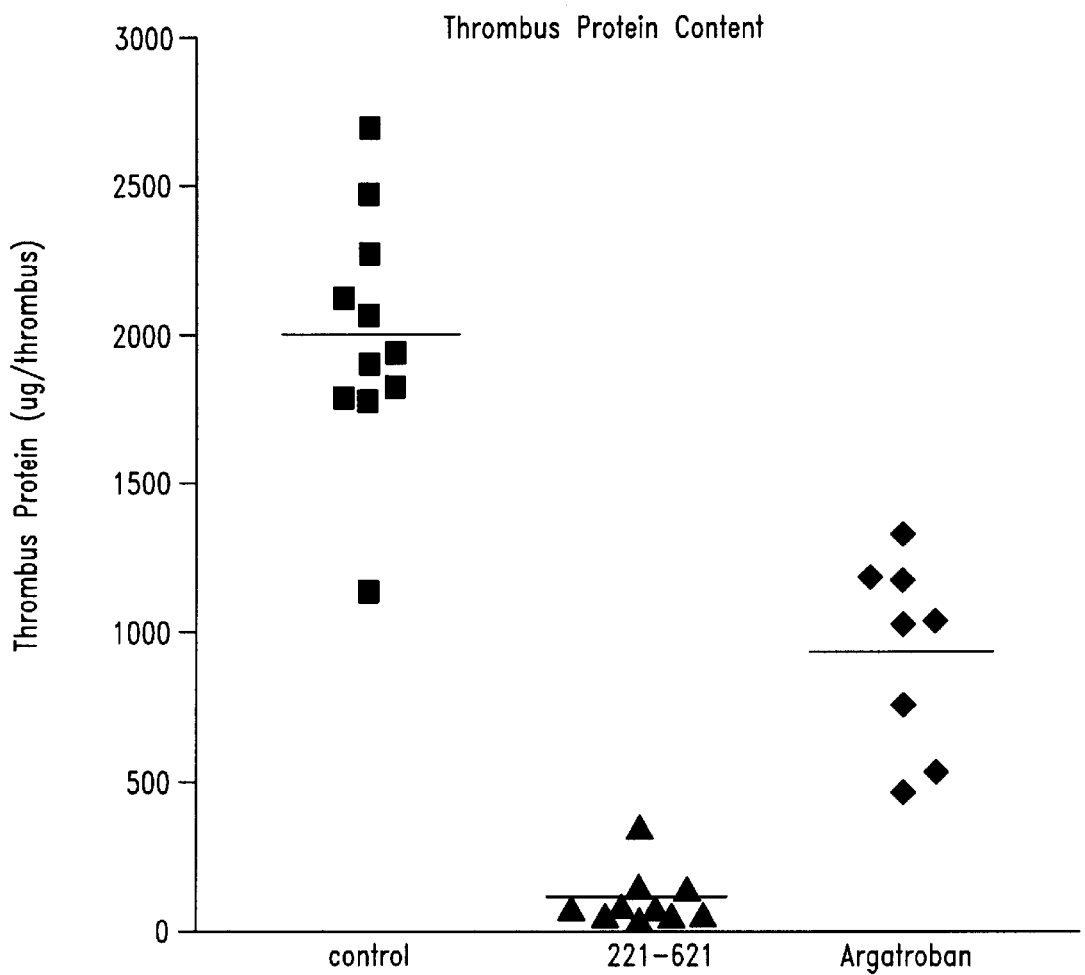

The results of these experiments are presented in FIGS. 5A and 5B, which plot thrombus protein (μg/thrombus) for each of a negative control (without added compound), compound 221-14 (FIG. 5A) or 221-21 (FIG. 5B) and Argatroban (a positive control). These results illustrate that both of the tested compounds significantly inhibit thrombus formation.

From the foregoing, it will be understood that, although specific embodiments of this invention have been described herein for purposes of illustration, various modifications may be made without departing from the spirit and scope of the invention. Accordingly, the invention is not limited except by the appended claims.

What is claimed is:

1. A compound having the structure:

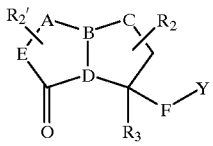

or a pharmaceutically acceptable salt thereof, wherein
A is selected from —C(=O)—, —(CH$_2$)$_{0-4}$—, —C(=O)(CH$_2$)$_{1-3}$—, —(CH$_2$)$_{1-2}$O— and —(CH$_2$)$_{1-2}$S—;
B is selected from N and CH;
C is selected from —C(=O)—, —C(=O)(CH$_2$)$_{1-3}$—, —(CH$_2$)$_{0-3}$—, —O—, —S—, —O—(CH$_2$)$_{1-2}$— and —S(CH$_2$)$_{1-2}$—;
D is selected from N and C(R$_4$),
E is selected from

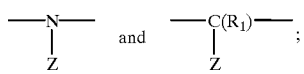

F is a direct bond or a carbonyl moiety;
R$_1$, R$_3$' and R$_4$ are independently selected from amino acid side chain moieties and derivatives thereof;
R$_2$ is selected from an amino acid side chain moiety and derivatives thereof, or taken together with C forms a fused substituted or unsubstituted homocyclic or heterocyclic ring;
R$_3$ is independently selected from an amino acid side chain moiety and derivatives thereof, or taken together with C forms a bridging moiety selected from —(CH$_2$)$_{1-2}$—, —O— and —S—;

Y and Z represent the remainder of the molecule; and
any two adjacent CH groups of the bicyclic ring do or do not form a double bond;
and wherein
when F is a carbonyl moiety, Y is anached to F by a C(=O)N bond, with the proviso that Y is not NH$_2$; and
when F is a direct bond, Y is selected from

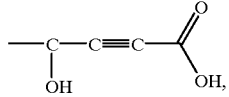

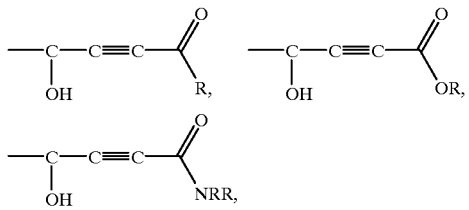

—CH(OH)CH=CHC(=O)OH, —CH(OH)CH=CHC(=O)R, —CH(OH)CH=CHC(=O)OR, —CH(OH)CH=CHC(=O)NRR, —CH=CHC(=O)SO$_2$R and —SO$_2$CH=CHR, wherein each occurrence of R is independently selected from a lower chain alkyl moiety, a lower chain aryl moiety, a lower chain aralkyl moiety and a heterocyclic moiety;
with the proviso that the compound is not 7-methoxy-1,3-dioxo-2-phenyl-N-[(1S)-1-phenylethyl]-2,3,5,8-tetrahydro-1H-[1,2,4]triazolo[1,2-α]pyridazine-5-carboxamide; 7-methoxy-2-phenyl-5-(1-piperidinylcarbonyl)-5,8-dihydro-1H-[1,2,4]triazolo[1,2-α]pyridazine-1,3(2H)dione; (3aR,7aS)-6-methoxy-2-phenyl-4-(1-pyrroldinylcarbonyl)-3a,4,7,7a-tetrahydro-1H-isoindole-1,3(2H)-dione; (3aR,7aS)-6-methoxy-2-phenyl-4-(1-piperidinylcarbonyl)-3a,4,7,7a-tetrahydro-1H)-isoindole-1,3(2H)-dione; 2-phenyl-8-(1-piperidinylcarbonyl)-5,8-dihydro-1H-[1,2,4]triazolo[1,2-α]pyridazine-1,3,6(2H,5H)trione; or (3aR,7aS)-2-phenyl-7-(1-piperidinylcarbonyl)-tetrahydro-1H-isoindole-1,3,5(2H,4H)-trione.

2. The compound according to claim 1 wherein F is a carbonyl moiety.

3. The compound according to claim 2 wherein E is

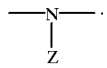

4. The compound according to claim 3 wherein A is —C(=O)—.

5. The compound according to claim 3 wherein C is —(CH$_2$)$_{0-3}$.

6. The compound according to claim 3 wherein R$_3$ is hydrogen.

7. the compound according to claim 3 wherein B is N and D is N.

8. the compound according to claim 7 wherein A is —C(=O)—.

9. The compound according to claim 7 wherein C is —C(CH$_2$)$_{0-3}$—.

10. The compound according to claim 9 wherein A is —C(=O)—.

11. The compound according to claim 10 wherein $R_3$ is hydrogen.

12. The compound according to claim 11 having the structure:

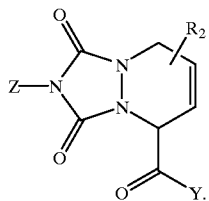

13. The compound according to claim 12 having the structure:

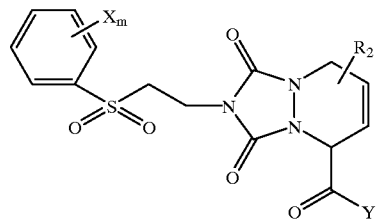

wherein X is a substituent and m=0–4.

14. The compound according to claim 12 having the structure:

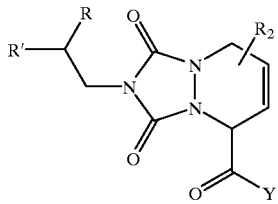

wherein R and R' are the same or different and are selected from

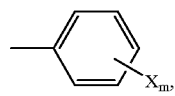

wherein X is a substituent and m=0–4.

15. The compound according to claim 14 having the structure:

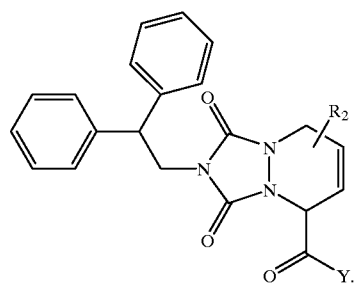

16. The compound according to claim 12 having the structure:

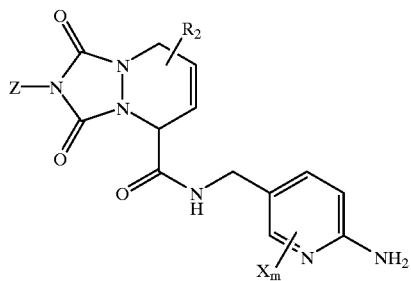

wherein X is a substituent and m=0–4.

17. The compound according to claim 12 having the structure:

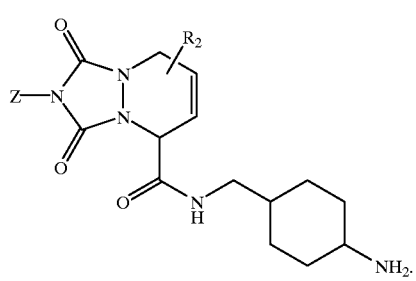

18. The compound according to claim 17 having the structure:

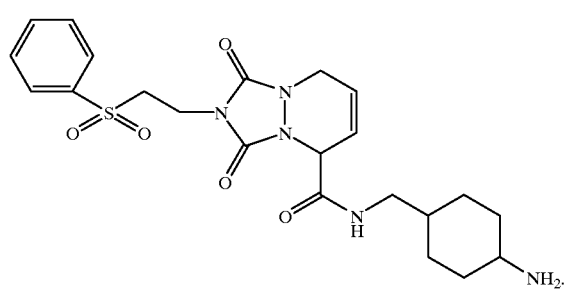

19. The compound according to claim 12 having the structure:

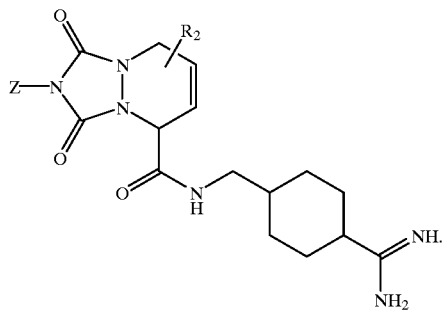

20. The compound according to claim 19 having the structure:

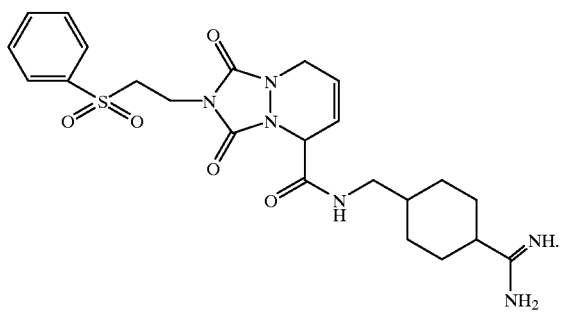

21. The compound according to claim 12 having the structure:

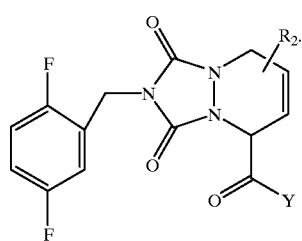

22. The compound according to claim 12 having the structure:

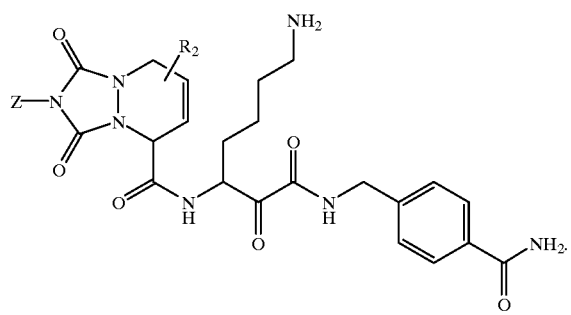

23. The compound according to claim 22 having the structure:

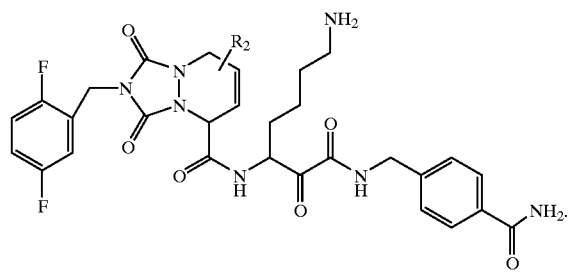

24. The compound according to claim 12 having the structure:

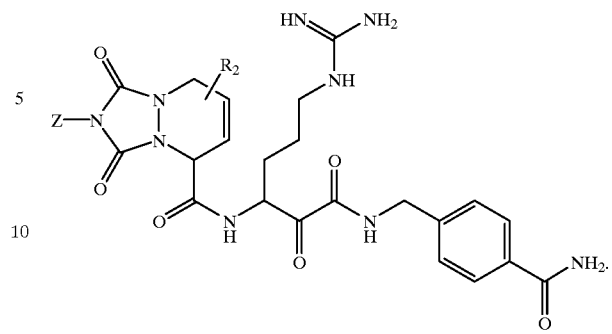

25. The compound according to claim 24 having the structure:

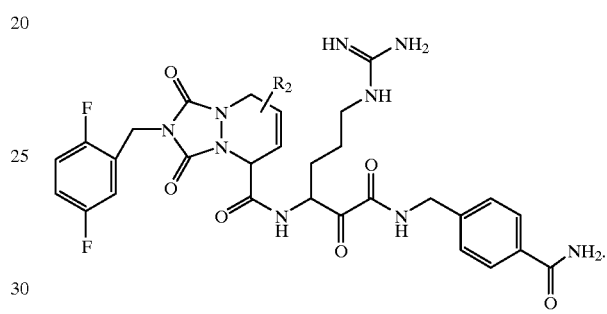

26. The compound according to claim 11 having the structure:

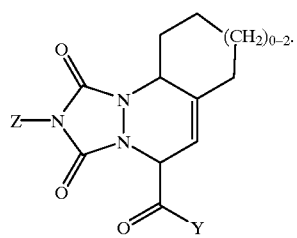

27. The compound according to claim 11 having the structure:

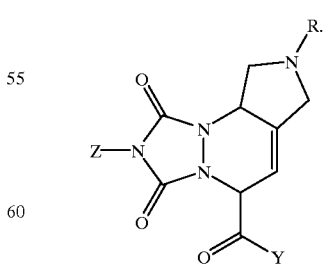

28. The compound according to claim 11 having the structure:

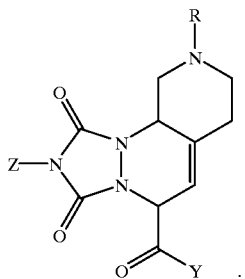

29. The compound according to claim 11 having the structure:

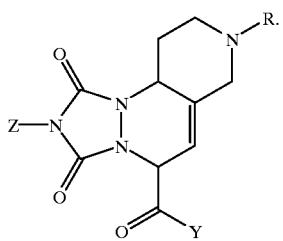

30. The compound according to claim 11 wherein $R_2$ and C taken together form a fused five-, seven-, or eight-membered ring having the structure:

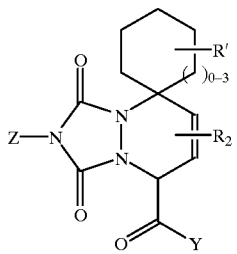

wherein R' represents one or more optional ring substituents.

31. The compound according to claim 30 having the structure:

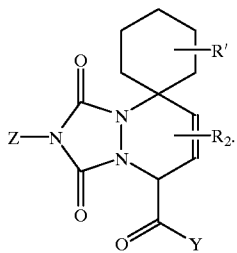

32. The compound according to claim 11 wherein $R_2$ and C taken together form a fused five, six-, seven- or eight-membered ring having the structure:

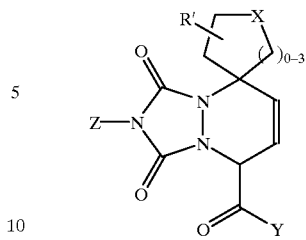

wherein X is selected from —C(=O)—, —NH—, —O— and —S—; and R' represents one or more optional ring substituents.

33. The compound according to claim 32 wherein X is —NH— and having the structure:

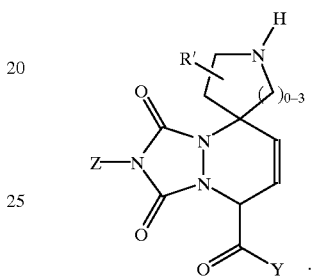

34. The compound according to claim 33 having the structure:

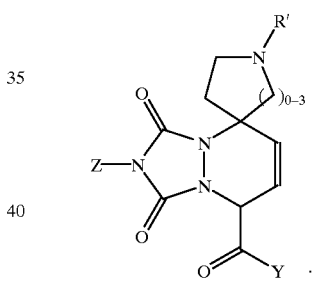

35. The compound according to claim 34 having the structure:

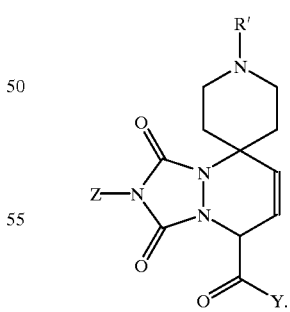

36. The compound according to claim 3 wherein B is CH and D is C($R_4$).

37. The compound according to claim 36 wherein C is —(CH$_2$)$_{0-3}$—.

38. The compound according to claim 36 wherein A is —C(=O)—.

39. The compound according to claim 38 wherein C is —(CH$_2$)$_{0-3}$—.

40. The compound according to claim 39 having the structure:

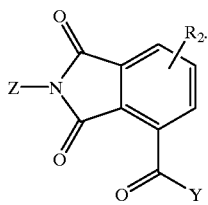

41. The compound according to claim 2 wherein E is

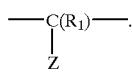

42. The compound according to claim 41 wherein A is —C(=O)—.

43. The compound according to claim 41 wherein C is —(CH$_2$)$_{0-3}$—.

44. The compound according to claim 41 wherein R$_3$ is hydrogen.

45. The compound according to claim 41 wherein B is N and D is N.

46. The compound according to claim 45 wherein A is —C(=O)—.

47. The compound according to claim 45 wherein C is —(CH$_2$)$_{0-3}$—.

48. The compound according to claim 47 wherein A is —C(=O)—.

49. The compound according to claim 48 wherein R$_3$ is hydrogen.

50. The compound according to claim 49 having the structure:

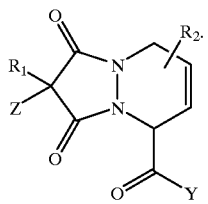

51. The compound according to claim 41 wherein B is CH and D is C(R$_4$).

52. The compound according to claim 51 wherein C is —(CH$_2$)$_{0-3}$—.

53. The compound according to claim 51 wherein A is —C(=O)—.

54. The compound according to claim 53 wherein C is —(CH$_2$)$_{0-3}$—.

55. The compound according to claim 54 having the structure:

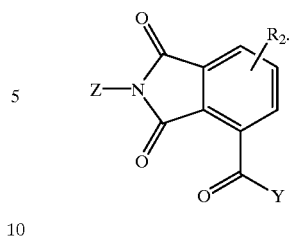

56. The compound according to claim 1, wherein F is a direct bond.

57. The compound according to claim 56 wherein Y is selected from

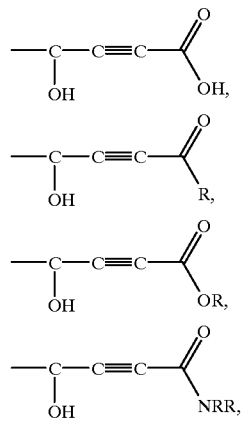

—CH(OH)CH=CHC(=O)OH, —CH(OH)CH=CHC(=O)R, —CH(OH)CH=CHC(=O)OR and —CH(OH)CH=CHC(=O)NRR.

58. The compound according to claim 57 wherein Y is selected from

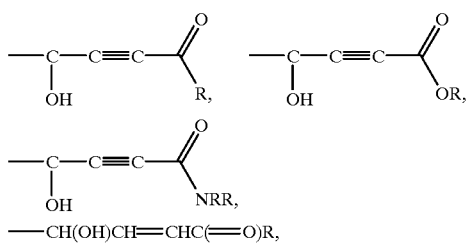

—CH(OH)CH=CHC(=O)R, —CH(OH)CH=CHC(=O)OR and —CH(OH)CH=CHC(=O)NRR.

59. The compound according to claim 58 wherein Y is selected from

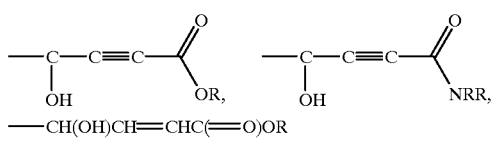

and —CH(OH)CH=CHC(=O)OR and —CH(OH)CH=CHC(=O)NRR.

60. The compound according to claim 59 wherein Y is selected from

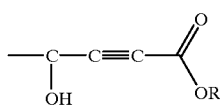

and —CH(OH)CH=CHC(=O)OR.

61. The compound according to claim 60 wherein Y is selected from

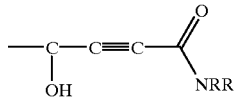

and —CH(OH)CH=CHC(=O)NRR.

62. A composition comprising the compound of claim 1 and a pharmaceutically acceptable carrier.

63. The composition according to clai 62 wherein F is a carbonyl moiety.

64. The composition according to claim 62 wherein F is a direct bond.

65. A method for inhibiting a protease, comprising administering to an animal in need thereof an effective amount of a compound having the structure:

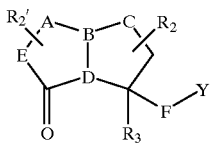

or a pharmaceutically acceptable salt thereof, wherein

A is selected from —C(=O)—, —(CH$_2$)$_{0-4}$—, —C(=O)(CH$_2$)$_{1-3}$—, —(CH$_2$)$_{1-2}$O— and —(CH$_2$)$_{1-2}$S—;

B is selected from N and CH;

C is selected from —C(=O)—, —C(=O)(CH$_2$)$_{1-3}$—, —(CH$_2$)$_{0-3}$—, —O—, —S—, —O—(CH$_2$)$_{1-2}$— and —S(CH$_2$)$_{1-2}$—;

D is selected from N and C(R$_4$);

E is selected from

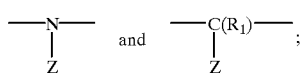

F is a direct bond or a carbonyl moiety;

R$_1$, R$_2$' and R$_4$ are independently selected ftom amino acid side chain moieties and derivatives thereof;

R$_2$ is selected from an amino acid side chain moiety and derivatives thereof, or taken together with C forms a fused substituted or unsubstituted homocyclic or heterocyclic ring;

R$_3$ is independently selected from an amino acid side chain moiety and derivatives thereof, or taken together with C forms a bridging moiety selected from —(CH$_2$)$_{1-2}$—, —O— and —S—;

Y and Z represent the remainder of the molecule; and any two adjacent CH groups of the bicyclic ring do or do not form a double bond, and wherein when F is a carbonyl moiety, Y is attached to F by a C(=O)N bond, with the proviso that Y is not NH$_2$; and when F is a direct bond, Y is selected from

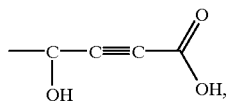

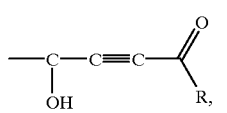

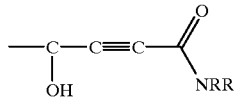

—CH(CH)CH=CHC(=O)OH, —CH(OH)CH=CHC(=O)R, —CH(OH)CH=CHC(=O)OR, —CH(OH)CH=CHC(=O)NRR, —CH=CHC(=O)SO$_2$R and —SO$_2$CH=CHR, wherein each occurrence of R is independently selected from a lower chain alkyl moiety, a lower chain aryl moiety, a lower chain aralkyl moiety and a heterocyclic moiety.

66. The method of claim 65 wherein E is

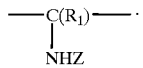

67. The method of claim 65 wherein E is

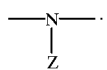

68. The method of claim 65 wherein E is

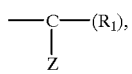

with the proviso that Z does not contain an —NH— moitey attached to the carbon atom bearing the R$_1$ substituent.

69. The method of claim 65 wherein the protease is a serine protease.

70. The method of claim 69 wherein the serine protease is selected from thrombin, Factor X, Factor IX, Factor VII, Factor XI, urokinase, HCV protease, chymase tryptase and kallikrein.

71. The method of claim 69 wherein the serine protease is thrombin.

72. The method of claim 69 wherein the serine protease is Factor VII.

73. The method of claim 65 wherein the protease is selected from an aspartic, cysteine and metalic protease.

* * * * *

UNITED STATES PATENT AND TRADEMARK OFFICE
CERTIFICATE OF CORRECTION

PATENT NO. : 6,372,744 B1
DATED : April 16, 2002
INVENTOR(S) : Maher N. Qabar et al.

It is certified that error appears in the above-identified patent and that said Letters Patent is hereby corrected as shown below:

<u>Title page,</u>
Item [60], Related U.S. Application Data, "Division of application No. 09/022,934, filed on Feb. 12, 1998, now Pat. No. 6,117,896, and a continuation-in-part of application No. 08/797,915, filed on Feb. 10, 1997, now abandoned, and a continuation-in-part of application No. 08/692,420, filed as application No. PCT/US97/13622 on Aug. 4, 1997, now abandoned" should be corrected to read -- Division of application No. 09/022,934, filed on Feb. 12, 1998, now Pat. No. 6,117,896, and a continuation-in-part of application No. 08/797,915 filed on Feb. 10, 1997, now abandoned, and a continuation-in-part of application No. 08/692,420, filed as application No. PCT/US97/13622 on Aug. 5, 1997, now abandoned --.

<u>Column 251,</u>
Line 57, "$R_1$, $R_3$' and $R_4$ are independently selected" should be corrected to read -- $R_1$, $R_2$' and $R_4$ are independently selected --.

<u>Column 252,</u>
Line 5, "Y is anached to F" should be corrected to read -- Y is attached to F --.

<u>Column 260,</u>
Line 1, the following formula "

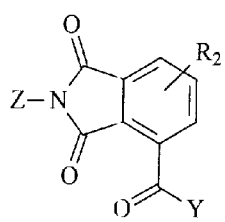

"

should be corrected to read --

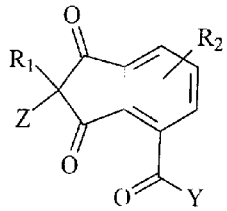

UNITED STATES PATENT AND TRADEMARK OFFICE
CERTIFICATE OF CORRECTION

PATENT NO. : 6,372,744 B1  
DATED : April 16, 2002  
INVENTOR(S) : Maher N. Qabar et al.

It is certified that error appears in the above-identified patent and that said Letters Patent is hereby corrected as shown below:

Column 260, cont'd.
Line 49, the following formula

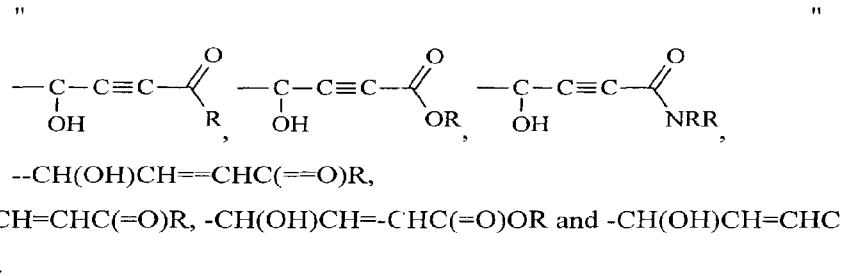

--CH(OH)CH==CHC(==O)R,

-CH(OH)CH=CHC(=O)R, -CH(OH)CH=-CHC(=O)OR and -CH(OH)CH=CHC(=O)NRR.

should be corrected to read --

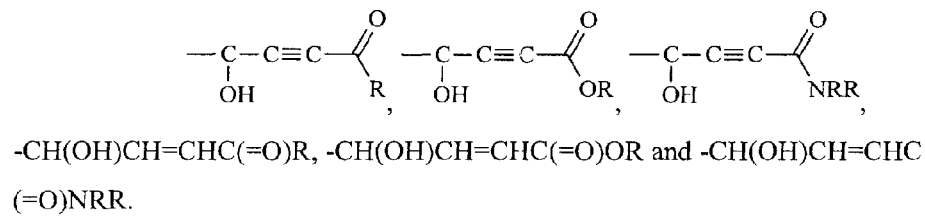

-CH(OH)CH=CHC(=O)R, -CH(OH)CH=CHC(=O)OR and -CH(OH)CH=CHC(=O)NRR.

Line 61, the following formula

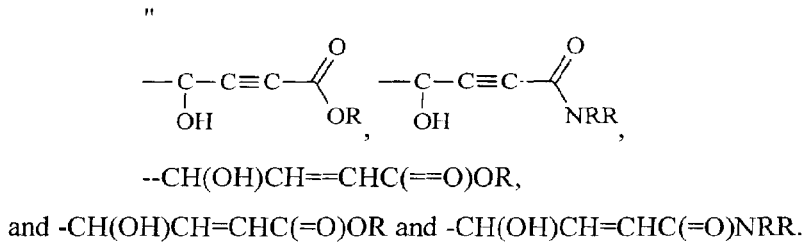

--CH(OH)CH==CHC(==O)OR, and -CH(OH)CH=CHC(=O)OR and -CH(OH)CH=CHC(=O)NRR.

should be corrected to read --

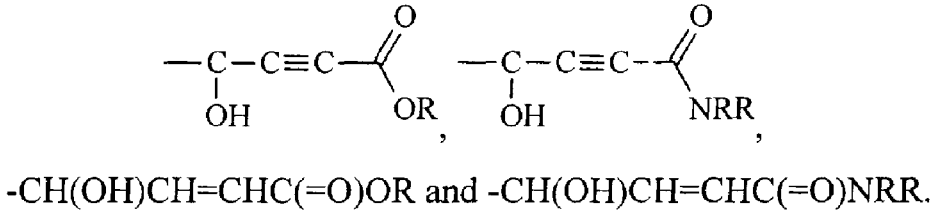

-CH(OH)CH=CHC(=O)OR and -CH(OH)CH=CHC(=O)NRR.

UNITED STATES PATENT AND TRADEMARK OFFICE
CERTIFICATE OF CORRECTION

PATENT NO. : 6,372,744 B1
DATED : April 16, 2002
INVENTOR(S) : Maher N. Qabar et al.

It is certified that error appears in the above-identified patent and that said Letters Patent is hereby corrected as shown below:

<u>Column 261,</u>
Line 20, "according to clai 62" should be corrected to read -- according to claim 62 --
Line 51, "are independently selected ftom" should be corrected to read -- are independently selected from --.

<u>Column 262,</u>
Line 56, "chymase tryptase and" should be corrected to read -- chymase, tryptase and --.
Line 63, "and metalic protease" should be corrected to read -- and metallo protease --.

Signed and Sealed this

Twelfth Day of November, 2002

Attest:

JAMES E. ROGAN
Attesting Officer
Director of the United States Patent and Trademark Office

UNITED STATES PATENT AND TRADEMARK OFFICE
CERTIFICATE OF CORRECTION

PATENT NO. : 6,372,744 B1
DATED : April 16, 2002
INVENTOR(S) : Maher N. Qabar et al.

It is certified that error appears in the above-identified patent and that said Letters Patent is hereby corrected as shown below:

Column 257,
Line 31, "form a fused five-, seven-, or" should read -- form a fused five-, six-, seven-, or --.

Column 262,
Lines 23-26, the following formula: "-CH(CH)CH=CHC(=O)OH, -CH(OH)CH=CHC(=O)R, -CH(OH)CH=CHC(=O)OR, -CH(OH)CH=CHC(=O)NRR, -CH=CHC(=O)SO$_2$R and -SO$_2$CH=CHR," should read -- -CH(OH)CH=CHC(=O)OH, -CH(OH)CH=CHC(=O)R, -CH(OH)CH=CHC(=O)OR, -CH(OH)CH=CHC(=O)NRR, -CH=CHC(=O)SO$_2$R and -SO$_2$CH=CHR, --.

Signed and Sealed this

Eighth Day of April, 2003

JAMES E. ROGAN
*Director of the United States Patent and Trademark Office*